United States Patent
Garred et al.

(10) Patent No.: US 11,945,848 B2
(45) Date of Patent: Apr. 2, 2024

(54) CHIMERIC INHIBITOR MOLECULES OF COMPLEMENT ACTIVATION

(71) Applicant: Omeros Corporation, Seattle, WA (US)

(72) Inventors: Peter Garred, Charlottelund (DK); Tina Hummelshoj Glue, Soborg (DK); Mikkel-Ole Skjodt, Frederiksberg C (DK)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 17/818,583

(22) Filed: Aug. 9, 2022

(65) Prior Publication Data

US 2023/0295252 A1 Sep. 21, 2023

Related U.S. Application Data

(60) Continuation of application No. 16/930,973, filed on Jul. 16, 2020, now Pat. No. 11,453,709, which is a continuation of application No. 15/729,924, filed on Oct. 11, 2017, now Pat. No. 10,752,661, which is a division of application No. 13/582,814, filed as application No. PCT/EP2011/053309 on Mar. 4, 2011, now Pat. No. 9,815,876.

(60) Provisional application No. 61/311,024, filed on Mar. 5, 2010.

(30) Foreign Application Priority Data

Mar. 5, 2010 (EP) ..................................... 10155621

(51) Int. Cl.
| | | |
|---|---|---|
| *A61K 38/17* | (2006.01) | |
| *A61K 38/00* | (2006.01) | |
| *A61K 45/06* | (2006.01) | |
| *C07K 14/47* | (2006.01) | |
| *C07K 14/705* | (2006.01) | |
| *C07K 14/81* | (2006.01) | |

(52) U.S. Cl.
CPC .......... *C07K 14/47* (2013.01); *A61K 38/1725* (2013.01); *A61K 45/06* (2013.01); *C07K 14/472* (2013.01); *C07K 14/4726* (2013.01); *C07K 14/70596* (2013.01); *C07K 14/8121* (2013.01); *H05K 999/99* (2013.01); *A61K 38/00* (2013.01); *C07K 2319/01* (2013.01); *C07K 2319/02* (2013.01); *C07K 2319/30* (2013.01); *C07K 2319/70* (2013.01); *Y02A 50/30* (2018.01)

(58) Field of Classification Search
None
See application file for complete search history.

(56) References Cited

U.S. PATENT DOCUMENTS

| | | |
|---|---|---|
| 9,573,984 B2 | 2/2017 | Garret et al. |
| 9,815,876 B2 | 11/2017 | Garred et al. |
| 2008/0221011 A1 | 9/2008 | Gilkeson et al. |
| 2008/0267980 A1 | 10/2008 | Tomlinson et al. |
| 2015/0210743 A1 | 7/2015 | Garred et al. |

FOREIGN PATENT DOCUMENTS

| | | |
|---|---|---|
| EP | 1539964 B1 | 12/2006 |
| JP | 2004-504027 A | 12/2004 |
| WO | WO 2002/006460 A2 | 1/2002 |
| WO | WO 2002/006460 A3 | 1/2002 |
| WO | WO 2004/050907 A2 | 6/2004 |
| WO | WO 2007/047995 A2 | 4/2007 |
| WO | WO 2007/117996 A2 | 10/2007 |
| WO | WO 2007/149567 A2 | 12/2007 |

OTHER PUBLICATIONS

Skjoedt et al. "A Novel Mannose-bindgni Lectin/Ficolin-associated Protein is Highly Expressed in Heart and Skeletal Muscle Tissues and Inhibits Complement Activation" J. Biol. Chem. 285:8234-8243. (Year: 2010).*
Atkinson, C., et al., "Targeted Complement Inhibitors Protect against Posttransplant Cardiac Ischemia and Reperfusion Injury and Reveal an Important Role for the Alternative Pathway of Complement Activation," *The Journal of Immunology*, 2010, vol. 185, pp. 7007-7013.
Banda, N.K., et al., "Targeted Inhibition of the Complement Alternative Pathway with Complement Receptor 2 and Factor H Attenuates Collagen Antibody-Induced Arthritis in Mice," *The Journal of Immunology*, 2009, vol. 183: 5928-5937, The American Association of Immunologists, Inc.
Beinrohr, L., et al., "C1, MBL-MASPs and C1-inhibitor: novel approaches for targeting complement-mediated inflammation," *Trends in Molecular Medicine*, 2008, vol. 14(12): 511-521, Institute of Enzymology, Budapest, Hungary.
EMBL Database Report for Accession No. ASQ27368, Sep. 18, 2008 (XP002637579).
European Examination Report for European Patent Application No. 10737833.3, dated May 12, 2015.
Fujita, T., "Evolution of the Lectin-Complement Pathway and its Role in Innate Immunity," *Nature Reviews | Immunology*, May 2002, 2: 346-353, Nature Publishing Group.
International Search Report for PCT/US2007/065274 dated Oct. 11, 2007.
International Search Report for PCT/US2007/014602 dated Mar. 6, 2008.

(Continued)

*Primary Examiner* — Sudhakar Katakam
*Assistant Examiner* — Zachary J Miknis
(74) *Attorney, Agent, or Firm* — Womble Bond Dickinson (US) LLP

(57) ABSTRACT

The present invention relates to novel chimeric molecules of ficolin-associated polypeptides, such as fusion polypeptides for the use in the treatment of conditions associated with inflammation, apoptosis, autoimmunity, coagulation, thrombotic or coagulopathic related diseases. The present invention further relates to nucleic acid molecules encoding such fusion polypeptides, vectors and host cells used in the production of the fusion polypeptides.

9 Claims, 45 Drawing Sheets

Figure 1:
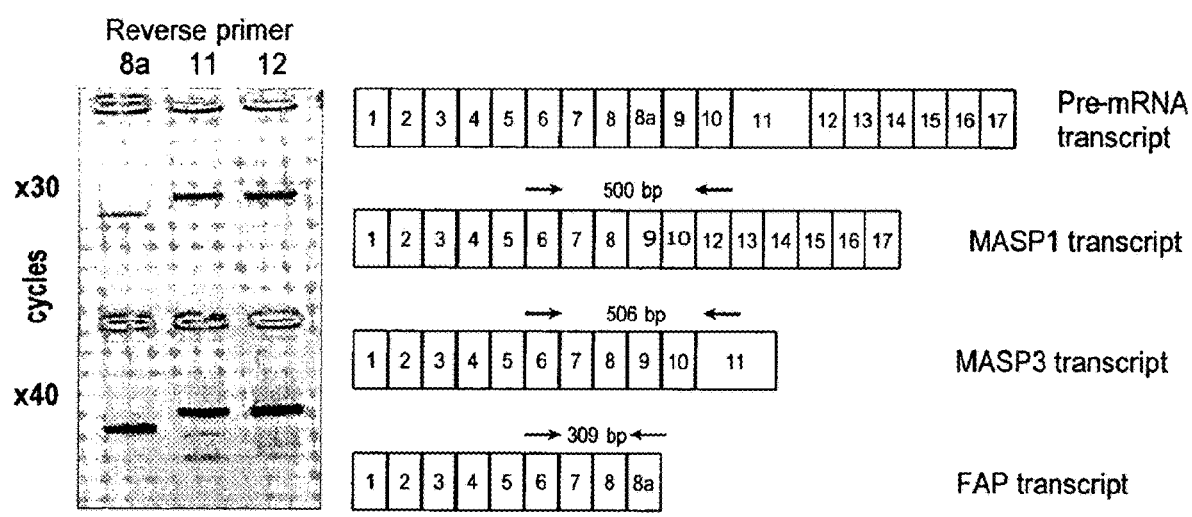

Specification includes a Sequence Listing.

(56) References Cited

OTHER PUBLICATIONS

Jenny, L., et al., "MASP-1 of the complement system enhances clot formation in a microvascular whole blood flow model," *PLoS ONE*, 2018, vol. 13(1), pp. 1-14.

Lambris, J.D., et al., "Complement evasion by human pathogens," *Nature Reviews |Microbiology*, Feb. 2008, 6: 132-142, Nature Publishing Group.

Larsen, et al., "Disease-associated Mutations in Human Mannose-binding Lectin Compromise Oligomerization and Activity of the Final Protein," *J. Biol Chem.*, vol. 279: 21302-21311. Published online Feb. 5, 2004.

Makrides, S., "Therapeutic Inhibition of the Complement System," *Pharmacological Reviews*, 1998, vol. 50, pp. 59-88.

Ratovitski, et al., "Variation in the biochemical/biophysical properties of mutant superoxide dismutase 1 enzymes and the rate of disease progression in familial amyotrophic lateral sclerosis kindreds," *Human Molecular Genetics*, vol. 8, pp. 1451-1460. Published 1999.

Skjoedt, et al., "A Novel Mannose-binding Lectin/Ficolin-associated Protein is Highly Expressed in Heart and Skeletal Muscle Tissues and Inhibits Complement Activation." *J. Biol. Chem.*, vol. 285:8234-8243. Published online Jan. 6, 2010.

Teillet, F., et al., "Crystal Structure of the CUB1-EGF-CUB2 Domain of Human MASP-1/3 and Identification of it Interaction Sites with Mannan-binding lectin and Ficolins," *The Journal of Biological Chemistry*, 2008, vol. 283(37), pp. 25715-25724.

UniprotKB—P48740 (MASP1_HUMAN), Deposited Feb. 1, 1996.

Wallis, R., "Interactions Between Mannose-Binding Lectin and Masps During Complement Activation by the Lectin Pathway," *Immunobiology*, 2007, vol. 212, pp. 289-299.

\* cited by examiner

| Immobilized ligand | Soluble analyte | $K_{on}$ (M$^{-1}$ s$^{-1}$) | $K_{off}$ (s$^{-1}$) | $K_D$ (nM) |
|---|---|---|---|---|
| rFicolin-2 | MASP-1 | $8.9 \times 10^4$ | $4.4 \times 10^{-4}$ | 5.0 |
| rFicolin-2 | MASP-3 | $1.0 \times 10^5$ | $3.0 \times 10^{-4}$ | 2.9 |

```
              10         20         30         40         50         60         70         80         90        100        110        120
         ....|....|....|....|....|....|....|....|....|....|....|....|....|....|....|....|....|....|....|....|....|....|....|....|
GULP     ETENMELKNKVQDLENQLRITQVSAPPAGSMTPKSPSTDIFDMIPFSPISHQSSMPTRNGTQPPPVPSRSTEIKRDLFGAEPFDPFNCGAADFPPDIQSKLDEMQVTILIDWPINDLFHF
FAP      --------EI-...SE.KSE..TE---------------------------------------------------------------------------------------------

130        140
         ....|....|....|....|
GULP     DMGQRECYVPKLWFPSIIFAIKTRLK
FAP      -------------------------
```

FIG. 12

MAP-1/FH expression vector:

MAP-1/FH protein:

MAP-1/FH protein with signal peptide:

MAP-1/C4bp expression vector:

or

MAP-1/C4bp protein:

or

MAP-1/C4bp protein with signal peptide:

or

C4bp constructs:

C4bpA or C4bpB or C4bpA C4bpB or C4bpB C4bpA

MAP-1/FI expression vector:

MAP-1/FI protein:

MAP-1/FI protein with signal peptide:

MAP-1/C1-inh expression vector:

or

MAP-1/C1-inh protein:

or

MAP-1/C1-inh protein with signal peptide:

or

CHIMERIC INHIBITOR MOLECULES OF COMPLEMENT ACTIVATION

CROSS-REFERENCE TO RELATED APPLICATIONS

This application is a continuation of U.S. application Ser. No. 16/930,973, filed Jul. 16, 2020, which is a continuation of U.S. application Ser. No. 15/729,924, filed Oct. 11, 2017, which is a divisional of U.S. patent application Ser. No. 13/582,814, filed Nov. 15, 2012 which was a national stage filing under 35 U.S.C. 371 of PCT/EP2011/053309, filed Mar. 4, 2011, which International Application was published by the International Bureau in English on Sep. 9, 2011, and which claims the benefit of U.S. Provisional Application No. 61/311,024, filed Mar. 5, 2010 and European Application No. 10155621.5, filed Mar. 5, 2010.

REFERENCE TO A SEQUENCE LISTING SUBMITTED ELECTRONICALLY AS AN XML FILE

The instant application contains a sequence listing which has been submitted in ST.26 format via USPTO Patent Center and is hereby incorporated by reference in its entirety. Said ST.26 copy, created on May 16, 2023, is named I88449 1060USD1C2-Seq_List-5-16-23, and is 121 KB in size.

FIELD OF THE INVENTION

The present invention relates to novel chimeric molecules of ficolin-associated polypeptides, such as fusion polypeptides for the use in the treatment of conditions associated with inflammation, apoptosis, autoimmunity, coagulation, thrombotic or coagulopathic related diseases. The present invention further relates to nucleic acid molecules encoding such fusion polypeptides, vectors and host cells used in the production of the fusion polypeptides.

BACKGROUND OF THE INVENTION

Activation of the complement system (C) is accomplished via three different initiation pathways: The alternative (AP), the classical (CP), or the lectin pathway (LCP).

AP activation occurs on foreign surfaces and is caused by a slow, spontaneous hydrolysis of C3 and the activity of the factors properdin, factor B and factor D to form the functional C3 convertase C3bBb. AP also functions as an amplification pathway (the amplification loop) of the two other pathways. Recently it has been shown that the alternative convertase assembly may also be initiated by non-covalent attachment of properdin to some target surfaces. CP activation on the other hand is initiated when C1q binds to immunoglobulins in complex with antigens, which triggers the activation of the C1q-associated serine proteases C1r and C1s. C1s cleaves and activates C4 and C2 to form the CP C3 convertase C4b2a. The LCP is activated when mannose-binding lectin (MBL) or ficolins binds to restricted patterns of carbohydrates or acetylated compounds e.g. on the surface of microorganisms or when exposed on dying host cells. Upon binding to the ligand the associated serine protease MASP-2 activates and cleaves C4 and C2 to form the LCP C3 convertase C4b2a. The function of MASP-1 has been suggested to involve a stabilization of MASP-2 cleavage of C2 and also direct low grade cleavage of C3. Yet other studies relate the function and activity of MASP-1 and MASP-2 to a coagulation system cross-talk involving prothrombin, fibrinogen and factor XIII. Using MASP1/3 knockout mice it was recently demonstrated that MASP-1 in fact contributes to the complement activity. The exact function of the most recently discovered MBL associated serine protease MASP-3 has yet to be elucidated. Studies indicating that MASP-3 associates with a limited range of MBL oligomers and that MASP-3 and the small MBL-associated protein (sMAP) are involved in regulation or inhibition of MBL dependent LCP complement activation have been reported.

MASP-1 and -3 are derived from the same MASP1/3 gene (present on chromosome 3q27-q28) through differential splicing. They contain an identical A-chain except for 15 C-terminal residues. The A chain is comprised of two CUB (C1r/C1s, Urchin-EGF, Bone morphogenetic protein) domains separated by an EGF (Epidermal Growth Factor) domain and followed by two CCP domains (complement control protein). The B-chain including the serine protease domain is different for MASP-1 and MASP-3. The MASP-2 and sMAP are also derived from the same gene (present on chromosome 1p36-p36.2) where sMAP is a truncated form lacking the serine protease domain and a major part of the A-chain. The MASP1/3 gene has been shown to be polymorphic, but the functional importance of this is still poorly understood. However, there is some evidence that polymorphisms in the MASP2/sMAP gene are associated with increased risk of infections. Expression of the MASPs is localized to liver hepatocytes, but a recent study described that human MASP-3 mRNA (as the only MASP-mRNA) was expressed in a broad range of tissues.

OBJECT OF THE INVENTION

It is an object of embodiments of the invention to provide chimeric molecules suitable for the treatment of conditions associated with inflammation, apoptosis, autoimmunity, coagulation, and/or thrombotic or coagulopathic related diseases. The chimeric molecules of the invention may further be suitable as biomarkers for the diagnosis and/or prognosis of these indications as well as for malignant diseases, such as cancers.

SUMMARY OF THE INVENTION

It has been found by the present inventor(s) that novel chimeric molecules that associate with the recognition molecules of the lectin complement pathway may be used in the treatment of specific medical conditions associated with inflammation, apoptosis, autoimmunity, coagulation, and/or thrombotic or coagulopathic related diseases.

So, in a first aspect the present invention relates to a chimeric molecule of a ficolin-associated polypeptide comprising:
a) a ficolin-associated polypeptide; and
b) a second modulator of complement activity;
which chimeric molecule is capable of inhibiting complement activation.

In a second aspect the present invention relates to an isolated nucleic acid molecule encoding a chimeric molecule, wherein the ficolin-associated polypeptide and the second modulator of complement activity are directly or indirectly fused to each other in the form of a fusion protein.

In a third aspect the present invention relates to vector comprising an isolated nucleic acid molecule encoding a chimeric molecule, wherein the ficolin-associated polypeptide and the second modulator of complement activity are directly or indirectly fused to each other in the form of a fusion protein.

In a fourth aspect the present invention relates to a host cell comprising a vector comprising an isolated nucleic acid molecule encoding a chimeric molecule, wherein the ficolin-associated polypeptide and the second modulator of complement activity are directly or indirectly fused to each other in the form of a fusion protein.

In a further aspect the present invention relates to a method for producing the chimeric molecule according to the invention, the method comprising cultivating a cell according to the invention in an appropriate growth medium under conditions allowing expression of the polynucleotide construct and recovering the resulting polypeptide from the culture medium.

In a further aspect the present invention relates to a composition comprising the chimeric molecule according to the invention.

In a further aspect the present invention relates to a pharmaceutical composition comprising the chimeric molecule according to the invention.

In a further aspect the present invention relates to a chimeric molecule according to the invention for use as a medicament.

In a further aspect the present invention relates to the use of a chimeric molecule according to the invention; for the preparation of a medicament.

In a further aspect the present invention relates to a chimeric molecule according to the invention as well as pharmaceutical composition comprising a chimeric molecule according to the invention for the treatment of any indications associated with inflammation, apoptosis and/or autoimmunity.

In a further aspect the present invention relates to a chimeric molecule according to the invention for the treatment of any indications associated with coagulation, thrombotic or coagulopathic related diseases.

In a further aspect the present invention relates to a method for the treatment of any indication associated with inflammation, apoptosis and/or autoimmunity, coagulation, thrombotic or coagulopathic related diseases, for preventing the occurrence of thromboembolic complications in identified high risk patients, treatment of a medical condition associated with the heart, or a medical condition associated with a deficiency in a ficolin-associated polypeptide; the method comprising administering a therapeutically or prophylactically effective amount of a chimeric molecule according to the invention to a subject in need thereof.

In a further aspect the present invention relates to the use of a composition according to the invention; for the preparation of a medicament.

In a further aspect the present invention relates to a method for the treatment of any indication described herein, the method comprising simultaneously or sequentially administering a therapeutically or prophylactically effective amount of a chimeric molecule according to the invention and one or more proteins selected from Ficolin-1, 2, 3, and mannose-binding lectin (MBL), C1q, lung surfactant proteins SP-A and/or SP-D, and intracellular collagen-like defence molecules, such as CL-L1.

LEGENDS TO THE FIGURES

FIG. 1: Alternative transcription of the MASP-1 gene. Alternative transcription of the MASP1 gene was detected in liver cDNA. The MASP1, MASP3, and FAP transcripts were amplified using a common forward primer located in exon 6 and specific reverse primers located in exon 12 (MASP1), exon 11 (MASP3), and exon 8a (FAP). Exon 8a as referred to herein may alternatively be referred to as exon 9 with a shift up in numbers of the following exons from 9-17 to 10-18 of the primary transcript. MASP1 generates a fragment of 500 bp, MASP3 generates a fragment of 506 bp and FAP generates a fragment of 309 bp.

Figure 2:
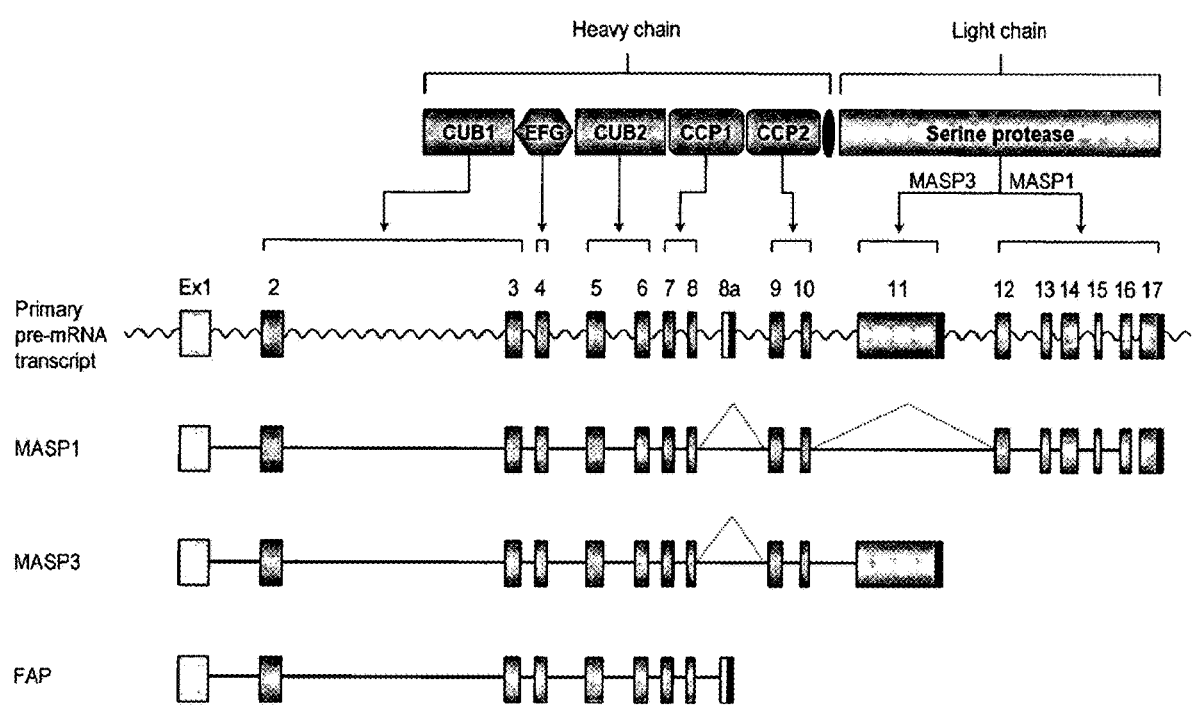

FIG. 2: Alternative splicing of the MASP1 gene. MASP1 is generated by splicing out of 8a and exon 11, which both contain a stop codon sequence (marked with black boxes). The MASP1 sequence contains a stop codon in exon 17. MASP3 is generated by splicing out of exon 8a and FAP is generated if no splicing out of exon 8a occurs. The FAP protein contains the two CUB domains, the EGF domain and the first CCP1 domain.

Figure 3:
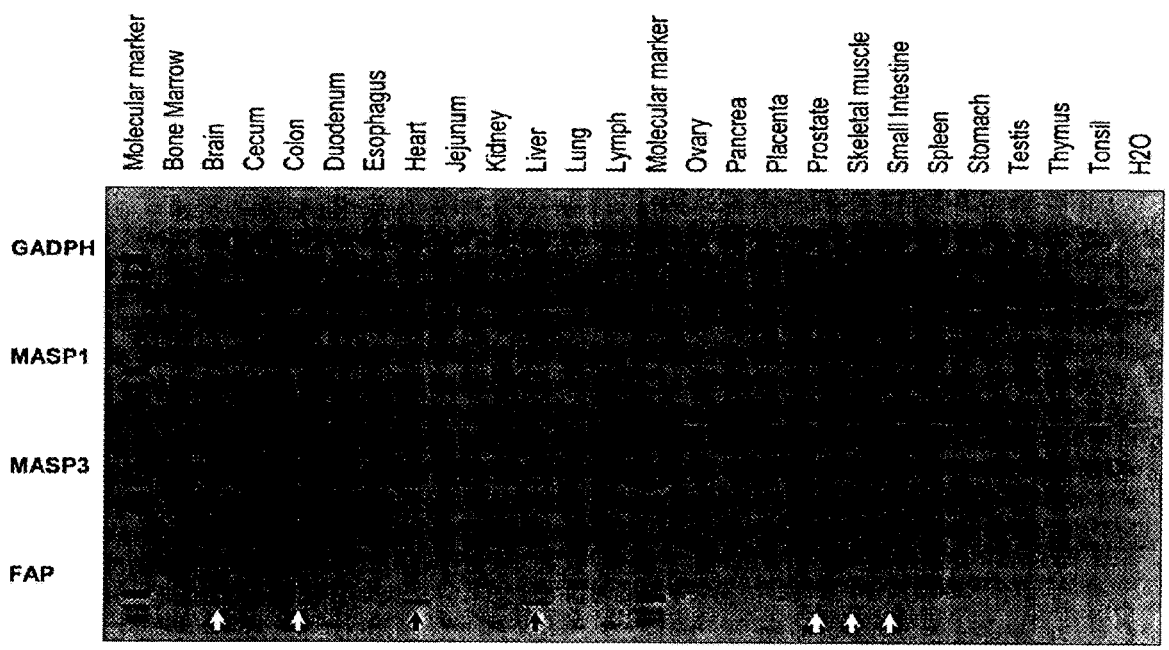

FIG. 3: Tissue expression of the FAP fragment. The tissue distributions of the MASP-1, MASP3, and FAP genes were investigated in cDNA panels from Clontech. MASP-1, MASP-3, and FAP transcripts were amplified using a common forward primer and specific reverse primers. GADPH was used as reference gene. All three genes were highly expressed in the liver, and additionally, FAP was strongly expressed in heart tissue (marked with black arrows). Minor expression of the FAP gene was detected in brain, colon, prostate, skeletal muscle, and small intestine (marked with white arrows).

FIG. 4: Alignment of MASP-1, MASP-3, and FAP (SEQ ID NO: 1). The protein sequences of MASP-1 (SEQ ID NO: 5), MASP-3 (SEQ ID NO:7), and FAP were aligned using the BioEdit Software. MASP-1 and MASP-3 contain different C-terminal serine protease domains whereas FAP does not contain any serine protease domain. Instead the protein contains 17 new amino acids in the C-terminal region.

FIG. 5: cDNA sequence and corresponding protein sequence of FAP (amino acid SEQ ID NO: 1; DNA SEQ ID NO:2). The cDNA sequence is shown in the upper row and the corresponding protein sequence is shown below. Exons regions are divided by black vertical lines. Amino acids believed to be involved in the binding to MBL/ficolins are marked with light-yellow boxes.

Figure 6:
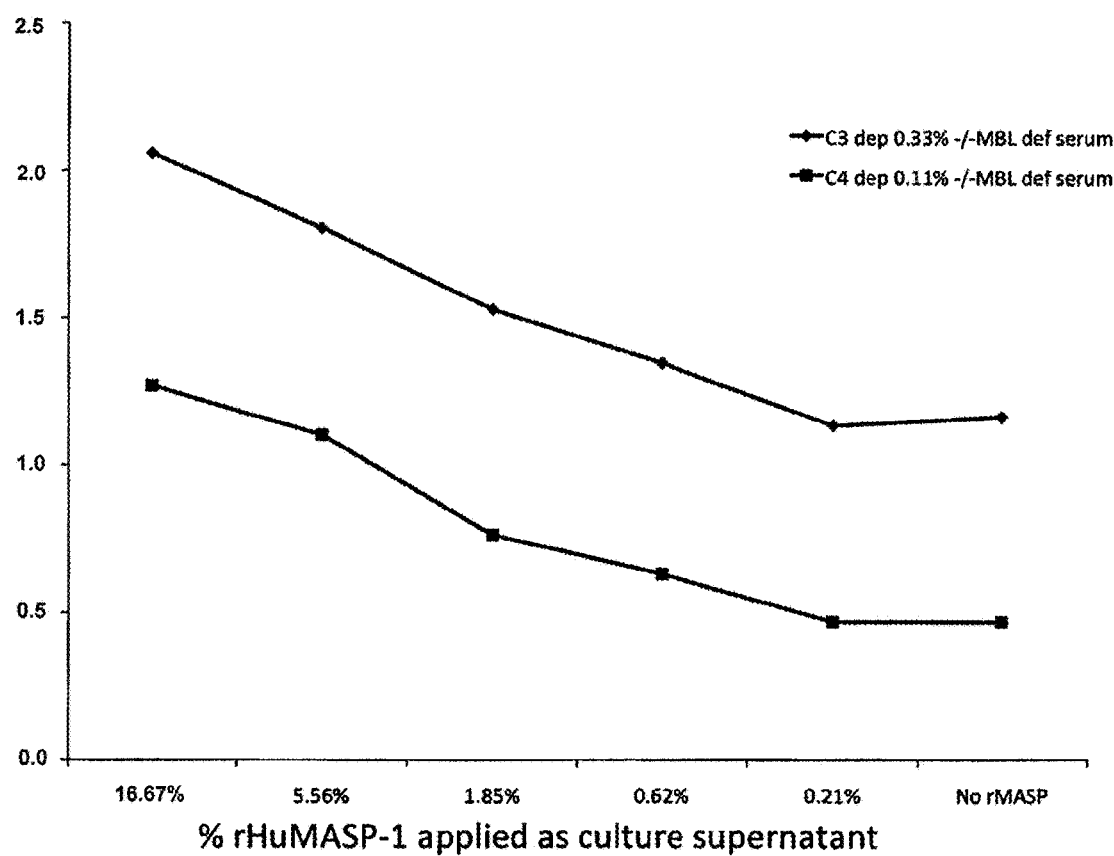

FIG. 6: MASP-1 complement activation. Human MBL were incubated with increased amount of MASP-1. MASP-1 were able to activate both the C3 and C4 complement proteins.

Figure 7:
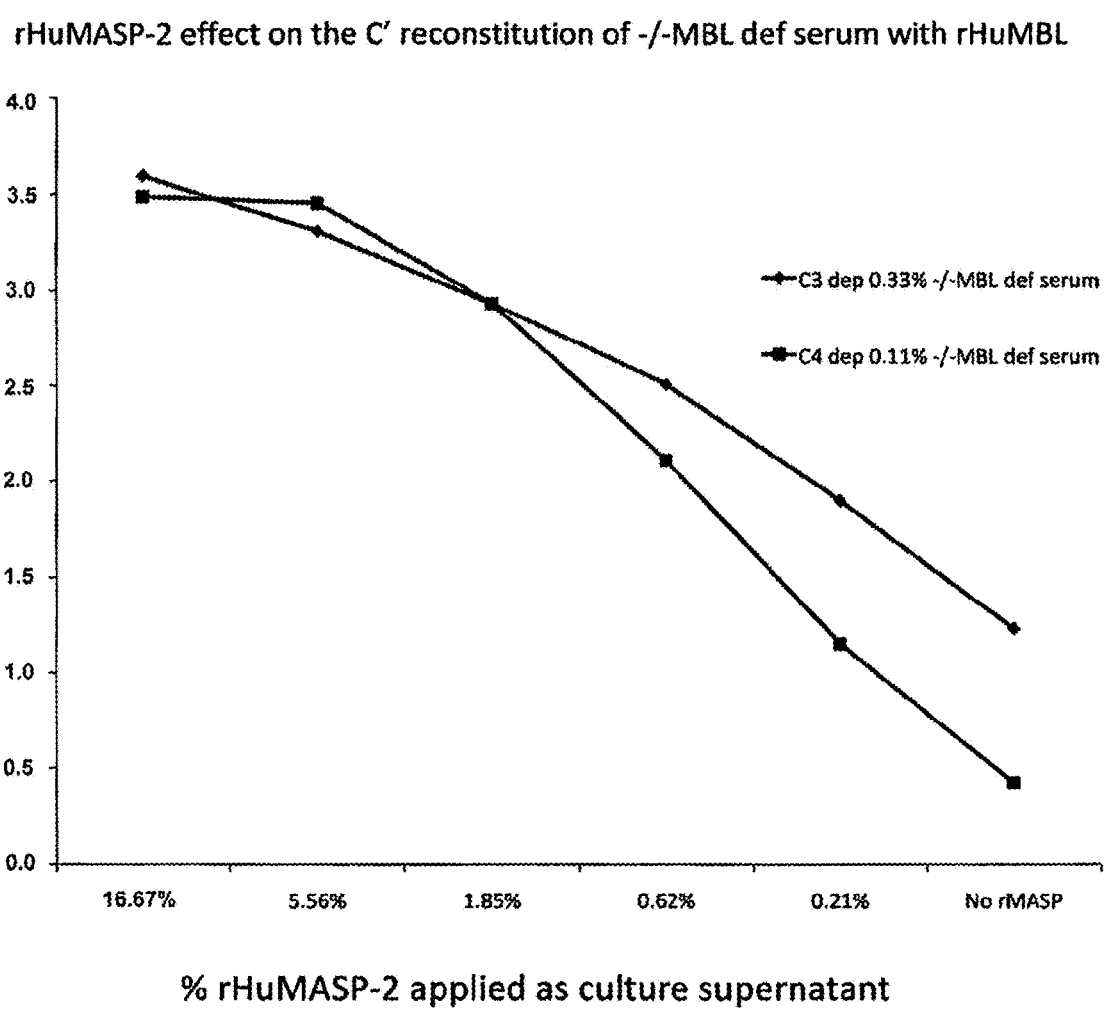

FIG. 7: MASP-2 complement activation. Human MBL were incubated with increased amount of MASP-2. MASP-2 were able to strongly activate both the C3 and C4 complement proteins.

Figure 8:
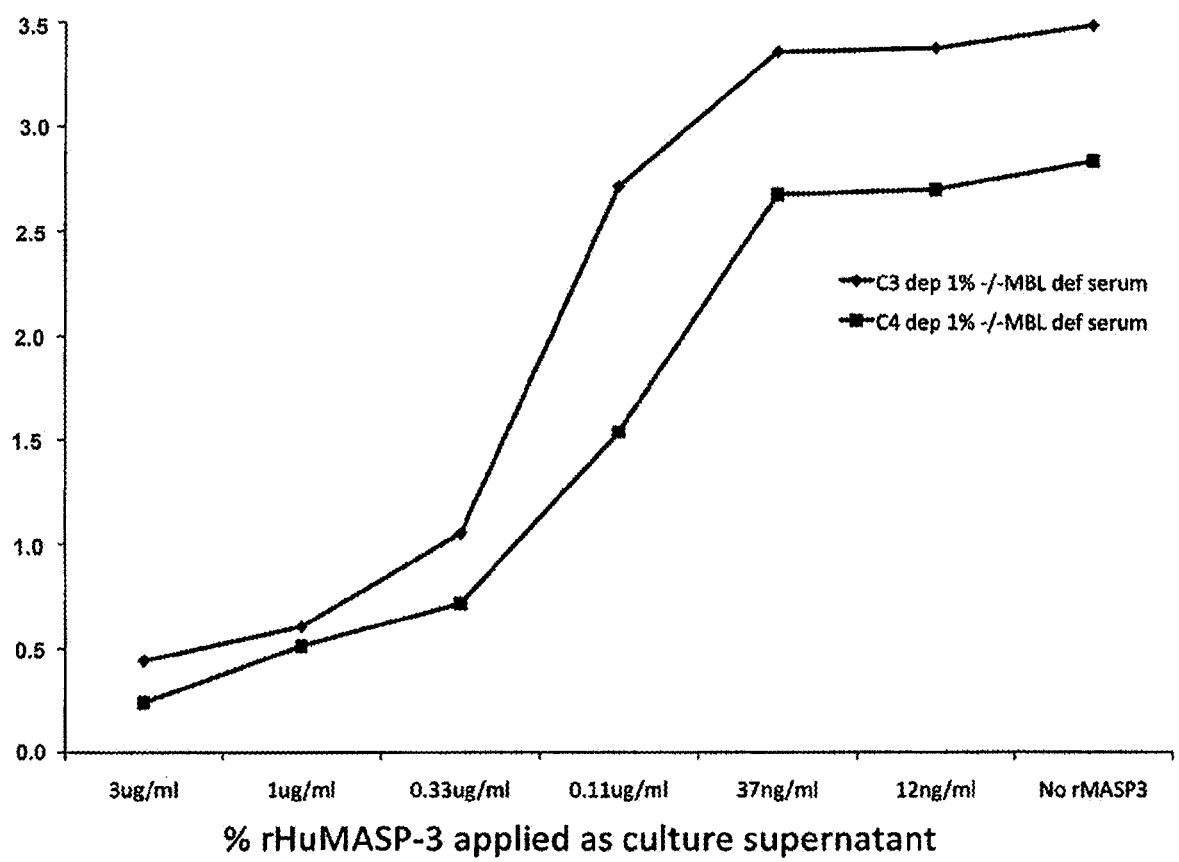

FIG. 8: MASP-3 inhibition of the complement. Human MBL were incubated with increased amount of MASP-3. MASP-3 were able to inhibit the activation of both the C3 and C4 complement proteins.

Figure 9:
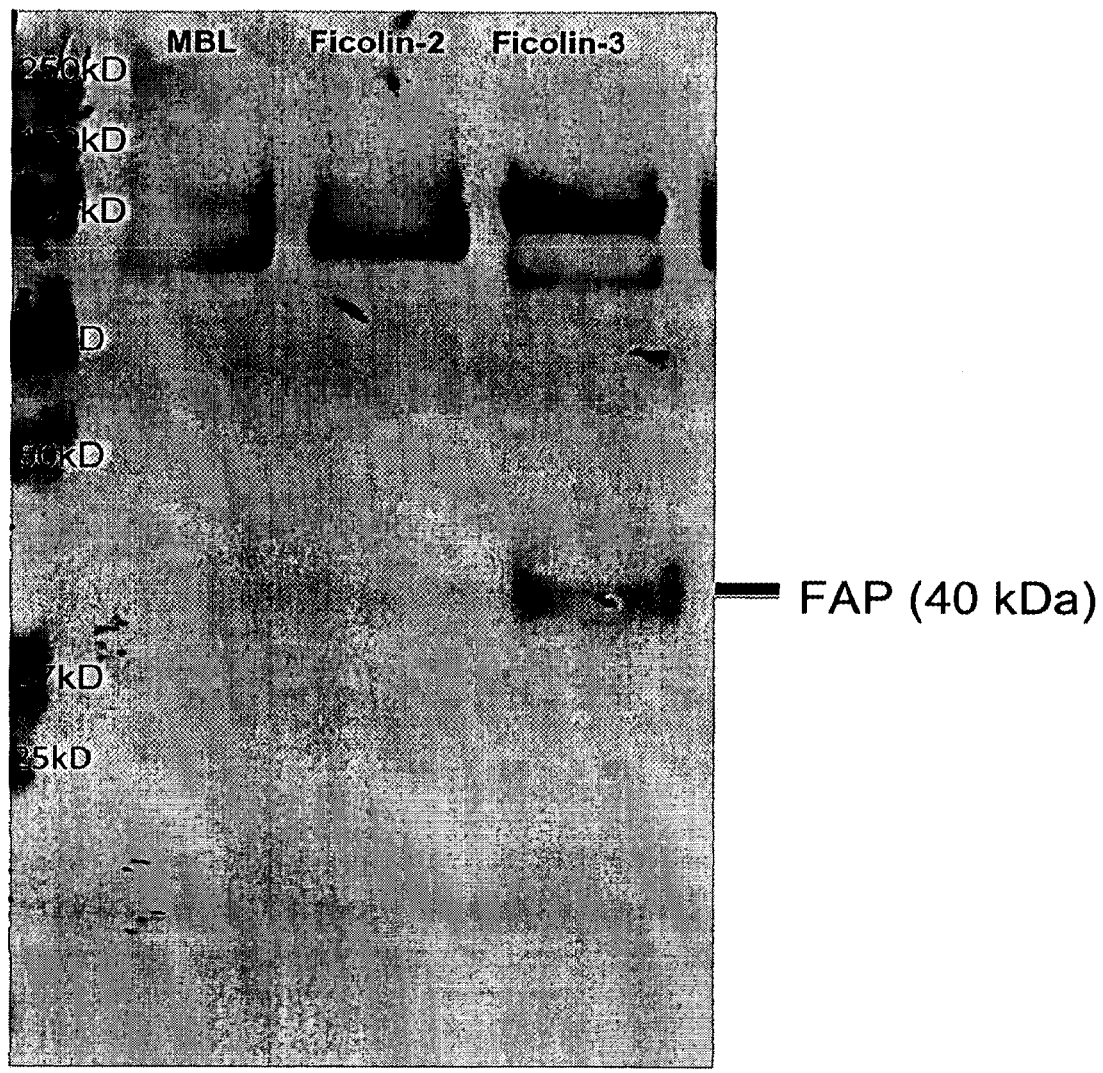

FIG. 9: Immunoprecipitation. Immunoprecipitation of serum Ficolin/MBL with mAb anti-MBL 131-11, anti-Ficolin-2 clone 219, and anti-Ficolin-3 clone 334. Followed by Dynal magnetic bead separation, SDS-PAGE, Western blot and biotin labeled anti-MASP-1/MASP-3 clone 8B3 as signal antibody.

Figure 10:
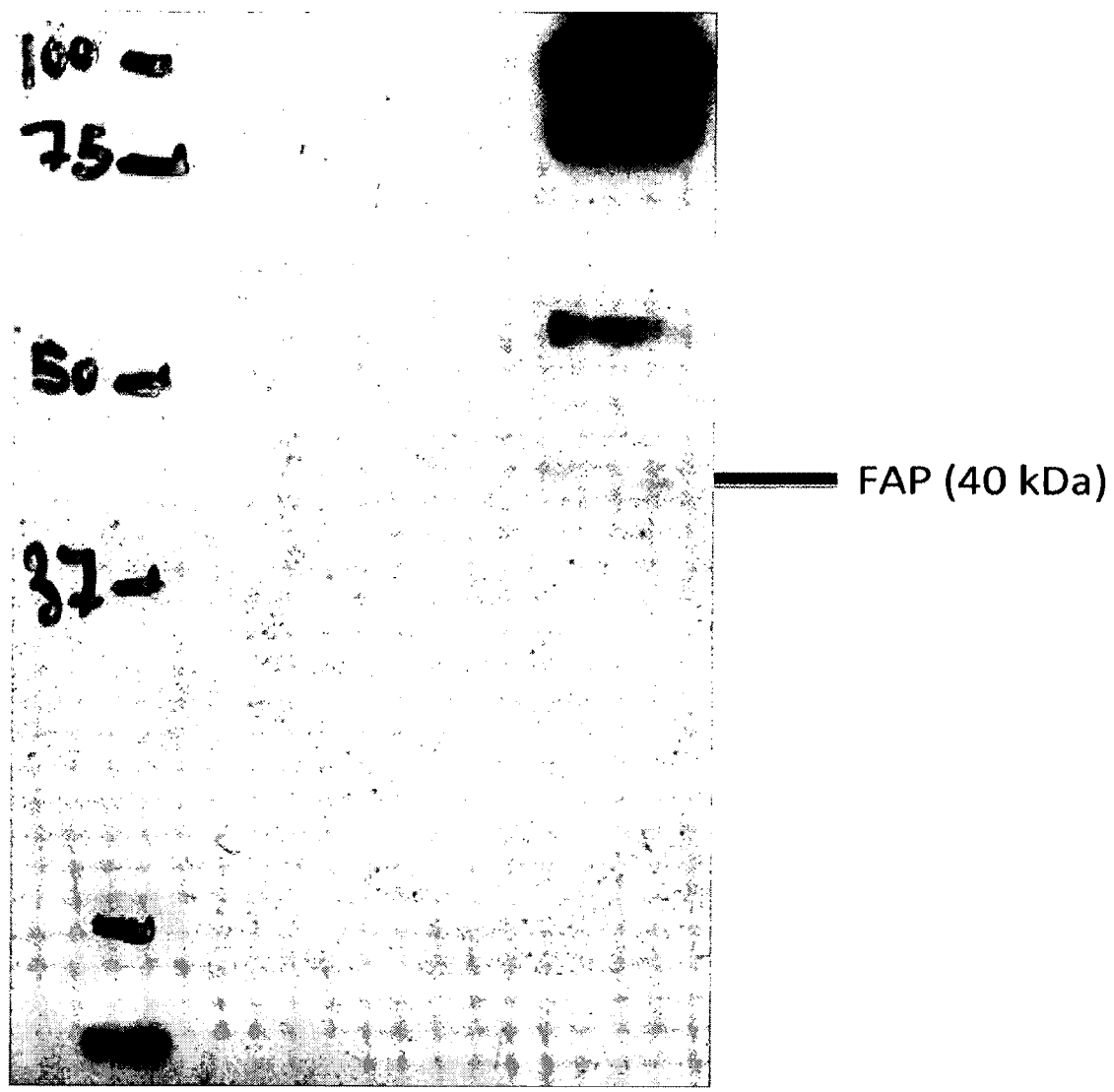

FIG. 10: FAP interact with Ficolin when bound to acetylated human serum albumin (AcHSA). Eluted serum Ficolin binding to AcHSA. Western blot with biotin labelled anti-MASP-1/MASP-3 clone 8B3 as signal antibody.

FIG. 11: Kinetics and dissociation constants for interaction between MASP-1 and MASP-3 and rFicolin-2 (Hummelshøj T et al., Mol. Immunol., 2007).

FIG. 12: Alignment of GULP (SEQ ID NO: 75) GULF and the 17 unique amino acids of FAP (SEQ ID NO:4).

Figure 13:
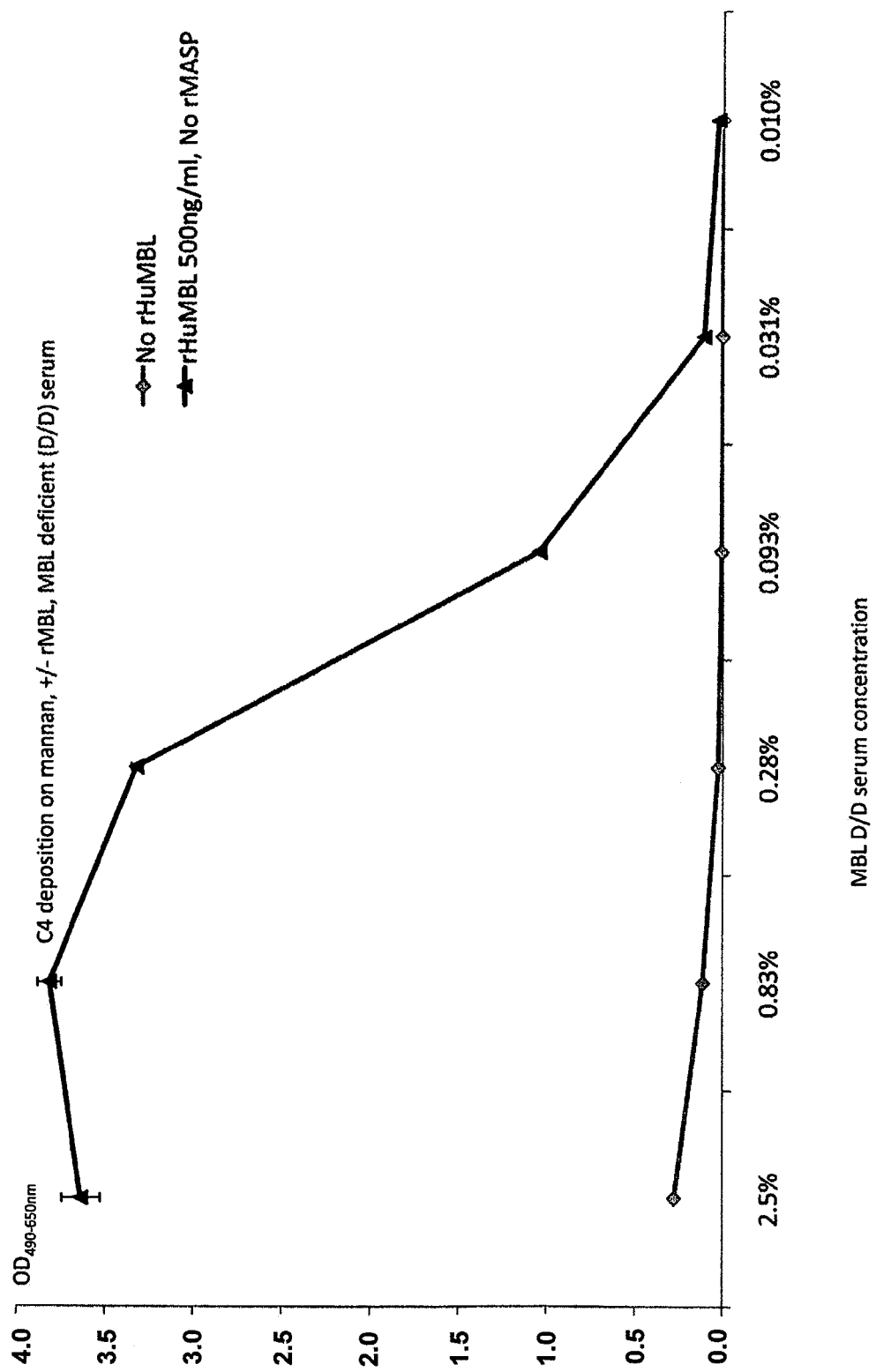

FIG. 13: Complement activation of C4 in a mannan/MBL ELISA assay. Mannan coated wells were incubated with or without recombinant human MBL followed by incubation with MBL homozygous deficient serum in serial dilutions. The C4 deposition was measured using polyclonal anti C4c antibodies. Error bars indicate two times the standard deviations on double determinations of each point on the curves.

Figure 14:
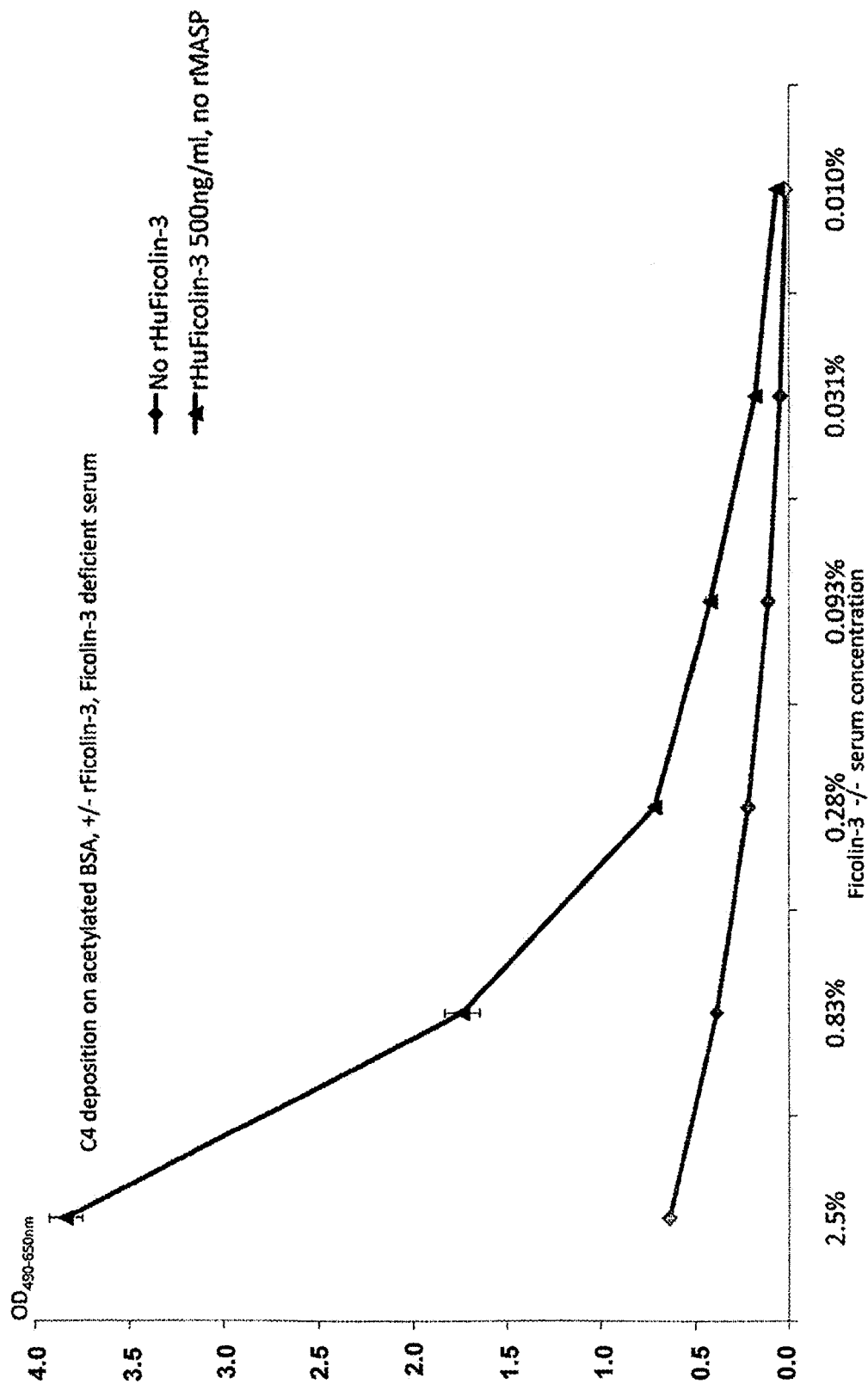

FIG. 14: Complement activation of C4 in an acetylated BSA/Ficolin-3 ELISA assay. AcBSA coated wells were incubated with or without recombinant human Ficolin-3 followed by incubation with Ficolin-3 homozygous deficient serum in serial dilutions. The C4 deposition was measured using polyclonal anti C4c antibodies. Error bars indicate two times the standard deviations on double determinations of each point on the curves.

Figure 15:
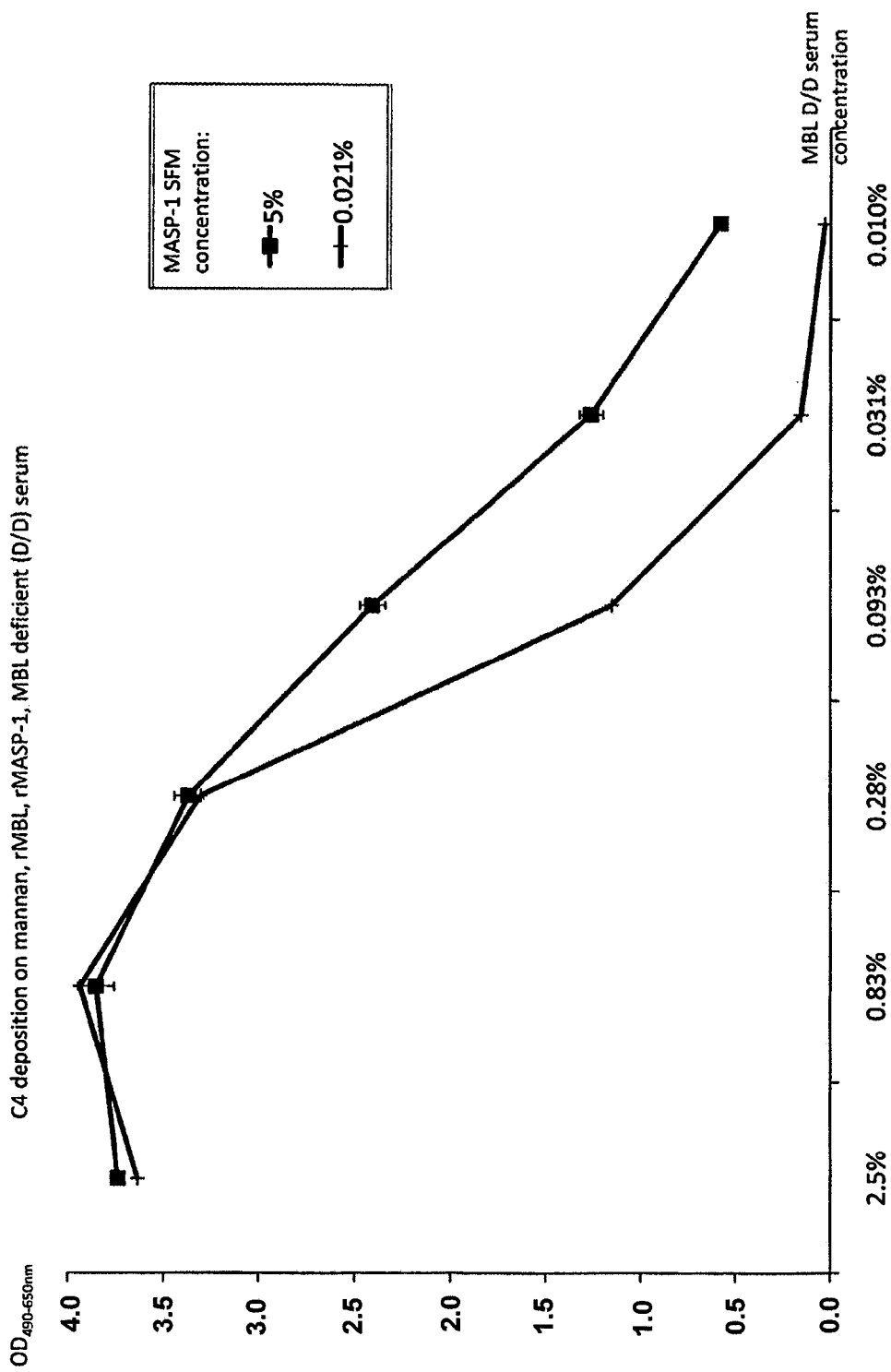

FIG. 15: Complement activation of C4 in a mannan/MBL ELISA assay. Mannan coated wells were incubated with recombinant human MBL followed by incubation with serial dilutions of rMASP-1 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 16:
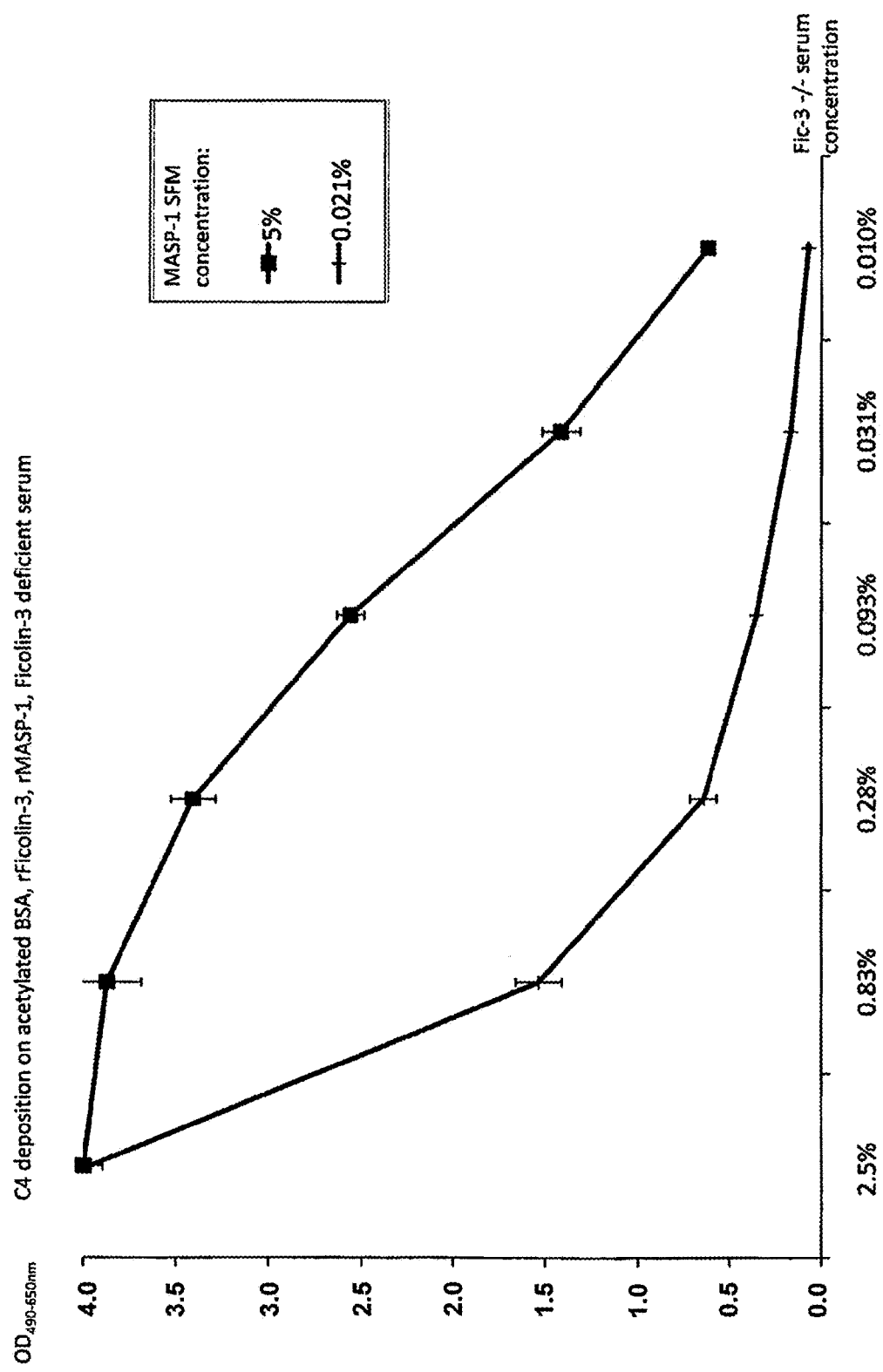

FIG. 16: Complement activation of C4 in an AcBSA/Ficolin-3 ELISA assay. AcBSA coated wells were incubated with recombinant human Ficolin-3 followed by incubation with serial dilutions of rMASP-1 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 17:
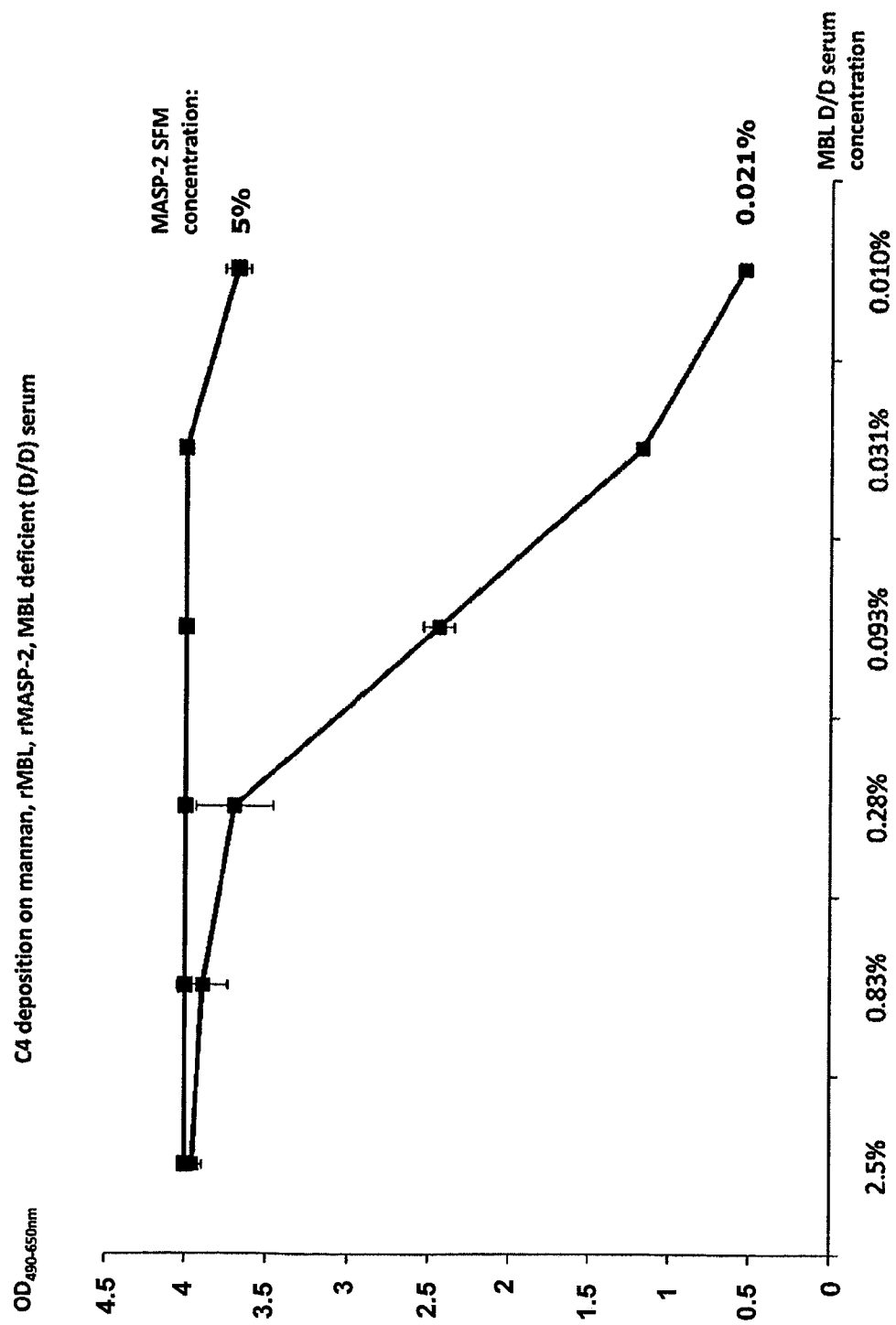

FIG. 17: Complement activation of C4 in a mannan/MBL ELISA. Mannan coated wells were incubated with recombinant human MBL followed by incubation with serial dilutions of rMASP-2 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 18:
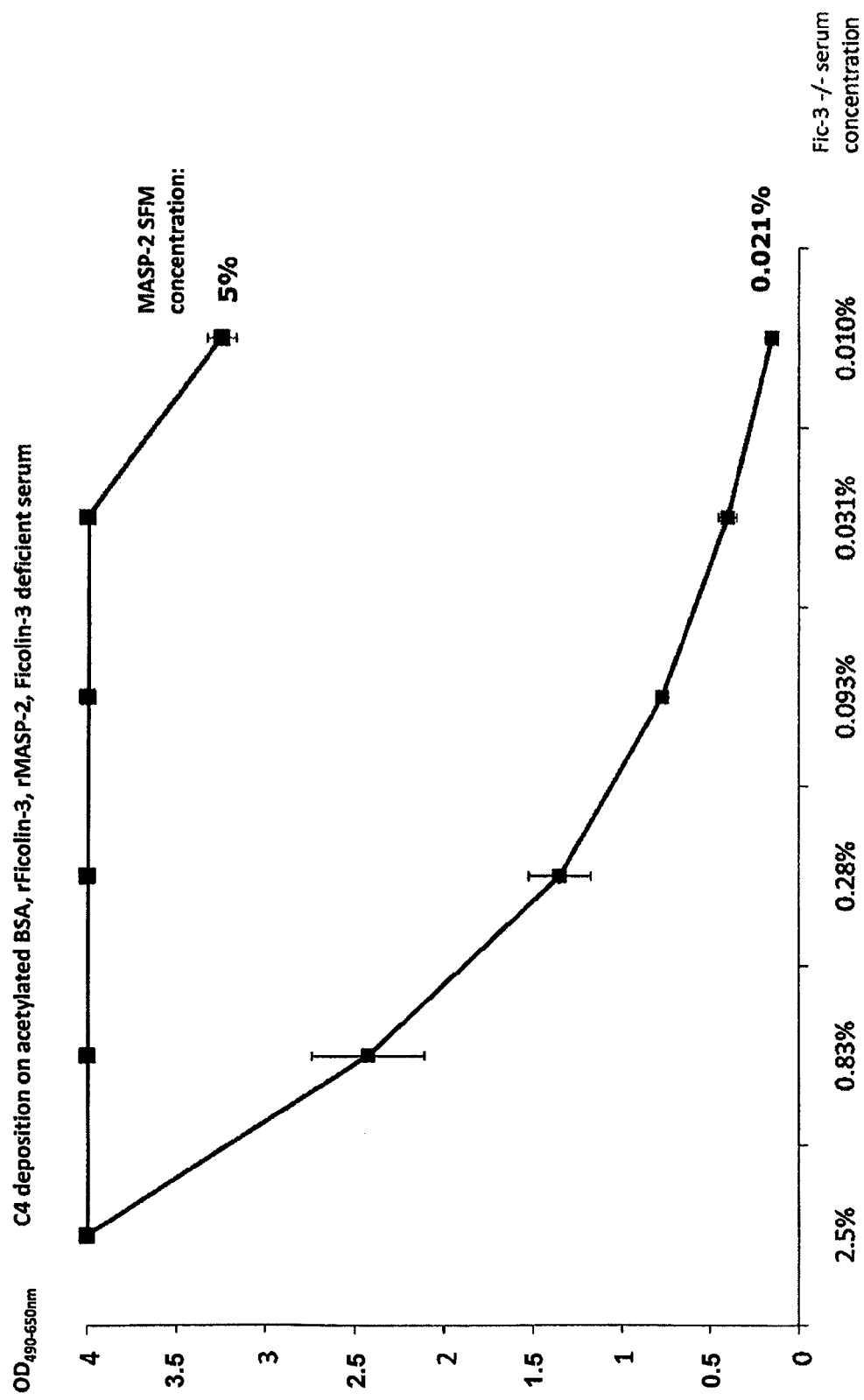

FIG. 18: Complement activation of C4 in an AcBSA/Ficolin-3 ELISA assay. AcBSA coated wells were incubated with recombinant human Ficolin-3 followed by incubation with serial dilutions of rMASP-2 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 19:
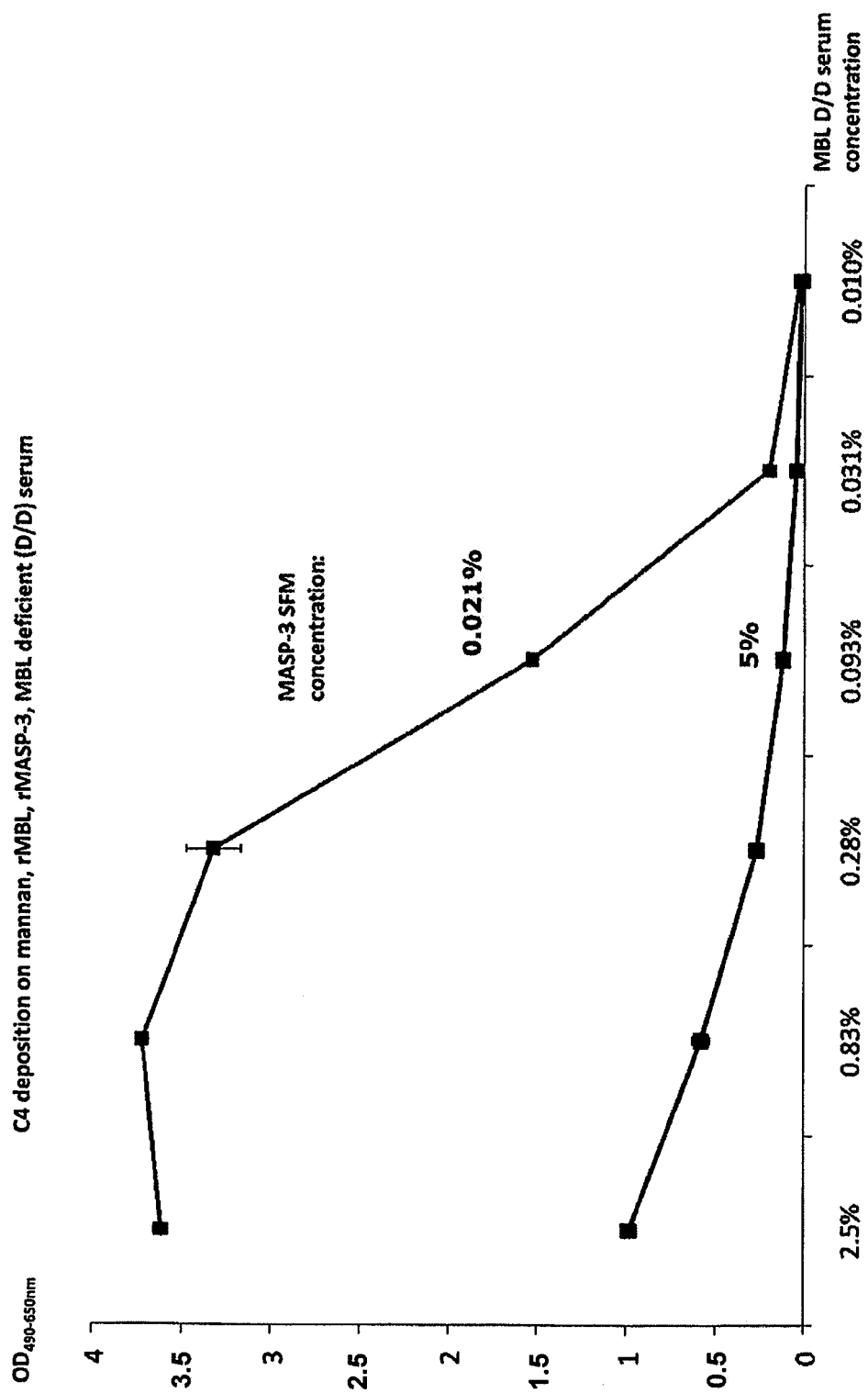

FIG. 19: Complement activation of C4 in a mannan/MBL ELISA assay. Mannan coated wells were incubated with recombinant human MBL followed by incubation with serial dilutions of rMASP-3 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 20:
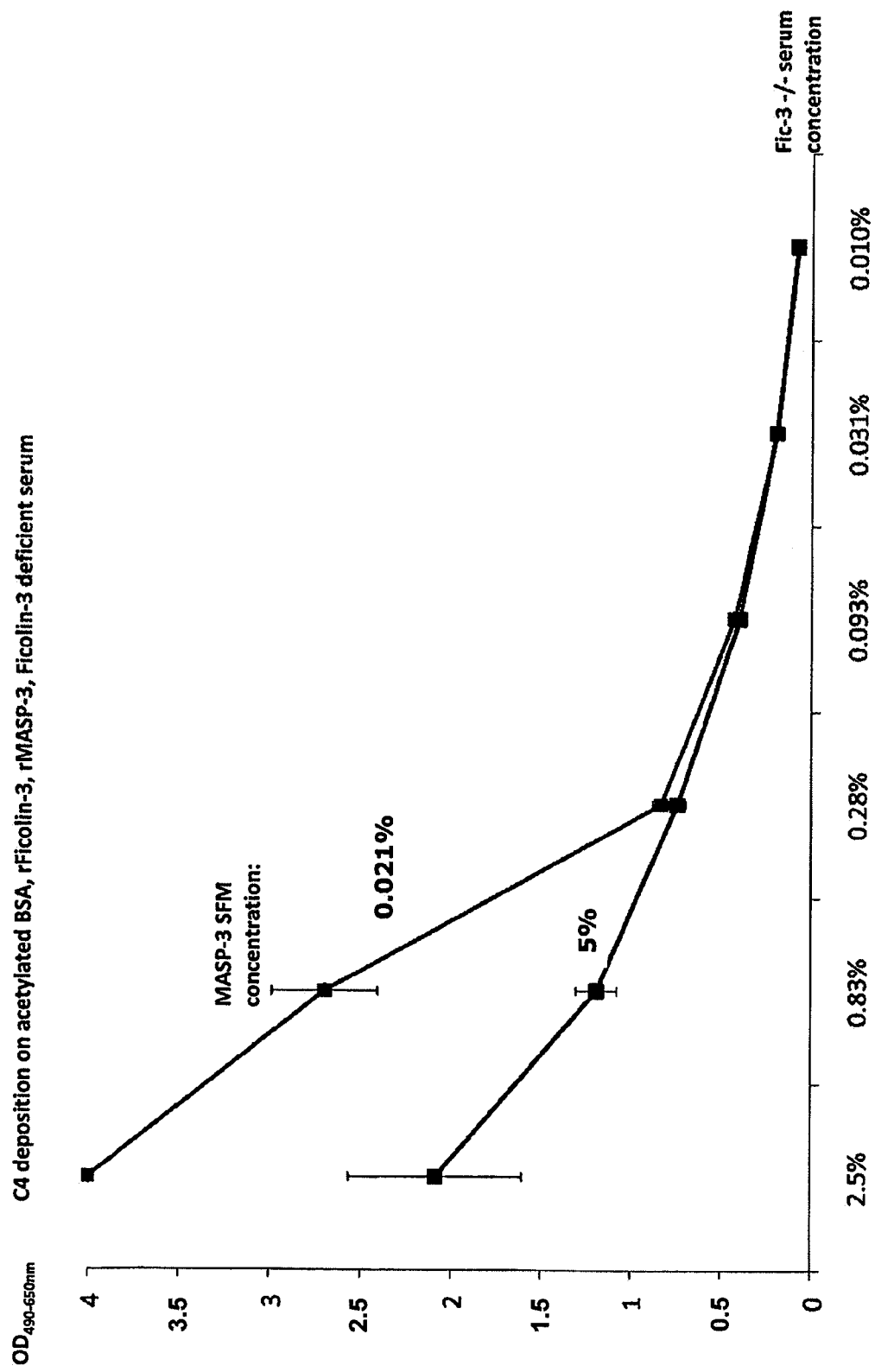

FIG. 20: Complement activation of C4 in an AcBSA/Ficolin-3 ELISA assay. AcBSA coated wells were incubated with recombinant human Ficolin-3 followed by incubation with serial dilutions of rMASP-3 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 21:
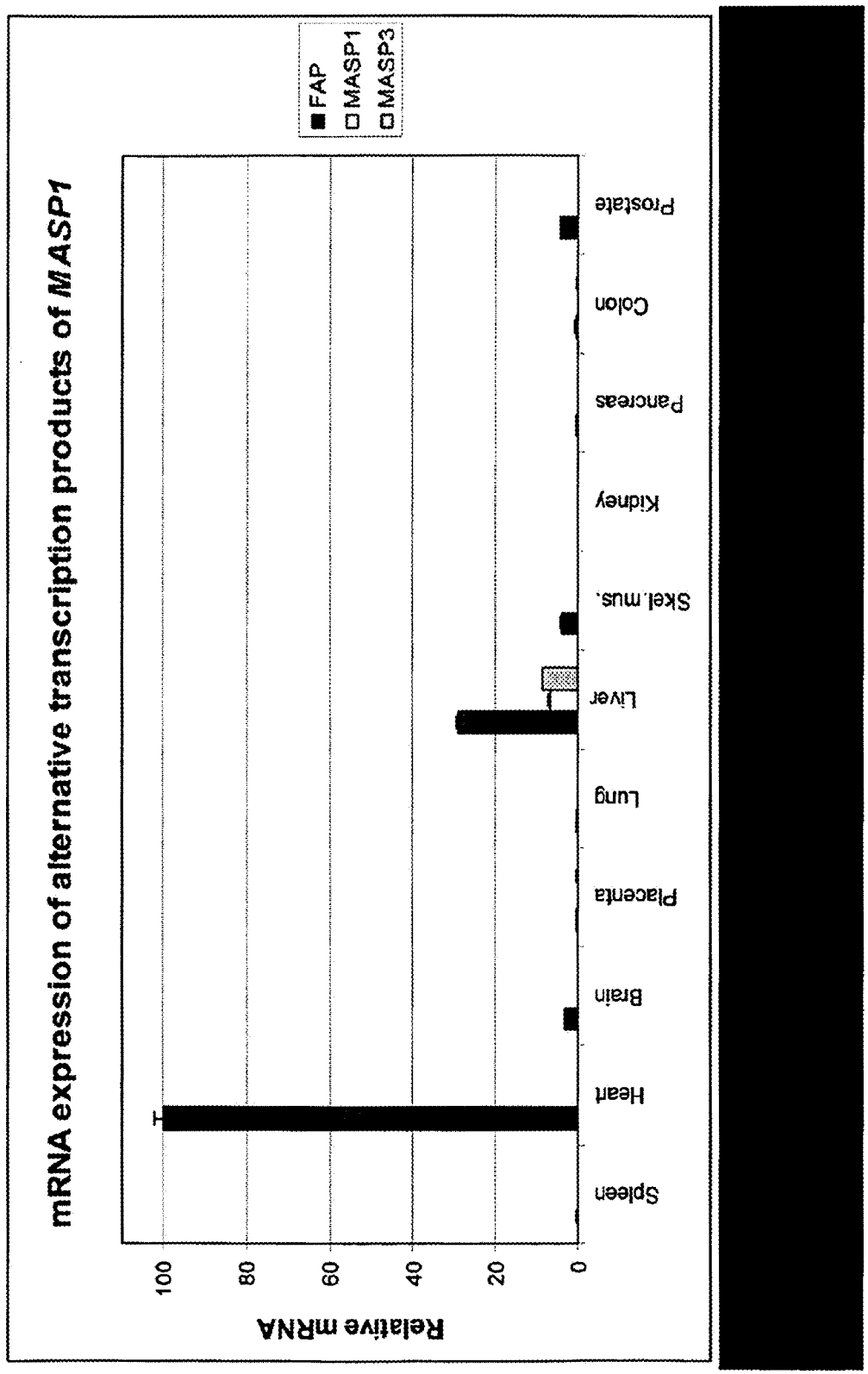

FIG. 21: Tissue distribution of FAP, MASP1 and MASP3. FAP was expressed much higher in the heart tissue compared to MASP1 and MASP3. FAP was expressed three times higher in the heart tissue compared to the FAP expression in liver. Furthermore, a higher FAP expression was observed in the liver compared to the MASP1 and MASP3 expression in the liver. Considerable FAP expression was also detected in brain, skeletal muscle and prostate tissues. The experiment was performed three times in duplicates. Standard error of the mean are indicated.

Figure 22:
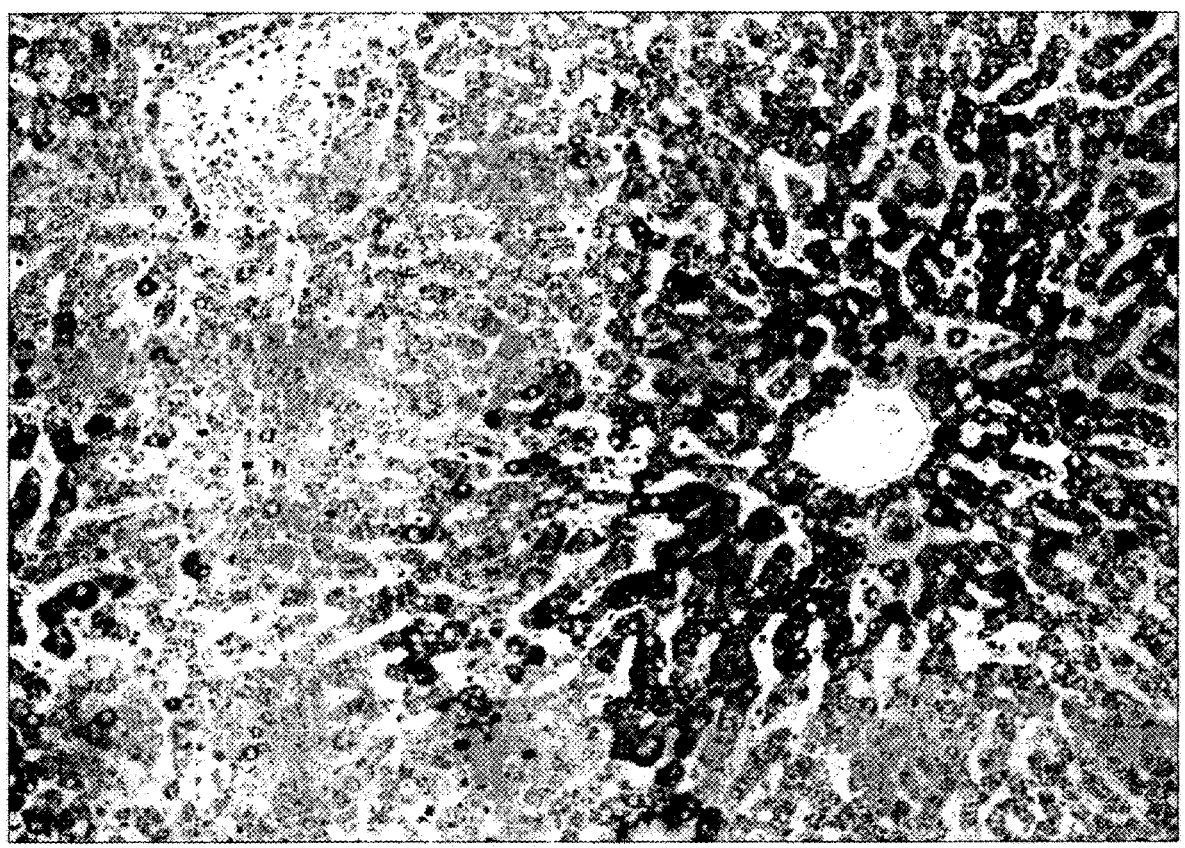

FIG. 22: Immunohistochemical liver localization of MAP-1 using polyclonal mouse antiserum raised against the 17 FAP specific C-terminal residues of the Protein. Control staining was negative. Several different polyclonal antibodies raised against FAP (rabbit and mouse) showed the same pattern staining.

Figure 23:

FIG. 23: Immunohistochemical analysis of MAP-1 tissue localization (OM×10). Left panel shows staining with a mAb (12B11) to MAP-1. Right panel shows the isotype control staining with a non-related IgG1k mAb. (A-B): Myocardium, (C-D): Skeletal muscle, (E-F): Liver sample, (G-H): Aortic tissue. Bottom right corner bar indicates 50 μm on all slides.

Figure 24:
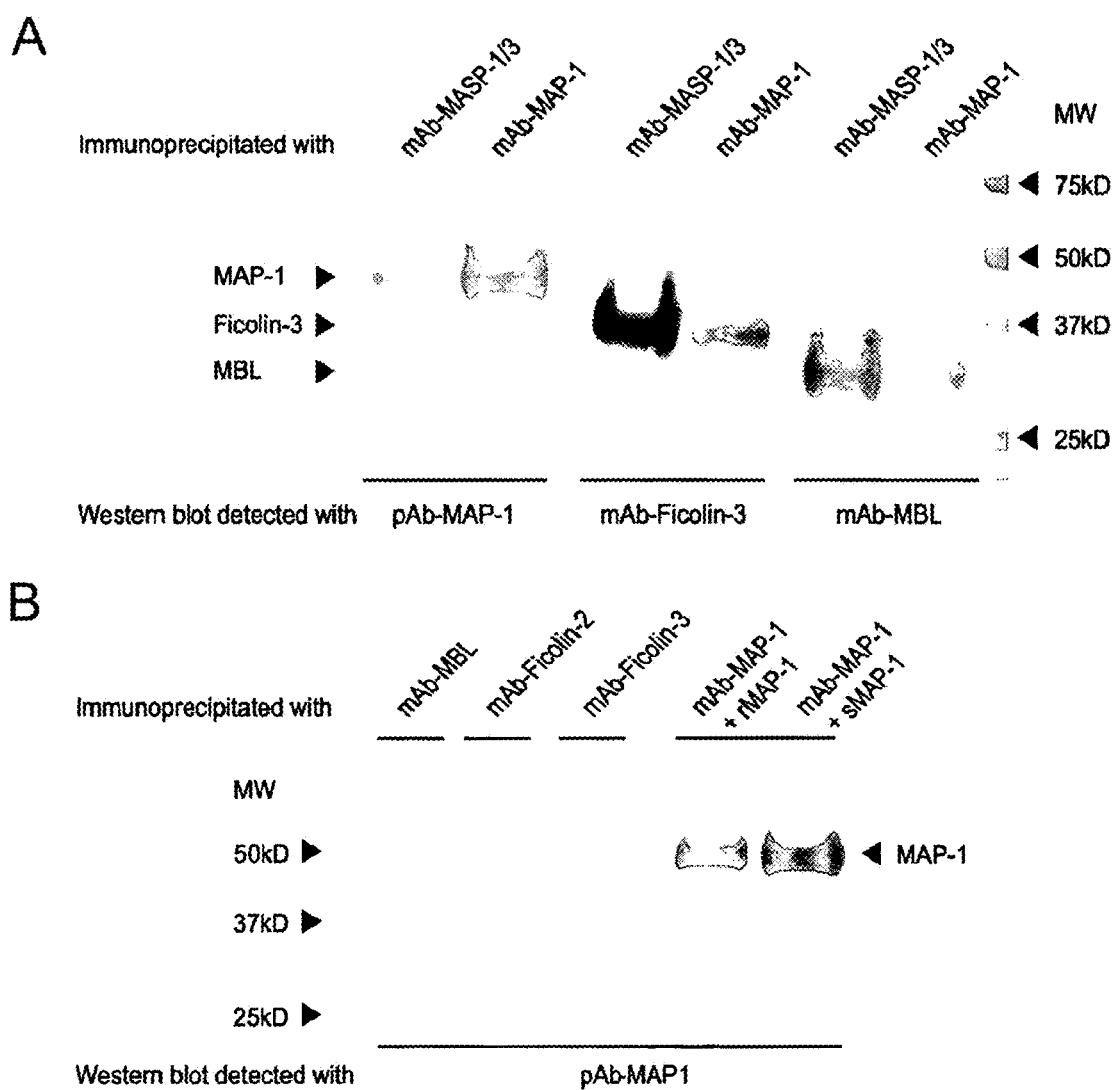

FIG. 24: Immunoprecipitation of MAP-1 and MASP-1/3 serum complexes. FIG. 24A: MAP-1 and MASP-1/3 was immunoprecipitated from serum using mAb 20C4 (anti MAP-1) and mAb 8B3 (anti MASP-1/3, with an epitope on the common heavy chain). Reduced samples were electroblotted and developed with pAb to MAP-1 or biotinylated mAbs to Ficolin-3 (FCN334) and MBL (Hyb 131-1). FIG. 24B: Immunoprecipitation with mAbs to MBL (Hyb 131-11), Ficolin-2 (FCN219) and Ficolin-3 (FCN334) from 1 ml, 300 μl and 100 μl serum, respectively (Left side). Controls were MAP-1 precipitated from serum (sMAP-1) and rMAP-1 from culture supernatant (rMAP-1) using anti MAP-1 mAb 20C4 (right side). The samples were analyzed by western blotting probed with pAb to MAP-1.

Figure 25:
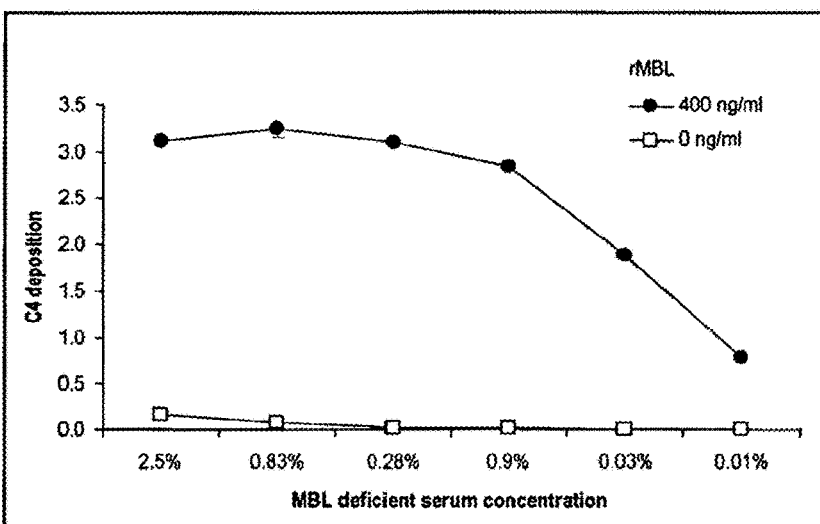
Figure 25:
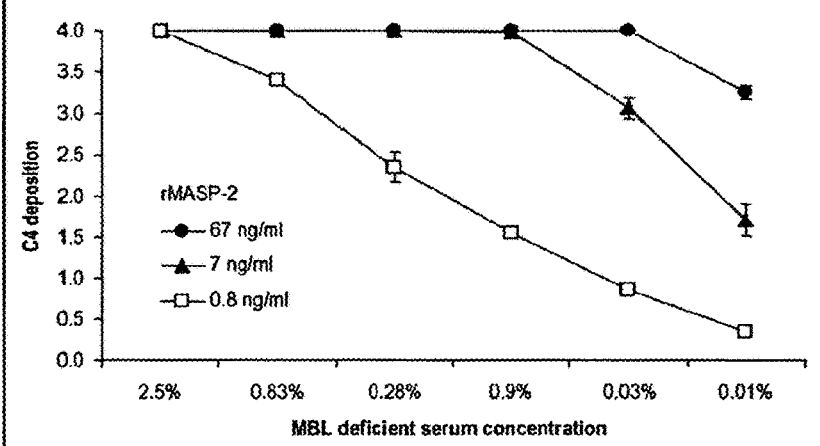
Figure 25:
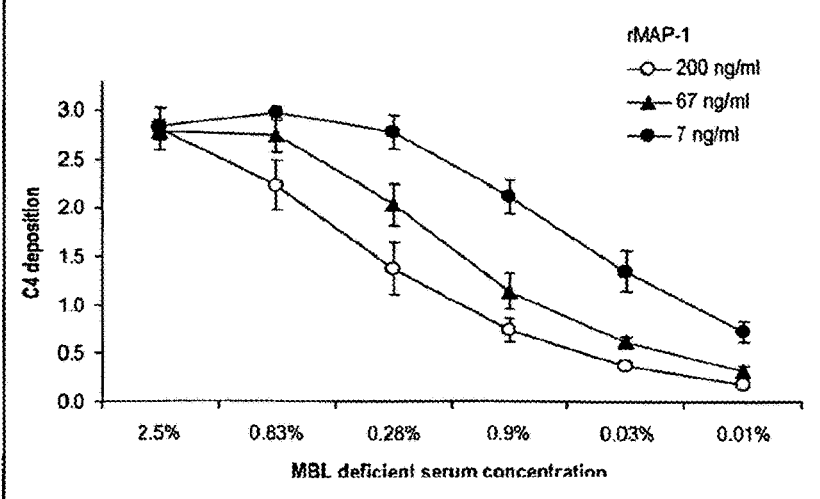
Figure 25:
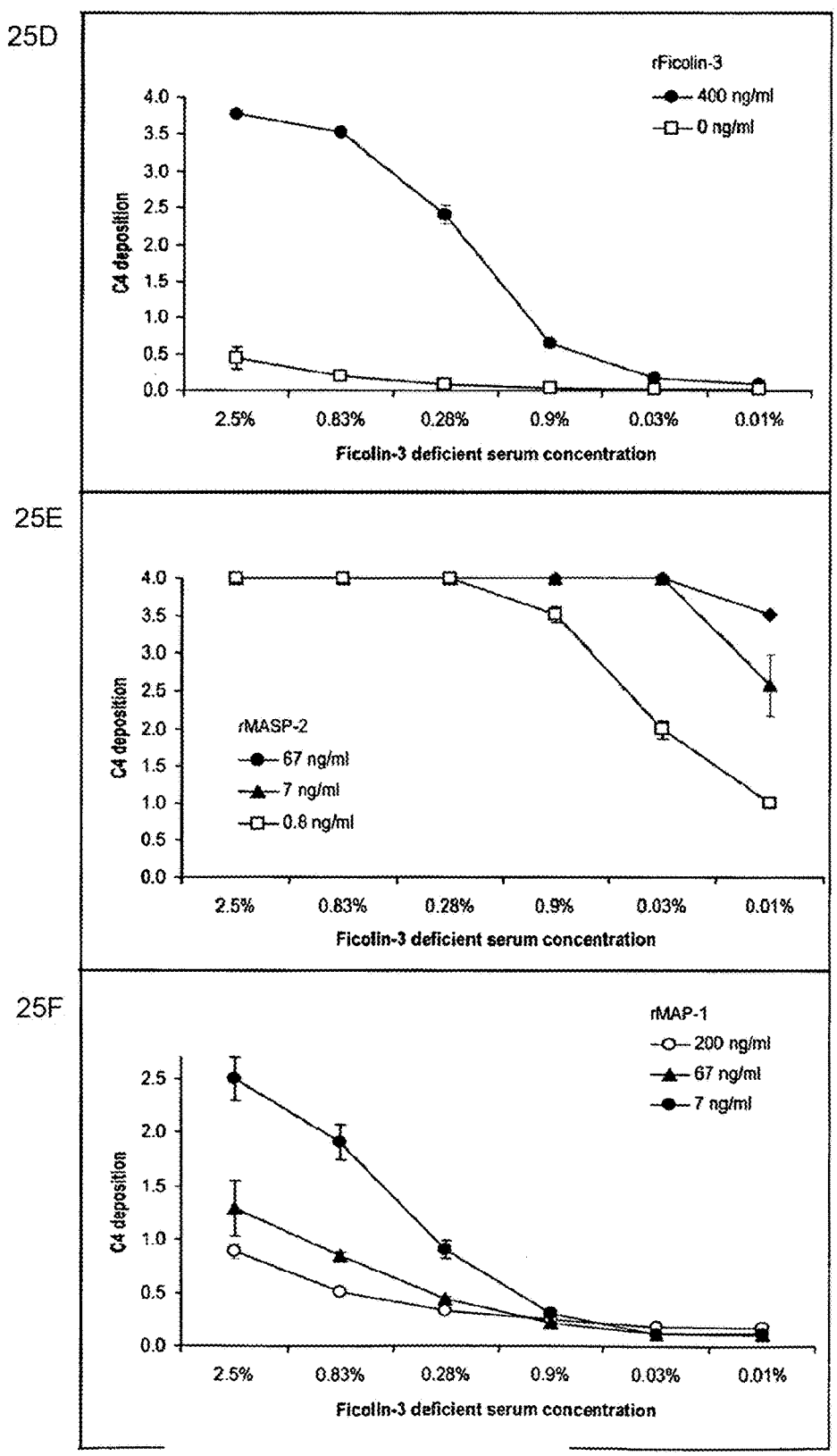

FIG. 25: Influence of MASP-2 and MAP-1 on MBL and Ficolin-3 mediated complement C4 deposition. The C4 depositions were measured using a polyclonal antibody to C4 and are given as $OD_{490-650\,nm}$ values. Error bars indicate two times the standard deviation of double determinations. Approximated concentrations of rMBL, rFicolin-3. rMAP-1 and rMASP-2 are given in the figure labels. FIG. 25A: Reconstitution of the C4 deposition on a mannan coated surface using MBL deficient serum with rMBL at 400 ng/ml. Control was without addition of rMBL. FIG. 25B: Dose dependent effect of rMASP-2 on the rMBL mediated C4 deposition. FIG. 25C: Dose dependent effect of rMAP-1 on the rMBL mediated C4 deposition. FIG. 25D: Reconstitution of the C4 deposition on an AcBSA coated surface using Ficolin-3 deficient serum with rFicolin-3 at 400 ng/ml. Control was without addition of rFicolin-3. FIG. 25E: Dose dependent effect of rMASP-2 on the rFicolin-3 mediated C4 deposition. FIG. 25F: Dose dependent effect of rMAP-1 on the rFicolin-3 mediated C4 deposition.

Figure 26:
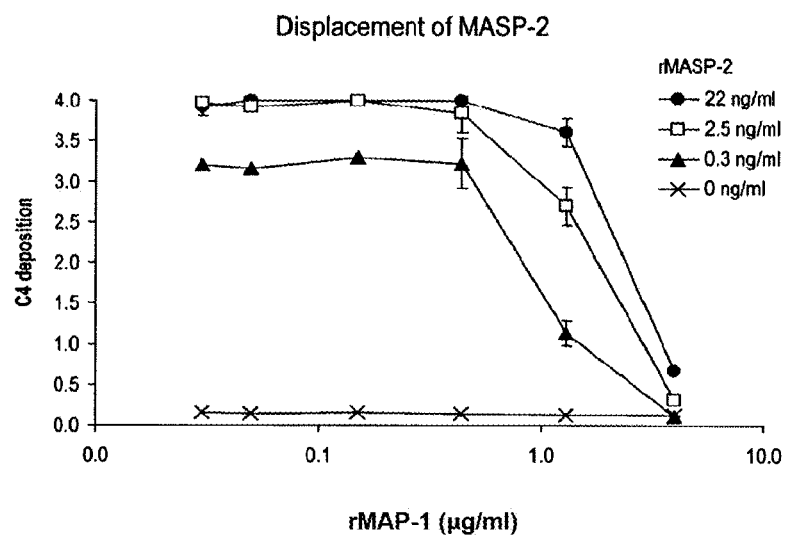

FIG. 26: Influence of MASP-2 and MAP-1 on the complement C4 deposition in a pure system. rMBL on a mannan surface was preincubated with serial dilutions of rMASP-2 in the first dimension. Serial dilutions of rMAP-1 were then applied in the second dimension followed by application of purified C4 at 1 µg/ml. The C4 depositions were measured with a pAb to C4 and are given as $OD_{490-650\ nm}$ values. Error bars indicate two times the standard deviation of double determinations. Approximated concentrations of rMAP-1 and rMASP-2 are given in the figure labels.

Figure 27:
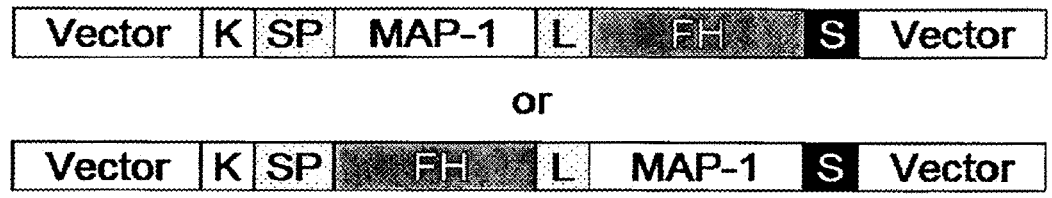
Figure 27:
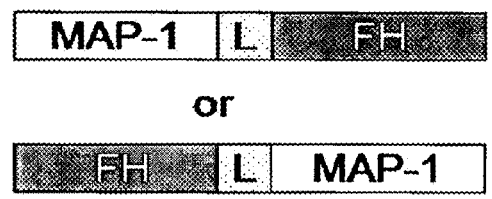
Figure 27:
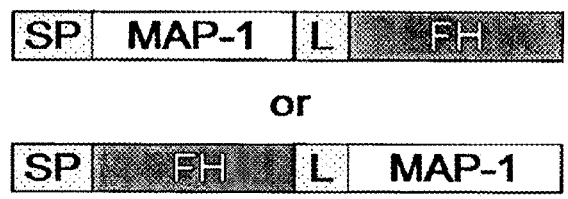

FIG. 27: Schematic diagram of an exemplary MAP-1/FH or FH/MAP-1 expression vector and chimeric constructs of MAP-1/FH or FH/MAP-1 protein. The chimeric expression plasmids contain a Kozak sequence (K), optional linker (L) and a stop codon (S). The vectors may also contain an optional signal peptide (SP).

Figure 28:
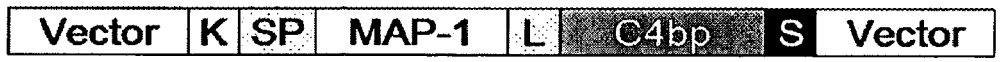
Figure 28:
Figure 28:
Figure 28:
Figure 28:
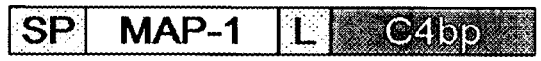
Figure 28:

FIG. 28: Schematic diagram of an exemplary MAP-1/C4 bp or C4 bp/MAP-1 expression vector and chimeric constructs of MAP-1/C4 bp or C4 bp/MAP-1 protein. The chimeric expression plasmids contain a Kozak sequence (K), optional linker (L) and a stop codon (S). The vectors may also contain an optional signal peptide (SP). C4 bp may be composed of either C4 bp alfa chain (C4bpA) or C4 bp beta chain (C4bpB) alone, or combination of the two chains.

Figure 29:
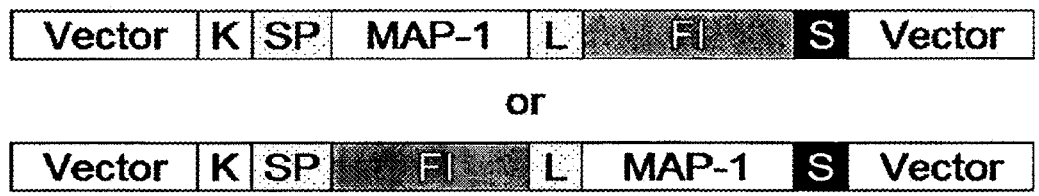
Figure 29:
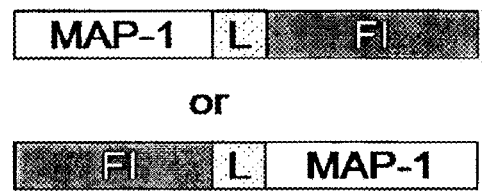
Figure 29:
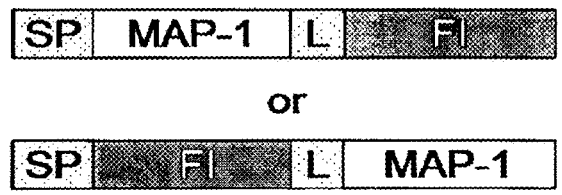

FIG. 29: Schematic diagram of an exemplary MAP-1/FI or FI/MAP-1 expression vector and chimeric constructs of MAP-1/FI or FI/MAP-1 protein. The chimeric expression plasmids contain a Kozak sequence (K), optional linker (L) and a stop codon (S). The vectors may also contain an optional signal peptide (SP).

Figure 30:
Figure 30:
Figure 30:
Figure 30:
Figure 30:
Figure 30:

FIG. 30: Schematic diagram of an exemplary MAP-1/C1-inh or C1-inh/MAP-1 expression vector and chimeric constructs of MAP-1/C1-inh or C1-inh/MAP-1 protein. The chimeric expression plasmids contain a Kozak sequence (K), optional linker (L) and a stop codon (S). The vectors may also contain an optional signal peptide (SP).

Figure 31:
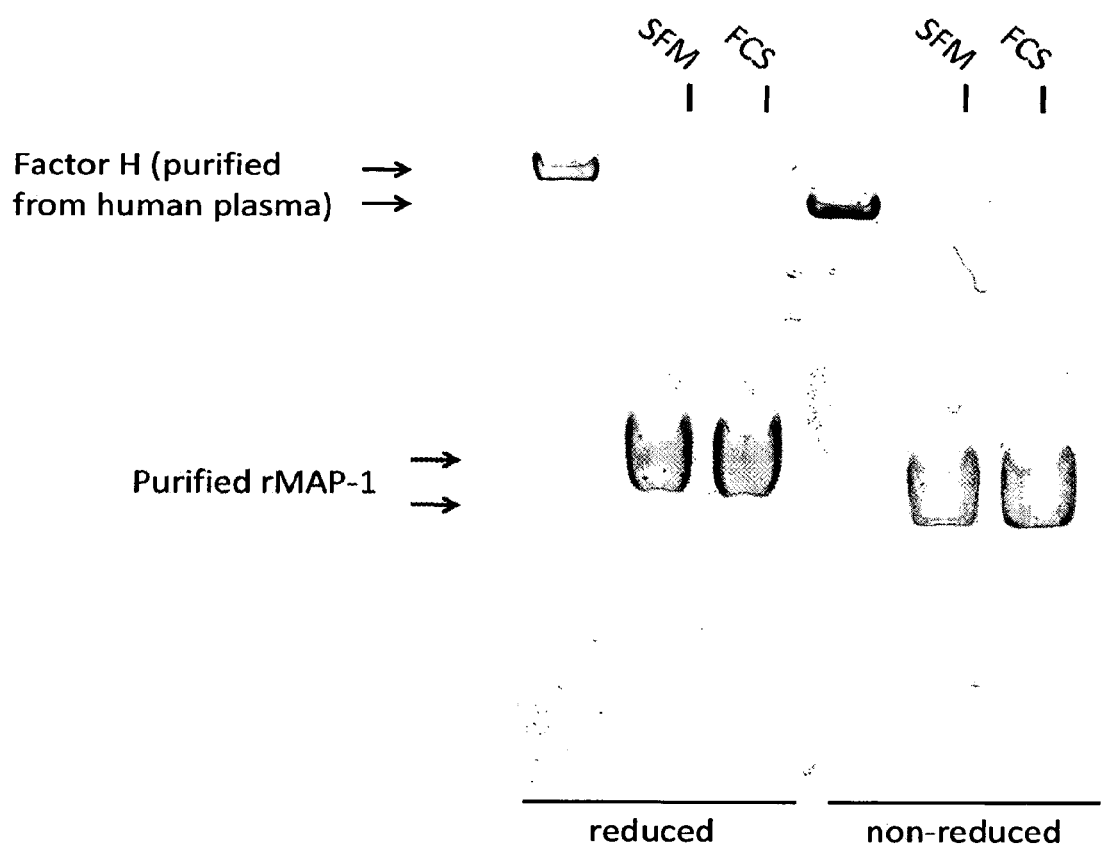

FIG. 31: Purified rMAP-1 and plasma Factor H in 4-12% Bis-Tris SDS-PAGE, Coomassie Brilliant Blue staining analysis of purified plasma Factor H and recombinant MAP-1 (from serum-free medium/SFM or medium with 10% fetal calf serum/FCS).

Figure 32:
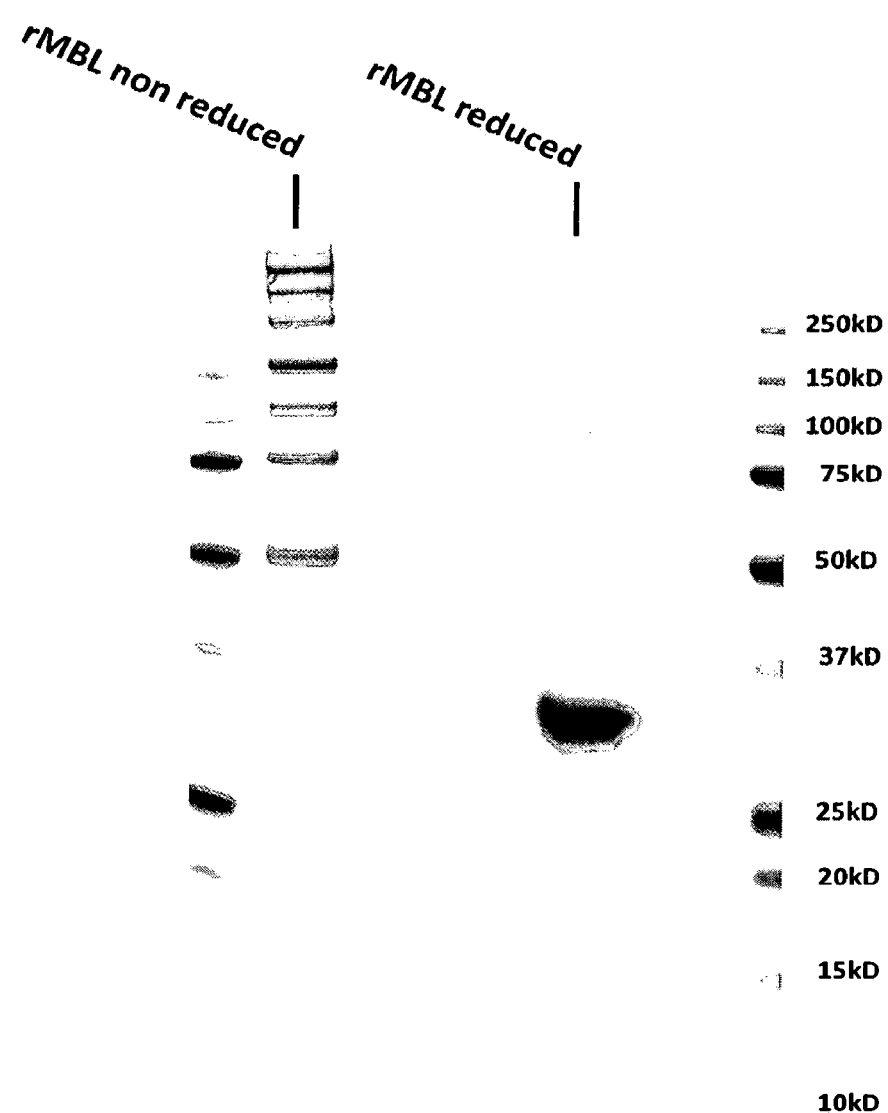

FIG. 32: Purified rMBL (SFM) in 4-12% Bis-Tris SDS-PAGE, Coomassie Brilliant Blue staining analysis of purified recombinant MBL (from serum-free medium/SFM).

Figure 33:
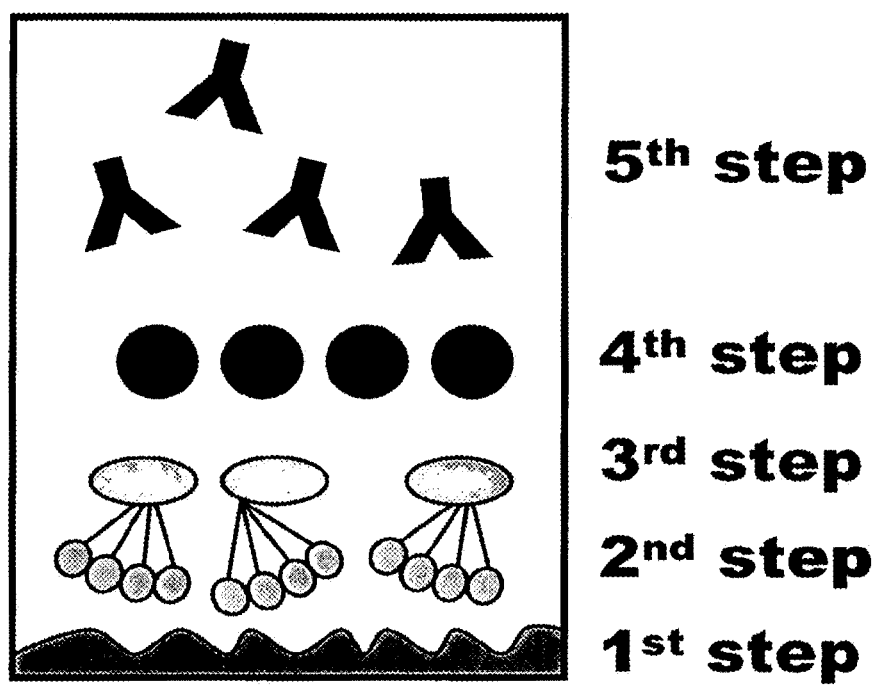

FIG. 33: MBL assay setup overview; Complement assay composition with included steps. Between each step are included three times washing/blocking. 1st step: Coating with Mannan; 2nd step: Application of rMBL, 400 ng/ml; 3rd step: Application of rMAP-1, fH or rMAP-1/fH hybrid in 1st dimension; 4th step: Application of MBL deficient serum (D/D) in 2nd dimension; 5th step: Measurement of C3 or C9 deposition, monoclonal antibodies to C3 or C9.

Figure 34:
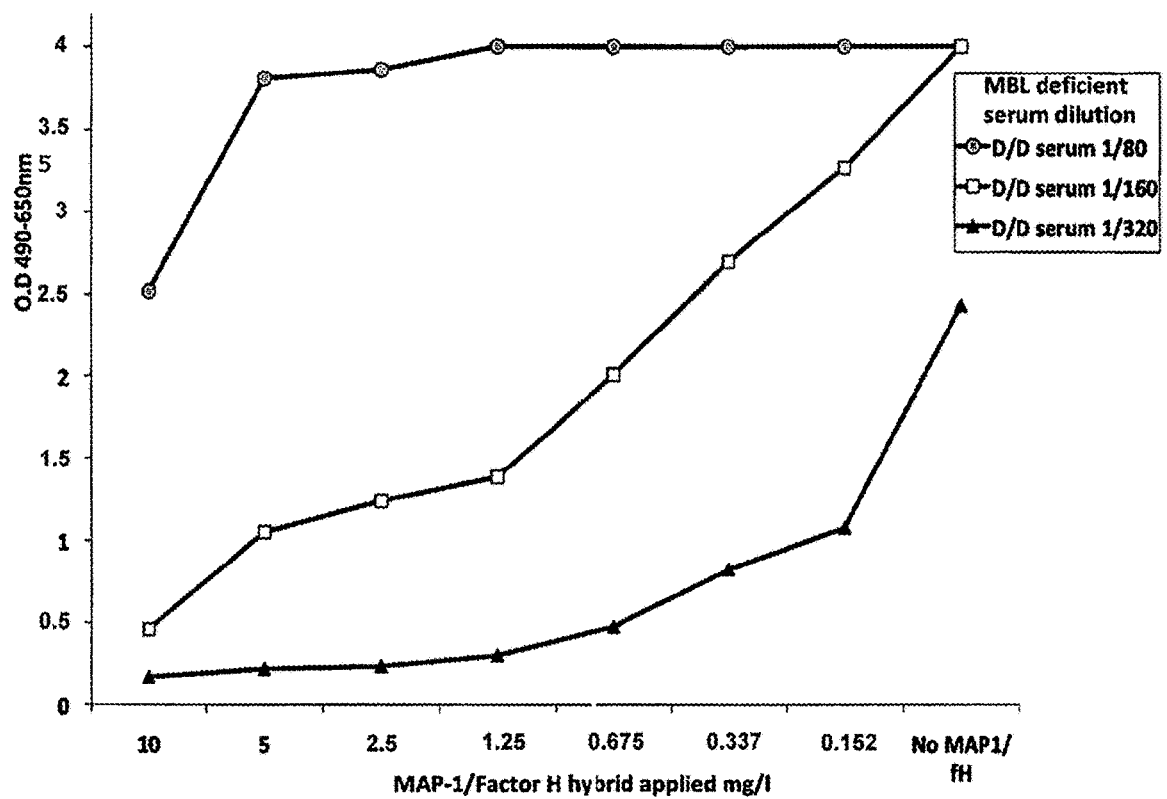

FIG. 34: MAP-1/Factor H hybrid molecule impact on the MBL mediated C3 deposition; Dose-dependent inhibition of complement C3 by a MAP-1/Factor H hybrid molecule.

Figure 35:
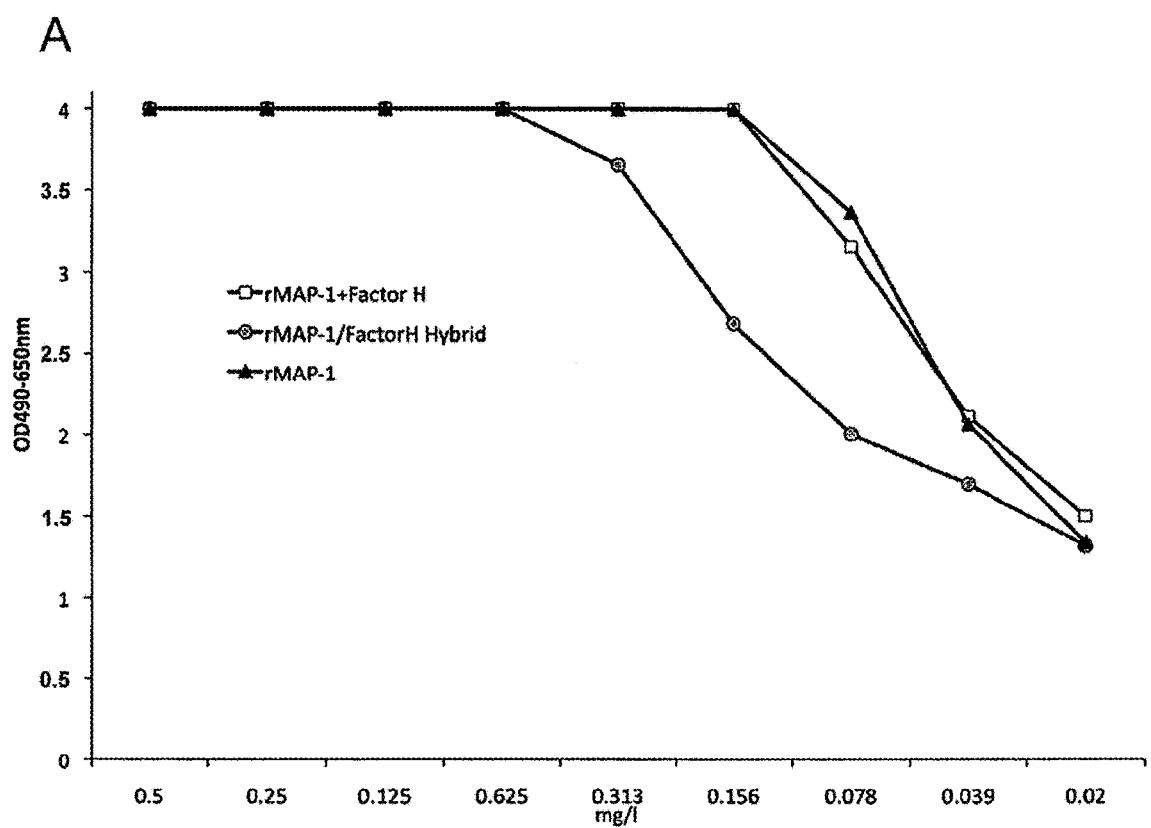
Figure 35:
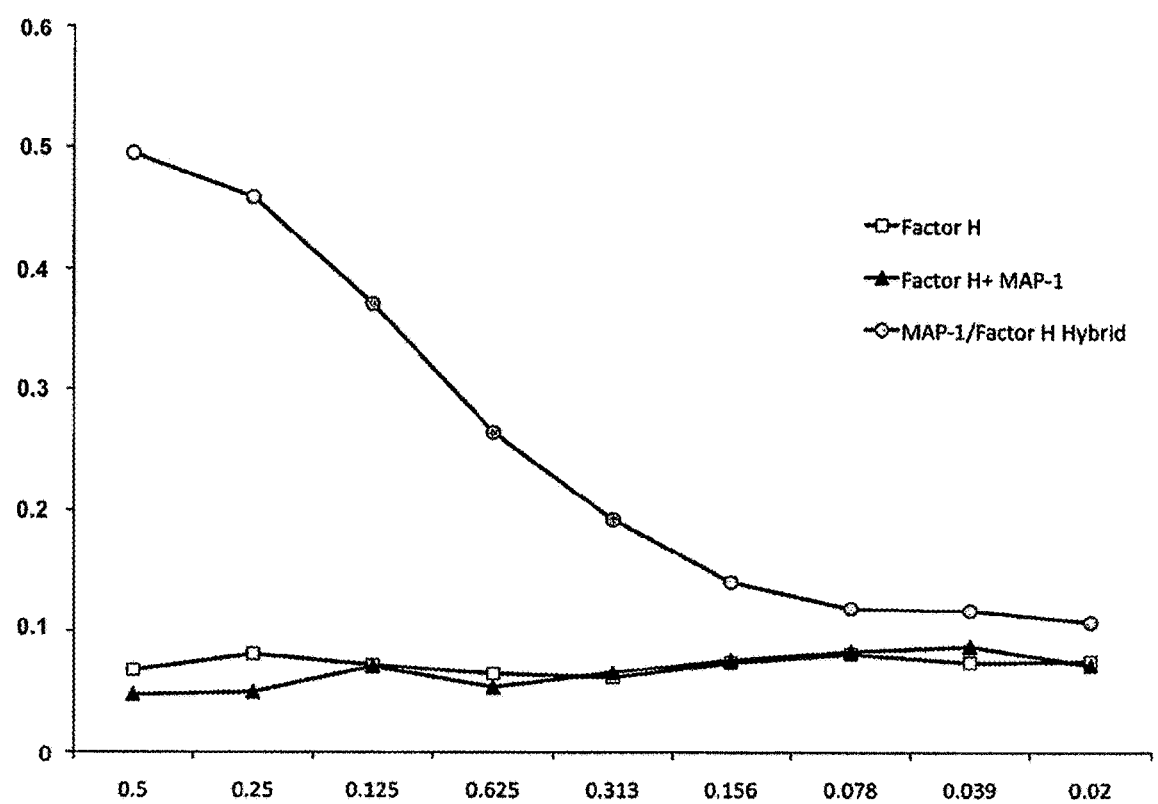

FIG. 35: Binding of specific antibodies to Factor H and MAP-1; FIG. 35A: rMAP-1 (SFM) association to rMBL bound to mannan; Detection of MAP-1 association with rMBL bound to mannan. Binding of rMAP-1, rMAP-1 with "free" Factor H and rMAP-1/Factor H Hybrid is detected with a monoclonal antibody to MAP-1. FIG. 35B: Detection of Factor H association with rMBL bound to mannan. Binding of Factor H, rMAP-1 with "free" Factor H and rMAP-1/Factor H Hybrid is detected with a monoclonal antibody to Factor H.

Figure 36:
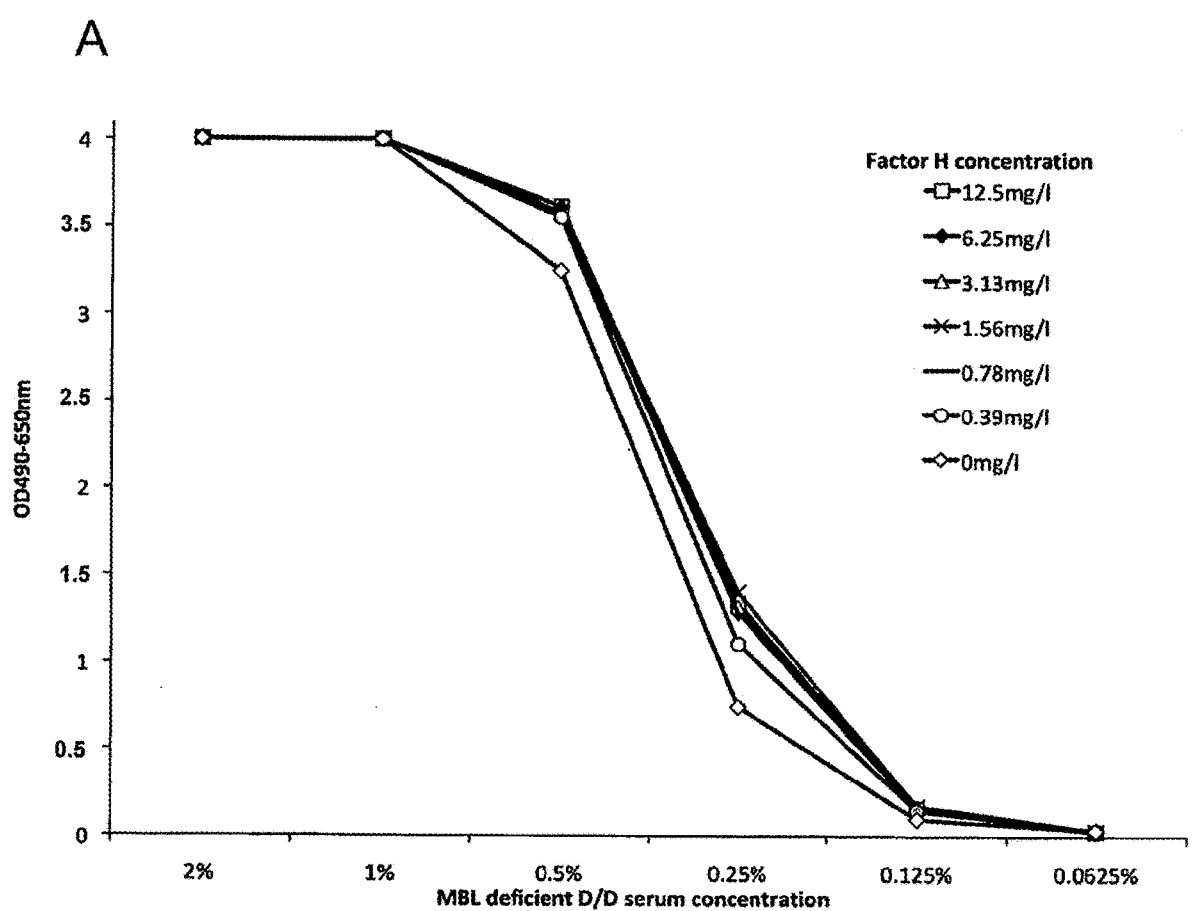
Figure 36:
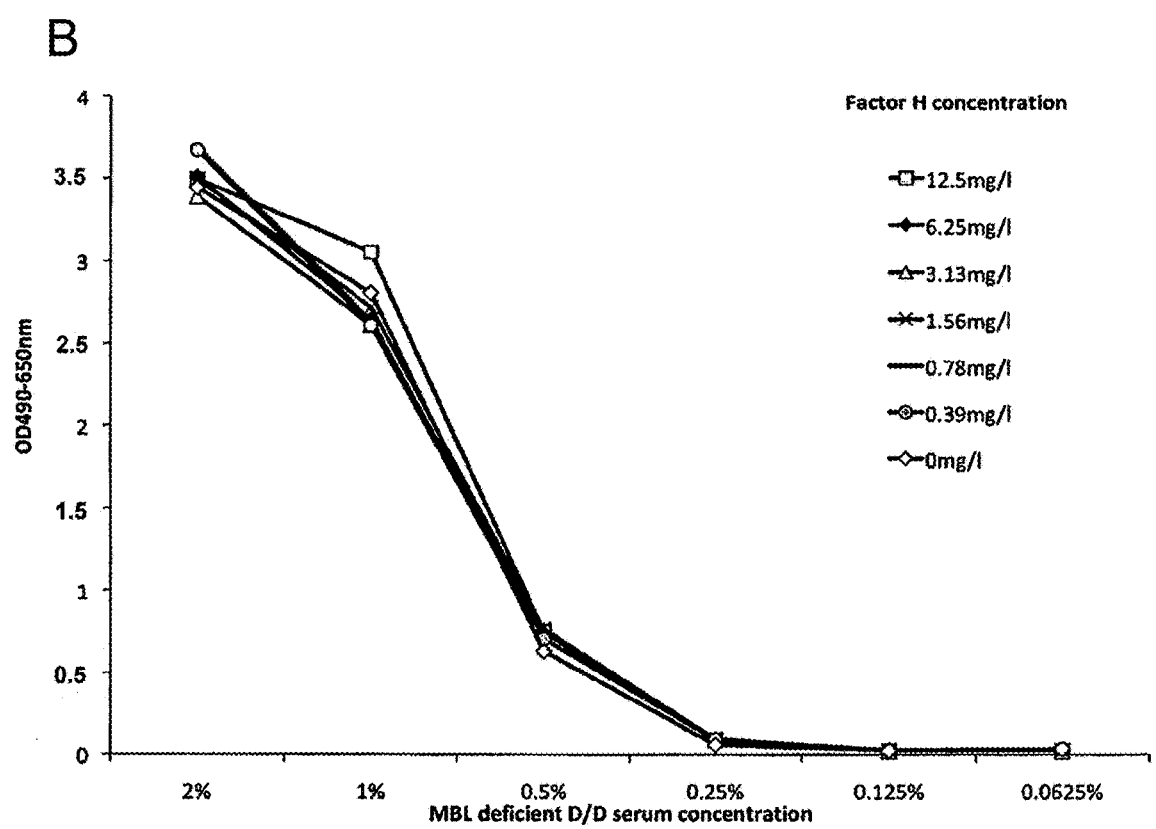

FIG. 36: Effect of Factor H on C3 and C9 deposition; FIG. 36A: Factor H impact on the MBL mediated C3 deposition; Dose-dependent inhibition of the MBL mediated complement C3 by purified "free" Factor H. FIG. 36B: Factor H impact on the MBL mediated C9 deposition (TCC); Dose-dependent inhibition of the MBL mediated complement C9 (terminal complement complex/TCC) by purified "free" Factor H.

Figure 37:
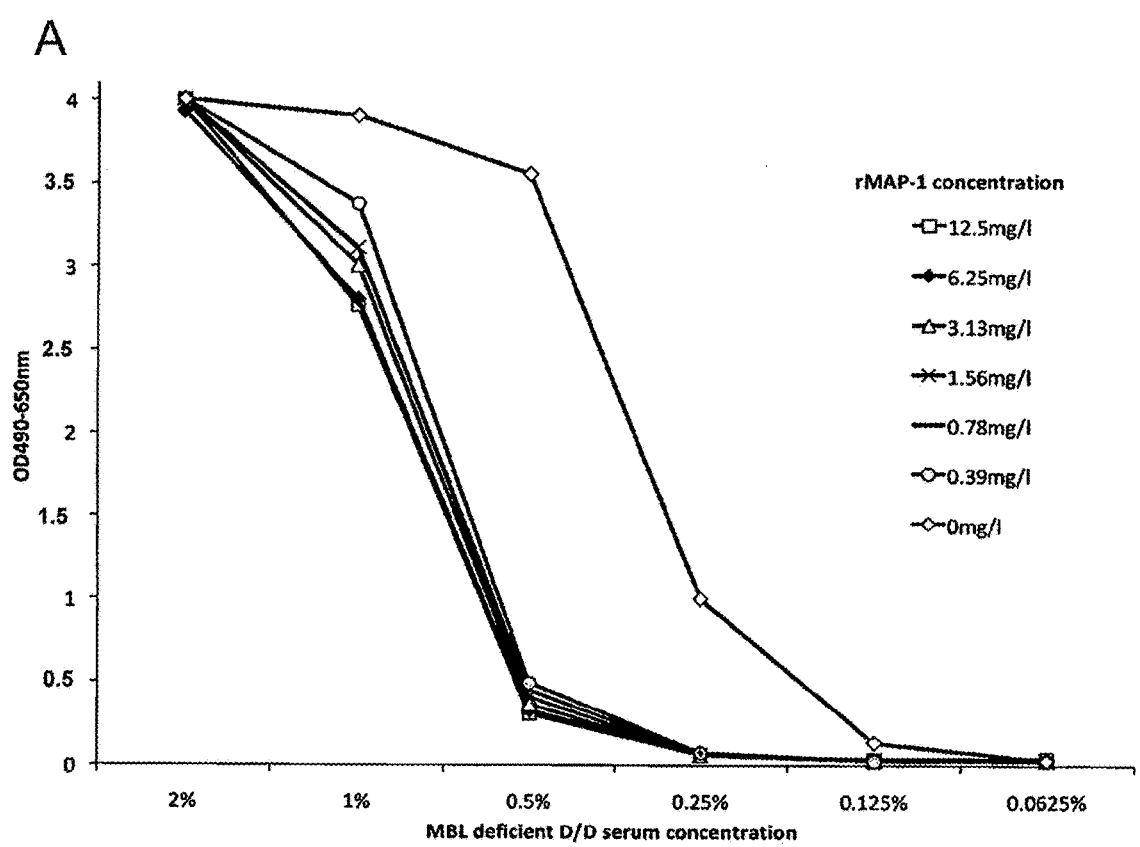
Figure 37:
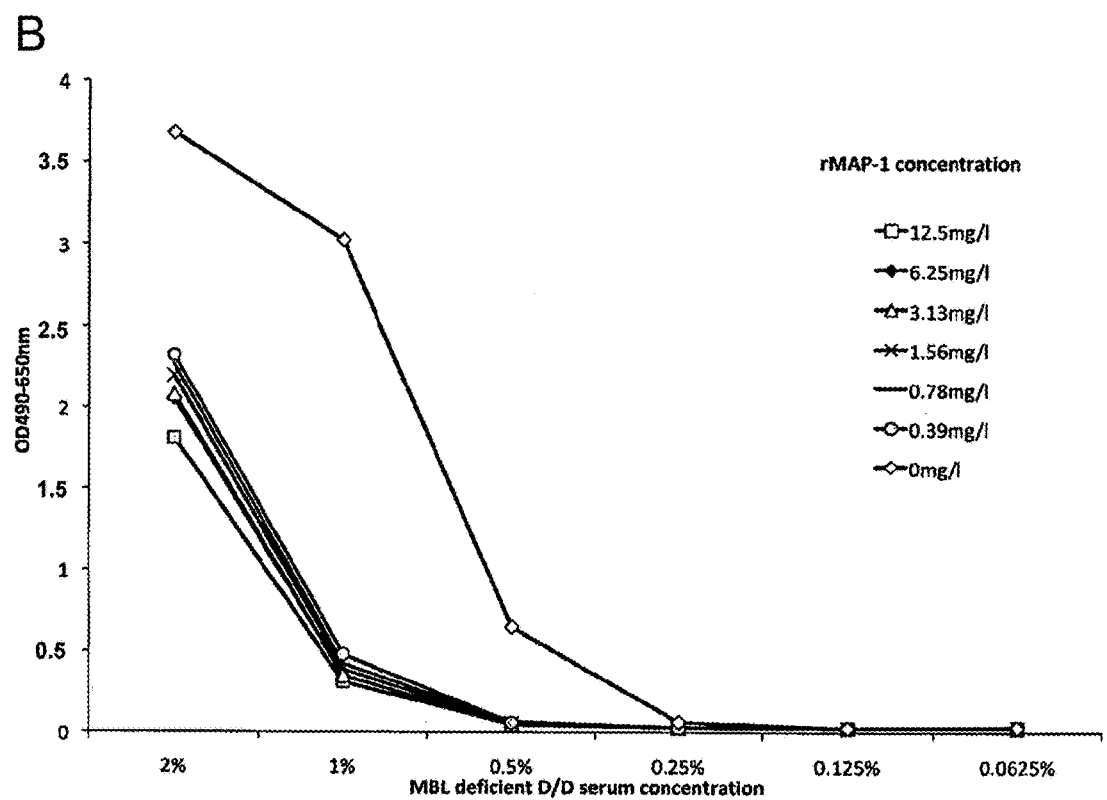

FIG. 37: Effect of rMAP-1 on C3 and C9 deposition; FIG. 37A: rMAP-1 impact on the MBL mediated C3 deposition; Dose-dependent inhibition of the MBL mediated complement C3 by purified recombinant MAP-1. FIG. 37B: rMAP-1 impact on the MBL mediated C9 deposition (TCC); Dose-dependent inhibition of the MBL mediated complement C9 (terminal complement complex/TCC) by purified recombinant MAP-1.

Figure 38:
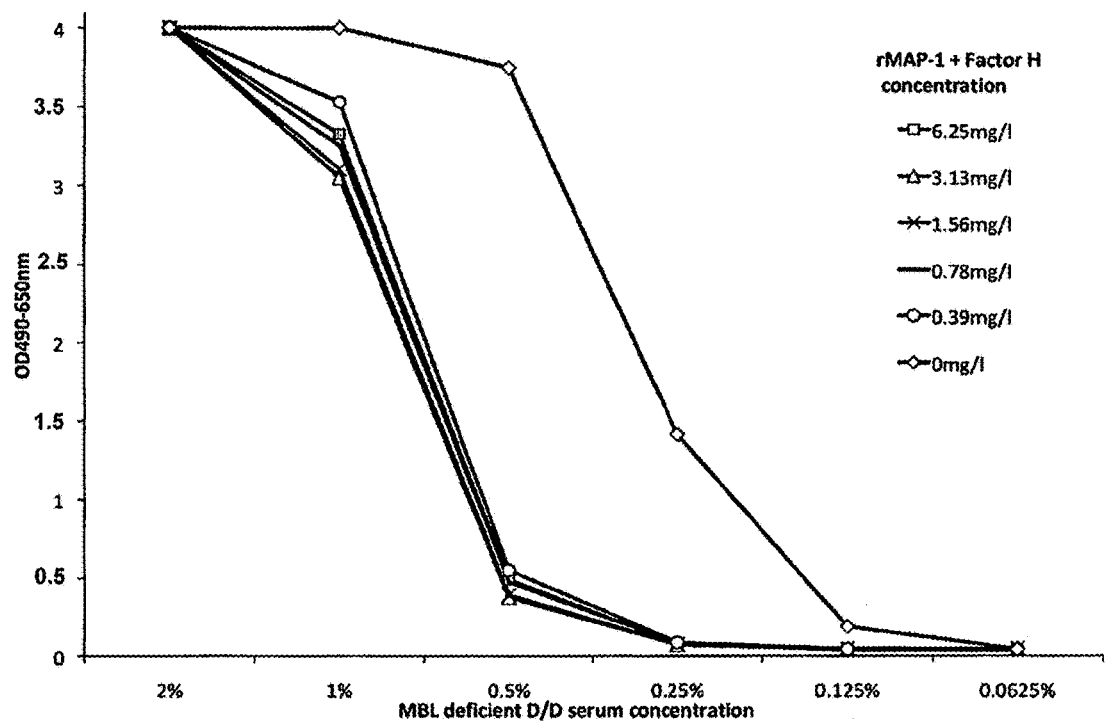
Figure 38:
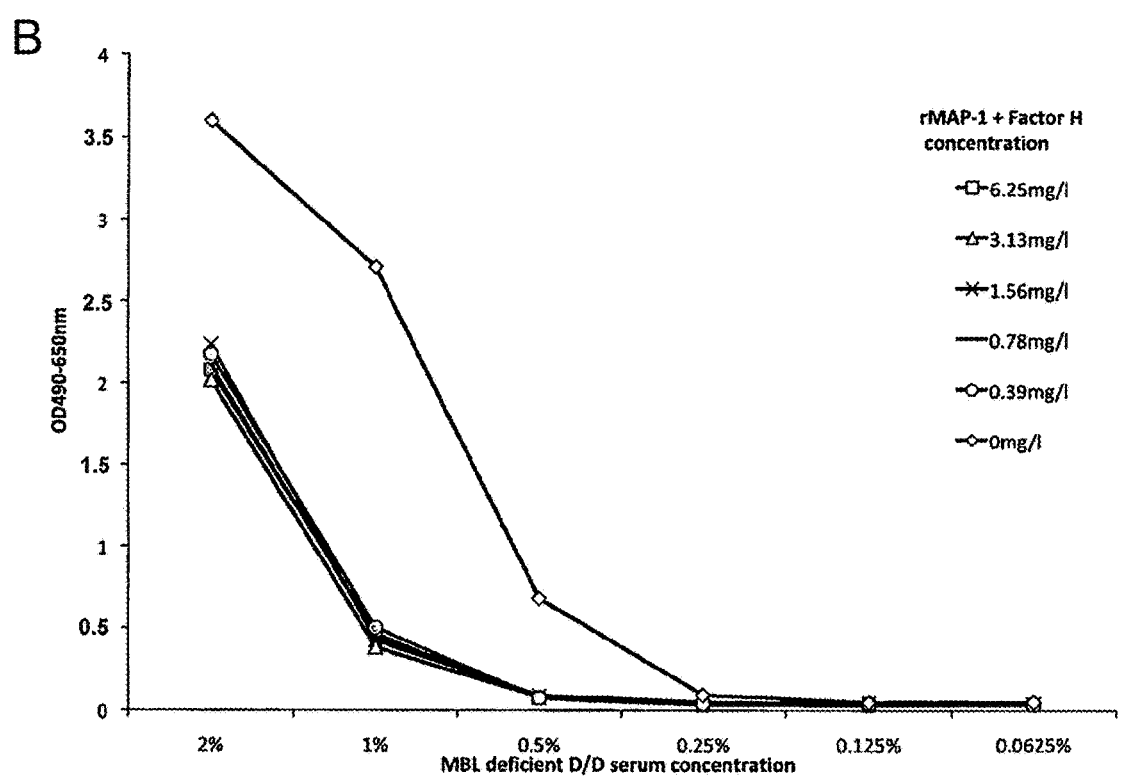

FIG. 38: Effect of rMAP-1+Factor H on C3 and C9 deposition; FIG. 38A: rMAP-1+Factor H impact on the MBL mediated C3 deposition; Dose-dependent inhibition of the MBL mediated complement C3 by recombinant MAP-1 and "free" Factor H. FIG. 38B: rMAP-1+Factor H impact on the MBL mediated C9 deposition (TCC); Dose-dependent inhibition of the MBL mediated complement C9 (terminal complement complex/TCC) by recombinant MAP-1 and "free" Factor H.

Figure 39:
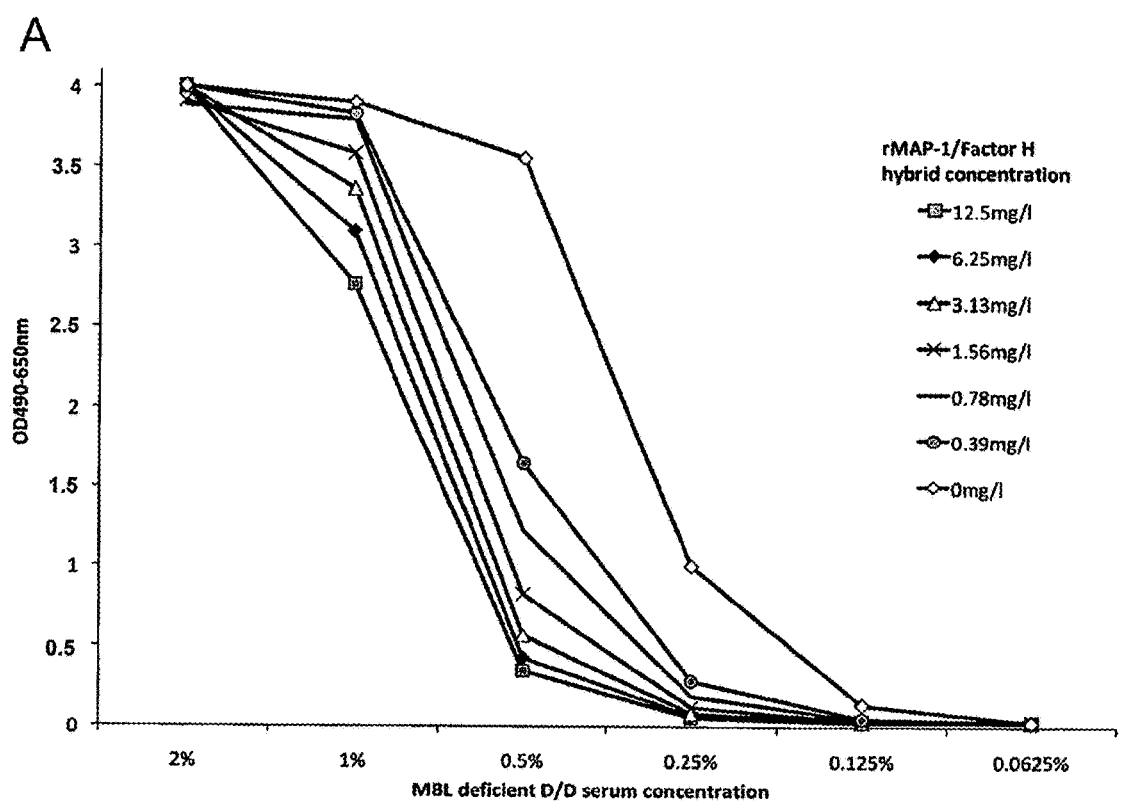
Figure 39:
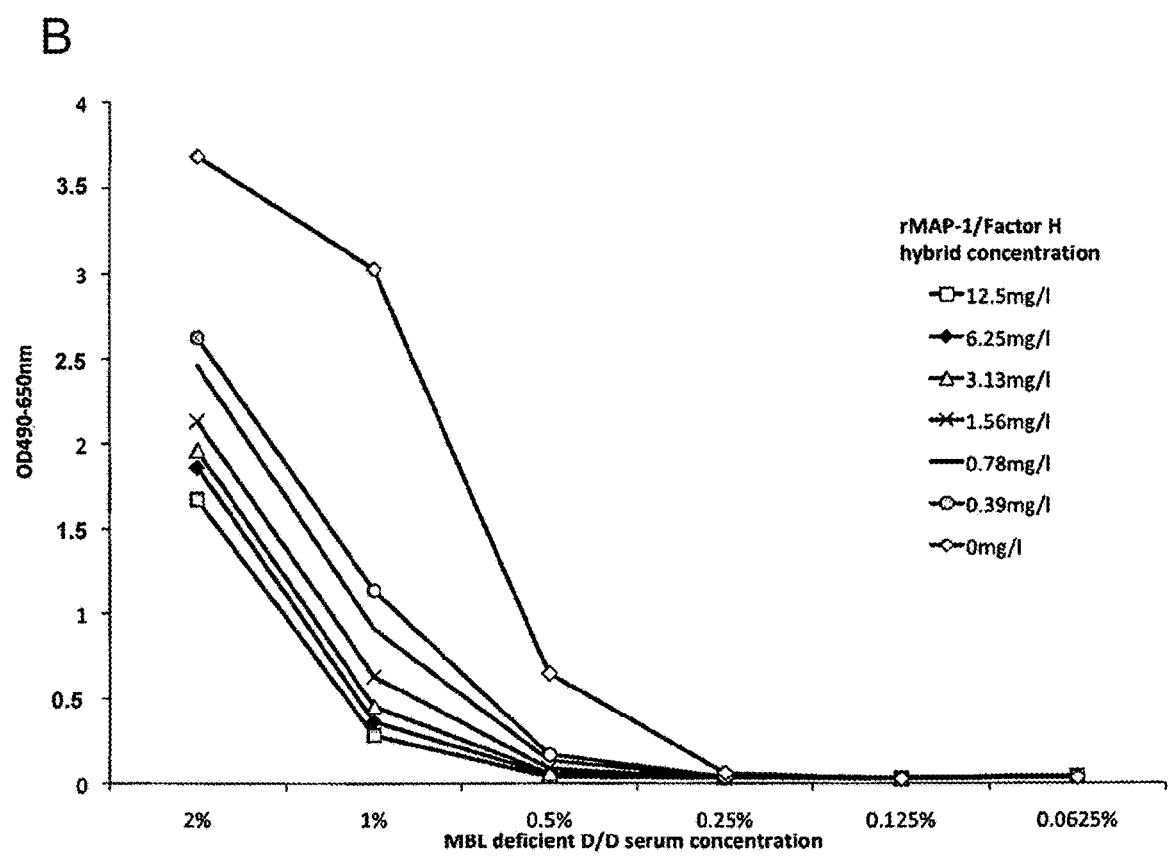

FIG. 39: Effect of rMAP-1/Factor H hybrid on C3 and C9 deposition; FIG. 39A: rMAP-1/Factor H hybrid impact on the MBL mediated C3 deposition; Dose-dependent inhibition of the MBL mediated complement C3 by rMAP-1/Factor H hybrid molecule. FIG. 39B: rMAP-1/Factor H hybrid impact on the MBL mediated C9 deposition (TCC); Dose-dependent inhibition of the MBL mediated complement C9 (terminal complement complex/TCC) by rMAP-1/Factor H hybrid molecule.

DETAILED DISCLOSURE OF THE INVENTION

The present inventors have discovered a novel plasma protein of 40 kDa associated with the recognition molecules of the lectin complement pathway and identified this as a new alternative transcript variant of MASP-1/MASP-3 that in turn corresponds to the newly discovered plasma protein.

The novel protein (by the inventors named FAP (Ficolin Associated Protein) or MAP-1 (MBL/Ficolin associated protein-1)) has been shown by the present inventors to lack an enzyme domain, but to contain the ficolin/MBL binding domain and is thus expected to be involved in regulation and inhibition of complement and coagulation functions through competitions and displacement of the MASPs or alternatively, but not mutually exclusive as a protein involved in scavenger or signaling functions.

Uncontrolled activation of the complement system and/or the coagulation cascade is strongly associated with fatal severe outcome in variety of diseases ranging from systemic inflammation and sepsis, through myocardial infarction and autoimmunity.

Inhibition of coagulation and complement activation has been shown to be a promising therapeutic tool.

MAP-1 is both a possible novel inhibitor of complement and of coagulation functions. However, the ficolin-associated polypeptides may have other functions, such as a scavenger and/or a signalling function. Moreover, they may be used as a biomarkers in several disease settings, including malignant diseases, autoimmune, metabolic and/or inflammatory conditions.

The inventors of the present invention found the plasma protein present in vivo and named it Ficolin Associated Protein (FAP). It is shown to be primarily associated with the ficolins (FIG. 9), but it may likely also be associated with mannose-binding lectin. By searching nucleotide database of NCBI the inventors of the present invention found a possible transcript variant that corresponds to a truncated of MASP-1. Based on this sequence, primers were designed in order to amplify the putative new gene transcript. Subsequently, using human liver cDNA a new alternative transcript variant of the MASP-1 gene (FIG. 1) was identified. This mRNA strain was sequenced and accordingly the amino acid sequence was determined, which corresponds to the molecular weight of the observed protein in plasma/serum of 40 kDa (FIG. 5). The new protein is partly identical to MASP-1 and MASP-3, but lacks a serine protease domain, but contain a novel exon encoding 17 amino acids followed by a stop codon. This exon is spliced out in the MASP1 and MASP3 transcript (FIG. 2). By using a panel of mRNA expression libraries the present inventors have found evidence that this protein is strongly expressed in the heart, the liver and in the skeletal muscle tissue (FIG. 3). Weak expression was observed in the brain, the digestive tract, prostata and in the spleen (FIG. 3). Taqman analysis confirmed the expression in heart and liver cells. FAP was expressed much higher in the heart tissue compared to MASP1 and MASP3. FAP was expressed three times higher in the heart tissue compared to the FAP expression in liver.

Furthermore, a higher FAP expression was observed in the liver compared to the MASP1 and MASP3 expression in the liver. Considerable FAP expression was also detected in brain, skeletal muscle and prostate tissues. The experiment was performed three times in duplicates.

The high expression in the heart is very prominent and has made the present inventors suggest a use of the polypeptides according to the present invention as a very useful protector against tissue damage in autoimmune, metabolic and/or inflammatory conditions, such as medical conditions associated with the heart.

The present inventors have established assays to assess complement activity initiated by ficolins and mannose-binding lectin and the present inventors have thus been able to show a possible functional complement inhibition of FAP.

The present inventors have establishing real time quantitative assays to measure the exact relative expression level in different tissues.

The ficolin-associated polypeptides as well as fusion proteins according to the present invention may be produced by recombinant techniques. Rabbits or mice may be immunized with a unique 17 amino acid long peptide in order to obtain FAP polyclonal and monoclonal specific antibodies, respectively.

Specific FAP antibodies may be used for quantitative measurement of FAP and immunohistochemical detection in different tissues.

Binding constants between FAP and different binding partners as described herein may be determined in ELISA and by using surface plasmon resonance technology (Biacore).

A FAP specific acceptor protein, such as a specific cell surface bound receptor may be identified by standard assays known to the person skilled in the art, such as assays wherein the protein is bound directly to cells.

The novel protein Ficolin Associated Protein (FAP) is an alternative splicing variant of MASP1. The protein lacks the serine protease domain but it still contains the domains that are involved in the binding to the initiators of the lectin pathway of the complement system. Thus, the present inventors expect the protein to be involved in regulation and inhibition of the function of MASP-1 and MASP-3 (complement, coagulation functions and other enzymes substrates) through competitions and displacement of the MASPs. Alternatively, but not mutually exclusive FAP may function as scavenger molecule facilitating removal of FAP/MBL/ficolin complexes bound to endogenous waste material or pathogens.

Uncontrolled activation of the complement system and the coagulation cascade are associated with adverse outcome and functional inhibitors, such as the polypeptides according to the present invention may be very useful for the control of the complement system and the coagulation cascade. In addition the polypeptides according to the present invention may be used in other settings. Another angle could be to use the protein as biomarker in different disease settings.

Chimeric molecules according to the present invention comprising the amino acid sequence of SEQ ID NO:4 or an immunologic fragment or variant thereof may have a specific function associated with this particular sequence of amino acids. It is suggested by the present inventors that such polypeptides may have a function or activity corresponding to the activity of one or more protein selected from DNMT1 DNA (cytosine-5-)-methyltransferase 1 (DNMT1), Golgin subfamily B member 1 (GOLGB1), A-kinase anchor protein 9 (AKAP9), B- and T-lymphocyte-associated protein)(CD272 antigen), PTB domain-containing engulfment adapter protein 1 (GULP), and MACRO domain-containing protein 2.

In some particular interesting embodiments the chimeric molecules according to the present invention have a function or activity corresponding to the activity of PTB domain-containing engulfment adapter protein 1 (GULP).

The ficolin-associated polypeptides are unique and may provide the basis for new drugs and/or new diagnostic tools.

Accordingly, the inventors of the present invention have provided chimeric molecules of a ficolin-associated polypeptide, which chimeric molecule further comprises a second modulator of complement activity.

Ficolin-associated polypeptides are expected to be effective in various clinical settings including indications associated with inflammation, apoptosis and/or autoimmunity. However, chimeric molecules, wherein a second modulator of complement activity, such as a complement inhibitor is fused, added, or conjugated to the ficolin-associated polypeptide are expected to offer significant potential advantages with regard to safety and efficacy.

Definitions

The term "ficolin-associated polypeptide" as used herein means any protein or polypeptide comprising the amino acid sequence 20-380 of native human ficolin-associated protein (FAP) (SEQ ID NO: 1) or amino acid sequence of 16-363 of SEQ ID NO:9, functional variants, functional truncated versions thereof as well as functional derivatives or conjugates, which polypeptide do not have complement activity, but posses the ability to compete with MASP-1, MASP-2, or MASP-3 for binding to ficolin-3, MBL, C1q, lung surfactant proteins SP-A and/or SP-D and/or CL-L1 (and other collectin family members). This includes but is not limited to human ficolin-associated polypeptide (FAP) having SEQ ID NO:1 and variants thereof.

The term "ficolin-associated protein (FAP)" as used herein means proteins that have the amino acid sequence 1-380 (with or without signal peptide, such as the amino acid sequence 20-380) of native human FAP (SEQ ID NO: 1), natural allelic variations and homologous thereof. It also includes proteins with a slightly modified amino acid sequence, for instance, a modified N- or C-terminal end including N- or C-terminal amino acid deletions or additions so long as those proteins substantially retain the activity of FAP. The term "ficolin-associated protein (FAP)" is used interchangeable herein with the terms "MAP-1" or "MBL/Ficolin associated protein-1". "FAP" within the above definition also includes natural allelic variations that may exist and occur from one individual to another. The term also includes proteins with homologous sequence and similar function derived from other species than human, such as bovine, pig, dog, horse, rat, and mouse. Also, degree and location of glycosylation or other post-translation modifications may vary depending on the chosen host cells and the nature of the host cellular environment.

The term "MBL-Associated Serine Protease-1" or "MASP-1" as used herein means proteins that have the amino acid sequence 1-699 (with or without signal peptide, such as the amino acid sequence 20-699) of native human MASP-1 (SEQ ID NO:5), natural allelic variations and homologous thereof. It is to be understood that the sequence may be in one or more peptide chains, such as in two chains, i.e. the heavy and light chains of the native human protein.

The term "MBL-Associated Serine Protease-3" or "MASP-3" as used herein means proteins that have the amino acid sequence 1-728 (with or without signal peptide, such as the amino acid sequence 20-728) of native human MASP-3 (SEQ ID NO:7), natural allelic variations and homologous thereof. It is to be understood that the sequence may be in one or more peptide chains, such as in two chains, i.e. the heavy and light chains of the native human protein.

The term "MBL-Associated Serine Protease-2" or "MASP-2" as used herein means proteins that have the amino acid sequence 1-686 (with or without signal peptide, such as the amino acid sequence 16-686) of native human MASP-2 (SEQ ID NO:9), natural allelic variations and homologous thereof. It is to be understood that the sequence may be in one or more peptide chains, such as in two chains, i.e. the heavy and light chains of the native human protein.

The terms "small MBL-associated protein", "sMAP", "MBL-associated plasma protein of 19 kD" or, "MAp19" as used herein means proteins that have the amino acid sequence 1-185 (with or without signal peptide, such as the amino acid sequence 16-185) of native human sMAP (SEQ ID NO:11), natural allelic variations and homologous thereof.

The terms "variant" or "variants", as used herein, is intended to designate any protein comprising naturally occurring polypeptide, such as a ficolin-associated polypeptide having the sequence of SEQ ID NO:1 or a polypeptide comprising the amino acid sequence of SEQ ID NO:4, wherein one or more amino acids have been substituted by another amino acid and/or wherein one or more amino acids have been deleted and/or wherein one or more amino acids have been inserted in the polypetide and/or wherein one or more amino acids have been added to the polypeptide. Such addition can take place either at the N-terminal end or at the C-terminal end or both. The "variant" or "variants" within this definition still have functional activity. In some embodiment a variant has 70% sequence identity with the sequence of SEQ ID NO:1. In some embodiments a variant has 80% sequence identity with the sequence of SEQ ID NO:1. In other embodiments a variant has 90% sequence identity with the sequence of SEQ ID NO:1. In a further embodiment a variant has 95% sequence identity with the sequence of SEQ ID NO:1.

In some embodiments a variant has 70% sequence identity with the sequence of SEQ ID NO:4. In some embodiments a variant has 80% sequence identity with the sequence of SEQ ID NO:4. In other embodiments a variant has 90% sequence identity with the sequence of SEQ ID NO:4. In a further embodiment a variant has 95% sequence identity with the sequence of SEQ ID NO:4.

The phrases "functional variant", "functional truncated versions", and "functional derivatives" of a chimeric ficolin-associated polypeptide as used herein refers to variants, truncated versions, as well as derivatives of SEQ ID NO:1, which polypeptides comprises essential sequence parts of SEQ ID NO:1 and at least posses the ability to compete with MASP-1 or MASP-3 for binding to the ficolins or MBL without having the complement activity and/or serine protease activity. It is to be understood that a chimeric molecule of a ficolin-associated polypeptide may have two or three features selected from being a both a variant, and/or truncated and/or a derivative.

A functional variant of a chimeric molecule of a ficolin-associated polypeptide encompass those that exhibit at least about 25%, such as at least about 50%, such as at least about 75%, such as at least about 90% of the specific activity of wild-type FAP that has been produced in the same cell type, when tested in the assays as described herein.

The term "immunologic fragment" as used herein refers to fragment of an amino acid sequence that posses essentially the same functional activities and the same spatial orientation to be recognized by an antibody. Accordingly a specific antibody will bind both the polypeptide and immunologic fragments thereof.

The term "another amino acid" as used herein means one amino acid that is different from that amino acid naturally present at that position. This includes but is not limited to amino acids that can be encoded by a polynucleotide. In some embodiments the different amino acid is in natural L-form and can be encoded by a polynucleotide.

The term "derivative" as used herein, is intended to designate a chimeric molecule of a ficolin-associated polypeptide exhibiting substantially the same or improved biological activity relative to wild-type human FAP, in which one or more of the amino acids of the parent peptide have been chemically modified, e.g. by alkylation, PEGylation, acylation, ester formation or amide formation or the like.

The term "complement activity" as used herein means the ability activate the complement system. The complement activity may be measured with assay as described in the section headed "Assays".

The term "mannose-binding lectin (MBL)" as used herein also means mannan-binding lectin, mannose-binding protein (MBP1), and mannan-binding protein, which terms may be used interchangeably.

The term "capable of associating" as used herein refers to the ability of the proteins according to the present invention to specifically bind in solution one or more of the initiators of the lectin pathway of the complement system or other proteins that may be involved in the effect of the polypeptide.

The term "modulator of complement activity" as used herein refers to any compound that directly or indirectly influences complement activity. The modulator of complement activity may be a direct inhibitor or an indirect inhibitor. Alternatively the modulator may be a homing domain that facilitates the transport and/or uptake at a particular site of complement activity, such as a site of inflammation. Alternatively the modulator may be an immunoglobulin molecule, such as an Fc domain, ligands for adhesion molecules, such as ligands for selectins. In some preferred embodiments, the modulator of complement activity is not a complement activator. The use of the term "second" for a modulator of complement activity simply refers to a modulator of complement activity, which is different from the ficolin-associated polypeptide. Inhibition or modulatory effect of complement activity may be measured according to the assays described herein or any one other assay known to the person skilled in the art.

The term "chimeric molecule" as used herein refers to a molecule comprising at least two domains which are not normally associated, comprising at least (i) a ficolin-associated polypeptide, and (ii) a second modulator of complement activity. The ficolin-associated polypeptide and the second modulator of complement activity may be linked together by any methods known in the art, as long as the desired functionalities of the two portions are maintained.

In some embodiments, the chimeric molecule is a fusion protein. "Fusion protein" used herein refers to two or more peptides, polypeptides, or proteins operably linked to each other. In some embodiments, the two portions are directly fused to each other. In some embodiments, the two portions are linked by an amino acid linker sequence. Examples of linker sequences are known in the art, and include, for example, $(Gly_4Ser)$(SEQ ID NO:67), $(Gly_4Ser)_2$(SEQ ID NO:68), $(Gly_4Ser)_3$(SEQ ID NO: 69), $(Gly_3Ser)_4$(SEQ ID NO: 70), $(SerGly_4)$(SEQ ID NO: 71), $(SerGly_4)_2$(SEQ ID NO: 72), $(SerGly_4)_3$(SEQ ID NO: 73), and $(SerGly_4)_4$(SEQ ID NO:74). Linking sequences can also comprise "natural" linking sequences found between different domains of complement factors. The order of the ficolin-associated polypeptide and the second modulator of complement activity in the fusion protein can vary. For example, in some embodiments, the C-terminus of the ficolin-associated polypeptide is fused (directly or indirectly) to the N-terminus of the second modulator of complement activity. In some embodiments, the N-terminus of the ficolin-associated polypeptide is fused (directly or indirectly) to the C-terminus of the second modulator of complement activity.

In some embodiments, the chimeric molecule comprising the ficolin-associated polypeptide and the second modulator of complement activity is linked via a chemical cross-linker. Linking of the two domains can occur on reactive groups located on the two portions. Reactive groups that can be targeted using a crosslinker include primary amines, sulfhydryls, carbonyls, carbohydrates, and carboxylic acids, or active groups that can be added to proteins. Examples of chemical linkers are well known in the art and include, but are not limited to, bismaleimidohexane, maleimidobenzoyl-N-hydroxysuccinimide ester, NHS-Esters-Maleimide Crosslinkers such as SPDP, carbodiimide, glutaraldehyde, MBS, Sulfo-MBS, SMPB, sulfo-SMPB, GMBS, Sulfo-GMBS, EMCS, Sulfo-EMCS, imidoester crosslinkers such as DMA, DMP, DMS, DTBP, EDC and DTME.

In some embodiments, the ficolin-associated polypeptide and the second modulator of complement activity are non-covalently linked. For example, the two portions may be brought together by two interacting bridging proteins (such as biotin and avidin or streptavidin), each linked to the ficolin-associated polypeptide or to the second modulator of complement activity.

In some embodiments, the chimeric molecules form dimers or multimers.

In some embodiments, the ficolin-associated polypeptide and the modulator of complement activity are directly fused (i.e. linked) to each other as a fusion protein. In some embodiments, the ficolin-associated polypeptide and the modulator of complement activity are indirectly linked via an amino acid linker sequence. In some embodiments, the C-terminus of the ficolin-associated polypeptide is linked (directly or indirectly) to the N-terminus of the modulator of complement activity. In some embodiments, the N-terminus of the ficolin-associated polypeptide is linked (directly or indirectly) to the C-terminus of the modulator of complement activity.

The term "construct" is intended to indicate a polynucleotide segment which may be based on a complete or partial naturally occurring nucleotide sequence encoding the polypeptide of interest. The construct may optionally contain other polynucleotide segments. In a similar way, the term "amino acids which can be encoded by polynucleotide constructs" covers amino acids which can be encoded by the polynucleotide constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln. The term "vector", as used herein, means any nucleic acid entity capable of the amplification in a host cell. Thus, the vector may be an autonomously replicating vector, i.e. a vector, which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to, plasmid vectors, phage vectors, viruses or cosmid vectors. Vectors usually contain a replication origin and at least one selectable gene, i.e., a gene which encodes a product which is readily detectable or the presence of which is essential for cell growth.

In a further aspect, the invention provides a recombinant host cell comprising the polynucleotide construct or the vector. In some embodiments the recombinant host cell is a eukaryotic cell. In other embodiments the recombinant host cell is of mammalian origin. In a further embodiment the recombinant host cell is selected from the group consisting of CHO cells, HEK cells and BHK cells.

The term "a host cell", as used herein, represent any cell, including hybrid cells, in which heterologous DNA can be expressed. Typical host cells includes, but are not limited to insect cells, yeast cells, mammalian cells, including human cells, such as BHK, CHO, HEK, and COS cells. In practicing the present invention, the host cells being cultivated are preferably mammalian cells, more preferably an established mammalian cell line, including, without limitation, CHO (e.g., ATCC CCL 61), COS-1 (e.g., ATCC CRL 1650), baby hamster kidney (BHK) and HEK293 (e.g., ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, MD 20852, under ATCC accession number CRL 10314. A tk⁻ ts13 BHK cell line is also available from the ATCC under accession number CRL 1632. Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci. USA* 77:4216-4220, 1980). Also useful are 3T3 cells, Namalwa cells, myelomas and fusions of myelomas with other cells.

In a further aspect, the invention provides a transgenic animal containing and expressing the polynucleotide construct.

In a further aspect, the invention provides a transgenic plant containing and expressing the polynucleotide construct.

In a further aspect, the invention relates to a method for producing the chimeric molecules of a ficolin-associated polypeptide of the invention, the method comprising cultivating a cell comprising the polynucleotide construct in an appropriate growth medium under conditions allowing expression of the polynucleotide construct and recovering the resulting polypeptide from the culture medium.

As used herein the term "appropriate growth medium" means a medium containing nutrients and other components required for the growth of cells and the expression of the nucleic acid sequence encoding the chimeric molecules of a ficolin-associated polypeptide of the invention.

In a further aspect, the invention relates to a method for producing the chimeric molecules of a ficolin-associated polypeptide, the method comprising recovering the polypeptide from milk produced by the transgenic animal.

In a further aspect, the invention relates to a method for producing the chimeric molecules of a ficolin-associated polypeptide, the method comprising cultivating a cell of a transgenic plant comprising the polynucleotide construct, and recovering the polypeptide from the resulting plant.

In the present context, the term "treatment" is meant to include both prevention of an expected condition involving inappropriate complement activation, such as inflammation and reperfusion injury and regulation of an already occurring condition, such as myocardial infarction and stroke with the purpose of inhibiting or minimising the tissue damage Prophylactic administration of the chimeric molecules of a ficolin-associated polypeptide according to the invention is thus included in the term "treatment".

The term "subject" as used herein is intended to mean any animal, in particular mammals, such as humans, and may, where appropriate, be used interchangeably with the term "patient".

The term "sequence identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or between polypeptides, as the case may be, as determined by the number of matches between strings of two or more nucleotide residues or two or more amino acid residues. "Identity" measures the percent of identical matches between the smaller of two or more sequences with gap alignments (if any) addressed by a particular mathematical model or computer program (i.e., "algorithms").

The term "similarity" is a related concept, but in contrast to "identity", refers to a sequence relationship that includes both identical matches and conservative substitution matches. If two polypeptide sequences have, for example, (fraction (10/20)) identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% ((fraction (15/20))). Therefore, in cases where there are conservative substitutions, the degree of similarity between two polypeptides will be higher than the percent identity between those two polypeptides.

Conservative modifications to the amino acid sequence of SEQ ID NO:1 (and the corresponding modifications to the encoding nucleotides) will produce ficolin-associated polypeptides having functional and chemical characteristics similar to those of naturally occurring FAP. In contrast, substantial modifications in the functional and/or chemical characteristics of a ficolin-associated polypeptide may be accomplished by selecting substitutions in the amino acid sequence of SEQ ID NO:1 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of a ficolin-associated polypeptide or a chimeric molecule of a ficolin-associated polypeptide, or to increase or decrease the affinity of a ficolin-associated polypeptide described herein.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human ficolin-associated polypeptide, or in the chimeric molecule of a ficolin-associated polypeptide that are homologous with non-human ficolin-associated polypeptides or into the non-homologous regions of the molecules.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids may be substituted for other amino acids having a similar hydropathic index or score and still retain a similar biological activity. In making changes based upon the hydropathic index, the substitution of amino acids whose hydropathic indices are within. ±2 is preferred, those that are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine ('3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those that are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in SEQ ID NO:1 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a ficolin-associated polypeptide or a second modulator of complement activity to such similar polypeptides. With such a comparison, one can identify residues and portions of the molecules that are conserved among similar polypeptides. It will be appreciated that changes in areas of a ficolin-associated polypeptide or of a second modulator of complement activity that are not conserved relative to such similar polypeptides would be less likely to adversely affect the biological activity and/or structure of the ficolin-associated polypeptide or the second modulator of complement activity. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a ficolin-associated polypeptide or in a second modulator of complement activity that correspond to amino acid residues that are important for activity or structure in similar polypeptides. One skilled in the art may opt for chemically similar amino acid substitutions for such predicted important amino acid residues of ficolin-associated polypeptides or second modulators of complement activity and other polypeptides of the invention.

One skilled in the art can also analyze the three-dimensional structure and amino acid sequence in relation to that structure in similar polypeptides. In view of that information, one skilled in the art may predict the alignment of amino acid residues of a ficolin-associated polypeptide or of a second modulator of complement activity with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays as described herein. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol, 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins, which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3):377-87 (1997); Sippl et al., Structure, 4(1):15-9 (1996)), "profile analysis" (Bowie et al., Science, 253:164-170 (1991); Gribskov et al., Meth. Enzymol., 183:146-159 (1990); Gribskov et al., Proc. Nat. Acad. Sci., 84(13):4355-4358 (1987)), and "evolutionary linkage" (See Home, supra, and Brenner, supra).

Identity and similarity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., Nucl. Acid. Res., 12:387 (1984); Genetics Computer Group, University of Wisconsin, Madison, Wis.), BLASTP, BLASTN, and FASTA (Altschul et al., J. Mol. Biol., 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in some embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA, 89:10915-10919 (1992) for the BLOSUM 62 comparison matrix) is also used by the algorithm.

Preferred parameters for a polypeptide sequence comparison include the following:

Algorithm: Needleman et al., J. Mol. Biol, 48:443-453 (1970); Comparison matrix: BLOSUM 62 from Henikoff et al., Proc. Natl. Acad. Sci. USA, 89:10915-10919 (1992); Gap Penalty: 12, Gap Length Penalty: 4, Threshold of Similarity: 0.

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following: Algorithm: Needleman et al., J. Mol Biol., 48:443-453 (1970); Comparison matrix: matches=+10, mismatch=0, Gap Penalty: 50, Gap Length Penalty: 3.

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Preparation of Ficolin-Associated Polypeptides and Other Chimeric Polypeptides of the Invention The invention also relates to a method of preparing human Ficolin-associated polypeptides and other chimeric polypeptides of the invention as mentioned above. The Ficolin-associated polypeptides and other polypeptides of the invention described herein may be produced by means of recombinant nucleic acid techniques. In general, a cloned wild-type FAP nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete amino acid and nucleotide sequences for human FAP is given by SEQ ID NO:1 and SEQ ID NO:2.

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of FAP, one may introduce the alteration(s) of choice. Likewise, procedures for preparing a DNA construct using polymerase chain reaction using specific primers are well known to per-sons skilled in the art (cf. PCR Protocols, 1990, Academic Press, San Diego, California, USA).

The polypeptides of the present invention can also comprise non-naturally occurring amino acid residues. Non-naturally occurring amino acids include, without limitation, beta-alanine, desaminohistidine, trans-3-methylproline, 2,4-methanoproline, cis-4-hydroxyproline, trans-4-hydroxyproline, N-methylglycine, allo-threonine, methylthreonine, hydroxyethylcys-teine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, nor-valine, 2-azaphenylalanine, 3-azaphenylalanine, 4-azaphenylalanine, and 4-fluorophenylalanine. Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Polypeptides are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oo-cytes by microinjection of mutated mRNA and chemically aminoacylated suppressor tRNAs (Turcatti et al., J. Biol. Chem. 271:19991-8, 1996). Within a third method, E. coli cells are cul-tured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

The nucleic acid construct encoding the Ficolin-associated polypeptides and other polypeptides of the invention of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Labora-tory, Cold Spring Harbor, New York, 1989).

The nucleic acid construct encoding a Ficolin-associated polypeptide and the second modulator of complement activity, as well as chimeric molecules of the invention may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors. The DNA sequences encoding the human Ficolin-associated polypeptides and the second modulator of complement activity, as well as chimeric molecules of the invention and other polypeptides of the invention may also be prepared by polymerase chain reaction using specific primers, for instance as described in U.S. Pat. No. 4,683, 202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of syn-thetic, genomic or cDNA origin (as appropriate), the fragments corresponding to various parts of the entire nucleic acid construct, in accordance with standard techniques.

The nucleic acid construct is preferably a DNA construct. DNA sequences for use in producing Ficolin-associated polypeptides, second modulators of complement activity, as well as chimeric molecules of the invention will typically encode a pre-pro polypeptide at the amino-terminus of FAP to obtain proper posttranslational processing and secretion from the host cell.

The DNA sequences encoding the human Ficolin-associated polypeptide and the second modulator of complement activity, as well as chimeric molecules of the invention are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the human Ficolin-associated polypeptide, the second modulator of complement activity, as well as chimeric molecules of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

Expression vectors for use in expressing Ficolin-associated polypeptide, the second modulator of complement activity, as well as chimeric molecules of the invention will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA encoding the human Ficolin-associated polypeptide, the second modulator of complement activity, as well as chimeric molecules of the invention in mammalian cells are the SV40 promoter (Subramani et al., Mol. Cell Biol. 1 (1981), 854-864), the MT-1 (metallothionein gene) promoter (Palmiter et al., Science 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

An example of a suitable promoter for use in insect cells is the polyhedrin promoter (U.S. Pat. No. 4,745,051; Vasuvedan et al., FEBS Lett. 311, (1992) 7-11), the P10 promoter J. M. Vlak et al., J. Gen. Virology 69, 1988, pp. 765-776), the *Autographa californica* polyhedrosis virus basic protein promoter (EP 397 485), the baculovirus immediate early gene 1 promoter (U.S. Pat. Nos. 5,155,037; 5,162,222), or the baculovirus 39K delayed-early gene promoter (U.S. Pat. Nos. 5,155,037; 5,162,222).

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652-654) promoters.

Examples of suitable promoters for use in filamentous fungus host cells are, for instance, the ADH3 promoter (McKnight et al., The EMBO J. 4 (1985), 2093-2099) or the tpiA promoter. Examples of other useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

The DNA sequences encoding the human Ficolin-associated polypeptide, the second modulator of complement activity, as well as chimeric molecules of the invention may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the FAP sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981) or the polyadenylation signal from the human FAP gene or the bovine FAP gene. The expression vectors may also include a noncoding viral leader sequence, such as the adenovirus 2 tripartite leader, located between the promoter and the RNA splice sites; and enhancer sequences, such as the SV40 enhancer.

To direct the human Ficolin-associated polypeptide, the second modulator of complement activity, as well as chimeric molecules of the invention into the secretory pathway of the host cells, a secretory signal sequence (also known as a leader sequence, prepro sequence or pre sequence) may be provided in the recombinant vector. The secretory signal sequence is joined to the DNA sequences encoding the human Ficolin-associated polypeptide, the second modulator of complement activity, or chimeric molecules of the invention in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed human Ficolin-associated polypeptide, the second modulator of complement activity, as well as chimeric molecules of the invention into the secretory pathway of the cell. The signal peptide may be naturally occurring signal peptide, or a functional part thereof, or it may be a synthetic peptide. Suitable signal peptides have been found to be the alpha-factor signal peptide (cf. U.S. Pat. No. 4,870,008), the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897), the yeast BAR1 signal peptide (cf. WO 87/02670), or the yeast aspartic protease 3 (YAP3) signal peptide (cf. M. Egel-Mitani et al., Yeast 6, 1990, pp. 127-137).

For efficient secretion in yeast, a sequence encoding a leader peptide may also be inserted downstream of the signal sequence and upstream of the DNA sequence encoding the human Ficolin-associated polypeptides, the second modulator of complement activity, as well as chimeric molecules of the invention. The function of the leader peptide is to allow the expressed peptide to be directed from the endoplasmic reticulum to the Golgi apparatus and further to a secretory vesicle for secretion into the culture medium (i.e. exportation of the human Ficolin-associated polypeptides, the second modulator of complement activity, as well as chimeric molecules of the invention across the cell wall or at least through the cellular membrane into the periplasmic space of the yeast cell). The leader peptide may be the yeast alpha-factor leader (the use of which is described in e.g. U.S. Pat. Nos. 4,546,082, 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral alpha-amylase, *A. niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran Manduca sexta adipokinetic hormone precursor signal peptide (cf. U.S. Pat. No. 5,023,328).

The procedures used to ligate the DNA sequences coding for the human Ficolin-associated polypeptides, the second modulator of complement activity, as well as chimeric molecules of the invention, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, New York, 1989).

Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841-845.

Cloned DNA sequences are introduced into cultured mammalian cells by, for example, calcium phosphate-mediated transfection (Wigler et al., Cell 14:725-732, 1978; Corsaro and Pearson, Somatic Cell Genetics 7:603-616, 1981; Graham and Van der Eb, Virology 52d:456-467, 1973) or electroporation (Neumann et al., EMBO J. 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (Mammalian Cell Technology, Butterworth Publishers, Stoneham, MA, incorporated herein by reference). The person skilled in the art will easily be able to choose suitable selectable markers.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the human Ficolin-associated polypeptide of interest. Media generally include a carbon source, a nitrogen source, essential amino acids, essential sugars, vitamins, salts, phospholipids, protein and growth factors. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby in-creasing expression levels. Clones of stably transfected cells are then screened for expression of the human Ficolin-associated polypeptide of interest.

The host cell into which the DNA sequences encoding the human Ficolin-associated polypeptides, the second modulator of complement activity, as well as chimeric molecules of the invention is introduced may be any cell, which is capable of producing the posttranslational modified human polypeptides and includes yeast, fungi and higher eucaryotic cells.

Examples of mammalian cell lines for use in the present invention are the COS-1 (ATCC CRL 1650), baby hamster kidney (BHK) and 293 (ATCC CRL 1573; Graham et al., J. Gen. Virol. 36:59-72, 1977) cell lines. A preferred BHK cell line is the tk⁻ ts13 BHK cell line (Waechter and Baserga, Proc. Natl. Acad. Sci. USA 79:1106-1110, 1982, incorporated herein by reference), hereinafter referred to as BHK 570 cells. The BHK 570 cell line has been deposited with the American Type Culture Collection, 12301 Parklawn Dr., Rockville, Md. 20852, under ATCC accession number CRL 10314. A tk⁻ ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, Proc. Natl. Acad. Sci. USA 77:4216-4220, 1980).

Examples of suitable yeasts cells include cells of *Saccharomyces* spp. or Schizosac-charomyces spp., in particular strains of *Saccharomyces cerevisiae* or *Saccharomyces kluyveri*. Methods for transforming yeast cells with heterologous DNA and producing heterologous poly-peptides there from are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the human Ficolin-associated polypeptides, the second modulator of complement activity, as well as chimeric molecules of the invention may be preceded by a signal sequence and optionally a leader sequence, e.g. as described above. Further examples of suitable yeast cells are strains of *Kluyveromyces*, such as *K. lactis*, *Hansenula*, e.g. *H. polymorpha*, or *Pichia*, e.g. *P. pastoris* (cf. Gleeson et al., J. Gen. Microbiol. 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, Gene 78: 147-156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162,222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting expression of the human Ficolin-associated polypeptide after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The human Ficolin-associated polypeptide produced by the cells may then be recovered from the culture medium by conventional procedures including separating the host cells from the medium by centrifugation or filtration, precipitating the proteinaqueous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

Transgenic animal technology may be employed to produce the Ficolin-associated polypeptides and other polypeptides of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta lactoglobulin, a lactalbumin, and whey acidic protein. The beta lactoglobulin (BLG) promoter is preferred. In the case of the ovine beta lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non coding portion of the beta lactoglobulin gene (see Whitelaw et al., Biochem. J. 286: 31 39 (1992)). Similar fragments of promoter DNA from other species are also suitable.

Other regions of the beta lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836 840 (1988); Palmiter et al., Proc. Natl. Acad. Sci. USA 88: 478 482 (1991); Whitelaw et al., Transgenic Res. 1: 3 13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta lactoglobulin gene, is preferred. One such region is a DNA segment that provides for intron splicing and RNA polyadenylation from the 3' non coding region of the ovine beta lactoglobulin gene. When substituted for the natural 3' non coding sequences of a gene, this ovine beta lactoglobulin segment can both enhance and stabilize expression levels of the protein or polypeptide of interest. Within other embodiments, the region surrounding the initiation ATG of the FAP sequence is replaced with corresponding sequences from a milk specific protein gene. Such replacement provides a putative tissue specific initiation environment to enhance expression. It is convenient to replace the entire FAP pre pro and 5' non coding sequences with those of, for example, the BLG gene, although smaller regions may be replaced.

For expression of Ficolin-associated polypeptides, the second modulator of complement activity, as well as chimeric molecules of the invention in transgenic animals, a DNA segment encoding FAP is operably linked to additional DNA segments required for its expression to produce expression units. Such additional segments include the above mentioned promoter, as well as sequences that provide for termination of transcription and polyadenylation of mRNA. The expression units will further include a DNA segment encoding a secretory signal sequence operably linked to the segment encoding modified FAP. The secretory signal sequence may be a native FAP secretory signal sequence or may be that of another protein, such as a milk protein (see, for example, von Heijne, Nucl. Acids Res. 14: 4683 4690 (1986); and Meade et al., U.S. Pat. No. 4,873, 316, which are incorporated herein by reference).

Construction of expression units for use in transgenic animals is conveniently carried out by inserting a FAP sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a FAP variant; thereby creating a gene fusion that includes the expression control sequences of the milk protein gene. In any event, cloning of the expression units in plasmids or other vectors facilitates the amplification of the FAP sequence. Amplification is conveniently carried out in bacterial (e.g. E. coli) host cells, thus the vectors will typically include an origin of replication and a selectable marker functional in bacterial host cells. The expression unit is then introduced into fertilized eggs (including early stage embryos) of the chosen host species. Introduction of heterologous DNA can be accomplished by one of several routes, including microinjection (e.g. U.S. Pat. No. 4,873,191), retroviral infection (Jaenisch, Science 240: 1468 1474 (1988)) or site directed integration using embryonic stem (ES) cells (reviewed by Bradley et al., Bio/Technology 10: 534 539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., Bio/Technology 6: 179 183 (1988); Wall et al., Biol. Reprod. 32: 645 651 (1985); Buhler et al., Bio/Technology 8: 140 143 (1990); Ebert et al., Bio/Technology 9: 835 838 (1991); Krimpenfort et al., Bio/Technology 9: 844 847 (1991); Wall et al., J. Cell. Biochem. 49: 113 120 (1992); U.S. Pat. Nos. 4,873,191; 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380 7384 (1980); Gordon and Ruddle, Science 214: 1244 1246 (1981); Palmiter and Brinster, Cell 41: 343 345 (1985); Brinster et al., Proc. Natl. Acad. Sci. USA 82: 4438 4442 (1985); and Hogan et al. (ibid.)). These techniques were subsequently adapted for use with larger animals, including livestock species (see, e.g., WO 88/00239, WO 90/05188, and WO 92/11757; and Simons et al., Bio/Technology 6: 179 183 (1988)). To summarise, in the most efficient route used to date in the generation of transgenic mice or livestock, several hundred linear molecules of the DNA of interest are injected into one of the pro nuclei of a fertilized egg according to established techniques. Injection of DNA into the cytoplasm of a zygote can also be employed.

Production in transgenic plants may also be employed. Expression may be generalised or directed to a particular organ, such as a tuber (see, Hiatt, Nature 344:469 479 (1990); Edelbaum et al., J. Interferon Res. 12:449 453 (1992); Sijmons et al., Bio/Technology 8:217 221 (1990); and EP 0 255 378).

FAP Purification

The Ficolin-associated polypeptides and other polypeptides of the invention may be recovered from cell culture medium or milk. The Ficolin-associated polypeptides and other polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-FAP antibody column. Additional purification may be achieved by conventional chemical purification means, such as high performance liquid chromatography. Other methods of purification, including barium citrate precipitation, are known in the art, and may be applied to the purification of the novel Ficolin-associated polypeptides and other polypeptides described herein (see, for example, Scopes, R., Protein Purification, Springer-Verlag, N.Y., 1982).

For therapeutic purposes it is preferred that the Ficolin-associated polypeptides and other polypeptides of the invention are substantially pure. Thus, in a preferred embodiment of the invention the polypeptides of the invention a purified to at least about 90 to 95% homogeneity, preferably to at least about 98% homogeneity. Purity may be assessed by e.g. gel electrophoresis and amino-terminal amino acid sequencing.

The term "isolated polypeptide" refers to a polypeptide of the present invention that (1) has been separated from at least about 50 percent of polynucleotides, lipids, carbohydrates or other materials (i.e., contaminants) with which it is naturally associated. Preferably, the isolated polypeptide is substantially free from any other contaminating polypeptides or other contaminants that are found in its natural environment, which would interfere with its therapeutic, diagnostic, prophylactic or research use.

The term "microorganism" as used herein refers to bacteria, fungi, archaea, protists; microscopic plants and animals (such as green algae or plankton), the planarian and amoeba. Included within this definition are pathogenic microorganisms.

Assays

A General Procedure for SDS-PAGE and Western Blotting:

Electrophoresis was performed on 10% or 4-12% (w/v) Bis-Tris Polyacrylamide-gels with discontinuous buffers using the NuPAGE® system (Invitrogen) as recommended by the manufacture. Western blotting was performed using polyvinylidene difluoride membranes (PVDF-HyBond, GE-healthcare, Hilleroed, Denmark, cat. no. RPN303F), 2 µg/ml of biotin labeled primary monoclonal antibody and secondary visualization by HRP conjugated streptavidin (P0397, Dako, Glostrup, Denmark) diluted to 1:1500 in PBS, 0.05% Tween20. The membranes were developed with 0.04% 3-amino-9-ethylcarbazole (Sigma-aldrich, Broenby, Denmark, cat. no. A5754-100G) in acetone and 0.015% $H_2O_2$ in 50 mM sodium acetate buffer pH 5.

Co-Immunoprecipitation:

Immunoprecipitation of mannose binding lectin (MBL) serum complexes: 1 ml of normal human serum was diluted 1:1 in TBS (10 mM Tris, 140 mM NaCl, pH 7.5) and incubated end over end for 1 hour at 4° C. with 5 µg of the MBL specific mouse monoclonal antibody Hyb 131-11 (Bioporto, Gentofte, Denmark).

Immunoprecipitation of Ficolin-2 serum complexes: 0.5 ml of normal human serum was diluted 1:1 in TBS (10 mM Tris, 140 mM NaCl, pH 7.5) and incubated end over end for 1 hour at 4° C. with 5 µg of the Ficolin-2 specific mouse monoclonal antibody Hyb 219 (Munthe-Fog L, et al.

Immunoprecipitation of Ficolin-3 serum complexes: 0.2 ml of normal human serum was diluted 1:1 in TBS (10 mM Tris, 140 mM NaCl, pH 7.5) and incubated end over end for 1 hour at 4° C. with 5 µg of the Ficolin-3 specific mouse monoclonal antibody Hyb 334 (Munthe-Fog L, et al.

Immune complex precipitation was conducted with sheep anti mouse IgG conjugated magnetic dynal beads (Dynal-Invitrogen, Cat. No. 112.02D): After incubation with serum and primary antibodies (as above) $5 \times 10^7$ sheep anti mouse conjugated magnetic dynal beads were added and incubated for 30 min 4° C. The beads were magnetically separated and washed for three times with TBS-tween-$Ca^{2+}$ (10 mM Tris, 140 mM NaCl, 0.05% tween, 5 mM $CaCl_2$), pH 7.5) and finally boiled in SDS-loading buffer and analyzed by SDS-PAGE and western blotting with biotin labeled monoclonal antibody mAb-8B3 (reacting with an epitope on the heavy chain/A-chain shared by MASP-1 and -3).

Immunoaffinity purification of FAP: 10 mg of mAb-8B3 (reacting with an epitope on the heavy chain/A-chain shared by FAP, MASP-1 and -3) or 10 mg of rabbit polyclonal anti FAP antibodies were conjugated to CNBr activated sepharose as recommended by the manufacturer (GE-healthcare, Hilleroed, Denmark, cat. no. 17-0430-01) and packed onto a column.

Purification from serum: 150 ml of a pool of normal human serum was diluted 1:1 with TBS+0.5 M NaCl+10 mM EDTA (10 mM Tris, 640 mM NaCl, 10 mM EDTA, pH 7.5) and loaded on the columns described above. The columns were washed with 1 l of TBS+0.5 M NaCl+10 mM EDTA and 1 ml fractions were eluted with 1 M Glycine-HCl, pH 2.5 and analyzed by SDS-PAGE and western blotting with biotin labeled monoclonal antibody mAb-8B3.

Purification of recombinant FAP: 2-3 l of culture supernatant (from CHO serum free medium/Gibco-Invitrogen, cat. no. 12651-014) from Chinese hamster ovarian cells (CHO cells) expressing recombinant FAP (rFAP) was loaded on the antibody columns described above. The columns were washed with 1.5 l of TBS+0.5 M NaCl+10 mM EDTA and 1 ml fractions were eluted with 1 M Glycine-HCl, pH 2.5. The eluted fractions were analyzed by SDS-PAGE and coomassie staining.

Recombinant expression of FAP: Full-length cDNA inserted into the pcDNA5/FRT vector (Invitrogen, cat. no. V6010-20) was ordered from Genscript (Genscript, New Jersey, USA) and co-transfected with the pOG44 vector (Invitrogen, cat. no. V6005-20) into the CHO Flp-In cell line (Invitrogen, cat. no. R758-07) and selected and cloned as recommended by the manufacturer (Invitrogen). The cells were grown in Freestyle CHO serum free medium (Invitrogen, cat. no. 12651-014) and culture supernatants were harvested and analyzed.

Production of mono- and polyclonal antibodies: A peptide construct (ordered from Genscript, New Jersey, USA) of the FAP specific 17 C-terminal residues were coupled onto the toxoid form of tetanus and diphtheria using the cysteine coupling method with m-Maleimidobenzoyl-N-hydroxysuccinimide ester as recommended by the manufacturer (Thermo Fisher Scientific/Pierce, Illinois, USA).

Six mice and two rabbits were each immunized three times (with 14 days intervals) with 25 µg antigen adsorbed onto $Al(OH)_3$ and Freunds incomplete adjuvant. The polyclonal antibody titers were assessed using ELISA with the different FAP peptides coupled to a protein carrier.

Polyclonal rabbit antiserum (≈10 ml) was harvested 14 days after the first, second and third immunization.

Two mice were used for production of monoclonal antibodies. Four days prior to the fusion the mice received an intravenous injection of 25 µg antigen. The fusion was conducted as described elsewhere (Kohler, G. and C. Milstein. 1975. Continuous cultures of fused cells secreting antibody of predefined specificity. Nature 256:495-497).

Clones were selected by differential ELISA screening against peptides coupled to different protein carriers.

Functional complement assays: Ficolin-3 and MBL homozygous defect sera were used to investigate the function of FAP.

Ficolin-3 assay: Maxisorp plates (NUNC, Roskilde, Denmark, cat. no. 439454) were coated with acetylated bovine serum albumin at 5 µg/ml for 12 hours at 4° C. in coating buffer (15 mM $Na_2CO_3$, 35 mM $NaHCO_3$, pH 9.5). After blocking/washing four times in barbital/tween buffer (4 mM barbital, 145 mM NaCl, 2 mM $CaCl_2$), 1 mM $MgCl_2$, pH 7.4+0.05% Tween), recombinant human Ficolin-3 was added at 500 ng/ml I barbital/tween buffer and incubated for 1.5 hours at 20° C. with shaking. After washing the plates twice in barbital/tween buffer, recombinant FAP, human MASP-1, -2 or -3 as serum free medium culture supernatants were added in serial dilutions in the $1^{st}$ dimension on separate plates and incubated for 1 hour at 20° C. with shaking. After washing the plates twice in barbital/tween buffer, Ficolin-3 or MASP-2 deficient serum were added in serial dilutions in the $2^{nd}$ dimension on the plates and incubated for 30 min at 37° C. After washing the plates four times in barbital/tween buffer the deposition of complement factor C4 was measured by incubation for 1 hour at 20° C. with polyclonal rabbit antibodies to human C4c (Dako, Glostrup, Denmark cat. no Q0369) diluted at 1:2000, followed by four washing steps and incubation with horseradish peroxidase conjugated swine anti rabbit antibodies (Dako, Glostrup, Denmark cat. no P0399) for 45 min at 20° C. The signal was obtained by the plates were developed with 100 µl/well of Ortho-phenylene-diamine (OPD) (0.4 mg/ml) dissolved in citrate buffer (35 mM citric acid, 65 mM $Na_2PO_4$, pH 5) with 0.12‰ (v/v) $H_2O_2$. The enzyme reaction was stopped with 1 M $H_2SO_4$ and optical density (OD) levels were measured at 490 nm-650 nm using a V-max Kinetic-reader (Molecular Devices).

Mannose-Binding Lectin assay: Maxisorp plates (NUNC, Roskilde, Denmark, cat. no. 439454) were coated with mannan (Sigma-aldrich, Broenby, Denmark, cat. no. M7504-1G) at 10 µg/ml for 12 hours at 4° C. in coating buffer (15 mM $Na_2CO_3$, 35 mM $NaHCO_3$, pH 9.5). After blocking/washing four times in barbital/tween buffer (4 mM barbital, 145 mM NaCl, 2 mM $CaCl_2$), 1 mM $MgCl_2$, pH 7.4+0.05% Tween) recombinant human Mannose-Binding Lectin was added at 0.5 µg/ml I barbital/tween buffer and incubated for 1.5 hours at 20° C. with shaking. After washing the plates twice in barbital/tween buffer, recombinant FAP, human MASP-1, -2 or -3 as serum free medium culture supernatants were added in serial dilutions in the $1^{st}$ dimension on separate plates and incubated for 1 hour at 20° C. with shaking. After washing the plates twice in barbital/tween buffer, MBL or MASP-2 deficient serum were added in serial dilutions in the $2^{nd}$ dimension on the plates and incubated for 45 min at 37° C. After washing the plates four times in barbital/tween buffer the deposition of complement factor C4 was measured by incubation for 1 hour at 20° C. with polyclonal rabbit antibodies to human C4c (Dako, Glostrup, Denmark cat. no Q0369) diluted at 1:2000, followed by four washing steps and incubation with horseradish peroxidase conjugated swine anti rabbit antibodies (Dako, Glostrup, Denmark cat. no P0399) for 45 min at 20° C. The signal was obtained by the plates were developed with 100 µl/well of Ortho-phenylene-diamine (OPD) (0.4 mg/ml) dissolved in citrate buffer (35 mM citric acid, 65 mM $Na_2PO_4$, pH 5) with 0.12‰ (v/v) $H_2O_2$. The enzyme reaction was stopped with 1 M $H_2SO_4$ and optical density (OD) levels were measured at 490 nm-650 nm using a V-max Kinetic-reader (Molecular Devices).

Genotyping assay: Different genotyping assays may be conducted where the genotype is determined in individuals using biological assays. Different kind of assays could be used such as:

Hybridization-based methods
    Dynamic allele-specific hybridization
    Molecular beacons
    SNP microarrays
Enzyme-based methods
    Restriction fragment length polymorphism
    PCR-based methods
    Flap endonuclease
    Primer extension
    5'-nuclease
    Oligonucleotide ligase assay
Other post-amplification methods based on physical properties of DNA
    Single strand conformation polymorphism
    Temperature gradient gel electrophoresis
    Denaturing high performance liquid chromatography
    High-Resolution Melting of the entire amplicon
    SNPlex
Sequencing
Administration and Pharmaceutical Compositions
Combination Treatments The ficolin-associated polypeptide as defined in the present specification may be administered simultaneously or sequentially with one or more proteins selected from Ficolin-1, 2, 3, and mannose-binding lectin (MBL). The factors may be supplied in single-dosage form wherein the single-dosage form contains both compounds, or in the form of a kit-of-parts comprising a preparation of a ficolin-associated polypeptide as a first unit dosage form and a preparation of the one or more other compound as a second unit dosage form. Whenever a first or second or third, etc., unit dose is mentioned throughout this specification this does not indicate the preferred order of administration, but is merely done for convenience purposes.

By "simultaneous" dosing of a preparation of a ficolin-associated polypeptide and a preparation of one or more other compound is meant administration of the compounds in single-dosage form, or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

Another object of the present invention is to provide a pharmaceutical formulation comprising a ficolin-associated polypeptide which is present in a serum/plasma concentration from 0 mg/ml to 1 mg/ml, and wherein the formulation has a pH from 2.0 to 10.0. The formulation may further comprise a buffer system, preservative(s), tonicity agent(s), chelating agent(s), stabilizers and surfactants. In some embodiments of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In other embodiments the pharmaceutical formulation is a freeze-dried formulation, whereto the physician or the patient adds solvents and/or diluents prior to use.

In other embodiments the pharmaceutical formulation is a dried formulation (e.g. freeze-dried or spray-dried) ready for use without any prior dissolution.

In a further aspect the invention relates to a pharmaceutical formulation comprising an aqueous solution of a ficolin-associated polypeptide, and a buffer, wherein the ficolin-associated polypeptide is present in a serum/plasma concentration from 0-1 mg/ml or above, and wherein the formulation has a pH from about 2.0 to about 10.0.

In a other embodiments of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19th edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In some embodiments the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In some embodiments the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In some embodiments, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: The Science and Practice of Pharmacy, 19th edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: The Science and Practice of Pharmacy, 19th edition, 1995.

In a further embodiment of the invention the formulation further comprises a stabilizer. The use of a stabilizer in pharmaceutical compositions is well-known to the skilled person. For convenience reference is made to Remington: The Science and Practice of Pharmacy, 19th edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-

59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In some embodiments, amino acids to use in preparing the compositions of the invention are those carrying a charged side chain, such as arginine, lysine, aspartic acid, and glutamic acid. Any stereoisomer (i.e., L, D, or DL isomer) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In some embodiments the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives- (e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl p-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: The Science and Practice of Pharmacy, 19th edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a ficolin-associated polypeptide according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

In some embodiments, the composition according to the invention is suitable for intraocular, intravenous, intraarterial, subcutaneous, intratracheal, or inhalational administration.

Topical administration may be a particular advantage in the treatment of conditions associated with local inflammation, such as in the treatment of inflammation associated with burn or other conditions associated with the skin. Accordingly, in some embodiments administration is by topical administration.

In some embodiments, the disease to be treated is a disease that involves local inflammation. In some particular embodiments, eye droplets may be used in conditions associated with the eye, such as keratitis, such as diffuse lamellar keratitis (DLK).

In some embodiments, the disease to be treated is a drusen-associated disease. For example, in some embodiments, there is provided a method of treating (such as reducing, delaying, eliminating, or preventing) formation of drusen, inflammation, loss of photoreceptors cells, visual acuity or visual field, and/or choroidal neovascularization (CNV) in the eye of an individual, comprising administering to the individual an effective amount of a composition comprising a chimeric molecule according to the invention.

In some embodiments, the disease to be treated does not involve the classical complement pathway.

In some embodiments, the disease to be treated is related to macular degeneration (such as age-related macular degeneration or AMD).

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the ficolin-associated polypeptide, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the ficolin-associated polypeptide, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the ficolin-associated polypeptide in the form of a nasal or pulmonal spray. As a still further option, the pharmaceutical compositions containing the ficolin-associated polypeptide of the invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In some embodiments of the invention the pharmaceutical formulation comprising the ficolin-associated polypeptide is stable for more than 6 weeks of usage and for more than 3 years of storage. In other embodiments of the invention the pharmaceutical formulation comprising the ficolin-associated polypeptide is stable for more than 4 weeks of usage and for more than 3 years of storage. In a further embodiment of the invention the pharmaceutical formulation comprising the ficolin-associated polypeptide is stable for more than 4 weeks of usage and for more than two years of storage. In an even further embodiment of the invention the pharmaceutical formulation comprising the ficolin-associated polypeptide is stable for more than 2 weeks of usage and for more than two years of storage.

The methods described herein may also be useful for treatment of certain renal diseases, such as membranoproliferative glomerulonephritis type II (MPGN II), hemolytic-uremic syndrome (HUS), lupus nephritis.

The methods described herein may also be useful for treatment of cardiovascular diseases. In some embodiments, the chimeric molecule according to the present invention is used for the treatment of ischemia reperfusion (including for example renal ischemia reperfusion and intestinal ischemia reperfusion).

Also provided are methods of treating organ transplant rejections. In some embodiments, there is provided methods of delaying onset of acute vascular rejection (such as antibody-mediated rejection of heart transplant), or for improving organ transplant survival in an individual by administration of a chimeric molecule according to the present invention.

In some embodiments, there is provided a method of improving organ transplant survival in an individual, the method comprises perfusing the organ to be transplanted to an individual with a composition comprising a chimeric molecule according to the present invention. In some embodiments, there is provided a method of improving survival of an organ transplant donor, comprising administering to the organ transplant donor an effective amount of a composition comprising a chimeric molecule according to the present invention.

Specific embodiments of the invention: As described above the present invention relates to chimeric molecules of a ficolin-associated polypeptide comprising a ficolin-associated polypeptide and a second modulator of complement activity.

In some embodiments the second modulator of complement activity is an inhibitor of complement activation.

In some embodiments the inhibitor of complement activation is selected from the list consisting of Factor H (FH), GAS6, Protein S, C1-inhibitor (C1-inh), complement component 4 binding protein (C4 bp), Factor I (FI), CR1, DAF (CD55), CD59, CR2, or a functional fragment thereof.

In some embodiments the inhibitor of complement activation is an inhibitory synthetic peptide, such as compstatin with a sequence of ICVVQDWGHHRCT (SEQ ID NO: 58), wherein Thr-13 is a C-terminal amide and C2 and C12 form a disulfide bridge.

In some embodiments the inhibitor of complement activation is a microbial evasion protein, such as any one selected from the list consisting of Extracellular fibrinogen-binding protein (Efb), Staphylococcal superantigen-like protein-7 (SSL-7), *Staphylococcus* complement inhibitor (SCIN), Complement C2 receptor trispanning protein (CRIT), and Chemotaxis inhibitory protein of *Staphylococcus aureus* (CHIPS).

In some embodiments the inhibitor of complement activation is a microbial evasion protein selected from table 1 derived from J D Lambris, D Ricklin, B V Geisbrecht "Complement evasion by human pathogens"—Nature Reviews Microbiology, February 2008, Vol. 6, page 132 the content of which is hereby incorporated by reference.

TABLE 1

| Microbial complement-targeting proteins Bacteria | Viruses: |
| --- | --- |
| *Actinobacillus* spp. | Herpes viruses |
| Omp100 Outer membrane protein 100 | gC1/2 Transmembrane glycoproteins C1, C2 (HSV) C3b |
| *Bordetella* spp. | gE + gI Glycoproteins E + I (HSV) |
| FHA Filamentous hemagglutinin | gp34,68 Glycoproteins 34, 68 (HCMV) |
| *Borrelia* spp. | gpI + gpIV Glycoproteins I + IV (VZV) |
| CRASP Complement regulator-acquiring surface proteins | KCP d Kaposi's sarkoma-associated complement control protein (KSHV) |
| Erp OspE/F-related proteins | Retroviruses |
| CD59-like protein | gp41 Envelope glycoprotein 41 (HIV) |
| *Escherichia* spp. | gp120 Envelope glycoprotein 120 (HIV) |
| OmpA Outer membrane protein A | Tat Transactivator of transcription (HIV) |
| StcE Secreted protease of C1 esterase inhibitor | Poxviruses |
| TraT TraT outer membrane protein | IMP Cowpox control inflammation modulatory protein (Cowpox Virus) |
| *Moraxella* spp. | MOPICE Monkeypox inhibitor of complement enzymes (monkeypox virus) |
| UspA1/2 Ubiquitous surface protein A1/A2 | SPICE Smallpox inhibitor of complement enzymes (variola virus) |
| *Neisseria* spp. | VCP Vaccinia virus complement control protein (vaccinia virus) |
| LOS Lipooligosaccharide | Filoviruses |
| GNA1870 Genome-derived neisserial antigen 1870 | NS1 Non-structural protein 1 (West Nile virus) |
| Por Outer membrane porins | Fungi: |
| Type IV pili | *Candida albicans* |
| *Porphyromonas* spp. | CRASP-1 Complement regulator-acquiring surface protein 1 |
| prtH prtH protease | Gpm1p Phosphoglycerate mutase |
| *Pseudomonas* spp. | Parasites: |
| PaE *Pseudomonas* elastase | *Echinococcus* spp. |
| PaAP *Pseudomonas* alkaline protease | Hydatid cyst wall |
| Tuf Elongation factor | *Ixodes* spp. |
| *Serratia* spp. | IRAC *Ixodes ricinus* anti-complement protein |
| n/a 56 kDa protease | ISAC *Ixodes scapularis* anti-complement protein |
| *Staphylococcus* spp. | *Onchocerca* spp. |
| CHIPS Chemotaxis inhibitory protein of *S. aureus* | mf Microfilariae |

TABLE 1-continued

| Microbial complement-targeting proteins | |
|---|---|
| Bacteria | Viruses: |
| Efb Extracellular fibrinogen-binding protein | *Ornithodoros* spp. |
| Ehp a Efb-homologous protein | OmCI *Ornithodoros moubata* complement inhibitor |
| SAK Staphylokinase | *Schistosoma* spp. |
| Sbi *S. aureus* IgG-binding protein | CRIT Complement C2 receptor trispanning |
| SCIN Staphylococcal complement inhibitor | m28 28 kDa membrane serine protease |
| SpA *S. aureus* protein A | Pmy e Paramyosin (Schistosome complement inhibitor protein 1 (SCIP-1)) |
| SSL-7 Staphylococcal superantigen-like protein 7 | *Trypanosoma* spp. |
| *Streptococcus* spp. | CRIT Complement C2 receptor trispanning |
| Bac -Protein | T-DAF *Trypanosoma* decay-accelerating factor |
| Fba Fibronectin-binding protein | |
| Hic b Factor H-binding inhibitor of complement | |
| IdeS IgG-degrading Enzyme of *S. pyrogenes* | |
| M b Surface proteins M family (Arp, Sir, etc.) | |
| PLY Pneumolysin | |
| PspA Pneumococcal surface protein A | |
| PspC c Pneumococcal surface protein C | |
| scpA/B Streptococcal C5a peptidase | |
| SIC Streptococcal inhibitor of complement | |
| SPE B Streptococcal pyrogenic exotoxin B | |
| SpG *Streptococcus* protein G | |
| *Yersinia* spp. | |
| YadA *Yersinia* adhesin A | |

In some embodiments the inhibitor of complement activation is Factor H, or a functional fragment thereof. In some embodiments the Factor H, or a functional fragment thereof comprises at least the first four SCR domains of Factor H.

In some embodiments the second modulator of complement activity is an immunoglobulin molecule or part thereof. In some embodiments the immunoglobulin molecule or part thereof is selected from the Fc component of human IgG1, IgG2, IgG3, and IgG4.

In some embodiments the ficolin-associated polypeptide is capable of associating with mannose-binding lectin (MBL).

In some embodiments the ficolin-associated polypeptide is capable of associating with any one of ficolin-1, ficolin-2, or ficolin-3.

In some embodiments the ficolin-associated polypeptide is capable of associating with any one of C1q, lung surfactant proteins SP-A and/or SP-D, and intracellular collagen-like defence molecules, such as CLL-11.

In some embodiments the ficolin-associated polypeptide is capable of associating with a specific acceptor protein, such as a specific receptor.

In some embodiments the ficolin-associated polypeptide comprises the amino acid sequence 20-297 of SEQ NO:3, or a functional variant thereof.

In some embodiments the ficolin-associated polypeptide comprises the amino acid sequence 20-380 of SEQ NO:1 or a functional variant thereof.

In some embodiments the ficolin-associated polypeptide comprises the amino acid sequence 16-296 of SEQ ID NO:9 or a functional variant thereof.

In some embodiments the ficolin-associated polypeptide has a molecular mass of about 40 kDa under non-reducing conditions on an SDS-PAGE.

In some embodiments the ficolin-associated polypeptide is N-linked glycosylated at one or two amino acids corresponding to a position selected from 49 and 178 of SEQ NO:1.

In some embodiments the ficolin-associated polypeptide is a recombinant protein.

In some embodiments the ficolin-associated polypeptide is in homodimer form.

In some embodiments the ficolin-associated polypeptide consists of the amino acid sequence 20-380 of SEQ ID NO 1.

In some embodiments the ficolin-associated polypeptide comprises the amino acid sequence of SEQ ID NO:4 or variants or immunologic fragments thereof.

In some embodiments the chimeric molecule according to the present invention mediates phagocytosis of dying or dead cells, such as apoptotic cells, and/or cellular debris.

In some embodiments the chimeric molecule according to the present invention mediates phagocytosis of a microorganism.

In some embodiments the ficolin-associated polypeptide has activity similar to other proteins with sequence homology, such as the engulfment adapter protein (GULP).

In some embodiments the ficolin-associated polypeptide and the second modulator of complement activity are directly or indirectly fused to each other in the form of a fusion protein.

In some embodiments the ficolin-associated polypeptide and the second modulator of complement activity are linked via a chemical crosslinker.

In some embodiments the ficolin-associated polypeptide and the second modulator of complement activity are non-covalently linked.

In some embodiments the host cell according the present invention is a eukaryotic cell.

In some embodiments the host cell according the present invention is of mammalian origin.

In some embodiments the host cell according to the present invention is selected from the group consisting of CHO cells, HEK cells and BHK cells.

In some embodiments the chimeric molecule according to the present invention is for the treatment of any indications associated with inflammation, apoptosis and/or autoimmunity.

In some embodiments the chimeric molecule according to the present invention is for the treatment of any autoimmune conditions such as Addison's disease, autoimmune hemolytic anemia, autoimmune thyroiditis, Crohn's disease, Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, psoriasis, various allergies.

In some embodiments the chimeric molecule according to the present invention is for the treatment of any inflammatory disorder selected from the group consisting of appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitis, hepatitis, Crohn's disease, enteritis, Whipple's disease, allergy, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumotransmicroscopicsilicovolcanoconiosis, alvealitis, bronchiolitis, pharyngitis, pleurisy, sinusitis, influenza, respiratory syncytial virus infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, ankylosing spondylitis, Berger's disease, Reiter's syndrome and Hodgkin's disease, keratitis, Type 2 diabetes, cystic fibrosis, myocardial infarction, reperfusion injury, stroke, dermatomyositis, metabolic syndrome, systemic inflammatory response syndrome, sepsis, multiple organ failure, disseminated intravascular coagulation, anaphylactic shock. Vascular complication and nephropathy associated with type 1 and/or type 2 diabetes, meningitis, bacterial septicaemia, complicated malaria, atypic haemolytic uremic syndrome, haemolytic uremic syndrome, age related macular degeneration, paroxysmal nocturnal hemoglobinuria, snake venom bite, burn injury, and complications to organ transplantations.

In some embodiments the chimeric molecule according to the present invention is for the treatment of any inflammatory disorder selected from the group consisting of organ ischemia, reperfusion injury, organ necrosis, vasulitis, endocarditis, atherosclerosis, thrombophlebitis, pericarditis, myocarditis, myocardial ischemia, periarteritis nodosa, rheumatic fever, congestive heart failure, adult respiratory distress syndrome, cerebral infarction, cerebral embolism. Vascular complications and nephropathy associated with type 1 and/or type 2 diabetes.

In some embodiments the chimeric molecule according to the present invention is for the treatment of any indications associated with coagulation, thrombotic or coagulopathic related diseases.

In some embodiments the chimeric molecule according to the present invention is for the treatment of an indication associated with coagulation, thrombotic or coagulopathic related diseases or disorders including inflammatory response and chronic thromboembolic diseases or disorders associated with fibrin formation including vascular disorders such as thrombosis, such as deep venous thrombosis, arterial thrombosis, post surgical thrombosis, coronary artery bypass graft (CABG), percutaneous transdermal coronary angioplasty (PTCA), platelet deposition stroke, tumor growth, tumor metastasis, angiogenesis, thrombolysis, atherosclerosis, restenosis, such as arteriosclerosis and/or restenosis following angioplasty, acute and chronic indications such as inflammation, sepsis, septic chock, septicemia, hypotension, adult respiratory distress syndrome (ARDS), systemic inflammatory response syndrome (SIRS), disseminated intravascular coagulopathy (DIC), pulmonary embolism, pathological platelet deposition, myocardial infarction, or the prophylactic treatment of mammals with atherosclerotic vessels at risk for thrombosis, venoocclusive disease following peripheral blood progenitor cell (PBPC) transplantation, hemolytic uremic syndrome (HUS), and thrombotic thrombocytopenic purpura (TTP) and rheumatic fever.

In some embodiments the chimeric molecule according to the present invention is for the treatment of an indication associated with coagulation, thrombotic or coagulopathic related diseases or disorders including inflammatory response and chronic thromboembolic diseases or disorders associated with fibrin formation including vascular disorders such as thrombosis, such as deep venous thrombosis, arterial thrombosis, post surgical thrombosis, coronary artery bypass graft (CABG), percutaneous transdermal coronary angioplasty (PTCA), platelet deposition stroke, tumor growth, tumor metastasis, angiogenesis, thrombolysis, atherosclerosis, restenosis, such as arteriosclerosis and/or restenosis following angioplasty, acute and chronic indications such as inflammation, pathological platelet deposition, myocardial infarction, or the prophylactic treatment of mammals with atherosclerotic vessels at risk for thrombosis, venoocclusive disease following peripheral blood progenitor cell (PBPC) transplantation, hemolytic uremic syndrome (HUS), and thrombotic thrombocytopenic purpura (TTP) and rheumatic fever.

In some embodiments the chimeric molecule according to the present invention is for preventing the occurrence of thromboembolic complications in identified high risk patients, such as those undergoing surgery or those with congestive heart failure.

In some embodiments the chimeric molecule according to the present invention is for the treatment of a medical condition associated with the heart.

In some embodiments the chimeric molecule according to the present invention is for the treatment of a medical condition associated with a deficiency in a ficolin-associated polypeptide.

Modulators of Complement Activity:

As discussed above the second modulator of complement activity used in the chimeric molecule of a ficolin-associated polypeptide may by any compound that directly or indirectly influences complement activity.

Natural complement inhibitors and regulatory proteins prevent the activation of the complement system, and include: (i) complement receptor 1 (CR1 or CD35) and DAF (decay accelerating factor or CD55), which compete with factor B for binding with C3b and block the alternative pathway, as well as similarly block the classical pathway C4b from interacting with C2, (ii) factor I, a plasma protease that cleaves C3b and C4b into their inactive forms to block formation of the convertases, and (iii) factor H which can compete with factor B, displace Bb from the convertase, act as a cofactor for factor I, and bind C3b that is already bound to cells. CD59 is a complement regulatory protein that inhibits MAC (C5b-9).

In some embodiments the modulator of complement activity used according to the present invention is Factor H. Factor H is a human plasma complement regulator that acts as a significant co-factor for Factor I in the cleavage and down-regulation of activated C4 and C3 and further downstream complement activation (Zipfel P F. Complement factor H: physiology and pathophysiology. Semin Thromb Hemost 2001; 27:191-9). Factor H thus works in at the central part of the complement system when initiation and activation have already occurred. In some embodiments, the Factor H is a wildtype Factor H, such as wildtype human Factor H. In some embodiments, the Factor H is a variant of wildtype Factor H.

In some embodiments the modulator of complement activity used according to the present invention is Protein S. This gene encodes a vitamin K-dependent plasma protein that functions as a cofactor for the anticoagulant protease, activated protein C (APC) to inhibit blood coagulation. It is found in plasma in both a free, functionally active form and also in an inactive form complexed with C4b-binding protein and helps to prevent coagulation and stimulating fibrinolysis. Mutations in this gene result in autosomal dominant hereditary thrombophilia. In some embodiments, the Protein S is a wildtype Protein S, such as wildtype human Protein S. In some embodiments, the Protein S is a variant of wildtype Protein S.

The amino acid sequences of human Protein S (SEQ ID NO:52) is one suitable example of a sequence that could be used as a modulator of complement activity of a chimeric protein according to the invention. Amino acid sequence of an exemplary human MAP-1/Protein S chimeric protein is illustrated by SEQ ID NO:56, and human Protein S/MAP1 chimeric protein by SEQ ID NO:57. For example, a Protein S variant may have an amino acid sequence that is at least about 70% identical to the amino acid sequence of a naturally occurring human Protein S (e.g., SEQ ID NO:52), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring Protein S (e.g., SEQ ID NO:52). In some embodiment, a variant of Protein S (or a fragment thereof) retains all the complement inhibition activity of Protein S (or a fragment thereof). In some embodiments, the variant of Protein S (or a fragment thereof) retains at least about 50%, for example, at least about any of 60%, 70%, 80%, 90%, or 95% of the complement inhibition activity of Protein S (or a fragment thereof).

In some embodiments the modulator of complement activity used according to the present invention is GAS6. This gene product is a gamma-carboxyglutamic acid (Gla)-containing protein thought to be involved in the stimulation of cell proliferation, and may play a role in thrombosis by amplifying platelet. It is a ligand for tyrosine-protein kinase receptors AXL, TYRO3 and MER whose signaling is implicated in cell growth and survival, cell adhesion and cell migration. Alternatively spliced transcript variants encoding different isoforms have been found for this gene. Transcript variant 1 is the predominant transcript and encodes the longest isoform. Transcript variant 2 is missing several 5'-exons and contains a different 5' UTR compared to transcript variant 1. This results in an isoform 2 with a shorter N-terminus, but retaining the two LamG domains at the C-terminus. Transcript variant 3 is missing several 5'-exons and contains a distinct 5' UTR compared to transcript variant 1. This results in an isoform 3 with a shorter N-terminus, but retaining the two LamG domains at the C-terminus. In some embodiments, the GAS6 is a wildtype GAS6, such as wildtype human GAS6. In some embodiments, the GAS6 is a variant of wildtype GAS6.

The amino acid sequences of human GAS6 (SEQ ID NO:46, SEQ ID NO:48, or SEQ ID NO:50) are suitable examples of sequences that could be used as a modulator of complement activity of a chimeric protein according to the invention. Amino acid sequence of an exemplary human MAP-1/GAS6 chimeric protein is illustrated by SEQ ID NO:54, and human GAS6/MAP1 chimeric protein by SEQ ID NO:55. For example, a GAS6 variant may have an amino acid sequence that is at least about 70% identical to the amino acid sequence of a naturally occurring human GAS6 (e.g., SEQ ID NO:46, SEQ ID NO:48, or SEQ ID NO:50), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring GAS6 (e.g., SEQ ID NO:46, SEQ ID NO:48, or SEQ ID NO:50). In some embodiment, a variant of GAS6 (or a fragment thereof) retains all the complement inhibition activity of GAS6 (or a fragment thereof). In some embodiments, the variant of GAS6 (or a fragment thereof) retains at least about 50%, for example, at least about any of 60%, 70%, 80%, 90%, or 95% of the complement inhibition activity of GAS6 (or a fragment thereof).

In some embodiments the complement inhibitor compound is an inhibitor of C5, C5a, or C5b. In some embodiments, the compound is a specific inhibitor of C5, C5a, or C5b. In other embodiments, the complement inhibitor compound is a polypeptide or a small molecule compound that inhibits C5, C5a, or C5b. In yet other embodiments, the inhibitor is an antibody that binds specifically to C5. In yet other embodiments, the inhibitor is a human monoclonal antibody against complement component C5, including eculizumab, pexelizumab or another anti-C5 antibody.

In yet a further embodiment the complement inhibitor compound is an inhibitor of C3 or C3 convertase. In some embodiments, the compound is a specific inhibitor of C3 or C3 convertase. In yet other embodiments, the complement inhibitor compound is a polypeptide, antibody or a small molecule compound that inhibits C3 or C3 convertase.

In yet a further embodiment the complement inhibitor compound is a potentiator of factor H. In some embodiments, the compound is a specific fragment of Factor H delivered to the joint. In yet other embodiments, the complement inhibitor compound is a polypeptide, antibody or a small molecule compound that potentiates Factor H. In yet other embodiments, the complement inhibitor consists in part of a monoclonal antibody specific for Factor H that promotes binding to the cartilage. In yet other embodiments, the monoclonal antibody is an isolated human monoclonal antibody.

In another embodiment, the complement inhibitor compound is an inhibitor of the membrane attack complex.

In another embodiment, the complement inhibitor compound is an inhibitor of proteases involved in the complement system. In some embodiments, the complement inhibitor is C1-INH. In yet other embodiments, the complement inhibitor is C1-INH purified from plasma or produced recombinantly in transgenic animals. In some embodiments, the C1-INH is recombinant human C1 inhibitor or functional equivalent thereof. In another embodiment, the complement inhibitor is a soluble complement regulator. In some embodiments, the complement inhibitor is soluble CR1 (sCR1), or analogues thereof. In other embodiments, the complement inhibitor compound is a CR2-Factor H fusion protein or a CR2-Crry fusion protein.

In other embodiments, the complement inhibitor compound is a small molecule. In yet other embodiments, the small molecule inhibits C5a or C3a. In other embodiments, the complement inhibitor compound is a compound that prevents cleavage of C2, C3, C4, or C5.

In other embodiments, the complement inhibitor compound is a Vaccinia complement control protein (Vaccinia CCP).

In other embodiments, the complement inhibitor compound is a decay-accelerating factor (DAF), a soluble decay-accelerating factor (sDAF), a membrane cofactor protein (MCP), a soluble membrane cofactor protein (sMCP), a fusion protein comprising sMCP fused to DAF (sMCP-DAF), CD59, a soluble CD59 protein (sCD59), or a fusion protein comprising DAF and CD59 (DAF-CD59). In yet other embodiments, the compound is an MCP-DAF fusion protein. In still other embodiments, the protein is CAB-2.

In other embodiments, the complement inhibitor compound is a variant or mutant C5a protein.

In other embodiments, the complement inhibitor compound is an antibody or functional fragment thereof that specifically binds C5, C3, C5a, C3a, C4a, C6, C7, C8, C9, factor B factor D, properdin (factor P), CD20, CD38, C5 receptor (C5R) or C5a receptor (C5aR).

In yet other embodiments, the antibody that specifically binds the C5 receptor is neutrazumab.

In yet other embodiments, the antibody that specifically binds C5 is eculizumab. In yet other embodiments, the antibody that binds CD38 is HuMax-CD38.

In yet other embodiments, the complement inhibitor compound is eculizumab.

In other embodiments, the complement inhibitor compound is a C5aR antagonist selected from the group consisting of N Me-FKPdChaWdR and F-(OpdChaWR) (Phe-[Orn-Pro-D-cyclohexylalanine-Trp-Arg]) C5aR.

In other embodiments, the complement inhibitor compound is an RNA aptamer. In yet other embodiments, the aptamer selectively binds and inhibits C5. In other embodiments, the complement inhibitor compound is a C3 inhibitor peptide or a functional analog thereof.

In other embodiments, the complement inhibitor compound is BCX-1470, FUT-175, K-76, recombinant human mannose-binding lectin (rhMBL), APT070, TNX-234, TNX-558, TA106, complement component 4 binding protein (C4 bp), Factor H, Factor I, carboxypeptidase N, vitronectin, clusterin, JSM-7717, JPE-1375, or OmCI protein.

In other embodiments, the complement inhibitor compound inhibits C5, C3, C5a, C3a, C4a, C6, C7, C8, C9, factor B factor D, properdin (factor p), CD20, CD38, C5 receptor (C5R), C5a receptor (C5aR), C1q, C1, C1 r, or C1s. In another embodiment, the method further comprises administering to the subject a further therapeutic treatment. In various embodiments, the further therapeutic treatment comprises administration of an active agent, such as an antiinflammatory agent, an analgesic, or a steroid. In other embodiments, the further therapeutic treatment is a physical therapy, exercise or a local heat treatment. In one embodiment, when the further therapeutic treatment is an active agent, the antiinflammatory agent is a non-steroidal anti-inflammatory agent or a cyclooxygenase-2 selective inhibitor, the analgesic is a non-opioid analgesic, or the steroid is a corticosteroid drug. In some embodiments the second modulator of complement activity of the chimeric molecule is Factor H (FH), or a functional fragment thereof.

In some embodiments, the chimeric molecule comprises one, two, or more (such as any of three, four, five, or more) Factor H portions. These Factor H portions may be the same or different, for example in terms of amino acid sequences, structures, and/or functions. For example, in some embodiments, the chimeric molecule (such as a fusion protein) comprises: 1) a ficolin-associated polypeptide, and 2) one, two or more Factor H portions comprising a FH or a fragment thereof.

In some embodiments, the Factor H portion comprises a full length Factor H. In some embodiments, the Factor H portion comprises a fragment of Factor H. In some embodiments, the Factor H portion comprises at least the first four N-terminal short consensus repeat (SCR) domains of Factor H. In some embodiments, the Factor H portion comprises at least the first five N-terminal SCR domains of Factor H. In some embodiments, the Factor H portion lacks a heparin binding site. In some embodiments, the Factor H portion comprises a Factor H or a fragment thereof having a polymorphism that is protective against age-related macular degeneration.

In some embodiments, the Factor H portion comprises at least the first 5, 6, 7, 8, 9, 10, 11, 12, 13, 14, or more N-terminal SCR domains of Factor H.

In some embodiments, the Factor H portion comprises amino acids 21 to 320 of SEQ ID NO:20.

In some embodiments, the polynucleotide encoding a fusion protein comprising a ficolin-associated polypeptide and a Factor H portion also comprises a sequence encoding a signal peptide operably linked at the 5' end of the sequence encoding the fusion protein. In some embodiments, a linker sequence is used for linking the ficolin-associated polypeptide and the Factor H portion.

In some embodiments, the disease to be treated is a disease that is associated with Factor H deficiencies (including for example decrease in level of Factor H, decrease in activity of Factor H, or lacking wild type or protective Factor H). In some embodiments, the disease to be treated is not a disease that is associated with Factor H deficiencies.

The terms "Factor H portion", "Factor H", or just "FH" refers to human Factor H according to SEQ ID NO: 20 or a functional fragment thereof.

The Factor H portion of the chimeric molecule described herein comprises Factor H or a fragment thereof. Complement factor H (FH) is a single polypeptide chain plasma glycoprotein. The protein is composed of 20 repetitive SCR domains of approximately 60 amino acids, arranged in a continuous fashion like a string of 20 beads. Factor H binds to C3b, accelerates the decay of the alternative pathway C3-convertase (C3Bb), and acts as a cofactor for the proteolytic inactivation of C3b. In the presence of factor H, C3b proteolysis results in the cleavage of C3b. Factor H has at least three distinct binding domains for C3b, which are located within SCR 1-4, SCR 5-8, and SCR 19-20. Each site of factor H binds to a distinct region within the C3b protein: the N-terminal sites bind to native C3b; the second site, located in the middle region of factor H, binds to the C3c fragment and the sited located within SCR19 and 20 binds to the C3d region. In addition, factor H also contains binding sites for heparin, which are located within SCR 7, SCR 5-12, and SCR 20 of factor H and overlap with that of the C3b binding site. Structural and functional analyses have shown that the domains for the complement inhibitory activity of Factor H are located within the first four N-terminal SCR domains.

SEQ ID NO:20 represents the full-length human Factor H protein sequence. Amino acids 1-18 correspond to the leader peptide, amino acids 21-80 correspond to SCR 1, amino acids 85-141 correspond to SCR 2, amino acids 146-205 correspond to SCR 3, amino acids 210-262 correspond to SCR4, amino acids 267-320 correspond to SCR5. It is understood that species and strain variations exist for the disclosed peptides, polypeptides, and proteins, and that the Factor H or a fragment thereof encompasses all species and strain variations.

The Factor H portion described herein refers to any portion of a Factor H protein having some or all the complement inhibitory activity of the FH protein, and includes, but is not limited to, full-length Factor H proteins, biologically active fragments of Factor H proteins, a Factor H fragment comprising SCR1-4, or any homologue or variant of a naturally occurring Factor H or fragment thereof, as described in detail below. In some embodiments, the Factor H portion has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In some embodiments, the Factor H portion comprises the first four N-terminal SCR domains of Factor H. In some embodiments, the construct comprises the first five N-terminal SCR domains of Factor H. In some embodiments, the construct comprises the first six N-terminal SCR domains of Factor H. In some embodiments, the Factor H portion comprises (and in some embodiments consists of or consisting essentially of) at least the first four N-terminal SCR domains of Factor H, including for example, at least any of the first 5, 6, 7, 8, 9, 10, 11, 12, 13, 14, or more N-terminal SCR domains of Factor H.

In some embodiments, the Factor H is a wildtype Factor H, such as wildtype human Factor H. In some embodiments, the Factor H is a variant of wildtype Factor H.

In some embodiments, the Factor H portion lacks a heparin binding site. This can be achieved, for example, by mutation of the heparin binding site on Factor H, or by selecting Factor H fragments that do not contain a heparin binding site. In some embodiments, the Factor H portion comprises a Factor H or a fragment thereof having a polymorphism that is protective to age-related macular degeneration. Hageman et al., Proc. Natl. Acad Sci. USA 102(20):7227.

A homologue or variant of a Factor H protein or a fragment thereof includes proteins which differ from a naturally occurring Factor H (or Factor H fragment) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a Factor H homologue or variant may have an amino acid sequence that is at least about 70% identical to the amino acid sequence of a naturally occurring human Factor H (e.g., SEQ ID NO:20), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% k identical to the amino acid sequence of a naturally occurring Factor H (e.g., SEQ ID NO:20). In some embodiment, a homologue or variant of Factor H (or a fragment thereof) retains all the complement inhibition activity of Factor H (or a fragment thereof). In some embodiments, the homologue or variant of Factor H (or a fragment thereof) retains at least about 50%, for example, at least about any of 60%, 70%, 80%, 90%, or 95% of the complement inhibition activity of Factor H (or a fragment thereof).

In some embodiments, the Factor H portion comprises at least the first four N-terminal SCR domains of a human Factor H, such as a Factor H portion having an amino acid sequence containing at least amino acids 21 through 262 of the human Factor H (SEQ ID NO:20). In some embodiments, the Factor H portion comprises at least the first four N-terminal SCR domains of human Factor H having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 262 of the human Factor H (SEQ ID NO:20).

In some embodiments, the Factor H portion comprises at least the first five N-terminal SCR domains of a human Factor H, such as a Factor H portion having an amino acid sequence containing at least amino acids 21 through 320 of the human Factor H (SEQ ID NO:20). In some embodiments, the Factor H portion comprises at least the first five N-terminal SCR domains of human Factor H having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 320 of the human Factor H (SEQ ID NO:20). In some embodiments, the Factor H portion comprises a full length or a fragment of factor-H like 1 molecule (FHL-1), a protein encoded by an alternatively spliced transcript of the factor H gene. The mature FHL-1 contains 431 amino acids. The first 427 amino acids organize seven SCR domains and are identical to the N-terminal SCR domains of Factor H. The remaining four amino acid residues Ser-Phe-Thr-Leu (SFTL) at the C-terminus are specific to FHL-1. FHL-1 has been characterized functionally and shown to have factor H complement regulatory activity. The term "Factor H portion" also encompasses full length or fragments of factor H related molecules, including, but are not limited to, proteins encoded by the FHR1, FHR2, FHR3, FHR4, FHR5 genes. These factor H related proteins are disclosed, for example, in de Cordoba et al., Molecular Immunology 2004, 41: 355-367.

In some embodiments the second modulator of complement activity of the chimeric molecule is C4 bp, or a functional fragment or portion thereof.

In some embodiments, the chimeric molecule comprises one, two, or more (such as any of three, four, five, or more) C4 bp portions. In some embodiments, the chimeric molecule comprises either the alfa chain or the beta chain or combination of both. These C4 bp portions may be the same or different, for example in terms of amino acid sequences, structures, and/or functions. For example, in some embodiments, the chimeric molecule (such as a fusion protein) comprises: 1) a ficolin-associated polypeptide, and 2) one, two or more C4 bp portions comprising a C4 bp or a fragment thereof.

In some embodiments, the C4 bp portion comprises a full length C4 bp. In some embodiments, the C4 bp portion comprises a fragment of C4 bp. In some embodiments, the C4 bp portion comprises at least the first three N-terminal short consensus repeat (SCR) domains of C4 bp alfa chain and/or the second SCR domain of C4 bp beta chain. In some embodiments, the C4 bp portion comprises a C4 bp or a fragment thereof having a polymorphism that is protective against age-related macular degeneration.

In some embodiments, the C4 bp portion comprises at least the first 3, 4, 5, 6, 7, 8 N-terminal SCR domains of C4 bp alfa.

In some embodiments, the C4 bp portion comprises at least the first 1, 2, 3 SCR domains of C4 bp beta.

In some embodiments, the C4 bp alfa portion comprises amino acids 21 to 597 of SEQ ID NO:21.

In some embodiments, the C4 bp beta portion comprises amino acids 21 to 252 of SEQ ID NO:22.

In some embodiments, the polynucleotide encoding a fusion protein comprising a ficolin-associated polypeptide and a C4 bp portion also comprises a sequence encoding a signal peptide operably linked at the 5' end of the sequence encoding the fusion protein. In some embodiments, a linker sequence is used for linking the ficolin-associated polypeptide and the C4 bp portion.

In some embodiments, the disease to be treated is a disease that is associated with C4 bp deficiencies (including for example decrease in level of C4 bp, decrease in activity of C4 bp, or lacking wild type or protective C4 bp). In some embodiments, the disease to be treated is not a disease that is associated with C4 bp deficiencies.

The terms "C4 bp portion", "C4 binding protein", or just "C4 bp" refers to human C4 bp according to SEQ ID NO: 21 and SEQ ID NO: 22 or a functional fragment thereof.

The C4 bp portion of the chimeric molecule described herein comprises C4 bp or a fragment thereof. Complement C4 binding protein (C4 bp) is a single polypeptide chain plasma glycoprotein. The protein is composed of seven identical alfa-chains and one beta chain linked by their C-terminal parts in a central core. It inhibits the action of C4. It splits C4 convertase and is a cofactor for factor I which cleaves C4b. C4BP binds necrotic cells and DNA, to clean up after swelling. C4 bp protein has at least two distinct binding domains for C4b, which are located within alfa SCR 1-3 and beta SCR 2.

SEQ ID NO:21 represents the full-length alfa chain of human C4 bp protein sequence. Amino acids 1-20 correspond to the leader peptide, amino acids 49-110 correspond to SCR 1, amino acids 111-172 correspond to SCR 2, amino acids 173-236 correspond to SCR 3, amino acids 237-296 correspond to SCR4, amino acids 297-362 correspond to SCR5, amino acids 363-424 correspond to SCR6, amino acids 425-482 correspond to SCR7, amino acids 483-540 correspond to SCR8. It is understood that species and strain variations exist for the disclosed peptides, polypeptides, and proteins, and that the C4 bp alfa chain or a fragment thereof encompasses all species and strain variations.

SEQ ID NO:22 represents the full-length beta chain of human C4 bp protein sequence. Amino acids 1-20 correspond to the leader peptide, amino acids 21-78 correspond to SCR 1, amino acids 79-136 correspond to SCR 2, amino acids 137-193 correspond to SCR 3. It is understood that species and strain variations exist for the disclosed peptides, polypeptides, and proteins, and that the C4 bp beta chain or a fragment thereof encompasses all species and strain variations.

The C4 bp portion described herein refers to any portion of a C4 bp protein having some or all the complement inhibitory activity of the C4 bp protein, and includes, but is not limited to, full-length C4 bp proteins, biologically active fragments of C4 bp proteins, a C4 bp fragment comprising SCR1-3, or any homologue or variant of a naturally occurring C4 bp or fragment thereof, as described in detail below. In some embodiments, the C4 bp portion has one or more of the following properties: (1) binding to C4, (2) binding to C3b/C4b, (3) accelerate the degradation of the C4bC2a complex by dissociating the complement fragment C2a.

In some embodiments the second modulator of complement activity of the chimeric molecule is Factor I (FI), or a functional fragment or portion thereof.

In some embodiments, the chimeric molecule comprises one, two, or more (such as any of three, four, five, or more) FI portions. These FI portions may be the same or different, for example in terms of amino acid sequences, structures, and/or functions. For example, in some embodiments, the chimeric molecule (such as a fusion protein) comprises: 1) a ficolin-associated polypeptide, and 2) one, two or more FI portions comprising a FI or a fragment thereof.

In some embodiments, the FI portion comprises a full length FI. In some embodiments, the FI portion comprises a fragment of FI. In some embodiments, the FI portion comprises at least the SP domain. In some embodiments, the FI portion comprises the FIMAC, SRCR, LDLRa1, LDLRb1 domains. In some embodiments, the FI portion comprises a FI or a fragment thereof having a polymorphism that is protective against age-related macular degeneration.

In some embodiments, the FI portion comprises amino acids 21 to 583 of SEQ ID NO:23.

In some embodiments, the polynucleotide encoding a fusion protein comprising a ficolin-associated polypeptide and a FI portion also comprises a sequence encoding a signal peptide operably linked at the 5' end of the sequence encoding the fusion protein. In some embodiments, a linker sequence is used for linking the ficolin-associated polypeptide and the FI portion.

In some embodiments, the disease to be treated is a disease that is associated with FI deficiencies (including for example decrease in level of FI, decrease in activity of FI, or lacking wild type or protective FI). In some embodiments, the disease to be treated is not a disease that is associated with FI deficiencies.

The terms "FI portion" or just "FI" refers to human Factor I according to SEQ ID NO: 23 or a functional fragment thereof.

The FI portion of the chimeric molecule described herein comprises FI or a fragment thereof. Factor I binding protein (FI) is a single polypeptide chain plasma glycoprotein. FI has restricted specificity limited to cleavage of arginyl bounds in its natural protein substrates C3b and C4b. Components such as FH, CR1, MCP or C4 bp are required as cofactors. FI is synthesized as a single polypeptide chain with an N-terminal heavy (317 amino acids) chain and a C-terminal light chain (244 amino acids). The FI heavy chain has four domains: a FIMAC domain, a Scavenger Receptor Cysteine Rich (SRCR) domain and two LDL-receptor Class A domains; the precise biological function of the heavy chain is not known, but it is likely to play a key role in recognising the FI cleavage substrates (C3b and C4b) and the cofactor proteins needed for cleavage of C3b (FH, CR1, MCP) and C4b (C4BP). The LDL-receptor domains are likely to contain one Calcium-binding site each. The FI light chain is the serine protease (SP) domain containing the catalytic triad responsible for specific cleavage of C3b and C4b.

SEQ ID NO:23 represents the full-length of human FI protein sequence. Amino acids 1-18 correspond to the leader peptide, amino acids 55-108 correspond to the FIMAC domain, amino acids 114-212 correspond to the Scavenger Receptor Cysteine Rich (SRCR) domain, amino acids 213-257 correspond to the LDL-receptor Class A1 domains, amino acids 258-294 correspond to the LDL-receptor Class A2 domains, amino acids 340-574 correspond to peptidase domain.

The FI portion described herein refers to any portion of a FI protein having some or all the complement inhibitory activity of the FI protein, and includes, but is not limited to, full-length FI proteins, biologically active fragments of FI proteins, a FI fragment comprising at least the serine protease domain, or any homologue or variant of a naturally occurring FI or fragment thereof, as described in detail below. In some embodiments, the FI portion has one or more of the following properties: (1) cleavage of C3b (2) cleavage of C4b.

In some embodiments the second modulator of complement activity of the chimeric molecule is C1-inhibitor (C1-inh), or a functional fragment or portion thereof.

In some embodiments, the chimeric molecule comprises one, two, or more (such as any of three, four, five, or more) C1-inh portions. These C1-inh portions may be the same or different, for example in terms of amino acid sequences, structures, and/or functions. For example, in some embodiments, the chimeric molecule (such as a fusion protein) comprises: 1) a ficolin-associated polypeptide, and 2) one, two or more C1-inh portions comprising a C1-inh or a fragment thereof.

In some embodiments, the C1-inh portion comprises a full length C1-inh. In some embodiments, the C1-inh portion comprises a fragment of C1-inh. In some embodiments, the C1-inh portion comprises at least part of the serpin domain. In some embodiments, the C1-inh portion comprises a C1-inh or a fragment thereof having a polymorphism that is protective against age-related macular degeneration.

In some embodiments, the C1-inh portion comprises amino acids 21 to 500 of SEQ ID NO:24.

In some embodiments, the polynucleotide encoding a fusion protein comprising a ficolin-associated polypeptide and a C1-inh portion also comprises a sequence encoding a signal peptide operably linked at the 5' end of the sequence encoding the fusion protein. In some embodiments, a linker sequence is used for linking the ficolin-associated polypeptide and the C1-inh portion.

In some embodiments, the disease to be treated is a disease that is associated with C1-inh deficiencies (including for example decrease in level of C1-inh, decrease in activity of C1-inh, or lacking wild type or protective C1-inh). In some embodiments, the disease to be treated is not a disease that is associated with C1-inh deficiencies.

The terms "C1-inh portion" or just "C1-inh" refers to human C1-inhibitor according to SEQ ID NO: 24 or a functional fragment thereof.

The C1-inh portion of the chimeric molecule described herein comprises C1-inh or a fragment thereof. Complement C1 inhibitor protein (C1-inh) is a serine protease inhibitor (serpin) protein, the main function of which is the inhibition of the complement system to prevent spontaneous activation. The C-terminal serpin domain is similar to other serpins, and this part of C1-inh provides the inhibitory activity of C1-inh. The N-terminal domain (also some times referred to as the N-terminal tail) is not essential for C1-inh to inhibit proteinases. This domain has no similarity to other proteins. C1-inh is highly glycosylated, bearing both N- and O-glycans. N-terminal domain is especially heavily glycosylated. C1-inh is an acute phase protein, it circulates in blood. C1-inh irreversibly binds to and inactivates C1r and C1s proteinases in the C1 complex of classical pathway of complement. MASP-1 and MASP-2 proteinases in MBL complexes of the lectin pathway are also inactivated. This way, C1-inh prevents the proteolytic cleavage of later complement components C4 and C2 by C1 and MBL. Although named after its complement inhibitory activity, C1-inh also inhibits proteinases of the fibrinolytic, clotting, and kinin pathways. Most notably, C1-inh is the most important physiological inhibitor of plasma kallikrein, fXIa and fXIIa.

SEQ ID NO:24 represents the full-length of human C1-inh protein sequence. Amino acids 1-22 correspond to the leader peptide, amino acids 23-500 correspond to the serpin domain. It is understood that species and strain variations exist for the disclosed peptides, polypeptides, and proteins, and that the C1-inh or a fragment thereof encompasses all species and strain variations.

The C1-inh portion described herein refers to any portion of a C1-inh protein having some or all the complement inhibitory activity of the C1-inh protein, and includes, but is not limited to, full-length C1-inh proteins, biologically active fragments of C1-inh proteins, a C1-inh fragment comprising SCR1-3, or any homologue or variant of a naturally occurring C1-inh or fragment thereof, as described in detail below. In some embodiments, the C1-inh portion has one or more of the following properties: (1) binding to C1r and C1s, (2) inhibits activity of MASP-1 and MASP-2 proteinases, (3) inhibits proteinases of the fibrinolytic, clotting, and kinin pathways, (4) inhibitor of plasma kallikrein, Factor XIa and Factor XIIa.

In other embodiments the second modulator of complement activity is a homing domain that facilitates the transport and/or uptake at a particular site of complement activity, such as a site of inflammation.

Accordingly, in some embodiments, the second modulator of complement activity is a targeting molecule or targeting moiety which increases the targeting efficiency of the chimeric molecule. For example, the second modulator of complement activity may be a ligand (such as an amino acid sequence) that has the capability to bind or otherwise attach to an endothelial cell of a blood vessel (referred to as "vascular endothelial targeting amino acid ligand"). Exemplary vascular endothelial targeting ligands include, but are not limited to, VEGF, FGF, integrin, fibronectin, I-CAM, PDGF, or an antibody to a molecule expressed on the surface of a vascular endothelial cell.

In some embodiments, the chimeric molecule of a ficolin-associated polypeptide is conjugated (such as fused) to a ligand for intercellular adhesion molecules. For example, the second modulator of complement activity may be one or more carbohydrate moieties that bind to an intercellular adhesion molecule. The carbohydrate moiety facilitates localization of the chimeric molecule to the site of injury. The carbohydrate moiety can be attached to the chimeric molecule by means of an extracellular event such as a chemical or enzymatic attachment, or can be the result of an intracellular processing event achieved by the expression of appropriate enzymes. In some embodiments, the carbohydrate moiety binds to a particular class of adhesion molecules such as integrins or selectins, including E-selectin, L-selectin or P-selectin. In some embodiments, the carbohydrate moiety comprises an N-linked carbohydrate, for example the complex type, including fucosylated and sialylated carbohydrates. In some embodiments, the carbohydrate moiety is related to the Lewis X antigen, for example the sialylated Lewis X antigen.

For treatment of eye diseases such as AMD, the second modulator of complement activity may be an antibody that recognizes a neoepitope of the drusen. Other targeting molecules such as small targeting peptide can also be used. Other modifications of the chimeric molecule include, for example, glycosylation, acetylation, phosphorylation, amidation, derivatization by known protectinglblocking groups, and the like.

The second modulator of complement activity may be an immunologically active domain, such as an antibody epitope or other tag, to facilitate targeting of the polypeptide. Other amino acid sequences that may be included in the chimeric molecule include functional domains, such as active sites from enzymes such as a hydrolase, glycosylation domains, and cellular targeting signals.

Domain for Increasing the Circulatory Half-Life:

In some embodiments the chimeric molecule according to the invention is further modified with a domain for increasing the circulatory half-life of the chimeric molecule as compared to the ficolin-associated polypeptide, which domain is a hydrophilic substituent.

The term "hydrophilic substituent", as used herein means a molecule that is capable of conjugation to an attachment point of the peptide and which is water-soluble. The terms "hydrophilic" and "hydrophobic" are generally defined in terms of a partition coefficient P, which is the ratio of the equilibrium concentration of a compound in an organic phase to that in an aqueous phase. A hydrophilic compound has a log P value less than 1.0, typically less than about –0.5, where P is the partition coefficient of the compound between octanol and water, while hydrophobic compounds will generally have a log P greater than about 3.0, typically greater than about 5.0.

The polymer molecule is a molecule formed by covalent linkage of two or more monomers wherein none of the monomers is an amino acid residue. Preferred polymers are polymer molecules selected from the group consisting of polyalkylene oxides, including polyalkylene glycol (PAG), such as polyethylene glycol (PEG) and polypropylene glycol (PPG), branched PEGs, polyvinyl alcohol (PVA), polycarboxylate, poly-vinylpyrolidone, polyethylene-co-maleic acid anhydride, polystyrene-co-maleic acid anhydride, and dextran, including carboxymethyl-dextran, PEG being particular preferred. The term "attachment group" is intended to indicate a functional group of the peptide capable of attaching a polymer molecule. Useful attachment groups are, for example, amine, hydroxyl, carboxyl, aldehyde, ketone, sulfhydryl, succinimidyl, maleimide, vinylsulfone, oxime or halo acetate.

The term "PAO" as used herein refers to any polyalkylene oxide, including polyalkylene glycol (PAG), such as polyethylene glycol (PEG) and polypropylene glycol (PPG), branched PEGs and methoxypolyethylene glycol (mPEG) with a molecular weight from about 200 to about 100.000 Daltons.

The polymer molecule to be coupled to the ficolin-associated polypeptide may be any suitable molecule such as natural or synthetic homo-polymer or hetero-polymer, typically with a molecular weight in the range of about 300-100.000 Da, such as about 500-20.000 Da, or about 500-15.000 Da, or 2-15 kDa, or 3-15 kDa, or about 10 kDa.

When the term "about" is used herein in connection with a certain molecular weight the word "about" indicates an approximate average molecular weight distribution in a given polymer preparation.

Examples of homo-polymers include a polyalcohol (i.e., poly-OH), a polyamine (i.e, poly-$NH_2$) and a polycarboxylic acid (i.e., poly-COOH). A hetero-polymer is a polymer comprising different coupling groups such as hydroxyl group and amine group.

Examples of suitable polymer molecules include polymer molecule selected from the group consisting of polyalkylene oxide, including polyalkylene glycol (PAG), such as polyethylene glycol (PEG) and polypropylene glycol (PPG), branched PEGs, polyvinyl alcohol (PVA), polycarboxylate, poly-vinylpyrolidone, polyethylene-co-maleic acid anhydride, polystyrene-co-maleic acid anhydride, dextran, including carboxymethyl-dextran, or any other polymer suitable for reducing immunicenicity and/or increasing functional in vivo half-life and/or serum half-life. Generally, polyalkyleneglycol-derived polymers are biocompatible, non-toxic, non-antigenic, and non-immunogenic, have various water solubility properties, and are easily secreted from living organism.

PEG is the preferred polymer molecule, since it has only a few reactive groups capable of cross-linking compared to e.g. polysaccharides such as dextran. In particular, monofunctional PEG, e.g., methoxypolyethylene glycol (mPEG) is of interest since its coupling chemistry is relatively simple (only one reactive group is available for conjugating with attachment groups the peptide).

To effect covalent attachment of the polymer molecule(s) to a ficolin-associated polypeptide, the hydroxyl end groups of the polymer molecule must be provided in activated form, i.e. with reactive functional groups (examples of which includes primary amino groups, hydrazide (HZ), thiol (SH), succinate (SUC), succinimidyl succinate (SS), succinimidyl succinamide (SSA), succinimidyl proprionate (SPA), succinimidyl 3-mercaptopropionate (SSPA), Norleucine (NOR), succinimidyl carboxymethylate (SCM), succinimidyl butanoate (SBA), succinimidyl carbonate (SC), succinimidyl glutarate (SG), acetaldehyde diethyl acetal (ACET), succinimidy carboxymethylate (SCM), benzotriazole carbonate (BTC), N-hydroxysuccinimide (NHS), aldehyde (ALD), trichlorophenyl carbonate (TCP) nitrophenylcarbonate (NPC), maleimide (MAL) vinylsulfone (VS), carbonylimidazole (CDI), isocyanate (NCO), iodine (IODO), expoxide (EPDX), iodoacetamide (IA), succinimidyl glutarate (SG) and tresylate (TRES).

Suitable activated polymer molecules are commercially available, e.g. from Nektar, formerly known as Shearwater Polymers, Inc., Huntsville, AL, USA, or from PolyMASC Pharmaceuticals plc, UK or from Enzon pharmaceuticals. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference).

Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, SCM-PEG, BTC-PEG, EPDX-PEG, NCO-PEG, NPC-PEG, CDI-PEG, ALD-PEG, TRES-PEG, VS-PEG, IODO-PEG, IA-PEG, ACET-PEG and MAL-PEG, and branched PEGs such as PEG2-NHS and those disclosed in U.S. Pat. Nos. 5,672,662, 5,932,462 and 5,643,575 both which are incorporated herein by reference. Furthermore the following publications, incorporated herein by reference, disclose useful polymer molecules and/or PEGylation chemistries: U.S. Pat. Nos. 4,179,337, 5,824, 778, 5,476,653, WO 97/32607, EP 229,108, EP 402,378, U.S. Pat. Nos. 4,902,502, 5,281,698, 5,122,614, 5,219,564, WO 92/16555, WO 94/04193, WO 94/14758, US 94/17039, WO 94/18247, WO 94,28024, WO 95/00162, WO 95/11924, WO 95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629, 384, WO 96/41813, WO 96/07670, U.S. Pat. Nos. 5,473, 034, 5,516,673, 305, 382, 657, EP 605 963, EP 510 356, EP 400 472, EP 183 503 and EP 154 316 and Roberts et al. *Adv. Drug Delivery Revl.* 54: 459-476 (2002) and references described herein. The conjugation between a ficolin-associated polypeptide and the activated polymer is conducted by conventional method. Conventional methods are known to those skilled in the art.

It will be understood that the polymer conjugation is designed so as to produce the optimal molecule with respect to the number of polymer molecules attached, the size and form of such molecules (e.g. whether they are linear or branched), and the attachment site(s) on ficolin-associated polypeptides. The molecular weight of the polymer to be used may e.g., be chosen on the basis of the desired effect to be achieved.

The hydrophilic substituent may be attached to an amino group of the ficolin-associated polypeptide moiety by means of a carboxyl group of the hydrophilic substituent which forms an amide bond with an amino group of the amino acid to which it is attached. As an alternative, the hydrophilic substituent may be attached to said amino acid in such a way that an amino group of the hydrophilic substituent forms an amide bond with a carboxyl group of the amino acid. As a further option, the hydrophilic substituent may be linked to the ficolin-associated polypeptide via an ester bond. Formally, the ester can be formed either by reaction between a carboxyl group of the ficolin-associated polypeptide and a hydroxyl group of the substituent-to-be or by reaction between a hydroxyl group of the ficolin-associated polypeptide and a carboxyl group of the substituent-to-be. As a further alternative, the hydrophilic substituent can be an alkyl group which is introduced into a primary amino group of the ficolin-associated polypeptide.

In one embodiment of the invention the hydrophilic substituent comprises $H(OCH_2CH_2)_nO$— wherein n>4 with a molecular weight from about 200 to about 100.000 daltons.

In one embodiment of the invention the hydrophilic substituent comprises $CH_3O$—$(CH_2CH_2O)_n$—$CH_2CH_2$—O— wherein n>4 with a molecular weight from about 200 to about 100.000 Daltons.

In one embodiment of the invention the hydrophilic substituent is polyethylen glycol (PEG) with a molecular weight from about 200 to about 5000 Daltons.

In one embodiment of the invention the hydrophilic substituent is polyethylen glycol (PEG) with a molecular weight from about 5000 to about 20.000 Daltons.

In one embodiment of the invention the hydrophilic substituent is polyethylen glycol (PEG) with a molecular weight from about 20.000 to about 100.000 Daltons.

In one embodiment of the invention the hydrophilic substituent comprises is a methoxy-PEG (mPEG) with a molecular weight from about 200 to about 5000 Daltons.

In one embodiment of the invention the hydrophilic substituent is methoxy-polyethylen glycol (mPEG) with a molecular weight from about 5000 to about 20.000 Daltons.

In one embodiment of the invention the hydrophilic substituent is methoxy-polyethylen glycol (mPEG) with a molecular weight from about 20.000 to about 100.000 daltons.

In one embodiment of the invention the hydrophilic substituent is attached to an amino acid residue in such a way that a carboxyl group of the hydrophilic substituent forms an amide bond with an amino group of the amino acid residue.

In one embodiment of the invention the hydrophilic substituent is attached to a Lys residue.

In one embodiment of the invention the hydrophilic substituent is attached to an amino acid residue in such a way that an amino group of the hydrophilic substituent forms an amide bond with a carboxyl group of the amino acid residue.

In some embodiments the chimeric molecule according to the invention is further modified with a domain for increasing the circulatory half-life of the chimeric molecule as compared to the ficolin-associated polypeptide, which domain is a lipophilic substituent.

The term "lipophilic substituent" is characterised by comprising 4-40 carbon atoms and having a solubility in water at 20° C. in the range from about 0.1 mg/100 ml water to about 250 mg/100 ml water, such as in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml.

In one embodiment of the invention the lipophilic substituent comprises from 4 to 40 carbon atoms.

In one embodiment of the invention the lipophilic substituent comprises from 8 to 25 carbon atoms.

In one embodiment of the invention the lipophilic substituent comprises from 12 to 20 carbon atoms.

In one embodiment of the invention the lipophilic substituent is attached to an amino acid residue in such a way that a carboxyl group of the lipophilic substituent forms an amide bond with an amino group of the amino acid residue.

In one embodiment of the invention the lipophilic substituent is attached to a Lys residue.

In one embodiment of the invention the lipophilic substituent is attached to an amino acid residue in such a way that an amino group of the lipophilic substituent forms an amide bond with a carboxyl group of the amino acid residue.

In one embodiment of the invention the lipophilic substituent is attached to the ficolin-associated polypeptide by means of a spacer.

In one embodiment of the invention the spacer is an unbranched alkane α,ω-dicarboxylic acid group having from 1 to 7 methylene groups, such as two methylene groups which spacer forms a bridge between an amino group of the ficolin-associated polypeptide and an amino group of the lipophilic substituent.

In one embodiment of the invention the spacer is an amino acid residue except a Cys residue, or a dipeptide. Examples of suitable spacers include p-alanine, gamma-aminobutyric acid (GABA), γ-glutamic acid, succinic acid, Lys, Glu or Asp, or a dipeptide such as Gly-Lys. When the spacer is succinic acid, one carboxyl group thereof may form an amide bond with an amino group of the amino acid residue, and the other carboxyl group thereof may form an amide bond with an amino group of the lipophilic substituent. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the ε-amino group of Lys and the lipophilic substituent. In one embodiment, such a further spacer is succinic acid which forms an amide bond with the ε-amino group of Lys and with an amino group present in the lipophilic substituent. In another embodiment such a further spacer is Glu or Asp which forms an amide bond with the ε-amino group of Lys and another amide bond with a carboxyl group present in the lipophilic substituent, that is, the lipophilic substituent is a $N^\alpha$-acylated lysine residue.

In one embodiment of the invention the spacer is selected from the list consisting of p-alanine, gamma-aminobutyric acid (GABA), γ-glutamic acid, Lys, Asp, Glu, a dipeptide containing Asp, a dipeptide containing Glu, or a dipeptide containing Lys. In one embodiment of the invention the spacer is p-alanine. In one embodiment of the invention the spacer is gamma-aminobutyric acid (GABA). In one embodiment of the invention the spacer is γ-glutamic acid.

In one embodiment of the invention a carboxyl group of the ficolin-associated polypeptide forms an amide bond with an amino group of a spacer, and the carboxyl group of the amino acid or dipeptide spacer forms an amide bond with an amino group of the lipophilic substituent.

In one embodiment of the invention an amino group of the ficolin-associated polypeptide forms an amide bond with a carboxylic group of a spacer, and an amino group of the spacer forms an amide bond with a carboxyl group of the lipophilic substituent.

In one embodiment of the invention the lipophilic substituent comprises a partially or completely hydrogenated cyclopentanophenathrene skeleton.

In one embodiment of the invention the lipophilic substituent is an straight-chain or branched alkyl group. In one embodiment of the invention the lipophilic substituent is the acyl group of a straight-chain or branched fatty acid.

In one embodiment of the invention the acyl group of a lipophilic substituent is selected from the group comprising $CH_3(CH_2)_nCO—$, wherein n is 4 to 38, such as $CH_3(CH_2)_6CO—$, $CH_3(CH_2)_8CO—$, $CH_3(CH_2)_{10}CO—$, $CH_3(CH_2)_{12}CO—$, $CH_3(CH_2)_{14}CO—$, $CH_3(CH_2)_{16}CO—$, $CH_3(CH_2)_{18}CO—$, $CH_3(CH_2)_{20}CO—$ and $CH_3(CH_2)_{22}CO—$.

In one embodiment of the invention the lipophilic substituent is an acyl group of a straight-chain or branched alkane α,ω-dicarboxylic acid.

In one embodiment of the invention the acyl group of the lipophilic substituent is selected from the group comprising $HOOC(CH_2)_mCO—$, wherein m is 4 to 38, such as $HOOC(CH_2)_{14}CO—$, $HOOC(CH_2)_{16}CO—$, $HOOC(CH_2)_{18}CO—$, $HOOC(CH_2)_{20}CO—$ and $HOOC(CH_2)_{22}CO—$.

In one embodiment of the invention the lipophilic substituent is a group of the formula $CH_3(CH_2)_p((CH_2)_qCOOH)CHNH—CO(CH_2)_2CO—$, wherein p and q are integers and p+q is an integer of from 8 to 40, such as from 12 to 35.

In one embodiment of the invention the lipophlic substituent is a group of the formula $CH_3(CH_2)_rCO—NHCH(COOH)(CH_2)_2CO—$, wherein r is an integer of from 10 to 24.

In one embodiment of the invention the lipophilic substituent is a group of the formula $CH_3(CH_2)_sCO—NHCH((CH_2)_2COOH)CO—$, wherein s is an integer of from 8 to 24.

In one embodiment of the invention the lipophilic substituent is a group of the formula $COOH(CH_2)_tCO—$ wherein t is an integer of from 8 to 24.

In one embodiment of the invention the lipophilic substituent is a group of the formula $—NHCH(COOH)(CH_2)_4NH—CO(CH_2)_uCH_3$, wherein u is an integer of from 8 to 18.

In one embodiment of the invention the lipophilic substituent is a group of the formula $—NHCH(COOH)(CH_2)_4NH—COCH((CH_2)_2COOH)NH—CO(CH_2)_wCH_3$, wherein w is an integer of from to 16.

In one embodiment of the invention the lipophilic substituent is a group of the formula $—NHCH(COOH)(CH_2)_4NH—CO(CH_2)_2CH(COOH)NH—CO(CH_2)_xCH_3$, wherein x is an integer of from to 16.

In one embodiment of the invention the lipophilic substituent is a group of the formula $—NHCH(COOH)(CH_2)_4NH—CO(CH_2)_2CH(COOH)NHCO(CH_2)_yCH_3$, wherein y is zero or an integer of from 1 to 22.

In one embodiment of the invention the lipophilic substituent is N-Lithocholoyl.

In one embodiment of the invention the lipophilic substituent is N-Choloyl.

In one embodiment of the invention the chimeric molecule of a ficolin-associated polypeptide has one lipophilic substituent. In one embodiment of the invention the chimeric molecule of a ficolin-associated polypeptide has two lipophilic substituents. In one embodiment of the invention the chimeric molecule of a ficolin-associated polypeptide has three lipophilic substituents. In one embodiment of the invention the chimeric molecule of a ficolin-associated polypeptide has four lipophilic substituents.

Example 1

Detection of alternative transcription of the MASP1 gene
Methods: In order to detect the three transcript variants of MASP1: MASP1, MASP3 and FAP, specific primers for each variant were design. PCR was set up with a common forward primer in exon 6 (5'-gcacccagagccacagtg-3 SEQ ID NO: 59) and specific reverse primers: MASP1 in exon 12 (5'-gccttccagtgtgtgggc-3 SEQ ID NO: 60), MASP3 in exon 11 (5-gccttccagagtgtggtca-3 SEQ ID NO: 61) and FAP in exon 8a (5'-cgatctggagagcgaactc-3 SEQ ID NO: 62) (FIG. 1). PCR amplifications were carried out in 20-μl volumes containing: 50 ng liver cDNA (Clontech), 0.25 μM of each primer, 2.5 mM $MgCl_2$, 0.2 mM dNTP, 50 mM KCl, 10 mM TrisHCl, pH 8.4, and 0.4 units of Platinum Taq DNA polymerase (Invitrogen). The PCR reactions were performed at the following cycling parameters: 10 min94° C., 30 or 40 cycles (30 sec94° C., 50 sec58° C., 90 sec72° C.), 10 min72° C. Samples were analysed on 2% agarose gels.

Results: Alternative transcription of the MASP1 gene was detected in liver cDNA. The MASP1, MASP3, and FAP transcripts were amplified using a common forward primer located in exon 6 and specific reverse primers located in exon 12 (MASP1), exon 11 (MASP3), and exon 8a (FAP). MASP1 generates a fragment of 500 bp, MASP3 generates a fragment of 506 bp and FAP generates a fragment of 309 bp.

Tissue Expression of the FAP Fragment
Methods: Commercially available human tissue cDNA panels (Clontech) were investigated for MASP1, MASP3, and FAP expression with the same PCR assays as described above. Samples were analysed on 2% agarose gels.

Results: The tissue distributions of the MASP1, MASP3, and FAP genes were investigated in cDNA panels from Clontech (FIG. 2). MASP1, MASP3, and FAP transcripts were amplified using a common forward primer and specific reverse primers. GADPH was used as reference gene. All three genes were highly expressed in the liver, and additionally, FAP was strongly expressed in heart tissue (marked with black arrows). Minor expression of the FAP gene was detected in brain, colon, prostate, skeletal muscle, and small intestine (marked with white arrows).

DNA Sequencing of the FAPexon8a of 100 Individuals.

Methods: Direct sequencing of the exon 8a including the intron-exon boundary of the MASP1/MASP3/FAP gene spanning from position +44,083 to +44,431 relative to the translation ATG start site, was performed on genomic DNA templates from 100 healthy Caucasian individuals. The fragment was amplified by using a single primer set (forward: 5 ctgttcttcacactggctg-3 SEQ ID NO: 63, reverse: 5'-ctgctgagatcatgttgttc-3 SEQ ID NO: 64), where the forward primers contained a 5'-T7 sequence (5'-ttatacgactcacta-3' SEQ ID NO: 65). PCR amplifications were carried out in 20-μl volumes containing: 50 ng genomic DNA, 0.25 μM of each primer, 2.5 mM $MgCl_2$, 0.2 mM dNTP, 50 mM KCl, 10 mM TrisHCl, pH 8.4, and 0.4 units of Platinum Taq DNA polymerase (Invitrogen). The PCR reactions were performed at the following cycling parameters: 2 min94° C., 15 cycles (30 sec94° C., 60 sec64° C., 60 sec72° C.), 15 cycles (30 sec94° C., 60 sec58° C., 60 sec72° C.), 5 min72° C. and were sequenced in the forward direction using the ABI BigDye cycle sequencing terminator kit (Applied Biosystems, Foster City, CA) according to the protocol using 5'-biotinylated sequence primers. Sequence reactions were purified on the PyroMark Vacuum Prep Workstation (Biotage) using streptavidin beads (GenoVision). Sequence analysis was performed on an ABI Prism 3100 Genetic Analyser (Applied Biosystems). The resulting DNA sequences were aligned using BioEdit software, and DNA polymorphisms were confirmed visually from sequence electropherograms.

Results: All sequences were aligned using BioEdit software. No genetic variations in the 100 healthy individuals were observed in the exon 8a or the exon-intron regions.

Example 2

Immunoprecipitation.

Specific immunoprecipitation of MAP-1 from serum was performed with the MAP-1 specific mAb 20C4 (raised against the 17 MAP-1 specific C-terminal peptide) or mAb 8B3, a monoclonal antibody reacting against the common heavy chain of MASP-1/3 used as control precipitation antibody. A total of 10 μg of anti MAP-1 or MASP-1/3 antibody was allowed to bind to sheep anti mouse or rabbit IgG Dynabeads (M-280, cat. 112.02D/112.04D, Dynal/Invitrogen). After a washing step the beads were applied to a pool of normal human serum (diluted 1:1 in TBS) and incubated end over end for 1 hour at 4° C. After final washing steps and magnetic separation the beads were boiled in SDS loading buffer and subjected to SDS-PAGE and western blotting probed with antibodies to MAP-1, MBL, and Ficolin-3.

The same precipitation procedure as described above was performed with mAbs to MBL (Hyb 131-11, Bioporto, Denmark), Ficolin-2 (FCN219) and Ficolin-3 (FCN334). To compensate for differences in serum concentrations of MBL, Ficolin-2 and -3 were precipitated from 1 ml, 300 μl and 100 μl serum, respectively. Samples were analyzed by SDS-PAGE and western blotting probed with pAb against MAP-1.

Immunohistochemistry.

CHO cells expressing rMAP-1 were grown in culture flasks in RPMI+10%. Cells were harvested at 80-90% confluence the cells were harvested and fixed for 24 h in 4% formaldehyde-PBS and subsequently embedded in paraffin. Six different human liver tissues and samples from two different myocardial tissues, two skeleton muscle tissues and two samples obtained from human aorta were also fixed and paraffin embedded as described above. Sections of 5 μm slices were obtained with a Leitz Wetzlar microtome and placed on glass slides and stored at 4° C. until assayed. Pre-treatments and analyses were performed as described previously. Primary antibodies were the MAP-1 specific monoclonal antibodies mAb 12B11 or affinity purified, monospecific rabbit anti-MAP-1 all diluted to 5 μg/ml. Isotype antibody controls were applied to the tissues at the same concentration. Secondary antibody was EnVision™ antibody (HRP-anti mouse or HRP-anti rabbit, Dako, Glostrup, Denmark). Analysis of staining patterns was conducted under a Leica DMLB2 microscope.

SDS-PAGE and Western Blotting.

Electrophoresis was performed on 10% or 4-12% (w/v) Bis-Tris Polyacrylamide-gels with discontinuous buffers using the NuPAGE® system (Invitrogen) essentially as described by the manufacturer. Western blotting was performed using polyvinylidene difluoride membranes (PVDF-HyBond, Amersham Bioscience), 2 μg/ml of primary mAbs and secondary visualization by HRP conjugated streptavidin (P0397, Dako) diluted to 1:1500 or HRP-Rabbit anti mouse IgG (P0260, Dako) diluted to 1:1000 in PBS, 0.05% Tween20. The membranes were developed with 3-amino-9-ethylcarbazole (Sigma) (0.04% in acetone) and 0.015% $H_2O_2$ in 50 mM sodium acetate buffer pH 5.

Complement Activation Assay.

The influence of MAP-1 on the MBL and Ficolin-3 mediated complement factor C4 deposition was assessed essentially as described previously. Briefly, mannan (MBL ligand) (Sigma-Aldrich M7504) or acetylated bovine serum albumin (Ficolin-3 ligand) was immobilized to Maxisorp ELISA plates (Nunc, Denmark) at 10 μg/ml. After washing with, rMBL or rFicolin-3 (0.4 μg/ml) was added and incubated for 1.5 hour. rMAP-1 or rMASP-2 was applied for 1 hour in two-fold serial dilutions in the first dimension followed by incubation for 45 min at 37° C. with serial dilutions of serum deficient of MBL or Ficolin-3 in the second dimension. The C4 deposition was measured using a pAb to C4c (Q0369, Dako, Glostrup/Denmark).

In addition we assessed the displacement of MASP-2 with MAP-1 using a pure system. rMASP-2 was pre-incubated for 45 min at 20° C. in serial dilutions in the first dimension on an rMBL/mannan matrix as described above followed by incubation with dilutions of rMAP-1 in the second dimension for 45 min at 20° C. Purified C4 (from Quidel, CA, USA) was added at a concentration of 1 μg/ml and incubated for 45 min at 37° C. Detection was conducted as above.

Results.

MAP-1 co-precipitates with Ficolin-2, Ficolin-3 and MBL To investigate a possible association of MAP-1 with MBL and Ficolin-3 we precipitated serum complexes using both anti MAP-1 mAb20C4 and a mAb against the common heavy chain of MASP-1 and MASP-3 (mAb8B3). The precipitates were subsequently analyzed by western blotting probed with antibodies to MAP-1, MBL, and Ficolin-3, respectively. We observed pronounced Ficolin-3 co-precipitation bands, but weaker bands were also seen with MBL (FIG. 24A). The samples wee not probed with antibodies against Ficolin-2 since they did not work in western blot. We then reversed the immunoprecipitation using mAbs against MBL, Ficolin-2 and Ficolin-3 to precipitate 1 ml, 300 µl and 100 µl serum, respectively, which was perform to adjust for differences in the serum concentration of MBL (2 µg/ml), Ficolin-2 (5 µg/ml) and Ficolin-3 (20 µg/ml), respectively. The samples were subsequently analyzed by western blotting probed with antibodies to MAP-1. Distinct MAP-1 bands were observed in the precipitates from Ficolin-2 and -3 and a much weaker band was apparent in the MBL precipitate, where immunoprecipitated rMAP-1 and serum MAP-1 served as controls (FIG. 24B).

MAP-1 Inhibits Complement Activity of the Lectin Pathway.

Serum deficient of MBL and Ficolin-3 in combination with rMBL and rFicolin-3 were used to reconstitute for MBL and Ficolin-3 complement C4 activation activity. Mannan and acetylated BSA served as ligands for MBL and Ficolin-3, respectively. Both rMBL and rFicolin-3 were able to initiate C4 deposition in MBL and Ficolin-3 deficient sera, respectively (FIGS. 25A and 25D). Application of rMASP-2 resulted in a strong positive dose dependent enhancement of the C4 deposition via both the Ficolin-3 and MBL activation pathways (FIGS. 25B and 25E), whereas application of rMAP-1 resulted in a pronounced dose dependent inhibition of the C4 deposition via both pathways (FIGS. 25C and 25F).

In addition we addressed a possible displacement of MASP-2 with MAP-1 using a system of pure components comprising only of rMBL, rMASP-2, rMAP-1 and purified C4. rMASP-2 was pre-incubated with mannan/rMBL complexes in serial dilutions. Thereafter, rMAP-1 was added in varying concentrations followed by addition of purified C4. Application of rMAP-1 to the system clearly resulted in a dose dependent inhibition of C4 deposition (FIG. 26).

Example 3

Chimeric molecules composed of MAP-1 and other complement inhibitory proteins are generated according to the following exemplary standard procedures. The MAP-1 protein (complete) is conjugated to following human proteins: Factor I, Factor H, C4 bp and C1inh using standard methods for covalent coupling, such as:
1) 1-Ethyl-3-[3-dimethylaminopropyl]carbodiimide hydrochloride (EDC, a zero-length crosslinker) is used to couple the MAP-1 protein to other conjugates via a carboxyl to primary amines group coupling as described by the manufacturer (Pierce, CAS nr. 25952-53-8).
2) Isuccinimidyl suberate (DSS) (with an 8-carbon spacer arm) is used to couple the MAP-1 protein to other conjugates via amine to amines group coupling as described by the manufacturer (Pierce, CAS nr. 68528-80-3).
3) EMCS ([N-e-Maleimidocaproyloxy]succinimide ester) (with a 9.4å spacer arm) is used to couple the MAP-1 protein to other conjugates via sulfhydryl to amino group coupling as described by the manufacturer (Pierce, product nr. 22308).

Example 4

The following list are examples of constructs of the present invention made in accordance with the teaching herein. The constructs all have the basic formula of MAP-1-linker-complement modulator or complement modulator-linker-MAP-1. The contructs may also be generated without any linker. Notations in parenthesis indicate details within a particular section of the composition. For example, "(complete)" means that the entire mature protein sequence with the amino acid sequence 20-380 of native human FAP (SEQ ID NO: 1) is used in the construct. It is understood that this list is not limiting and only provides examples of some of the constructs disclosed in the present application.

MAP-1 (complete)-(Gly4Ser)3(SEQ ID NO: 69)-DAF
MAP-1 (complete)-(Gly4Ser)3(SEQ ID NO: 69)-Factor H
MAP-1 (complete)-(Gly4Ser)3(SEQ ID NO: 69)-human CD59
MAP-1 (complete)-(Gly4Ser)3(SEQ ID NO: 69-MCP
MAP-1 (complete)-(Gly4Ser)3(SEQ ID NO: 69)-R1
MAP-1 (complete)-(Gly4Ser)3(SEQ ID NO: 69)-Crry
MAP-1 (complete)-(Gly4Ser)3(SEQ ID NO: 69)-mouse CD59
MAP-1 (complete)-(Gly4Ser)3(SEQ ID NO: 69)-human IgG1 Fc
MAP-1 (complete)-(Gly4Ser)3(SEQ ID NO: 69)-human IgM Fc
MAP-1 (complete)-(Gly4Ser)3(SEQ ID NO: 69)-murine IgG3 Fc
MAP-1 (complete)-(Gly4Ser)3(SEQ ID NO: 69)-murine IgM Fc
MAP-1 (complete)-(Gly4Ser)3(SEQ ID NO: 69)-Factor I
MAP-1 (complete)-(Gly4Ser)3(SEQ ID NO: 69)-C4 bp
MAP-1 (complete)-(Gly4Ser)3(SEQ ID NO: 69)-C1inh
MAP-1 (complete)-(Gly3Ser)4(SEQ ID NO: 70)-DAF
MAP-1 (complete)-(Gly3Ser)4(SEQ ID NO: 70)-Factor H
MAP-1 (complete)-(Gly3Ser)4(SEQ ID NO: 70)-human CD59
MAP-1 (complete)-(Gly3Ser)4(SEQ ID NO: 70)-MCP
MAP-1 (complete)-(Gly3Ser)4(SEQ ID NO: 70)-CR1
MAP-1 (complete)-(Gly3Ser)4(SEQ ID NO: 70)-Crry
MAP-1 (complete)-(Gly3Ser)4(SEQ ID NO: 70)-mouse CD59
MAP-1 (complete)-(Gly3Ser)4(SEQ ID NO: 70)-human IgG1 Fc
MAP-1 (complete)-(Gly3Ser)4(SEQ ID NO: 70)-human IgM Fc
MAP-1 (complete)-(Gly3Ser)4(SEQ ID NO: 70)-murine IgG3 Fc
MAP-1 (complete)-(Gly3Ser)4(SEQ ID NO: 70)-murine IgM Fc
MAP-1 (complete)-(Gly3Ser)4(SEQ ID NO: 70)-Factor I
MAP-1 (complete)-(Gly3Ser)4(SEQ ID NO: 70)-C4 bp
MAP-1 (complete)-(Gly3Ser)4(SEQ ID NO: 70)-C1inh
MAP-1 (complete)-(Gly4Ser)3(SEQ ID NO: 69)-DAF (SCRs 2-4)
MAP-1 (complete)-(Gly3Ser)4(SEQ ID NO: 70)-DAF (SCRs 2-4)
MAP-1 (complete)-(Gly4Ser)3(SEQ ID NO: 69)-CR1 (LP-SCR1-4-SCR8-11-SCR15-18)
MAP-1 (complete)-(Gly4Ser)3(SEQ ID NO: 69)-Crry (5 N-terminal SCRs)
MAP-1 (complete)-VSVFPLE (SEQ ID NO: 66)-DAF
MAP-1 (complete)-VSVFPLE (SEQ ID NO: 66)-Factor H
MAP-1 (complete)-VSVFPLE (SEQ ID NO: 66)-human CD59
MAP-1 (complete)-VSVFPLE (SEQ ID NO: 66)-MCP
MAP-1 (complete)-VSVFPLE (SEQ ID NO: 66)-CR1

MAP-1 (complete)-VSVFPLE (SEQ ID NO: 66)-Crry
MAP-1 (complete)-VSVFPLE (SEQ ID NO: 66)-mouse CD59
MAP-1 (complete)-VSVFPLE (SEQ ID NO: 66)-human IgG1 Fc
MAP-1 (complete)-VSVFPLE (SEQ ID NO: 66)-human IgM Fc
MAP-1 (complete)-VSVFPLE (SEQ ID NO: 66)-murine IgG3 Fc
MAP-1 (complete)-VSVFPLE (SEQ ID NO: 66)-murine IgM Fc
MAP-1 (complete)-VSVFPLE (SEQ ID NO: 66)-Factor I
MAP-1 (complete)-VSVFPLE (SEQ ID NO: 66)-C4 bp
MAP-1 (complete)-VSVFPLE (SEQ ID NO: 66)-C1inh
MAP-1 (complete)-m-Maleimidobenzoyl-N-hydroxysuccinimide ester-DAF
MAP-1 (complete)-m-Maleimidobenzoyl-N-hydroxysuccinimide ester-human CD59
MAP-1 (complete)-m-Maleimidobenzoyl-N-hydroxysuccinimide ester-MCP
MAP-1 (complete)-m-Maleimidobenzoyl-N-hydroxysuccinimide ester-CR1
MAP-1 (complete)-m-Maleimidobenzoyl-N-hydroxysuccinimide ester-Crry
MAP-1 (complete)-m-Maleimidobenzoyl-N-hydroxysuccinimide ester-mouse CD59
MAP-1 (complete)-m-Maleimidobenzoyl-N-hydroxysuccinimide ester-human IgG1 Fc
MAP-1 (complete)-m-Maleimidobenzoyl-N-hydroxysuccinimide ester-human IgM Fc
MAP-1 (complete)-m-Maleimidobenzoyl-N-hydroxysuccinimide ester-murine IgG3 Fc
MAP-1 (complete)-m-Maleimidobenzoyl-N-hydroxysuccinimide ester-murine IgM Fc
MAP-1 (complete)-m-Maleimidobenzoyl-N-hydroxysuccinimide ester-Factor I
MAP-1 (complete)-m-Maleimidobenzoyl-N-hydroxysuccinimide ester-C4 bp
MAP-1 (complete)-m-Maleimidobenzoyl-N-hydroxysuccinimide ester-C1inh
MAP-1 (complete)-m-Maleimidobenzoyl-N-hydroxysuccinimide ester-Factor H
MAP-1 (complete)-bismaleimidohexane-DAF
MAP-1 (complete)-bismaleimidohexane-Factor H
MAP-1 (complete)-bismaleimidohexane-human CD59
MAP-1 (complete)-bismaleimidohexane-MCP
MAP-1 (complete)-bismaleimidohexane-CR1
MAP-1 (complete)-bismaleimidohexane-Crry
MAP-1 (complete)-bismaleimidohexane-mouse CD59
MAP-1 (complete)-bismaleimidohexane-human IgG1 Fc
MAP-1 (complete)-bismaleimidohexane-human IgM Fc
MAP-1 (complete)-bismaleimidohexane-murine IgG3 Fc
MAP-1 (complete)-bismaleimidohexane-murine IgM Fc
MAP-1 (complete)-bismaleimidohexane-Factor I
MAP-1 (complete)-bismaleimidohexane-C4 bp
MAP-1 (complete)-bismaleimidohexane-C1inh

Example 5

Exemplary specific sequences of MAP-1 chimeric molecules, which may be produced as fusion proteins:

Human fusion proteins containing a ficolin-associated polypeptide portion and a second modulator of complement activity may be made by recombinant DNA cloning and gene expression method.

Amino acid sequence of an exemplary human MAP-1/FH chimeric protein (SEQ ID NO:25) and an exemplary polynucleotide sequence encoding the human MAP-1/FH chimeric protein (SEQ ID NO:26). The construct is illustrated in FIG. 27.

Amino acid sequence of an exemplary human FH/MAP-1 chimeric protein (SEQ ID NO:27) and an exemplary polynucleotide sequence encoding the human FH/MAP-1 chimeric protein (SEQ ID NO:28). The construct is illustrated in FIG. 27. The amino acid sequences of human MAP-1 (SEQ ID NO:29-31) are all suitable examples of sequences that could be used as the MAP-1 portion of a chimeric protein according to the invention. The amino acid sequences of human FH (SEQ ID NO:32-36) are all suitable examples of sequences that could be used as a FH portion of a chimeric protein according to the invention.

In the following examples the FH portion may be replaced by any one of C4 bp, FI, or C1-inh:

The amino acid sequences of human C4 bp (SEQ ID NO:37-40) are all suitable examples of sequences that could be used as a C4 bp portion of a chimeric protein according to the invention. The construct is illustrated in FIG. 28.

The amino acid sequences of human FI (SEQ ID NO:41-44) are all suitable examples of sequences that could be used as a FI portion of a chimeric protein according to the invention. The construct is illustrated in FIG. 29.

The amino acid sequences of human C1-inh (SEQ ID NO:45) are all suitable examples of sequences that could be used as a C1-inh portion of a chimeric protein according to the invention. The construct is illustrated in FIG. 30.

Example 6

Detailed Exemplary Procedure for the Production of MAP-1/FH Fusion Protein:

Construction of Expression Vectors

The pEDdC vector, which carries a cloning sequence for insertion of the target gene followed by the selectable and amplifiable marker (dhfr), will be used for expression of the fusion gene.

Two sets of primers are designed for each gene to be linked. These primers contain restriction enzyme sequences adaptable with the expression vector. The primers are developed in order to amplify the two fusion protein, MAP-1 and FH. MAP-1 and FH will have identical restriction enzyme sequences in the region to be linked. Optional linker sequence may be incorporated.

In order to be able to obtain the protein expression in cell culture supernatant, a construct containing optional signal peptide may be incorporated. For cytoplasmic expression of chimeric protein, the construct does not contain the signal peptide. In this way, the fusion protein would be expressed and accumulated in the cytoplasmic area of the host cell rather than that of the supernatant.

Fusion Gene Construction

Cloning of MAP-1/FH is performed briefly as follows. The MAP-1 and FH genes are amplified from human liver cDNA and run at agarose gel. The gene is then cut out of the gel, purified, and digested with respective restriction enzymes. The products are purified and the two genes ligated. After ligation, the gene construct is purified and inserted into the pED vector and characterized. The pEDdC/MAP-1/FH vector is transformed into *Escherichia coli* bacteria and plated on selective LB medium (containing 100 μg/mL ampicillin) and grown overnight at 37° C. Bacterial colonies are screened for the presence of both gene by colony PCR. Positive colonies are picked, streaked, and cultured in LB. Plasmids are purified and sequenced in order to confirm the sequence.

Transfection and MAP-1/FH Expression

The pEDdC/MAP-1/FH construct is transfected into the Chinese hamster ovary (CHO) DG44 cell line. This CHO clone is a double deletion mutant that contains no copies of the hamster dhfr gene. Untransfected cells are grown in IMDM supplemented by 10% dFBS, 100 units/ml penicillin, 0.1 mg/ml streptomycin, 2 mM L-glutamine, 10 mM hypoxanthine, and 1.6 mM thymidine (HT-supplement) in a 37° C. humidified atmosphere containing 5% $CO_2$. Cells are passaged using 0.05% trypsin in PBS. Stable transfections are performed using the LipofectAMINE PLUS reagent kit. Transfection is performed by seeding $8\times10^5$ cells in 6-cm culture wells on day 0. On day 1, cell medium is replaced and the cells transfected according to the manufacturer's protocol, adding 60 µl of LipofectAMINE, 0.2 µg of $pSV_2neo$, and 20 µg of the pEDdC/MAP-1/FH vector. On day 3, cells are transferred to 25 cm2 flasks, and on day 5, cells are transferred to a medium containing 0.5 mg/ml G418 and lacking hypoxanthine and thymidine. G418-resistant clones are usual obtained after 12 days. Selection and gene amplification with MTX are initiated by cultivating cells in cell medium containing 0.5 mg/ml G418, 50 nM MTX, which lacked hypoxanthine and thymidine. When cells regain normal growth rate and morphology, the concentration of MTX is gradually increased to 200 nM.

Example 7

Chimeric Proteins of rMAP-1 and Factor H.

Purification of Proteins

Factor H from human plasma was purified essentially as described by Laine et al. J Immunol 2007; 178:3831-6 with the modification that the monoclonal anti human Factor H antibody Hyb 268-01 (Bioporto A/S, Gentofte, Denmark) was coupled to the purification matrix and used to affinity purify plasma Factor H.

Recombinant, full-length, non-tagged MBL/Ficolin associated protein-1 (rMAP-1) was expressed in CHO DG 44 cells in serum-free medium (SFM) (CHO CD-1, Lonza) and RPMI 1640 with 10% fetal calf serum (FCS) and purified as described previously Skjoedt M O, et al. Serum concentration and interaction properties of MBL/ficolin associated protein-1. Immunobiology doi:101016/jimbio201009011.

Recombinant, full-length, non-tagged mannose-binding lectin (rMBL) was expressed in CHO DG 44 cells in serum-free medium (SFM) (CHO CD-1, Lonza) and purified by affinity chromatography on a mannan-agarose column as described previously Skjoedt M O, et al. J Biol Chem 2010; 285:8234-43.

SDS-PAGE 4-12% Bis-Tris SDS-PAGE and coomassie staining was used to determine the molecular composition and purity of the proteins mentioned above. The conditions were according to the instructions from the manufacturer (Invitrogen).

Protein Coupling rMAP-1 and Factor H was covalently linked by glutaraldehyde coupling according to the recommendations by Carter J M. Conjugation of Peptides to Carrier Proteins via Glutaraldehyde The Protein Protocols Handbook, Part VII, 679-687, DOI: 101007/978-1-60327-259-9_117: Springer, 1996. The conjugated product is named rMAP-1/Factor H hybrid molecule.

Complement Activation Assays

The MBL dependent complement activation was analyzed with the purified proteins described above. The methods and reagents used in these assays have previously been described (Skjoedt M O, et al. J Biol Chem 2010; 285:8234-43, and Palarasah Y, et al. J Clin Microbiol; 48:908-14), except for the inclusion of plasma Factor H and rMAP-1/Factor H hybrid molecule described here.

Results and Discussion

Protein Analysis

Analysis of the purified recombinant MAP-1 revealed an expected non-reduced molecular mass of ≈45 kDa (FIG. 31). No dysfunctional disulfide bridge formation was observed. Analysis of the purified plasma Factor H revealed an expected molecular mass of ≈150 kDa (FIG. 31). A high purity was observed for both rMAP-1 and Factor H.

Analysis of the purified recombinant MBL revealed an expected reduced molecular mass of ≈30 kDa. A high purity was observed for rMBL (FIG. 32). Analysis non-reduced pattern of rMBL revealed a disulfide bridge mediated oligomerization comparable with native serum derived MBL (FIG. 32).

Complement Deposition Assays

A simple scheme illustrates the composition of the assays employed in the following (FIG. 33).

Initially the rMAP-1/Factor H hybrid molecule was introduced to the MBL dependent complement assay to investigate if this chimeric protein is able to inhibit the activation and deposition of complement factor C3. FIG. 34 illustrates a clear dose dependent inhibition mediated by the chimeric protein of the MBL dependent C3 activation.

To further investigate if rMAP-1 and Factor H binds to rMBL under the conditions employed here, we measured the association with specific monoclonal antibodies to MAP-1 and Factor H, respectively. FIG. 35A shows the binding of rMAP-1 to rMBL bound to mannan. The rMAP-1/Factor H hybrid molecule shows a reduced binding to rMBL compared with the non-conjugated rMAP-1, suggesting that a part of the rMAP-1 linked to Factor H is conformational changed. FIG. 35B shows the binding of Factor H to rMBL. As expected only the Factor H in the rMAP-1/Factor H hybrid form is able to bind to the MBL/mannan complex.

The purified plasma Factor H shows no effect on the C3 deposition (FIG. 36A) or the C9/Terminal complement complex formation (FIG. 36B) in the MBL assay. In contrast to this the purified rMAP-1 showed a significant inhibition of the C3 deposition (FIG. 37A) and the C9/Terminal complement complex formation (FIG. 37B). When non-conjugated purified rMAP-1 and Factor H are applied together in the assays, the deposition patterns are equivalent to the results obtained with rMAP-1 alone (FIG. 38A-B). These data show that Factor H does not play a role unless it is covalently attached to rMAP-1. When the rMAP-1/Factor H hybrid molecule is employed in the complement activation assays a pronounced dose-dependent inhibition of both the C3 deposition (FIG. 39A) and the C9/Terminal complement complex formation (FIG. 39B). This is in spite of the fact that a large proportion of the rMAP-1 presumably is not able to bind to rMBL due to misfolding after the glutaraldehyde coupling (see FIG. 35A). A combined MAP-1/Factor H hybrid molecule might thus be a potent regulator of adverse in vivo inflammation caused by complement activation and could perhaps also operate at levels where lectin pathway related proteins have been shown to play a role (apoptosis, necrosis, thrombosis and coagulation).

SEQ ID NO: 1. The complete 380 amino acid sequences for human FAP. (Two potential glycosylation sites identified at amino acid position 49 and 178 are highlighted):
MRWLLLYYALCFSLSKASAHTVELNNMFGQIQSPGYPDSYPSDSEVTWNITVPDGFRIKLYFMHFNLESSYLCEYDYVKVETEDQV
LATFCGRETTDTEQTPGQEVVLSPGSFMSITFRSDFSNEERFTGFDAHYMAVDVDECKEREDEELSCDHYCHNYIGGYYCSCRFGY
ILHTDNRTCRVECSDNLFTQRTGVITSPDFPNPYPKSSECLYTIELEEGFMVNLQFEDIFDIEDHPEVPCPYDYIKIKVGPKVLGP
FCGEKAPEPISTQSHSVLILFHSDNSGENRGWRLSYRAAGNECPELQPPVHGKIEPSQAKYFFKDQVLVSCDTGYKVLKDNVEMDT
FQIECLKDGTWSNKIPTCKKNEIDLESELKSEQVTE SEQ ID NO: 2. The complete cDNA nucleotide sequences for human FAP:
atgaggtggctgctgctctctattatgctctgtgcttctccctgtcaaaggcttcagcccacaccgtggagctaaacaatatgtt
tggccagatccagtcgcctggttatccagactcctatcccagtgattcagaggtgacttggaatatcactgtcccagatgggt
ttggatcaagctttacttcatgcacttcaacttggaatcctcctacctttgtaatatgactatgtgaaggtagaaactgag
gaccaggtgctggcaaccttctgtggcagggagaccacagacacagagcagactcccggccaggaggtggtcctctcccctgg
ctccttcatgtccatcacttttcggtcagatttctccaatgaggagcgtttcacaggctttgatgcccactacatggctgtgg
atgtggacgagtgcaaggagagggaggacgaggagctgtcctgtgaccactactgccacaactacattggCggctactactgc
tcctgccgcttcggctacatcctccacacagacaacaggacctgccgagtggagtgcagtgacaacctcttcactcaaaggac
tggggtgatcaccagccctgacttcccaaaccctacccaagagctctgaatgcctgtataccatcgagctggaggagggtt
tcatggtcaacctgcagtttgaggacatatttgacattgacattgcagtgcgcctgccctatgactacatcaagatc
aaagttggtccaaaagttttggggcctttctgtggagagaaagcccagaacccatcagcacccagagccacagtgtcctgat
cctgttccatagtgacaactcgggagagaaccggggctggaggctctcatacagggctgcaggaaatgagtgcccagagctac
agcctcctgtccatgggaaaatcgagccctccaagccaagtatttcttcaaagaccaagtgctcgtcagctgtgacacaggc
tacaaagtgctgaaggataatgtggagatggacacattccagattgagtgtctgaaggatgggacgtggagtaacaagattcc
cacctgtaaaaaaaatgaaatcgatctggagagcgaactcaagtcagagcaagtgacagagtga SEQ NO: 3. Minimum sequence of a ficolin-associated polypeptide comprising the CUB1-EGF-CUB2 domains including a signal peptide of amino acids 1-19. The sequence corresponds to exon 2 to exon 6:
MRWLLLYYALCFSLSKASAHTVELNNMFGQIQSPGYPDSYPSDSEVTWNITVPDGFRIKLYFMHFNLESSYLCEYDYVKVETEDQ
VLATFCGRETTDTEQTPGQEVVLSPGSFMSITFRSDFSNEERFTGFDAHYMAVDVDECKEREDEELSCDHYCHNY
IGGYYCSCRFGYILHTDNRTCRVECSDNLFTQRTGVITSPDFPNPYPKSSECLYTIELEEGFMVNLQFEDIFDIEDHPEVPCPYD
YIKIKVGPKVLGPFCGEKAPEPISTQSHSVLILFHSDNSGENRGWRLSYRAA SEQ ID NO: 4. Unique terminal 17 amino acids of FAP:
KNEIDLESELKSEQVTE SEQ ID NO: 5 Protein sequence of human MASP-1:
MRWLLLYYALCFSLSKASAHTVELNNMFGQIQSPGYPDSYPSDSEVTWNITVPDGFRIKLYFMHFNLESSYLCEYDYVKVETE
DQVLATFCGRETTDTEQTPGQEVVLSPGSFMSITFRSDFSNEERFTGFDAHYMAVDVDECKEREDEELSCDHYCHNYIGGYYC
SCRFGYILHTDNRTCRVECSDNLFTQRTGVITSPDFPNPYPKSSECLYTIELEEGFMVNLQFEDIFDIEDHPEVPCPYDYIKI
KVGPKVLGPFCGEKAPEPISTQSHSVLILFHSDNSGENRGWRLSYRAAGNECPELQPPVHGKIEPSQAKYFFKDQVLVSCDTG
YKVLKDNVEMDTFQIECLKDGTWSNKIPTCKIVDCRAPGELEHGLITFSTRNNLTTYKSEIKYSCQEPYYKMLNNNTGIYTCS
AQGVWMNKVLGRSLPTCLPVCGLPKFSRKLMARIFNGRPAQKGTTPWIAMLSHLNGQPFCGGSLLGSSWIVTAAHCLHQSLDP
EDPTLRDSDLLSPSDFKIILGKHWRLRSDENEQHLGVKHTTLHPQYDPNTFENDVALVELLESPVLNAFVMPICLPEGPQQEG
AMVIVSGWGKQFLQRFPETLMEIEIPIVDHSTCQKAYAPLKKKVTRDMICAGEKEGGKDACAGDSGGPMVTLNRERGQWYLVG
TVSWGDDCGKKDRYGVYSYIHHNKDWIQRVTGVRN SEQ ID NO: 6 cDNA sequence of human MASP-1:
GAAGTCAGCCACACAGGATAAAGGAGGGAAGGGAAGGAGCAGATCTTTTCGGTAGGAAGACAGATTTTGTTGTCAGGTTCCTGGG
AGTGCAAGAGCAAGTCAAAGGAGAGAGAGAGGAGAGAGGAAAAGCCAGAGGGAGAGAGGGGGAGAGGGGATCTGTTGCAGGCAGG
GGAAGGCGTGACCTGAATGGAGAATGCCAGCCAATTCCAGAGACACACAGGGACCTCAGAACAAAGATAAGGCATCACGGACACC
ACACCGGGCACGAGCTCACAGGCAAGTCAAGCTGGGAGGACCAAGGCCGGGCAGCCGGGAGCACCCAAGGCAGGAAAATGAGGTG
GCTGCTTCTCTATTATGCTCTGTGCTTCTCCCTGTCAAAGGCTTCAGCCCACACCGTGGAGCTAAACAATATGTTTGGCCAGATC
CAGTCGCCTGGTTATCCAGACTCCTATCCCAGTGATTCAGAGGTGACTTGGAATATCACTGTCCCAGATGGGTTTCGGATCAAGC
TTTACTTCATGCACTTCAACTTGGAATCCTCCTACCTTTGTGAATATGACTATGTGAAGGTAGAAACTGAGGACCAGGTGCTGGC
AACCTTCTGTGGCAGGGAGACCACAGACACAGAGCAGACTCCCGGCCAGGAGGTGGTCCTCTCCCCTGGCTCCTTCATGTCCATC
ACTTTCCGGTCAGATTTCTCCAATGAGGAGCGTTTCACAGGCTTTGATGCCCACTACATGGCTGTGGATGTGGACGAGTGCAAGG
AGAGGGAGGACGAGGAGCTGTCCTGTGACCACTACTGCCACAACTACATTGGCGGCTACTACTGCTCCTGCCGCTTCGGCTACAT
CCTCCACACAGACAACAGGACCTGCCGAGTGGAGTGCAGTGACAACCTCTTCACTCAAAGGACTGGGGTGATCACCAGCCCTGAC
TTCCCAAACCCTTACCCCAAGAGCTCTGAATGCCTGTATACCATCGAGCTGGAGGAGGGTTTCATGGTCAACCTGCAGTTTGAGG
ACATATTTGACATTGAGGACCATCCTGAGGTGCCCTGCCCCTATGACTACATCAAGATCAAAGTTGGTCCAAAAGTTTTGGGGCC
TTTCTGTGGAGAGAAAGCCCCAGAACCCATCAGCACCCAGAGCCACAGTGTCCTGATCCTGTTCCATAGTGACAACTCGGGAGAG
AACCGGGGCTGGAGGCTCTCATACAGGGCTGCAGGAAATGAGTGCCCAGAGCTACAGCCTCCTGTCCATGGGAAAATCGAGCCCT
CCCAAGCCAAGTATTTCTTCAAAGACCAAGTGCTCGTCAGCTGTGACACAGGCTACAAAGTGCTGAAGGATAATGTGGAGATGGA
CACATTCCAGATTGAGTGTCTGAAGGATGGGACGTGGAGTAACAAGATTCCCACCTGTAAAATTGTAGACTGTAGAGCCCCAGGA
GAGCTGGAACACGGGCTGATCACCTTCTCTACAAGGAACAACCTCACCACATACAAGTCTGAGATCAAATACTCCTGTCAGGAGC
CCTATTACAAGATGCTCAACAATAACACAGGTATATATACCTGTTCTGCCCAAGGAGTCTGGATGAATAAAGTATTGGGGAGAAG
CCTACCCACCTGCCTTCCAGTGTGTGGGCTCCCCAAGTTCTCCCGGAAGCTGATGGCCAGGATCTTCAATGGACGCCCAGCCCAG
AAAGGCACCACTCCCTGGATTGCCATGCTGTCACACCTGAATGGGCAGCCTTTCTGCGGAGGCTCCCTTCTAGGGCTCCAGCTGGA
TCGTGACCGCCGCACACTGCCTCCACCAGTCACTCGATCCGGAAGATCCGACCCTACGTGATTCAGACTTGCTCAGCCCTTCTGA
CTTCAAAATCATCCTGGGCAAGCATTGGAGGCTCCGGTCAGATGAAAATGAACAGCATCTCGGCGTCAAACACACCACTCTCCAC
CCCCAGTATGATCCCAACACATTCGAGAATGACGTGGCTCTGGTGGAGCTGTTGGAGAGCCCAGTGCTGAATGCCTTCGTGATGC
CCATCTGTCTGCCTGAGGGACCCCAGCAGGAGGGAGCCATGGTCATCGTCAGCGGCTGGGGGAAGCAGTTCTTGCAAAGGTTCCC
AGAGACCCTGATGGAGATTGAAATCCCGATTGTTGACCACAGCACCTGCCAGAAGGCTTATGCCCCGCTGAAGAAGAAAGTGACC
AGGGACATGATCTGTGCTGGGGAGAAGGAAGGGGGAAAGGACGCCTGTGCGGGTGACTCTGGAGGCCCCATGGTGACCCTGAATA
GAGAAAGAGGCCAGTGGTACCTGGTGGGCACTGTGTCCTGGGGTGATGACTGTGGGAAGAAGGACCGCTACGGAGTATACTCTTA
CATCCACCACAACAAGGACTGGATCCAGAGGGTCACCGGAGTGAGGAACTGAATTTGGCTCCTCCAGCCCCAGCACCACCAGCTGT
GGGCAGTCAGTAGCAGAGGACGATCCTCCGATGAAAGCAGCCATTTCTCCTTTCCTTCCTCCCATCCCCCCTCCTTGGCCTATC
CATTACTGGGCAATAGAGCAGGTATCTTCACCCCCTTTTCACTCTCTTTAAAGATGGACAAGAGAGTGGTCAGAACACAGGC
CGAATCCAGGCTCTATCACTTACTAGTTTGCAGTGCTGGGCAGGTGACTTCATCTCTTCGAACTTCAGTTTCTTCATAAGATGGA
AATGCTATACCTTACCTACCTCGTAAAAGTCTGATGAGGAAAGATTAACTAATAGATGCATAGCACTTAACAGAGTGCATAGCA
TACACTGTTTTCAATAAATGCACCTTAGCAGAAGGTCGATGTGTCTACCAGGCAGACGAAGCTCTCTTACAAACCCCTGCCTGGG -continued

```
TCTTAGCATTGATCAGTGACACACCTCTCCCCTCAACCTTGACCATCTCCATCTGCCCTTAAATGCTGTATGCTTTTTTGCCACC
GTGCAACTTGCCCAACATCAATCTTCACCCTCATCCCTAAAAAAGTAAAACAGACAAGGTTCTGAGTCCTGTGGTATGTCCCCTA
GCAAATGTAACTAGGAACATGCACTAGATGACAGATTGCGGGAGGGCCTGAGAGAAGCAGGGACAGGAGGGAGCCTGGGGATTGT
GGTTTGGGAAGGCAGACACCTGGTTCTAGAACTAGCTCTGCCCTTAGCCCCCTGTATGACCCTATGCAAGTCCTCCTCCCTCATC
TCAAAGGGTCCTCAAAGCTCTGACGATCTAAGATACAATGAAGCCATTTTCCCCCTGATAAGATGAGGTAAAGCCAATGTAACCA
AAAGGCAAAAATTACAATCGGTTCAAAGGAACTTTGATGCAGACAAAATGCTGCTGCTGCTGCTCCTGAAATACCCACCCCTTTC
CACTACGGGTGGGTTCCCAAGGACATGGGACAGGCAAAGTGTGAGCCAAAGGATCCTTCCTTATTCCTAAGCAGAGCATCTGCTC
TGGGCCCTGGCCTCCTTCCCTTCTTGGGAAACTGGGCTGCATGAGGTGGGCCCTGGTAGTTTGTACCCCAGGCCCCTATACTCTT
CCTTCCTATGTCCACAGCTGACCCCAAGCAGCCGTTCCCCGACTCCTCACCCCTGAGCCTCACCCTGAACTCCCTCATCTTGCAA
GGCCATAAGTGTTTTCCAAGCAAAATGCCTCTCCCATCCTCTCTCAGGAAGCTTCTAGAGACTTTATGCCCTCCAGAGCTCCAAG
ATATAAGCCCTCCAAGGGATCAGAAGCTCCAAGTTCCTGTCTTCTGTTTTATAGAAATTGATCTTCCCTGGGGGACTTTAACTCT
TGACCTGTATGCAGCTGTTGGAGTAATTCCAGGTCTCTTGAAAAAAAAGAGGAAGATAATGGAGAATGAGAACATATATATATAT
ATATTAAGCCCCAGGCTGAATACTCAGGGACAGCAATTCACAGCCTGCCTCTGGTTCTATAAACAAGTCATTCTACCTCTTTGTG
CCCTGCTGTTTATTCTGTAAGGGGAAGGTGGCAATGGGACCCAGCTCCATCAGACACTTGTCAAGCTAGCAGAAACTCCATTTTC
AATGCCAAAGAAGAACTGTAATGCTGTTTTGGAATCATCCCAAGGCATCCCAAGACACCATATCTTCCCATTTCAAGCACTGCCT
GGGCACACCCCAACATCCCAGGCTGTGGTGGCTCCTGTGGGAACTACCTAGATGAAGAGAGTATCATTTATACCTTCTAGGAGCT
CCTATTGGGAGACATGAAACATATGTAATTGACTACCATGTAATAGAACAAACCCTGCCAAGTGCTGCTTTGGAAAGTCATGGAG
GTAAAAGAAAGACCATTC
```

SEQ ID NO: 7 Protein sequence of human MASP-3:
MRWLLLYYALCFSLSKASAHTVELNNMFGQIQSPGYPDSYPSDSEVTWNITVPDGFRIKLYFMHFNLESSYLCEYDYVKVETE
DQVLATFCGRETTDTEQTPGQEVVLSPGSFMSITFRSDFSNEERFTGFDAHYMAVDVDECKEREDEELSCDHYCHNYIGGYYC
SCRFGYILHTDNRTCRVECSDNLFTQRTGVITSPDFPNPYPKSSECLYTIELEEGFMVNLQFEDIFDIEDHPEVPCPYDYIKI
KVGPKVLGPFCGEKAPEPISTQSHSVLILFHSDNSGENRGWRLSYRAAGNECPELQPPVHGKIEPSQAKYFFKDQVLVSCDTG
YKVLKDNVEMDTFQIECLKDGTWSNKIPTCKIVDCRAPGELEHGLITFSTRNNLTTYKSEIKYSCQEPYYKMLNNNTGIYTCS
AQGVWMNKVLGRSLPTCLPECGQPSRSLPSLVKRIIGGRNAEPGLFPWQALIVVEDTSRVPNDKWFGSGALLSASWILTAAHV
LRSQRRDTTVIPVSKEHVTVYLGLHDVRDKSGAVNSSAARVVLHPDFNIQNYNHDIALVQLQEPVPLGPHVMPVCLPRLEPEG
PAPHMLGLVAGWGISNPNVTVDEIISSGTRTLSDVLQYVKLPVVPHAECKTSYESRSGNYSVTENMFCAGYYEGGKDTCLGDS
GGAFVI FDDLSQRWVVQGLVSWGGPEECGSKQVYGVYTKVSNYVDWVWEQMGLPQSVVEPQVER SEQ ID NO: 8 cDNA sequence of human MASP-3:
```
GAAGTCAGCCACACAGGATAAAGGAGGGAAGGGAAGGAGCAGATCTTTTCGGTAGGAAGACAGATTTTGTTGTCAGGTTCCTGGG
AGTGCAAGAGCAAGTCAAAGGAGAGAGAGAGGAGAGAGGAAAAGCCAGAGGGAGAGAGGGGGAGAGGGGATCTGTTGCAGGCAGG
GGAAGGCGTGACCTGAATGGAGAATGCCAGCCAATTCCAGAGACACACAGGGACCTCAGAACAAAGATAAGGCATCACGGACACC
ACACCGGGCACGAGCTCACAGGCAAGTCAAGCTGGGAGGACCAAGGCCGGGCAGCCGGGAGCACCCAAGGCAGGAAAATGAGGTG
GCTGCTTCTCTATTATGCTCTGTGCTTCTCCCTGTCAAAGGCTTCAGCCCACACCGTGGAGCTAAACAATATGTTTGGCCAGATC
CAGTCGCCTGGTTATCCAGACTCCTATCCCAGTGATTCAGAGGTGACTTGGAATATCACTGTCCCAGATGGGTTTCGGATCAAGC
TTTACTTCATGCACTTCAACTTGGAATCCTCCTACCTTTGTGAATATGACTATGTGAAGGTAGAAACTGAGGACCAGGTGCTGGC
AACCTTCTGTGGCAGGGAGACCACAGACACAGAGCAGACTCCCGGCCAGGAGGTGGTCCTCTCCCCTGGCTCCTTCATGTCCATC
ACTTTCCGGTCAGATTTCTCCAATGAGGAGCGTTTCACAGGCTTTGATGCCCACTACATGGCTGTGGATGTGGACGAGTGCAAGG
AGAGGGAGGACGAGGAGCTGTCCTGTGACCACTACTGCCACAACTACATTGGCGGCTACTACTGCTCCTGCCGCTTCGGCTACAT
CCTCCACACAGACAACAGGACCTGCCGAGTGGAGTGCAGTGACAACCTCTTCACTCAAAGGACTGGGGTGATCACCAGCCCTGAC
TTCCCAAACCCTTACCCCAAGAGCTCTGAATGCCTGTATACCATCGAGCTGGAGGAGGGGTTTCATGGTCAACCTGCAGTTTGAGG
ACATATTTGACATTGAGGACCATCCTGAGGTGCCCTGCCCCTATGACTACATCAAGATCAAAGTTGGTCCAAAAGTTTTGGGGCC
TTTCTGTGGAGAGAAAGCCCCAGAACCCATCAGCACCCAGAGCCACAGTGTCCTGATCCTGTTCCATAGTGACAACTCGGGAGAG
AACCGGGGCTGGAGGCTCTCATACAGGGCTGCAGGAAATGAGTGCCCAGAGCTACAGCCTCCTGTCCATGGGAAAATCGAGCCCT
CCCAAGCCAAGTATTTCTTCAAAGACCAAGTGCTCGTCAGCTGTGACACAGGCTACAAAGTGCTGAAGGATAATGTGGAGATGGA
CACATTCCAGATTGAGTGTCTGAAGGATGGGACGTGGAGTAACAAGATTCCCACCTGTAAAATTGTAGACTGTAGAGCCCCAGGA
GAGCTGGAACACGGGCTGATCACCTTCTCTACAAGGAACAACCTCACCACATACAAGTCTGAGATCAAATACTCCTGTCAGGAGC
CCTATTACAAGATGCTCAACAATAACACAGGTATATATACCTGTTCTGCCCAAGGAGTCTGGATGAATAAAGTATTGGGGAGAAG
CCTACCCACCTGCCTTCCAGAGTGTGGTCAGCCCTCCCGCTCCCTGCCCAAGCCTGGTCAAGAGGATCATTGGGGGCCGAAATGCT
GAGCCTGGCCTCTTCCCGTGGCAGGCCCTGATAGTGGTGGAGGACACTTCGAGAGTGCCAAATGACAAGTGGTTTGGGAGTGGGG
CCCTGCTCTCTGCGTCCTGGATCCTCACAGCAGCTCATGTGCTGCGTCCCAGCGTAGAGACACCACGGTGATACCAGTCTCCAA
GGAGCATGTCACCGTCTACCTGGGCTTGCATGATGTGCGAGACAAATCGGGGGCAGTCAACAGCTCAGCTGCCCGAGTGGTGCTC
CACCCAGACTTCAACATCCAAAACTACAACCACGATATAGCTCTGGTGCAGCTGCAGGAGCCTGTGCCCCTGGGACCCCACGTTA
TGCCTGTCTGCCTGCCAAGGCTTGAGCCTGAAGGCCCGGCCCCCACATGCTGGGCCTGGTGGCCGGCTGGGGCATCTCCAATCC
CAATGTGACAGTGGATGAGATCATCAGCAGTGGCACACGGACCCTTGTCAGATGTCCTGCAGTATGTCAAGTTACCCGTGGTGCCT
CACGCTGAGTGCAAAACTAGCTATGAGTCCCGCTCGGGCAATTACAGCGTCACGGAGAACATGTTCTGTGCTGGCTACTACGAGG
GCGGCAAAGACACGTGCCTTGGAGATAGCGGTGGGGCCTTTGTCATCTTTGATGACTTGAGCCAGCGCTGGGTGGTGCAAGGCCT
GGTGTCCTGGGGGGGACCTGAAGAATGCGGCAGCAAGCAGGTCTATGGAGTCTACACAAAGGTCTCCAATTACGTGGACTGGGTG
TGGGAGCAGATGGGCTTACCACAAAGTGTTGTGGAGCCCCAGGTGGAACGGTGAGCTGACTTACTTCCTCGGGGCCTGCCTCCCC
TGAGCGAAGCTACACCGCACTTCCGACAGCACACTCCACATTACTTATCGACATATGGAATGACACACTGACCTAGCGGTG
GCTTCTCCTACCGAGACAGCCCCAGGACCCTGAGAGGCAGAGTGTGGTATAGGGAAAAGGCTCCAGGCAGGAGACCTGTGTTCC
TGAGCTTGTCCAAGTCTCTTTCCCTGTCTGGGCCTCACTCTACCGAGTAATACAATGCAGGAGCTCAACCAAGGCCTCTGTGCCA
ATCCCAGCACTCCTTTCCAGGCCATGCTTCTTACCCCAGTGGCCTTTATTCACTCCTGACCACTTATCAAACCCATCGGTCCTAC
TGTTGGTATAACTGAGCTTGGACCTGACTATTAGAAAATGGTTTCTAACATTGAACTGAATGCCGCATCTGTATATTTTCCTGCT
CTGCCTTCTGGGACTAGCCTTTGGCCTAATCCTTCCTCTAGGAGAAGACCATTCAGGTTTGGGAGATGGCTCATAGCCAAGCCCC
TCTCTCTTAGTGTGATCCCTTGGAGCACCTTCATGCCTGGGGTTTCTCTCCCAAAAGCTTCTTGCAGTCTAAGCCTTTATCCTTA
TGTTCCCCATTAAAGGAATTTCAAAAGACATGGAGAAAGTTGGGAAGGTTTGTGCTGACTGCTGGGAGCAGAATAGCCGTGGGAG
GCCCACCAAGCCCTTAAATTCCCATTGTCAACTCAGAACACATTTGGGCCCATATGCCACCCTGGAACACCAGCTGACACCATGG
GCGTCCACACCTGCTGCTCCAGACAAGCACAAAGCAATCTTTCAGCCTTGAAATGTATTATCTGAAAGGCTACCTGAAGCCCAGG
CCCGAATATGGGGACTTAGTCGATTACCTGGAAAAAGAAAAGACCCACACTGTCTCTGCTGTTTTGGGCAGGAAAATGGAA
GAAAGAGTGGGGTGGGCACATTAGAAGTGCACCCAAATCCTGCCAGGCTGCCTGGCATCCCTGGGGCATGAGCTGGGCGGAGAATC
CACCCCGCAGGATGTTCAGAGGGACCCACTCCTTCATTTTTCAGAGTCAAAGGAATCAGAGGCTCACCCATGGCAGGCAGTGAAA
AGAGCCAGGAGTCCTGGGTTCTAGTCCCTGCTCTGCCCCAACTGGCTGTATAACCTTGAAAAATCATTTTCTTTGTCTGAGTC
TCTGGTTCTCCGTCAGCAACAGGCTGGCATAAGGTCCCCTGCAGGTTCCTTCAGCTGGAGCACTCAGAGCTTCCCTGACTGCTA
GCAGCCTCTCTGGCCCTCACAGGGCTGATTGTTCTCCTTCTCCCTGGAGCTCTCTCCTGAAAATCTCCATCAGAGCAAGGCAG
CCAGAGAAGCCCCTGAGAGGGAATGATTGGGAAGTGTCCACTTTCTCAACCGGCTCATCAAACACACTCCTTTGTCTATGAATGG

```
CACATGTAAATGATGTTATATTTTGTATCTTTTATATCATATGCTTCACCATTCTGTAAAGGGCCTCTGCATTGTTGCTCCCATC
AGGGGTCTCAAGTGGAAATAAACCCTCGTGGATAACCAAAAAAAAAAAAAAAAAAA

SEQ ID NO: 9 Protein sequence of human MASP-2:
MRLLTLLGLLCGSVATPLGPKWPEPVFGRLASPGFPGEYANDQERRWTLTAPPGYRLRLYFTHFDLELSHLCEYDFVKLSSGA
KVLATLCGQESTDTERAPGKDTFYSLGSSLDITFRSDYSNEKPFTGFEAFYAAEDIDECQVAPGEAPTCDHHCHNHLGGFYCS
CRAGYVLHRNKRTCSALCSGQVFTQRSGELSSPEYPRPYPKLSSCTYSISLEEGFSVILDFVESFDVETHPETLCPYDFLKIQ
TDREEHGPFCGKTLPHRIETKSNTVTITFVTDESGDHTGWKIHYTSTAQPCPYPMAPPNGHVSPVQAKYILKDSFSIFCETGY
ELLQGHLPLKSFTAVCQKDGSWDRPMPACSIVDCGPPDDLPSGRVEYITGPGVTTYKAVIQYSCEETFYTMKVNDGKYVCEAD
GFWTSSKGEKSLPVCEPVCGLSARTTGGRIYGGQKAKPGDFPWQVLILGGTTAAGALLYDNWVLTAAHAVYEQKHDASALDIR
MGTLKRLSPHYTQAWSEAVFIHEGYTHDAGFDNDIALIKLNNKVVINSNITPICLPRKEAESFMRTDDIGTASGWGLTQRGFL
ARNLMYVDIPIVDHQKCTAAYEKPPYPRGSVTANMLCAGLESGGKDSCRGDSGGALVFLDSETERWFVGGIVSWGSMNCGEAG
QYGVYTKVINYIPWIENIISDF SEQ ID NO: 10 cDNA sequence of human MASP-2:
GGCCAGCTGGACGGGCACACCATGAGGCTGCTGACCCTCCTGGGCCTTCTGTGTGGCTCGGTGGCCACCCCCTTGGGCCC
GAAGTGGCCTGAACCTGTGTTCGGGCGCCTGGCATCCCCCGGCTTTCCAGGGGAGTATGCCAATGACCAGGAGCGGCGCT
GGACCCTGACTGCACCCCCCGGCTACCGCCTGCGCCTCTACTTCACCCACTTCGACCTGGAGCTCTCCCACCTCTGCGAG
TACGACTTCGTCAAGCTGAGCTCGGGGGCCAAGGTGCTGGCCACGCTGTGCGGGCAGGAGAGCACAGACACGGAGCGGGC
CCCTGGCAAGGACACTTTCTACTCGCTGGGCTCCAGCCTGGACATTACCTTCCGCTCCGACTACTCCAACGAGAAGCCGT
TCACGGGGTTCGAGGCCTTCTATGCAGCCGAGGACATTGACGAGTGCCAGGTGGCCCCGGGAGAGGCGCCCACCTGCGAC
CACCACTGCCACAACCACCTGGGCGGTTTCTACTGCTCCTGCCGCGCAGGCTACGTCCTGCACCGTAACAAGCGCACCTG
CTCAGCCCTGTGCTCCGGCCAGGTCTTCACCCAGAGGTCTGGGGAGCTCAGCAGCCCTGAATACCCACGGCCGTATCCCA
AACTCTCCAGTTGCACTTACAGCATCAGCCTGGAGGAGGGGTTCAGTGTCATTCTGGACTTTGTGGAGTCCTTCGATGTG
GAGACACACCCTGAAACCCTGTGTCCCTACGACTTTCTCAAGATTCAAACAGACAGAGAAGAACATGGCCCATTCTGTGG
GAAGACATTGCCCCACAGGATTGAAACAAAAAGCAACACGGTGACCATCACCTTTGTCACAGATGAATCAGGAGACCACA
CAGGCTGGAAGATCCACTACACGAGCACAGCGCAGCCTTGCCCTTATCCGATGGCGCCACCTAATGGCCACGTTTCACCT
GTGCAAGCCAAATACATCCTGAAAGACAGCTTCTCCATCTTTTGCGAGACTGGCTATGAGCTTCTGCAAGGTCACTTGCC
CCTGAAATCCTTTACTGCAGTTTGTCAGAAAGATGGATCTTGGGACCGGCCAATGCCCGCGTGCAGCATTGTTGACTGTG
GCCCTCCTGATGATCTACCCAGTGGCCGAGTGGAGTACATCACAGGTCCTGGAGTCACCACCTACAAAGCTGTGATTCAG
TACAGCTGTGAAGAGACCTTCTACACAATGAAAGTGAATGATGGTAAATATGTGTGTGAGGCTGATGGATTCTGGACGAG
CTCCAAAGGAGAAAAATCACTCCCAGTCTGTGAGCCTGTTTGTGGACTATCAGCCCGCACAACAGGAGGGCTATATATG
GAGGGCAAAAGGCAAAACCTGGTGATTTTCCTTGGCAAGTCCTGATATTAGGTGGAACCACAGCAGCAGGTGCACTTTTA
TATGACAACTGGGTCCTAACAGCTGCTCATGCCGTCTATGAGCAAAAACATGATGCATCCGCCCTGGACATTCGAATGGG
CACCCTGAAAAGACTATCACCTCATTATACACAAGCCTGGTCTGAAGCTGTTTTTATACATGAAGGTTATACTCATGATG
CTGGCTTTGACAATGACATAGCACTGATTAAATTGAATAACAAAGTTGTAATCAATAGCAACATCACGCCTATTTGTCTG
CCAAGAAAAGAAGCTGAATCCTTTATGAGGACAGATGACATTGGAACTGCATCTGGATGGGGATTAACCCAAAGGGGTTT
TCTTGCTAGAAATCTAATGTATGTCGACATACCGATTGTTGACCATCAAAAGTGTACTGCTGCATATGAAAAGCCACCCT
ATCCAAGGGGAAGTGTAACTGCTAACATGCTTTGTGCTGGCTTAGAAAGTGGGGGCAAGGACAGCTGCAGAGGTGACAGC
GGAGGGGCACTGGTGTTCTAGATAGTGAAACAGAGAGGTGGTTTGTGGGAGGAATAGTGTCCTGGGGTTCCATGAATTG
TGGGGAAGCAGGTCAGTATGGAGTCTACACAAAAGTTATTAACTATATTCCCTGGATCGAGAACATAATTAGTGATTTTT
AACTTGCGTGTCTGCAGTCAAGGATTCTTCATTTTTAGAAATGCCTGTGAAGACCTTGGCAGCGACGTGGCTCGAGAAGC
ATTCATCATTACTGTGGACATGGCAGTTGTTGCTCCACCCAAAAAAACAGACTCCAGGTGAGGCTGCTGTCATTTCTCCA
CTTGCCAGTTTAATTCCAGCCTTACCCATTGACTCAAGGGGACATAAACCACGAGAGTGACAGTCATCTTTGCCCACCCA
GTGTAATGTCACTGCTCAAATTACATTTCATTACCTTAAAAAGCCAGTCTCTTTTCATACTGGCTGTTGGCATTTCTGTA
AACTGCCTGTCCATGCTCTTTGTTTTTAAACTTGTTCTTATTGAAAAAAAAAAAAAAAAA SEQ ID NO: 11 Protein sequence of human sMAP (MAp19):
MRLLTLLGLLCGSVATPLGPKWPEPVFGRLASPGFPGEYANDQERRWTLTAPPGYRLRLYFTHFDLELSHLCEYDFVKLSSGA
KVLATLCGQESTDTERAPGKDTFYSLGSSLDITFRSDYSNEKPFTGFEAFYAAEDIDECQVAPGEAPTCDHHCHNHLGGFYCS
CRAGYVLHRNKRTCSEQSL SEQ ID NO: 12 cDNA sequence of human sMAP (MAp19):
GGCCAGCTGGACGGGCACACCATGAGGCTGCTGACCCTCCTGGGCCTTCTGTGTGGCTCGGTGGCCACCCCCTTGGGCCCGAAGT
GGCCTGAACCTGTGTTCGGGCGCCTGGCATCCCCCGGCTTTCCAGGGGAGTATGCCAATGACCAGGAGCGGCGCTGGACCCTGAC
TGCACCCCCGGCTACCGCCTGCGCCTCTACTTCACCCACTTCGACCTGGAGCTCTCCCACCTCTGCGAGTACGACTTCGTCAAG
CTGAGCTCGGGGGCCAAGGTGCTGGCCACGCTGTGCGGGCAGGAGAGCACAGACACGGAGCGGGCCCCTGGCAAGGACACTTTCT
ACTCGCTGGGCTCCAGCCTGGACATTACCTTCCGCTCCGACTACTCCAACGAGAAGCCGTTCACGGGGTTCGAGGCCTTCTATGC
AGCCGAGGACATTGACGAGTGCCAGGTGGCCCCGGGAGAGGCGCCCACCTGCGACCACCACTGCCACAACCACCTGGGCGGTTTC
TACTGCTCCTGCCGCGCAGGCTACGTCCTGCACCGTAACAAGCGCACCTGCTCAGACAGAGCCTCTAGCCTCCCCTGGAGCTCC
GGCCTGCCCAGCAGGTCAGAAGCCAGAGCCAGCCTGCTGGCCTCAGCTCCGGGTTGGGCTGAGATGGCTGTGCCCCAACTCCCAT
TCACCCACCATGGACCCAATAATAAACCTGGCCCCACCCCAAAAAAAAAAAAAAAAAAA
```

DNA Primers:

```
SEQ ID NO: 13: 5'-gcacccagagccacagtg-3'

SEQ ID NO: 14: 5'-gccttccagtgtgtgggc-3'

SEQ ID NO: 15: 5-gccttccagagtgtggtca-3'

SEQ ID NO: 16: 5'-cgatctggagagcgaactc-3'
```

-continued

SEQ ID NO: 17: 5'-ctgttcttcacactggctg-3'

SEQ ID NO: 18: 5'-ctgctgagatcatgttgttc-3'

SEQ ID NO: 19: 5'-TTATACGACTCACTA-3'

SEQ ID NO: 20 (Amino acid sequence of human Factor H):
MRLLAKIICLMLWAICVAEDCNELPPRRNTEILTGSWSDQTYPEGTQAIYKCRPGYRSLGNVIMVCRKGEWVALNPLRKCQKR
PCGHPGDTPFGTFTLTGGNVFEYGVKAVYTCNEGYQLLGEINYRECDTDGWTNDIPICEVVKCLPVTAPENGKIVSSAMEPDR
EYHFGQAVRFVCNSGYKIEGDEEMHCSDDGFWSKEKPKCVEISCKSPDVINGSPISQKIIYKENERFQYKCNMGYEYSERGDA
VCTESGWRPLPSCEEKSCDNPYIPNGDYSPLRIKHRTGDEITYQCRNGFYPATRGNTAKCTSTGWIPAPRCTLKPCDYPDIKH
GGLYHENMRRPYFPVAVGKYYSYYCDEHFETPSGSYWDHIHCTQDGWSPAVPCLRKCYFPYLENGYNQNHGRKFVQGKSIDVA
CHPGYALPKAQTTVTCMENGWSPTPRCIRVKTCSKSSIDIENGFISESQYTYALKEKAKYQCKLGYVTADGETSGSIRCGKDG
WSAQPTCIKSCDIPVFMNARTKNDFTWFKLNDTLDYECHDGYESNTGSTTGSIVCGYNGWSDLPICYERECELPKIDVHLVPD
RKKDQYKVGEVLKFSCKPGFTIVGPNSVQCYHFGLSPDLPICKEQVQSCGPPPELLNGNVKEKTKEEYGHSEVVEYYCNPRFL
MKGPNKIQCVDGEWTTLPVCIVEESTCGDIPELEHGWAQLSSPPYYYGDSVEFNCSESFTMIGHRSITCIHGVWTQLPQCVAI
DKLKKCKSSNLIILEEHLKNKKEFDHNSNIRYRCRGKEGWIHTVCINGRWDPEVNCSMAQIQLCPPPPQIPNSHNMTTTLNYR
DGEKVSVLCQENYLIQEGEEITCKDGRWQSIPLCVEKIPCSQPPQIEHGTINSSRSSQESYAHGTKLSYTCEGGFRISEENET
TCYMGKWSSPPQCEGLPCKSPPEISHGVVAHMSDSYQYGEEVTYKCFEGFGIDGPAIAKCLGEKWSHPPSCIKTDCLSLPSFE
NAIPMGEKKDVYKAGEQVTYTCATYYKMDGASNVTCINSRWTGRPTCRDTSCVNPPTVQNAYIVSRQMSKYPSGERVRYQCRS
PYEMFGDEEVMCLNGNWTEPPQCKDSTGKCGPPPPIDNGDITSFPLSVYAPASSVEYQCQNLYQLEGNKRITCRNGQWSEPPK
CLHPCVISREIMENYNIALRWTAKQKLYSRTGESVEFVCKRGYRLSSRSHTLRTTCWDGKLEYPTCAKR SEQ ID NO: 21 (Amino acid sequence of human C4bp alfa):
MHPPKTPSGALHRKRKMAAWPFSRLWKVSDPILFQMTLIAALLPAVLGNCGPPPTLSFAAPMDITLTETRFKTGTTLKYTCLP
GYVRSHSTQTLTCNSDGEWVYNTFCIYKRCRHPGELRNGQVEIKTDLSFGSQIEFSCSEGFFLIGSTTSRCEVQDRGVGWSHP
LPQCEIVKCKPPPDIRNGRHSGEENFYAYGFSVTYSCDPRFSLLGHASISCTVENETIGVWRPSPPTCEKITCRKPDVSHGEM
VSGFGPIYNYKDTIVFKCQKGFVLRGSSVIHCDADSKWNPSPPACEPNSCINLPDIPHASWETYPRPTKEDVYVGTVLRYRC
HPGYKPTTDEPTTVICQKNLRWTPYQGCEALCCPEPKLNNGEITQHRKSRPANHCVYFYGDEISFSCHETSRFSAICQGDGTW
SPRTPSCGDICNFPPKIAHGHYKQSSSYSFFKEEIIYECDKGYILVGQAKLSCSYSHWSAPAPQCKALCRKPELVNGRLSVDK
DQYVEPENVTIQCDSGYGVVGPQSITCSGNRTWYPEVPKCEWETPEGCEQVLTGKRLMQCLPNPEDVKMALEVYKLSLEIEQL
ELQRDSARQSTLDKEL SEQ ID NO: 22 (Amino acid sequence of human C4bp beta):
MFFWCACCLMVAWRVSASDAEHCPELPPVDNSIFVAKEVEGQILGTYVCIKGYHLVGKKTLFCNASKEWDNTTTECRLGHCPD
PVLVNGEFSSSGPVNVSDKITFMCNDHYILKGSNRSQCLEDHTWAPPFPICKSRDCDPPGNPVHGYFEGNNFTLGSTISYYCE
DRYYLVGVQEQQCVDGEWSSALPVCKLIQEAPKPECEKALLAFQESKNLCEAMENFMQQLKESGMTEELKYSLELKKAELKA
KLL SEQ ID NO: 23 (Amino acid sequence of human FI):
MKLLHVFLLFLCFHLRFCKVTYTSQEDLVEKKCLAKKYTHLSCDKVFCQPWQRCIEGTCVCKLPYQCPKNGTAVCATNRRSFP
TYCQQKSLECLHPGTKFLNNGTCTAEGKFSVSLKHGNTDSEGIVEVKLVDQDKTMFICKSSWSMREANVACLDLGFQQGADTQ
RRFKLSDLSINSTECLHVHCRGLETSLAECTFTKRRTMGYQDFADVVCYTQKADSPMDDFFQCVNGKYISQMKACDGINDCGD
QSDELCCKACQGKGFHCKSGVCIPSQYQCNGEVDCITGEDEVGCAGFASVAQEETEILTADMDAERRRIKSLLPKLSCGVKNR
MHIRRKRIVGGKRAQLGDLPWQVAIKDASGITCGGIYIGGCWILTAAHCLRASKTHRYQIWTTVVDWIHPDLKRIVIEYVDRI
IFHENYNAGTYQNDIALIEMKKDGNKKDCELPRSIPACVPWSPYLFQPNDTCIVSGWGREKDNERVFSLQWGEVKLISNCSKF
YGNRFYEKEMECAGTYDGSIDACKGDSGGPLVCMDANNVTYVWGVVSWGENCGKPEFPGVYTKVANYFDWISYHVGRPFISQY
NV SEQ ID NO: 24 (Amino acid sequence of human C1-inh):
MASRLTLLTLLLLLLAGDRASSNPNATSSSSQDPESLQDRGEGKVATTVISKMLFVEPILEVSSLPTTNSTTNSATKITANTT
DEPTTQPTTEPTTQPTIQPTQPTTQLPTDSPTQPTTGSFCPGPVTLCSDLESHSTEAVLGDALVDFSLKLYHAFSAMKKVETN
MAFSPFSIASLLTQVLLGAGENTKTNLESILSYPKDFTCVHQALKGFTTKGVTSVSQIFHSPDLAIRDTFVNASRTLYSSSPR
VLSNNSDANLELINTWVAKNTNNKISRLLDSLPSDTRLVLLNAIYLSAKWKTTFDPKKTRMEPFHFKNSVIKVPMMNSKKYPV
AHFIDQTLKAKVGQLQLSHNLSLVILVPQNLKHRLEDMEQALSPSVFKAIMEKLEMSKFQPTLLTLPRIKVTTSQDMLSIMEK
LEFFDFSYDLNLCGLTEDPDLQVSAMQHQTVLELTETGVEAAAASAISVARTLLVFEVQQPFLFVLWDQQHKFPVFMGRVYDP
RA SEQ ID NO: 25 (Amino acid sequence of human MAP1/FH):
HTVELNNMFGQIQSPGYPDSYPSDSEVTWNITVPDGFRIKLYFMHFNLESSYLCEYDYVKVETEDQVLATFCGRETTDT
EQTPGQEVVLSPGSFMSITFRSDFSNEERFTGFDAHYMAVDVDECKEREDEELSCDHYCHNYIGGYYCSCRFGYILHTD
NRTCRVECSDNLFTQRTGVITSPDFPNPYPKSSECLYTIELEEGFMVNLQFEDIFDIEDHPEVPCPYDYIKIKVGPKVL
GPFCGEKAPEPISTQSHSVLILFHSDNSGENRGWRLSYRAAGNECPELQPPVHGLEPSQAKYFFKDQVLVSCDTGKYV
LKDNVEMDTFQIECLKDGTWSNKIPTCKKNEIDLESELKSEQVTEGGGSGGGGSCVAEDCNELPPRRNTEILTGSWSD
QTYPEGTQAIYKCRPGYRSLGNVIMVCRKGEWVALNPLRKCQKRPCGHPGDTPFGTFTLTGGNVFEYGVKAVYTCNEGY
QLLGEINYRECDTDGWTNDIPICEVVKCLPVTAPENGKIVSSAMEPDREYHFGQAVRFVCNSGYKIEGDEEMHCSDDGF
WSKEKPKCVEISCKSPDVINGSPISQKIIYKENERFQYKCNMGYEYSERGDAVCTESGWRPLPSCEEKSCDNPYIPNGD
YSPLRIKHRTGDEITYQCRNGFYPATRGNTAKCTSTGWIPAPRCTLKP SEQ ID NO: 26 (Nucleic acid sequence of human MAP-1/FH):
CACACCGTGGAGCTAAACAATATGTTTGGCCAGATCCAGTCGCCTGGTTATCCAGACTCCTATCCCAGTGATTCAGAGG
TGACTTGGAATATCACTGTCCCAGATGGGTTTCGGATCAAGCTTTACTTCATGCACTTCAACTTGGAATCCTCCTACCT
TTGTGAATATGACTATGTGAAGGTAGAAACTGAGGACCAGGTGCTGGCAACCTTCTGTGGCAGGGAGACCACAGACACA
GAGCAGACTCCCGGCCAGGAGGTGGTCCTCTCCCTGGCTCCTTCATGTCCATCACTTTCCGGTCAGATTTCTCCAATG
AGGAGCGTTTCACAGGCTTTGATGCCCACTACATGGCTGTGGATGTGGACGAGTGCAAGGAGAGGGAGGACGAGGAGCT
GTCCTGTGACCACTACTGCCACAACTACATTGGCGGCTACTACTGCTCCTGCCGCTTCGGCTACATCCTCCACACAGAC
AACAGGACCTGCCGAGTGGAGTGCAGTGACAACCTCTTCACTCAAAGGACTGGGGTGATCACCAGCCCTGACTTCCCAA
ACCCTTACCCCAAGAGCTCTGAATGCCTGTATACCATCGAGCTGGAGGAGGGTTTCATGGTCAACCTGCAGTTTGAGGA
CATATTTGACATTGAGGACCATCCTGAGGTGCCCTGCCCCTATGACTACATCAAGATCAAAGTTGGTCCAAAAGTTTTG

```
GGGCCTTTCTGTGGAGAGAAAGCCCCAGAACCCATCAGCACCCAGAGCCACAGTGTCCTGATCCTGTTCCATAGTGACA
ACTCGGGAGAGAACCGGGGCTGGAGGCTCTCATACAGGGCTGCAGGAAATGAGTGCCCAGAGCTACAGCCTCCTGTCCA
TGGGAAAATCGAGCCCTCCCAAGCCAAGTATTTCTTCAAAGACCAAGTGCTCGTCAGCTGTGACACAGGCTACAAAGTG
CTGAAGGATAATGTGGAGATGGACACATTCCAGATTGAGTGTCTGAAGGATGGGACGTGGAGTAACAAGATTCCCACCT
GTAAAAAAAATGAAATCGATCTGGAGAGCGAACTCAAGTCAGAGCAAGTGACAGAGGGCGGAGGTGGGTCGGGTGGCGG
CGGATCTTGTGTAGCAGAAGATTGCAATGAACTTCCTCCAAGAAGAAATACAGAAATTCTGACAGGTTCCTGGTCTGAC
CAAACATATCCAGAAGGCACCCAGGCTATCTATAAATGCCGCCCTGGATATAGATCTCTTGGAAATGTAATAATGGTAT
GCAGGAAGGGAGAATGGGTTGCTCTTAATCCATTAAGGAAATGTCAGAAAAGGCCCTGTGGACATCCTGGAGATACTCC
TTTTGGTACTTTTACCCTTACAGGAGGAAATGTGTTTGAATATGGTGTAAAAGCTGTGTATACATGTAATGAGGGGTAT
CAATTGCTAGGTGAGATTAATTACCGTGAATGTGACACAGATGGATGGACCAATGATATTCCTATATGTGAAGTTGTGA
AGTGTTTACCAGTGACAGCACCAGAGAATGGAAAATTGTCAGTAGTGCAATGGAACCAGATCGGGAATACCATTTTGGG
ACAAGCAGTACGGTTTGTATGTAACTCAGGCTACAAGATTGAAGGAGATGAAGAAATGCATTGTTCAGACGATGGTTTT
TGGAGTAAAGAGAAACCAAAGTGTGTGGAAATTTCATGCAAATCCCCAGATGTTATAAATGGATCTCCTATATCTCAGA
AGATTATTTATAAGGAGAATGAACGATTTCAATATAAATGTAACATGGGTTATGAATACAGTGAAAGAGGAGATGCTGT
ATGCACTGAATCTGGATGGCGTCCGTTGCCTTCATGTGAAGAAAATCATGTGATAATCCTTATATTCCAAATGGTGAC
TACTCACCTTTAAGGATTAAACACAGAACTGGAGATGAAATCACGTACCAGTGTAGAAATGGTTTTTATCCTGCAACCC
GGGGAAATACAGCAAATGCACAAGTACTGGCTGGATACCTGCTCCGAGATGTACCT

SEQ ID NO: 27 (Amino acid sequence of human FH/MAP-1):
CVAEDCNELPPRRNTEILTGSWSDQTYPEGTQAIYKCRPGYRSLGNVIMVCRKGEWVALNPLRKCQKRPCGHPGDTPFG
TFTLTGGNVFEYGVKAVYTCNEGYQLLGEINYRECDTDGWTNDIPICEVVKCLPVTAPENGKIVSSAMEPDREYHFGQA
VRFVCNSGYKIEGDEEMHCSDDGFWSKEKPKCVEISCKSPDVINGSPISQKIIYKENERFQYKCNMGYEYSERGDAVCT
ESGWRPLPSCEEKSCDNPYIPNGDYSPLRIKHRTGDEITYQCRNGFYPATRGNTAKCTSTGWIPAPRCTLKPGGGGSGG
GGSHTVELNNMFGQIQSPGYPDSYPSDSEVTWNITVPDGFRIKLYFMHFNLESSYLCEYDYVKVETEDQVLATFCGRET
TDTEQTPGQEVVLSPGSFMSITFRSDFSNEERFTGFDAHYMAVDVDECKEREDEELSCDHYCHNYIGGYYCSCRFGYIL
HTDNRTCRVECSDNLFTQRTGVITSPDFPNPYPKSSECLYTIELEEGFMVNLQFEDIFDIEDHPEVPCPYDYIKIKVGP
KVLGPFCGEKAPEPISTQSHSVLILFHSDNSGENRGWRLSYRAAGNECPELQPPVHGKIEPSQAKYFFKDQVLVSCDTG
YKVLKDNVEMDTFQIECLKDGTWSNKIPTCKKNEIDLESELKSEQVTE SEQ ID NO: 28 (Nucleic acid sequence of human FH/MAP-1):
TGTGTAGCAGAAGATTGCAATGAACTTCCTCCAAGAAGAAATACAGAAATTCTGACAGGTTCCTGGTCTGACCAAACAT
ATCCAGAAGGCACCCAGGCTATCTATAAATGCCGCCCTGGATATAGATCTCTTGGAAATGTAATAATGGTATGCAGGAA
GGGAGAATGGGTTGCTCTTAATCCATTAAGGAAATGTCAGAAAAGGCCCTGTGGACATCCTGGAGATACTCCTTTTGGT
ACTTTTACCCTTACAGGAGGAAATGTGTTTGAATATGGTGTAAAAGCTGTGTATACATGTAATGAGGGGTATCAATTGC
TAGGTGAGATTAATTACCGTGAATGTGACACAGATGGATGGACCAATGATATTCCTATATGTGAAGTTGTGAAGTGTTT
ACCAGTGACAGCACCAGAGAATGGAAAATTGTCAGTAGTGCAATGGAACCAGATCGGGAATACCATTTTGGGACAAGCA
GTACGGTTTGTATGTAACTCAGGCTACAAGATTGAAGGAGATGAAGAAATGCATTGTTCAGACGATGGTTTTTGGAGTA
AAGAGAAACCAAAGTGTGTGGAAATTTCATGCAAATCCCCAGATGTTATAAATGGATCTCCTATATCTCAGAAGATTAT
TTATAAGGAGAATGAACGATTTCAATATAAATGTAACATGGGTTATGAATACAGTGAAAGAGGAGATGCTGTATGCACT
GAATCTGGATGGCGTCCGTTGCCTTCATGTGAAGAAAATCATGTGATAATCCTTATATTCCAAATGGTGACTACTCAC
CTTTAAGGATTAAACACAGAACTGGAGATGAAATCACGTACCAGTGTAGAAATGGTTTTTATCCTGCAACCCGGGGAAA
TACAGCAAATGCACAAGTACTGGCTGGATACCTGCTCCGAGATGTACCTGCGCAGGTGGGTCGGGTGGCGGCGGATC
TCACACCGTGGAGCTAAACAATATGTTTGGCCAGATCCAGTCGCCTGGTTATCCAGACTCCTATCCCAGTGATTCAGAG
GTGACTTGGAATATCACTGTCCCAGATGGGTTTCGGATCAAGCTTTACTTCATGCACTTCAACTTTGGAATCCTCCTACC
TTTGTGAATATGACTATGTGAAGGTAGAAACTGAGGACCAGGTGCTGGCAACCTTCTGTGGCAGGGAGACCACAGACAC
AGAGCAGACTCCCGGCCAGGAGGTGGTCCTCTCCCCTGGCTCCTTCATGTCCATCACTTTCCGGTCAGATTTCTCCAAT
GAGGAGCGTTTCACAGGCTTTGATGCCCACTACATGGCTGTGGATGTGGACGAGTGCAAGGAGAGGGAGGACGAGGAGC
TGTCCTGTGACCACTACTGCCACAACTACATTGGCGGCTACTACTGCTCCTGCCGCTTCGGCTACATCCTCCACGACAGA
CAACAGGACCTGCCGAGTGGAGTGCAGTGACAACCTCTTCACTCAAAGGACTGGGGTGATCACCAGCCCTGACTTCCCA
AACCCTTACCCCAAGAGCTCTGAATGCCTGTATACCATCGAGCTGGAGGAGGGTTTCATGGTCAACCTGCAGTTTGAGG
ACATATTTGACATTGAGGACCATCCTGAGGTGCCCTGCCCCTATGACTACATCAAGATCAAAGTTGGTCCAAAAGTTTT
GGGGCCTTTCTGTGGAGAGAAAGCCCCAGAACCCATCAGCACCCAGAGCCACAGTGTCCTGATCCTGTTCCATAGTGAC
AACTCGGGAGAGAACCGGGGCTGGAGGCTCTCATACAGGGCTGCAGGAAATGAGTGCCCAGAGCTACAGCCTCCTGTCC
ATGGGAAAATCGAGCCCTCCCAAGCCAAGTATTTCTTCAAAGACCAAGTGCTCGTCAGCTGTGACACAGGCTACAAAGT
GCTGAAGGATAATGTGGAGATGGACACATTCCAGATTGAGTGTCTGAAGGATGGGACGTGGAGTAACAAGATTCCCACC
TGTAAAAAAAATGAAATCGATCTGGAGAGCGAACTCAAGTCAGAGCAAGTGACAGAG SEQ ID NO: 29 (Amino acid sequence of human MAP-1: CUB1, EGF; CUB2, CCP1, without
unique 17 amino acids):
MRWLLLYYALCFSLSKASAHTVELNNMFGQIQSPGYPDSYPSDSEVTWNITVPDGFRIKLYFMHFNLESSYLCEYDYVK
VETEDQVLATFCGRETTDTEQTPGQEVVLSPGSFMSITFRSDFSNEERFTGFDAHYMAVDVDECKEREDEELSCDHYCH
NYIGGYYCSCRFGYILHTDNRTCRVECSDNLFTQRTGVITSPDFPNPYPKSSECLYTIELEEGFMVNLQFEDIFDIEDH
PEVPCPYDYIKIKVGPKVLGPFCGEKAPEPISTQSHSVLILFHSDNSGENRGWRLSYRAAGNECPELQPPVHGKIEPSQ
AKYFFKDQVLVSCDTGYKVLKDNVEMDTFQIECLKDGTWSNKIPTCK SEQ ID NO: 30 (Amino acid sequence of human MAP-1: CUB1, EGF, CUB2):
WLLLYYALCFSLSKASAHTVELNNMFGQIQSPGYPDSYPSDSEVTWNITVPDGFRIKLYFMHFNLESSYLCEYDYVKVE
TEDQVLATFCGRETTDTEQTPGQEVVLSPGSFMSITFRSDFSNEERFTGFDAHYMAVDVDECKEREDEELSCDHYCHNY
IGGYYCSCRFGYILHTDNRTCRVECSDNLFTQRTGVITSPDFPNPYPKSSECLYTIELEEGFMVNLQFEDIFDIEDHPE
VPCPYDYIKIKVGPKVLGPFCGEKAPEPISTQSHSVLILFHSDNSGENRGWRLSYRAA SEQ ID NO: 31 (Amino acid sequence of human MAP-1: CUB2, CCP1):
VECSDNLFTQRTGVITSPDFPNPYPKSSECLYTIELEEGFMVNLQFEDIFDIEDHPEVPCPYDYIKIKVGPKVLGPFCG
EKAPEPISTQSHSVLILFHSDNSGENRGWRLSYRAAGNECPELQPPVHGKIEPSQAKYFFKDQVLVSCDTGYKVLKDNV
EMDTFQIECLKDGTWSNKIPTCKKNEIDLESELKSEQVTE SEQ ID NO: 32 (Amino acid sequence of human FH, SCR 1-4):
MRLLAKIICLMLWAICVAEDCNELPPRRNTEILTGSWSDQTYPEGTQATYKCRPGYRSLGNVIMVCRKGEWVALNPLRK
CQKRPCGHPGDTPFGTFTLTGGNVFEYGVKAVYTCNEGYQLLGEINYRECDTDGWTNDIPICEVVKCLPVTAPENGKIV
```

```
SSAMEPDREYHFGQAVRFVCNSGYKIEGDEEMHCSDDGFWSKEKPKCVEISCKSPDVINGSPISQKITYKENERFQYKC
NMGYEYSERGDAVCTESGWRPLPSCEE

SEQ ID NO: 33 (Amino acid sequence of human FH, SCR 7-20):
RKCYFPYLENGYNQNHGRKFVQGKSIDVACHPGYALPKAQTTVTCMENGWSPTPRCIRVKTCSKSSIDIENGFISESQY
TYALKEKAKYQCKLGYVTADGETSGSIRCGKDGWSAQPTCIKSCDIPVFMNARTKNDFTWFKLNDTLDYECHDGYESNT
GSTTGSIVCGYNGWSDLPICYERECELPKIDVHLVPDRKKDQYKVGEVLKFSCKPGFTIVGPNSVQCYHFGLSPDLPIC
KEQVQSCGPPPELLNGNVKEKTKEEYGHSEVVEYYCNPRFLMKGPNKIQCVDGEWTTLPVCIVEESTCGDIPELEHGWA
QLSSPPYYYGDSVEFNCSESFTMIGHRSITCIHGVWTQLPQCVAIDKLKKCKSSNLIILEEHLKNKKEFDHNSNIRYRC
RGKEGWIHTVCINGRWDPEVNCSMAQIQLCPPPPQIPNSHNMTTTLNYRDGEKVSVLCQENYLIQEGEEITCKDGRWQS
IPLCVEKIPCSQPPQIEHGTINSSRSSQESYAHGTKLSYTCEGGFRISEENETTCYMGKWSSPPQCEGLPCKSPPEISH
GVVAHMSDSYQYGEEVTYKCFEGFGIDGPAIAKCLGEKWSHPPSCIKTDCLSLPSFENAIPMGEKKDVYKAGEQVTYTC
ATYYKMDGASNVTCINSRWTGRPTCRDTSCVNPPTVQNAYIVSRQMSKYPSGERVRYQCRSPYEMFGDEEVMCLNGNWT
EPPQCKDSTGKCGPPPPIDNGDITSFPLSVYAPASSVEYQCQNLYQLEGNKRITCRNGQWSEPPKCLHPCVISREIMEN
YNIALRWTAKQKLYSRTGESVEFVCKRGYRLSSRSHTLRTTCWDGKLEYPTCAKR SEQ ID NO: 34 (Amino acid sequence of human FH, SCR 7-14):
KTCSKSSIDIENGFISESQYTYALKEKAKYQCKLGYVTADGETSGSIRCGKDGWSAQPTCIKSCDIPVFMNARTKNDFT
WFKLNDTLDYECHDGYESNTGSTTGSIVCGYNGWSDLPICYERECELPKIDVHLVPDRKKDQYKVGEVLKFSCKPGFTI
VGPNSVQCYHFGLSPDLPICKEQVQSCGPPPELLNGNVKEKTKEEYGHSEVVEYYCNPRFLMKGPNKIQCVDGEWTTLP
VCIVEESTCGDIPELEHGWAQLSSPPYYYGDSVEFNCSESFTMIGHRSITCIHGVWTQLPQCVAIDKLKKCKSSNLIIL
EEHLKNKKEFDHNSNIRYRCRGKEGWIHTVCINGRWDPEVNCSMAQIQLCPPPPQIPNSHNMTTTLNYRDGEKVSVLCQ
ENYLIQEGEEITCKDGRWQSIPLCVEKIPCSQPPQIEHGTINSSRSSQESYAHGTKLSYTCEGGFRISEENETTCYMGK
WSSPPQCEG SEQ ID NO: 35 (Amino acid sequence of human FH, SCR 12-14):
ESTCGDIPELEHGWAQLSSPPYYYGDSVEFNCSESFTMIGHRSITCIHGVWTQLPQCVAIDKLKKCKSSNLIILEEHLK
NKKEFDHNSNIRYRCRGKEGWIHTVCINGRWDPEVNCSMAQIQLCPPPPQIPNSHNMTTTLNYRDGEKVSVLCQENYLI
QEGEEITCKDGRWQSIPLCVEK SEQ ID NO: 36 (Amino acid sequence of human FH, SCR 19-20):
TGKCGPPPPIDNGDITSFPLSVYAPASSVEYQCQNLYQLEGNKRITCRNGQWSEPPKCLHPCVISREIMENYNIALRWT
AKQKLYSRTGESVEFVCKRGYRLSSRSHTLRTTCWDGKLEYPTCAKR SEQ ID NO: 37 (Amino acid sequence of human C4bp, alfa chain, SCR 1-3):
NCGPPPTLSFAAPMDITLTETRFKTGTTLKYTCLPGYVRSHSTQTLTCNSDGEWVYNTFCIYKRCRHPGELRNGQVEIK
TDLSFGSQIEFSCSEGFFLIGSTTSRCEVQDRGVGWSHPLPQCEIVKCKPPPDIRNGRHSGEENFYAYGFSVTYSCDPR
FSLLGHASISCTVENETIGVWRPSPPTCEK SEQ ID NO: 38 (Amino acid sequence of human C4bp, alfa chain, SCR 1-3 + beta chain, SCR
2):
NCGPPPTLSFAAPMDITLTETRFKTGTTLKYTCLPGYVRSHSTQTLTCNSDGEWVYNTFCIYKRCRHPGELRNGQVEIK
TDLSFGSQIEFSCSEGFFLIGSTTSRCEVQDRGVGWSHPLPQCEIVKCKPPPDIRNGRHSGEENFYAYGFSVTYSCDPR
FSLLGHASISCTVENETIGVWRPSPPTCEKGHCPDPVLVNGEFSSSGPVNVSDKITFMCNDHYILKGSNRSQCLEDHTW
APPFPICKS SEQ ID NO: 39 (Amino acid sequence of human C4bp, alfa chain, SCR 1-3 + beta chain,
SCR 1-2):

NCGPPPTLSFAAPMDITLTETRFKTGTTLKYTCLPGYVRSHSTQTLTCNSDGEWVYNTFCIYKRCRHPGELRNGQVEIK
TDLSFGSQIEFSCSEGFFLIGSTTSRCEVQDRGVGWSHPLPQCEIVKCKPPPDIRNGRHSGEENFYAYGFSVTYSCDPR
FSLLGHASISCTVENETIGVWRPSPPTCEKEHCPELPPVDNSIFVAKEVEGQILGTYVCIKGYHLVGKKTLFCNASKEW
DNTTTECRLGHCPDPVLVNGEFSSSGPVNVSDKITFMCNDHYILKGSNRSQCLEDHTWAPPFPICKS

SEQ ID NO: 40 (Amino acid sequence of human C4bp, alfa chain, SCR 1-8 + beta chain,
SCR 1-3):
NCGPPPTLSFAAPMDITLTETRFKTGTTLKYTCLPGYVRSHSTQTLTCNSDGEWVYNTFCIYKRCRHPGELRNGQVEIK
TDLSFGSQIEFSCSEGFFLIGSTTSRCEVQDRGVGWSHPLPQCEIVKCKPPPDIRNGRHSGEENFYAYGFSVTYSCDPR
FSLLGHASISCTVENETIGVWRPSPPTCEKITCRKPDVSHGEMVSGFGPIYNYKDTIVFKCQKGFVLRGSSVIHCDADS
KWNPSPPACEPNSCINLPDIPHASWETYPRPTKEDVYVVGTVLRYRCHPGYKPTTDEPTTVICQKNLRWTPYQGCEALC
CPEPKLNNGEITQHRKSRPANHCVYFYGDEISFSCHETSFSAICQDGEWSPRTPSCGDICNFPPKIAHGHYKQSSSY
SFFKEEIIYECDKGYILVGQAKLSCSYSHWSAPAPQCKALCRKPELVNGRLSVDKDQYVEPENVTIQCDSGYGVVGPQS
ITCSGNRTWYPEVPKCEWEHCPELPPVDNSIFVAKEVEGQILGTYVCIKGYHLVGKKTLFCNASKEWDNTTTECRLGHC
PDPVLVNGEFSSSGPVNVSDKITFMCNDHYILKGSNRSQCLEDHTWAPPFPICKSRDCDPPGNPVHGYFEGNNFTLGST
ISYYCEDRYYLVGVQEQQCVDGEWSSALPVCKL SEQ ID NO: 41 (Amino acid sequence of human FI, SRCR, LDLRa1, LDLRb1, SP):
KFSVSLKHGNTDSEGIVEVKLVDQDKTMFICKSSWSMREANVACLDLGFQQGADTQRRFKLSDLSINSTECLHVHCRGL
ETSLAECTFTKRRTMGYQDFADVVCYTQKADSPMDDFFQCVNGKYISQMKACDGINDCGDQSDELCCKACQGKGFHCKS
GVCIPSQYQCNGEVDCITGEDEVGCAGFASVAQEETEILTADMDAERRRIKSLLPKLSCGVKNRMHIRRKRIVGGKRAQ
LGDLPWQVAIKDASGITCGGIYIGGCWILTAAHCLRASKTHRYQIWTTVVDWIHPDLKRIVIEYVDRIIFHENYNAGTY
QNDIALIEMKKDGNKKDCELPRSIPACVPWSPYLFQPNDTCIVSGWGREKDNERVFSLQWGEVKLISNCSKFYGNRFYE
KEMECAGTYDGSIDACKGDSGGPLVCMDANNVTYVWGVVSWGENCGKPEFPGVYTKVANYFDWISYHVGRPFISQYNV SEQ ID NO: 42 (Amino acid sequence of human FI, LDLRa1, LDLRb1, SP):
KADSPMDDFFQCVNGKYI SQMKACDGINDCGDQSDELCCKACQGKGFHCKSGVCIPSQYQCNGEVDCITGEDEVGCAGF
ASVAQEETEILTADMDAERRRIKSLLPKLSCGVKNRMHIRRKRIVGGKRAQLGDLPWQVAIKDASGITCGGIYIGGCWI
```

LTAAHCLRASKTHRYQIWTTVVDWIHPDLKRIVIEYVDRIIFHENYNAGTYQNDIALIEMKKDGNKKDCELPRSIPACV
PWSPYLFQPNDTCIVSGWGREKDNERVFSLQWGEVKLISNCSKFYGNRFYEKEMECAGTYDGSIDACKGDSGGPLVCMD
ANNVTYVWGVVSWGENCGKPEFPGVYTKVANYFDWISYHVGRPFISQYNV

SEQ ID NO: 43 (Amino acid sequence of human FI, LDLRb1, SP):
KACQGKGFHCKSGVCIPSQYQCNGEVDCITGEDEVGCAGFASVAQEETEILTADMDAERRRIKSLLPKLSCGVKNRMHI
RRKRIVGGKRAQLGDLPWQVAIKDASGITCGGIYIGGCWILTAAHCLRASKTHRYQIWTTVVDWIHPDLKRIVIEYVDR
IIFHENYNAGTYQNDIALIEMKKDGNKKDCELPRSIPACVPWSPYLFQPNDTCIVSGWGREKDNERVFSLQWGEVKLIS
NCSKFYGNRFYEKEMECAGTYDGSIDACKGDSGGPLVCMDANNVTYVWGVVSWGENCGKPEFPGVYTKVANYFDWISYH
VGRPFISQYNV SEQ ID NO: 44 (Amino acid sequence of human FI, SP):
VAQEETEILTADMDAERRRIKSLLPKLSCGVKNRMHIRRKRIVGGKRAQLGDLPWQVAIKDASGITCGGIYIGGCWILT
AAHCLRASKTHRYQIWTTVVDWIHPDLKRIVIEYVDRIIFHENYNAGTYQNDIALIEMKKDGNKKDCELPRSIPACVPW
SPYLFQPNDTCIVSGWGREKDNERVFSLQWGEVKLISNCSKFYGNRFYEKEMECAGTYDGSIDACKGDSGGPLVCMDAN
NVTYVWGVVSWGENCGKPEFPGVYTKVANYFDWISYHVGRPFISQYNV SEQ ID NO: 45 (Amino acid sequence of human C1-inh, serpin domain):
HSTEAVLGDALVDFSLKLYHAFSAMKKVETNMAFSPFSIASLLTQVLLGAGENTKTNLESILSYPKDFTCVHQALKGFT
TKGVTSVSQIFHSPDLAIRDTFVNASRTLYSSSPRVLSNNSDANLELINTWVAKNTNNKISRLLDSLPSDTRLVLLNAI
YLSAKWKTTFDPKKTRMEPFHFKNSVIKVPMMNSKKYPVAHFIDQTLKAKVGQLQLSHNLSLVILVPQNLKHRLEDMEQ
ALSPSVFKAIMEKLEMSKFQPTLLTLPRIKVTTSQDMLSIMEKLEFFDFSYDLNLCGLTEDPDLQVSAMQHQTVLELTE
TGVEAAAASAISVARTLLVFEVQQPFLFVLWDQQHKFPVFMGRVYDPRA Amino acid sequence of human GAS6 growth arrest-specific 6, transcript variant 1
(SEQ ID NO 46)
MAPSLSPGPAALRRAPQLLLLLLAAECALAALLPAREATQFLRPRQRRAFQVFEEAKQGHLERECVEELCSR
EEAREVFENDPETDYFYPRYLDCINKYGSPYTKNSGFATCVQNLPDQCTPNPCDRKGTQACQDLMGNFFC
LCKAGWGGRLCDKDVNECSQENGGCLQICHNKPGSFHCSCHSGFELSSDGRTCQDIDECADSEACGEA
RCKNLPGSYSCLCDEGFAYSSQEKACRDVDECLQGRCEQVCVNSPGSYTCHCDGRGGLKLSQDMDTCE
DILPCVPFSVAKSVKSLYLGRMFSGTPVIRLRFKRLQPTRLVAEFDFRTFDPEGILLFAGGHQDSTWIVLAL
RAGRLELQLRYNGVGRVTSSGPVINHGMWQTISVEELARNLVIKVNRDAVMKIAVAGDLFQPERGLYHLN
LTVGGIPFHEKDLVQPINPRLDGCMRSWNWLNGEDTTIQETVKVNTRMQCFSVTERGSFYPGSGFAFYSL
DYMRTPLDVGTESTWEVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLRSPVLTFAGGLPDVP
VTSAPVTAFYRGCMTLEVNRRLLDLDEAAYKHSDITAHSCPPVEPAAA Nucleic acid sequence of human GAS6 growth arrest-specific 6, transcript variant 1
(SEQ ID NO 47)
gccacctgcgtgcaaaacctgcctgaccagtgcacgcccaaccctgcgataggaaggggacccaagcctgccaggacctcatgg
gcaacttcttctgcctgtgtaaagctggctgggggggccggctctgcgacaaagatgtcaacgaatgcagccaggagaacggggg
ctgcctccagatctgccacaacaagccgggtagcttccactgttcctgccacagcggcttcgagctctcctctgatggcaggacctgcc
aagacatagacgagtgcgcagactcggaggcctgcggggaggcgcgctgcaagaacctgccccggctcctactcctgcctctgtgac
gagggctttgcgtacagctcccaggagaaggcttgccgagatgtggacgagtgtctgcagggccgctgtgagcaggtctgcgtgaa
ctccccaggggagctacacctgccactgtgacgggcgtgggggcctcaagctgtcccaggacatggacacctgtgaggacatcttgc
cgtgcgtgcccttcagcgtggccaagagtgtgaagtccttgtacctgggccggatgttcagtgggacccccgtgatccgactgcgctt
caagaggctgcagcccaccaggctggtagctgagtttgacttccggaccttcgacccagagggcatcctcctttgccggaggccac
caggacagcacctggatcgtgctggccctgagagccggccggctggagctgcagctgcgctacaacggtgtcggccgtgtcaccag
cagcggcccggtcatcaaccatggcatgtggcagacaatctctgttgaggagctggcgcggaatctggtcatcaaggtcaacaggg
atgctgtcatgaaaatcgcggtggccggggacttgttccaaccggagcgaggactgtatcatctgaacctgaccgtgggaggtattc
ccttccatgaaggacctcgtgcagcctataaaccctcgtctgatggctgcatgaggagctgaactggctgaacggagaagac
accaccatccaggaaacggtgaaagtgaacacgaggatgcagtgcttctcggtgacggagagaggctcttctactcccgggagcg
gcttcgccttctacagcctggactacatgcggacccctctgacgtcgggactgaatcaacctgggaagtagaagtcgtggctcacat
ccgcccagccgcagacacaggcgtgctgtttgcgctctgggcccccgaccctccgtgccgtgcctctctctgtggcactggtagactatc
actccacgaagaaactcaagaagcagctggtggtcctggccgtggagcatacggccttggccctaatggagatcaaggtctgcgac
ggccaagagcacgtggtcaccgtctcgctggaggacggtgaggccaccctggaggtggacggcaccagggcaggcgaggt
gagcgccgcgcagctgcaggagaggctggccgtgctcgagaggcacctgcggagcccgtgctcacctttgctggcggctgcca
gatgtgccggtgacttcagcgccagtcaccgcgttctaccgcggctgcatgacactggaggtcaaccggaggctgctggacctgga
cgaggcggcgtacaagcacagcgacatcacggcccactcctgccccccgtggagcccgccgcagcctaggccccacgggacgc
ggcaggcttctcagtctctgtccgagacagccgggaggagcctggggctcctcaccacgtggggccatgctgagagctgggctttc
ctctgtgaccatcccggcctgtaacatatctgtaaatagtgagatggacttggggcctctgacgccgcgcactcagccgtgggcccgg
gcgcggggaggccggccgcagcgcagagcgggctcgaagaaaataattctctattattttttattaccaagcgcttctttctgactctaa
aatatggaaaataaaatatttacagaaagctttgtaaaaaaaaaaaaaaaaaa Amino acid sequence of human GAS6 growth arrest-specific 6, transcript variant 2
(SEQ ID NO 48)
MDTCEDILPCVPFSVAKSVKSLYLGRMFSGTPVIRLRFKRLQPTRLVAEFDFRTFDPEGILLFAGGHQDST
WIVLALRAGRLELQLRYNGVGRVTSSGPVINHGMWQTISVEELARNLVIKVNRDAVMKIAVAGDLFQPER
GLYHLNLTVGGIPFHEKDLVQPINPRLDGCMRSWNWLNGEDTTIQETVKVNTRMQCFSVTERGSFYPGS
GFAFYSLDYMRTPLDVGTESTWEVEVVAHIRPAADTGVLFALWAPDLRAVPLSVALVDYHSTKKLKKQLV
VLAVEHTALALMEIKVCDGQEHVVTVSLRDGEATLEVDGTRGQSEVSAAQLQERLAVLERHLRSPVLTFA
GGLPDVPVTSAPVTAFYRGCMTLEVNRRLLDLDEAAYKHSDITAHSCPPVEPAAA Nucleic acid sequence of human GAS6 growth arrest-specific 6, transcript variant 2
(SEQ ID NO 49)
ttgattgaaaccagtaaatgcttctctttgggggtgggggttttagtttcaaatgccccgggggttacttttttacggcccccgtgtcctgt
agcaccgtcattaaatggaacagcacagcgtgcaccgccgcccccacccctccaccaagcagggcccttcccagctctccacctg
ctgggctgaagtcagccttcccagccgggccttgatcagaagcgtgcaccaacaccccgggagctgcccggtcaggggaggaggg
cagggaaatggggcagggcgcgctggcccccacagagtctggatgcgacctctggggtggtgccctggccagtccctgcagccgcct -continued

```
gccccagccccgtctgagatgccgctgtgctgcggttggccggttttttttgcttgcagacatagacgagtgcgcagactcggaggc
ctgcggggaggcgcgctgcaagaacctgcccggctcctactcctgcctctgtgacgagggctttgcgtacagctcccaggagaagg
cttgccgagatgtggacgagtgtctgcagggccgctgtgagcaggtctgcgtgaactcccagggagctacacctgccactgtgacg
ggcgtgggggcctcaagctgtcccaggacatggacacctgtgaggacatcttgccgtgcgtgcccttcagcgtggccaagagtgtg
aagtccttgtacctgggccggatgttcagtgggaccccgtgatccgactgcgcttcaaggagctgcagcccaccaggctggtagct
gagtttgacttccggacctttgaccccgagggcatcctcctcttgccggaggccaccaggacagcacctggatcgtgctggccctga
gagccggccggctggagctgcagctgcgctacaacggtgtcggccgtgtcaccagcagcggcccggtcatcaaccatggcatgtgg
cagacaatctctgttgaggagctggcgcggaatctggtcatcaaggtcaacagggatgctgtcatgaaaatcgcggtggccgggga
cttgttccaaccggagcgaggactgtatcatctgaacctgaccgtggaggtattccctccatgagaaggacctcgtgcagcctata
aaccctcgtctggatggctgcatgaggagctggaactggctgaacggagaagacaccaccatccaggaaacggtgaaagtgaac
acgaggatgcagtgcttctcggtgacggagagaggctcttctaccccgggagcggcttcgccttctacagcctggactacatgcgg
acccctctggacgtcgggactgaatcaacctgggaagtagaagtcgtggctcacatccgcccagccgcagacacaggcgtgctgttt
gcgctctgggccccgacctccgtgccgtgcctctctctgtggcactggtagactatcactccacgaagaaactcaagaagcagctgg
tggtcctggccgtggagcatacggccttggccctaatggagatcaaggtctgcgacggccaagagcacgtggtcaccgtctcgctga
gggacggtgaggccaccctggaggtggacggcaccagggtccagagcgaggtgagcgccgcgcagctgcaggagaggctggc
cgtgctcgagaggcacctgcggagcccgtgctcaccttcgctggcggcctgccagatgtgccggtgacttcagcgccagtcaccgc
gttctaccgcggctgcatgacactggaggtcaaccggaggctgctggacctggacgaggcggcgtacaagcacagcgacatcacg
gcccactcctgccccccgtggagcccgccgcgagcctaggccccccacgggacgcggcaggcttctcagtctctgtccgagacagccg
ggaggagcctggggctcctcaccacgtggggccatgctgagagctgggctttcctctgtgaccatcccggcctgtaacatatctgta
aatagtgagatggacttggggcctctgacgccgcgcactcagccgtgggcccgggcgcggggaggccggcgcagcgcagagcgg
gctcgaagaaataattctctattattttttattaccaagcgcttctttctgactctaaaatatggaaaataaaatatttacagaaagctttt
gtaaaaaaaaaaaaaaaaaa
```

Amino acid sequence of human GAS6 growth arrest-specific 6, transcript variant 3 (SEQ ID
NO 50)
MFSGTPVIRLRFKRLQPTRLVAEFDFRTFDPEGILLFAGGHQDSTWIVLALRAGRLELQLRYNGVGRVTSS
GPVINHGMWQTISVEELARNLVIKVNRDAVMKIAVAGDLFQPERGLYHLNLTVGGIPFHEKDLVQPINPRL
DGCMRSWNWLNGEDTTIQETVKVNTRMQCFSVTERGSFYPGSGFAFYSLDYMRTPLDVGTESTWEVEV
VAHIRPAADTGVLFALWAPDLRAVPLSVALVDYHSTKKLKKQLVVLAVEHTALALMEIKVCDGQEHVVTV
SLRDGEATLEVDGTRGQSEVSAAQLQERLAVLERHLRSPVLTFAGGLPDVPVTSAPVTAFYRGCMTLEVN
RRLLDLDEAAYKHSDITAHSCPPVEPAAA Nucleic acid sequence of human GAS6 growth arrest-specific 6, transcript variant 3 (SEQ ID
NO 51)
```
cacaccgacctgtcacaccggtgcctgtcacaccactgcctgtcacactgacttgtcaccggtgtctgtcacaccgacctgtcacactg
gtgcctgtcacactggtgcctgtcacaccgacctgtcacaccggtgcctgtcacaccgacctgtcacactgacctgtcacaccggtag
gaatgcagtacccacatgtggacgtttctgggcagggcggctcttgtctttcctcttcagcctgggcctgtgcctgggggttgatgaga
gtgagcatttatttaaaaagcaaaaccacaggtggaaagagtcaccaggacagcttctcggagtcgcagacctgggatgcagccgt
ggggctcttgggtctggctgcgacgttcagggcttccagccagccctcgccttgaggttctttgcctcgctgcctcatgtactcatgca
gagggtgtcggaccctgcgagatgtccagctcaccctggctgcccacggtgggcagggcaggcctggctcagcccccagcccctcc
atcttccagggtgtcagctcacaccggctttggttctgtccccttcgggcagcgtggagaaaccacagcccagaacagggaacttt
ccaggacagccatcttcaaggcatccatatctatttcataatagtgtatacttttaatgattctctgtaatttttgtatgcttgaaatatt
tcataatttaaaaataaagggtcaagggaaatgagcaggggaaggagatgacgggaccccccgagaagccctgtgggaagcggctg
ctgcaagcccgcccttcacctgggagtcccagtggggcaggtgtgacagcctctgggtctcagcagctagaggcggggtggccac
tcccgaggcacaggagggacagtggacccgctgcgcggccggggcgtggggctcaggggagcaggagtgaaggccacatcccc
gaccggcgtggcccccgtccgtggcaggacatcttgccgtgcgtgcccttcagcgtggccaagagtgtgaagtccttgtacctgggc
cggatgttcagtgggaccccgtgatccgactgcgcttcaaggaggctgcagcccaccaggctggtagctgagtttgacttccggacct
tgaccccgagggcatcctcctcttgccggaggccaccaggacagcacctggatcgtgctggccctgagagccggccggctggag
ctgcagctgcgctacaacggtgtcggccgtgtcaccagcagcggcccggtcatcaaccatggcatgtggcagacaatctctgttgag
gagctggcgcggaatctggtcatcaaggtcaacagggatgctgtcatgaaaatcgcggtggccggggacttgttccaaccggagc
gaggactgtatcatctgaacctgaccgtggaggtattccctccatgagaaggacctcgtgcagcctataaaaccctcgtctggatgg
ctgcatgaggagctggaactggctgaacggagaagacaccaccatccaggaaacggtgaaagtgaacacgaggatgcagtgctt
ctcggtgacggagagaggctcttctaccccgggagcggcttcgccttctacagcctggactacatgcggacccctctggacgtcgg
gactgaatcaacctgggaagtagaagtcgtggctcacatccgcccagccgcagacacaggcgtgctgtttgcgctctgggccccg
acctccgtgccgtgcctctctctgtggcactggtagactatcactccacgaagaaactcaagaagcagctggtggtcctggccgtgga
gcatacggccttggccctaatggagatcaaggtctgcgacggccaagagcacgtggtcaccgtctcgctgagggacggtgaggcc
acccctggaggtggacggcaccagggtccagagcgaggtgagcgccgcgcagctgcaggagaggctggccgtgctcgagaggca
cctgcggagcccgtgctcaccttcgctggcggcctgccagatgtgccggtgacttcagcgccagtcaccgcgttctaccgcggctgc
atgacactggaggtcaaccggaggctgctggacctggacgaggcggcgtacaagcacagcgacatcacgccccactcctgcccc
ccgtggagcccgccgcagcctaggccccacgggacgcggcaggcttctcagtctctgtccgagacagccggaggagcctgggg
gctcctcaccacgtggggccatgctgagagctgggctttcctctgtgaccatcccggcctgtaacatatctgtaaatagtgagatgga
cttggggcctctgacgccgcgcactcagccgtgggcccgggcgcggggaggccggcgcagcgcagagcgggctcgaagaaata
attctctattattttttattaccaagcgcttctttctgactctaaaatatggaaaataaaatatttacagaaagctttgtaaaaaaaaaaaa
aaaaaa
```

Amino acid sequence of human Protein S (PROS1)(alpha) (SEQ ID NO 52)
MRVLGGRCGALLACLLLVLPVSEANFLSKQQASQVLVRKRRANSLLEETKQGNLERECIEELCNKEEAREV
FENDPETDYFYPKYLVCLRSFQTGLFTAARQSTNAYPDLRSCVNAIPDQCSPLPCNEDGYMSCKDGKASFT
CTCKPGWQGEKCEFDINECKDPSNINGGCSQICDNTPGSYHCSCKNGFVMLSNKKDCKDVDECSLKPSI
CGTAVCKNIPGDFECECPEGYRYNLKSKSCEDIDECSENMCAQLCVNYPGGYTCYCDGKKGFKLAQDQK
SCEVVSVCLPLNLDTKYELLYLAEQFAGVVLYLKFRLPEISRFSAEFDFRTYDSEGVILYAESIDHSAWLLIA
LRGGKIEVQLKNEHTSKITTGGDVINNGLWNMVSVEELEHSISIKIAKEAVMDINKPGPLFKPENGLLETK
VYFAGFPRKVESELIKPINPRLDGCIRSWNLMKQGASGIKEIIQEKQNHCLVTVEKGSYYPGSIAQFHI
DYNNVSSAEGWHVNVTLNIRPSTGTGVMLALVSGNNTVPFAVSLVDSTSEKSQDILLSVENTVIYRIQAL
SLCSDQQSHLEFRVNRNNLELSTPLKIETISHEDLQRQLAVLDKAMKAKVATYLGGLPDVPFSATPVNAFY
NGCMEVNINGVQLDLDEAISKHNDIRAHSCPSVWKKTKNS Nucleic acid sequence of human Protein S (PROS1)(alpha) (SEQ ID NO 53)
```
tttggaaacgtcacactgtggaggaaaagcagcaactagggagctggtgaagaaggatgtctcagcagtgtttactaggcctccaa
cactagagcccatccccagctccgaaaagcttcctggaaatgtccttgttatcacttccctctcgggctgggcgctgggagcgggc
ggtctcctccgcccggctgttccgccgaggctcgctgggtcgctggcgccgccgcgcagcacggctcagaccgaggcgcacagg
ctcgcagctccgcggcgcctagcgctccggtcccgccgagacggcgccaccgtccctgccggcgcctccgcgcgcttcgaaatgagg
gtcctgggtgggcgctgcggggcgctgctggcgtgtctcctcctagtgcttcccgtctcagaggcaaacttttttgtcaaagcaacagg
cttcacaagtcctggttaggaagcgtcgtgcaaattctttacttgaagaaaccaaacagggtaatcttgaaagagaatgcatcgaag
aactgtgcaataaagaagaagccagggaggtctttgaaaatgacccggaaacggattattttatccaaaatacttagtttgtcttcg
ctcttttcaaactgggttattcactgctgcacgtcagtcaactaatgcttatcctgacctaagaagctgtgtcaatgccattccagacca
gtgtagtcctctgccatgcaatgaagatggatatatgagctgcaaagatggaaaagcttctttacttgcacttgtaaaccaggttggc
aaggagaaaagtgtgaatttgacataaatgaatgcaaagatccctcaaatataaatggaggttgcagtcaaatttgtgataatacac
ctggaagttaccactgttcctgtaaaaatggttttgttatgctttcaaataagaaagattgtaaagatgtggataatgctctttgaagc
caagcattttgtggcacagctgtgtgcaagaacatcccaggagattttgaatgtgaatgccccgaaggctacagatataatctcaaat
caaagtcttgtgaagatatagatgaatgctctgagaacatgtgtgctcagctttgtgtcaattaccctggaggttacacttgctattgtg
atgggaagaaaggattcaaacttgcccaagatcagaagagttgtgaggttgtttcagtgtgccttcccttgaaccttgacacaaagta
tgaattacttacttggcggagcagtttgcagggttgttttatatttaaaatttcgtttgccagaaatcagcagatttttcagcagaattt
gatttccggacatatgattcagaaggcgtgatactgtacgcagaatctatcgatcactcagcgtggctcctgattgcacttcgtggtgg
aaagattgaagttcagcttaaggaatgaacatacatccaaaatcacaactggaggtgatgttattaataatggtctatggaatatggtg
tctgtggaagaattagaacatagtattagcattaaaatagctaaagaagctgtgatggatataaataaacctggacccctttttaagc
cggaaaatggattgctggaaaccaaagtatacttgcaggattccctcggaaagtggaaagtgaactcattaaaccgattaaccctc
gtctagatggatgtacgaagctggaatttgatgaagcaaggagcttctggaataaaggaaattattcaagaaaaacaaaataag
cattgcctggttactgtggagaagggctcctactatcctggttctggaattgctcaatttcacatagattataatggtatccagtgctg
agggttggcatgtaaatgtgaccttgaatattcgtccatccacgggcactggtgttatgcttgccttggtttctggtaacaacacagtgc
cctttgctgtgccttggtggactccacctctgaaaaatcacaggatattctgttatctgttgaaaatactgtaatatatcggatacaggc
cctaagtctatgttccgatcaacaatctcatctggaatttagagtcaacagaaacaatctggagttgtcgacaccacttaaaatagaa
accatctcccatgaagaccttcaaagacaacttgccgtcttggacaaagcaatgaaagcaaaagtgggccacatacctgggtggcctt
ccagatgttccattcagtgccacaccagtgaatgcctttttataatggctgcatggaagtgaatattaatggtgtacagttggatctgga
tgaagccatttctaaacataatgatattagagctcactcatgtccatcagtttggaaaaagacaaagaattcttaaggcatcttttctct
gcttataatacctttccttgtgtgtaattatacttatgtttcaataacagctgaagggtttatttacaatgtgcagtctttgattattt
gtggtccttttcctggattttaaaaggtcctttgtcaaggaaaaaaattctgttgtgatataaacagtaaagaaattcttacttctctt
gctatctaagaatagtgaaaaataacaattttaaatttgaatttttttcctacaaatgacagtttcaattttttgtttgtaaaactaaattttta
attttatcatcatgaactagtgtctaaatacctatgtttttttcagaaagcaaggaagtaaactcaaacaaaagtgcgtgtaattaaatact
attaatcataggcagatactattttgtttatgttttttgtttttttcctgatgaaggcagaagagatggtggtctattaaatatgaattgaat
ggagggtcctaatgccttatttcaaaacaattcctcaggggaacagctttggcttcatctttctcttgtgtggcttcacatttaaaccag
tatcttattgaattagaaaacaagtgggacatattttcctgagagcagcacaggaatcttcttggcagctgcagtctgtcaggat
gagatatcagattaggttggataggtggggaaatctgaagtgggtacattttttaaattttgctgtgtgggtcacacaaggtctacatt
acaaaagacagaattcagggatggaaaggagaatgaacaaatgtgggagttcatagttttccttgaatccaacttttaattaccaga
gtaagttgccaaaatgtgattgttgaagtacaaaaggaactatgaaaaccagaacaaattttaacaaaaggacaaccacagaggg
atatagtgaatatcgtatcattgtaatcaaagaagtaaggaggtaagattgccacgtgcctgctggtactgtgatgcatttcaagtgg
cagttttatcacgtttgaatctaccattcatagccagatgtgtatcagatgtttcactgacagttttttaacaataaattcttttcactgtatt
ttatatcacttataataatcggtgtaattttaaaatgcatgtgaatatctttattatatcaactgtttgaataaaacaaaattacataat
agacatttaactcttcaaaaaaaaaaaaaaa
```

Amino acid sequence of human MAP-1/GAS6 transcript variant 1 (SEQ ID NO 54)
```
HTVELNNMFGQIQSPGYPDSYPSDSEVTWNITVPDGFRIKLYFMHFNLESSYLCEYDYVKVETEDQVLATF
CGRETTDTEQTPGQEVVLSPGSFMSITFRSDFSNEERFTGFDAHYMAVDVDECKEREDEELSCDHYCHN
YIGGYYCSCRFGYILHTDNRTCRVECSDNLFTQRTGVITSPDFPNPYPKSSECLYTIELEEGFMVNLQFEDI
FDIEDHPEVPCPYDYIKIKVGPKVLGPFCGEKAPEPISTQSHSVLILFHSDNSGENRGWRLSYRAAGNECP
ELQPPVHGKIEPSQAKYFFKDQVLVSCDTGYKVLKDNVEMDTFQIECLKDGTWSNKIPTCKKNEIDLESEL
KSEQVTEGGGGSGGGGSALLPAREATQFLRPRQRRAFQVFEEAKQGHLERECVEELCSREEAREVFEND
PETDYFYPRYLDCINKYGSPYTKNSGFATCVQNLPDQCTPNPCDRKGTQACQDLMGNFFCLCKAGWGGR
LCDKDVNECSQENGGCLQICHNKPGSFHCSCHSGFELSSDGRTCQDIDECADSEACGEARCKNLPGSY
SCLCDEGFAYSSQEKACRDVDECLQGRCEQVCVNSPGSYTCHCDGRGGLKLSQDMDTCEDILPCVPFSV
AKSVKSLYLGRMFSGTPVIRLRFKRLQPTRLVAEFDFRTFDPEGILLFAGGHQDSTWIVLALRAGRLELQLR
YNGVGRVTSSGPVINHGMWQTISVEELARNLVIKVNRDAVMKIAVAGDLFQPERGLYHLNLTVGGIPFHE
KDLVQPINPRLDGCMRSWNWLNGEDTTIQETVKVNTRMQCFSVTERGSFYPGSGFAFYSLDYMRTPLDV
GTESTWEVEVVAHIRPAADTGVLFALWAPDLRAVPLSVALVDYHSTKKLKKQLVVLAVEHTALALMEIKVC
DGQEHVVTVSLRDGEATLEVDGTRGQSEVSAAQLQERLAVLERHLRSPVLTFAGGLPDVPVTSAPVTAFY
RGCMTLEVNRRLLDLDEAAYKHSDITAHSCPPVEPAAA
```

Amino acid sequence of human GAS6 transcript variant 1/MAP1 (SEQ ID NO 55)
```
ALLPAREATQFLRPRQRRAFQVFEEAKQGHLERECVEELCSREEAREVFENDPETDYFYPRYLDCINKYGS
PYTKNSGFATCVQNLPDQCTPNPCDRKGTQACQDLMGNFFCLCKAGWGGRLCDKDVNECSQENGGCL
QICHNKPGSFHCSCHSGFELSSDGRTCQDIDECADSEACGEARCKNLPGSYSCLCDEGFAYSSQEKACR
DVDECLQGRCEQVCVNSPGSYTCHCDGRGGLKLSQDMDTCEDILPCVPFSVAKSVKSLYLGRMFSGTPV
IRLRFKRLQPTRLVAEFDFRTFDPEGILLFAGGHQDSTWIVLALRAGRLELQLRYNGVGRVTSSGPVINHG
MWQTISVEELARNLVIKVNRDAVMKIAVAGDLFQPERGLYHLNLTVGGIPFHEKDLVQPINPRLDGCMRS
WNWLNGEDTTIQETVKVNTRMQCFSVTERGSFYPGSGFAFYSLDYMRTPLDVGTESTWEVEVVAHIRPA
ADTGVLFALWAPDLRAVPLSVALVDYHSTKKLKKQLVVLAVEHTALALMEIKVCDGQEHVVTVSLRDGEA
TLEVDGTRGQSEVSAAQLQERLAVLERHLRSPVLTFAGGLPDVPVTSAPVTAFYRGCMTLEVNRRLLDLDE
AAYKHSDITAHSCPPVEPAAAGGGSGGGGSHTVELNNMFGQIQSPGYPDSYPSDSEVTWNITVPDGFR
IKLYFMHFNLESSYLCEYDYVKVETEDQVLATFCGRETTDTEQTPGQEVVLSPGSFMSITFRSDFSNEERFT
GFDAHYMAVDVDECKEREDEELSCDHYCHNYIGGYYCSCRFGYILHTDNRTCRVECSDNLFTQRTGVITS
PDFPNPYPKSSECLYTIELEEGFMVNLQFEDIFDIEDHPEVPCPYDYIKIKVGPKVLGPFCGEKAPEPISTQS
HSVLILFHSDNSGENRGWRLSYRAAGNECPELQPPVHGKIEPSQAKYFFKDQVLVSCDTGYKVLKDNVE
MDTFQIECLKDGTWSNKIPTCKKNEIDLESELKSEQVTE
```

Amino acid sequence of human MAP-1/Protein S (SEQ ID NO 56)
HTVELNNMFGQIQSPGYPDSYPSDSEVTWNITVPDGFRIKLYFMHFNLESSYLCEYDYVKVETEDQVLATF
CGRETTDTEQTPGQEVVLSPGSFMSITFRSDFSNEERFTGFDAHYMAVDVDECKEREDEELSCDHYCHN
YIGGYYCSCRFGYILHTDNRTCRVECSDNLFTQRTGVITSPDFPNPYPKSSECLYTIELEEGFMVNLQFEDI
FDIEDHPEVPCPYDYIKIKVGPKVLGPFCGEKAPEPISTQSHSVLILFHSDNSGENRGWRLSYRAAGNECP
ELQPPVHGKIEPSQAKYFFKDQVLVSCDTGYKVLKDNVEMDTFQIECLKDGTWSNKIPTCKKNEIDLESEL
KSEQVTEGGGGSGGGGSGSGGGGSNFLSKQQASQVLVRKRRANSLLEETKQGNLERECIEELCNKEEA
REVFENDPETDYFYPKYLVCLRSFQTGLFTAARQSTNAYPDLRSCVNAIPDQCSPLPCNEDGYMSCKDGK
ASFTCTCKPGWQGEKCEFDINECKDPSNINGGCSQICDNTPGSYHCSCKNGFVMLSNKKDCKDVDECS
LKPSICGTAVCKNIPGDFECECPEGYRYNLKSKSCEDIDECSENMCAQLCVNYPGGYTCYCDGKKGFKLA
QDQKSCEVVSVCLPLNLDTKYELLYLAEQFAGVVLYLKFRLPEISRFSAEFDFRTYDSEGVILYAESIDHSA
WLLIALRGGKIEVQLKNEHTSKITTGGDVINNGLWNMVSVEELEHSISIKIAKEAVMDINKPGPLFKPENG
LLETKVYFAGFPRKVESELIKPINPRLDGCIRSWNLMKQGASGIKEIIQEKQNKHCLVTVEKGSYYPGSGIA
QFHIDYNNVSSAEGWHVNVTLNIRPSTGTGVMLALVSGNNTVPFAVSLVDSTSEKSQDILLSVENTVIYRI
QALSLCSDQQSHLEFRVNRNNLELSTPLKIETISHEDLQRQLAVLDKAMKAKVATYLGGLPDVPFSATPVN
AFYNGCMEVNINGVQLDLDEAISKHNDIRAHSCPSVWKKTKNS Amino acid sequence of human Protein S/MAP1 (SEQ ID NO 57)
NFLSKQQASQVLVRKRRANSLLEETKQGNLERECIEELCNKEEAREVFENDPETDYFYPKYLVCLRSFQTG
LFTAARQSTNAYPDLRSCVNAIPDQCSPLPCNEDGYMSCKDGKASFTCTCKPGWQGEKCEFDINECKDP
SNINGGCSQICDNTPGSYHCSCKNGFVMLSNKKDCKDVDECSLKPSICGTAVCKNIPGDFECECPEGYR
YNLKSKSCEDIDECSENMCAQLCVNYPGGYTCYCDGKKGFKLAQDQKSCEVVSVCLPLNLDTKYELLYLA
EQFAGVVLYLKFRLPEISRFSAEFDFRTYDSEGVILYAESIDHSAWLLIALRGGKIEVQLKNEHTSKITTGG
DVINNGLWNMVSVEELEHSISIKIAKEAVMDINKPGPLFKPENGLLETKVYFAGFPRKVESELIKPINPRLD
GCIRSWNLMKQGASGIKEIIQEKQNKHCLVTVEKGSYYPGSGIAQFHIDYNNVSSAEGWHVNVTLNIRPS
TGTGVMLALVSGNNTVPFAVSLVDSTSEKSQDILLSVENTVIYRIQALSLCSDQQSHLEFRVNRNNLELST
PLKIETISHEDLQRQLAVLDKAMKAKVATYLGGLPDVPFSATPVNAFYNGCMEVNINGVQLDLDEAISKHN
DIRAHSCPSVWKKTKNSGSGGGSHTVELNNMFGQIQSPGYPDSYPSDSEVTWNITVPDGFRIKLYFMH
FNLESSYLCEYDYVKVETEDQVLATFCGRETTDTEQTPGQEVVLSPGSFMSITFRSDFSNEERFTGFDAHY
MAVDVDECKEREDEELSCDHYCHNYIGGYYCSCRFGYILHTDNRTCRVECSDNLFTQRTGVITSPDFPNP
YPKSSECLYTIELEEGFMVNLQFEDIFDIEDHPEVPCPYDYIKIKVGPKVLGPFCGEKAPEPISTQSHSVLILF
HSDNSGENRGWRLSYRAAGNECPELQPPVHGKIEPSQAKYFFKDQVLVSCDTGYKVLKDNVEMDTFQIE
CLKDGTWSNKIPTCKKNEIDLESELKSEQVTE

```

The invention claimed is:

1. A method of treating a subject suffering from an autoimmune disorder comprising administering a composition comprising a chimeric molecule of a ficolin-associated polypeptide, wherein said chimeric molecule of a ficolin-associated polypeptide comprises: (a) a human ficolin-associated polypeptide comprising the amino acid sequence set forth in SEQ ID NO:1 or a variant thereof having at least 80% sequence identity to the amino acid sequence set forth in SEQ ID NO:1; and (b) an inhibitor of complement activation, wherein said inhibitor of complement activation is selected from the list consisting of Factor H (FH), GAS6, Protein S, C1-inhibitor (C1-inh), complement component 4 binding protein (C4 bp), Factor I (FI), CR1, DAF(CD55), CD59, CR2, or a fragment thereof that inhibits complement activation, or an immunoglobulin molecule or part thereof that is an inhibitor of complement activation, and wherein said chimeric molecule inhibits complement activation in a subject suffering from an autoimmune disorder, wherein said autoimmune disorder is selected from the group consisting of Addison's disease, autoimmune hemolytic anemia, autoimmune thyroiditis, Crohn's disease, Graves' disease, Guillain-Barre syndrome, systemic lupus erythematosus, lupus nephritis, multiple sclerosis, myasthenia gravis, psoriasis, primary biliary cirrhosis, rheumatoid arthritis, uveitis, asthma, atherosclerosis, type I diabetes, and allergies.

2. The method according to claim 1, wherein said ficolin-associated polypeptide comprises the amino acid sequence of residues 20-297 of SEQ ID NO:3, or a functional variant thereof having at least 80% sequence identity to the amino acid sequence of residues 20-297 of SEQ ID NO:3.

3. The method according to claim 1, wherein said ficolin-associated polypeptide comprises the amino acid sequence of residues 20-380 of SEQ ID NO:1, or a functional variant thereof having at least 80% sequence identity to the amino acid sequence of residues 20-380 of SEQ ID NO:1.

4. The method according to claim 1, wherein said ficolin-associated polypeptide is in homodimer form.

5. The method according to claim 1, wherein said ficolin-associated polypeptide consists of the amino acid sequence of residues 20-380 of SEQ ID NO:1.

6. The method according to claim 1, wherein said ficolin-associated polypeptide comprises the amino acid sequence of SEQ ID NO:4 or variants or immunologic fragments thereof having at least 80% sequence identity to the amino acid sequence of SEQ ID NO:4.

7. The method according to claim 1, wherein said ficolin-associated polypeptide and said inhibitor of complement activation are directly fused to each other in the form of a fusion protein.

8. The method according to claim 1, wherein said inhibitor of complement activation is Factor H, or a fragment thereof that inhibits complement activation, wherein said fragment of Factor H comprises at least the first four SCR domains of Factor H.

9. The method according to claim 1, wherein said immunoglobulin molecule or part thereof consists of the Fc component of human IgG1, IgG2, IgG3, or IgG4.

* * * * *

                            SEQUENCE LISTING

Sequence total quantity: 75
SEQ ID NO: 1            moltype = AA    length = 380
FEATURE                 Location/Qualifiers
source                  1..380
                        mol_type = protein
                        organism = Homo sapiens
SEQUENCE: 1
MRWLLLYYAL CFSLSKASAH TVELNNMFGQ IQSPGYPDSY PSDSEVTWNI TVPDGFRIKL   60
YFMHFNLESS YLCEYDYVKV ETEDQVLATF CGRETTDTEQ TPGQEVVLSP GSFMSITFRS  120
DFSNEERFTG FDAHYMAVDV DECKEREDEE LSCDHYCHNY IGGYYCSCRF GYILHTDNRT  180
CRVECSDNLF TQRTGVITSP DFPNPYPKSS ECLYTIELEE GFMVNLQFED IFDIEDHPEV  240
PCPYDYIKIK VGPKVLGPFC GEKAPEPIST QSHSVLILFH SDNSGENRGW RLSYRAAGNE  300
CPELQPPVHG KIEPSQAKYF FKDQVLVSCD TGYKVLKDNV EMDTFQIECL KDGTWSNKIP  360
TCKKNEIDLE SELKSEQVTE                                              380

SEQ ID NO: 2            moltype = DNA    length = 1143
FEATURE                 Location/Qualifiers
source                  1..1143
                        mol_type = other DNA
                        organism = Homo sapiens
SEQUENCE: 2
atgaggtggc tgcttctcta ttatgctctg tgcttctccc tgtcaaaggc ttcagcccac   60
accgtggagc taaacaatat gtttggccaa atccagtcgc ctggttatcc agactcctat  120
cccagtgatt cagaggtgac ttggaatatc actgtcccag atgggtttcg gatcaagctt  180
tacttcatgc acttcaactt ggaatcctcc tacctttgtg aatatgacta tgtgaaggta  240
gaaactgagg accaggtgct ggcaaccttc tgtggcaggg agaccacaga cacagagcag  300
actcccggcc aggaggtggt cctctcccct ggctccttca tgtccatcac tttccggtca  360
gatttctcca atgaggagcg tttcacaggc tttgatgccc actacatggc tgtggatgtg  420
gacgagtgca aggagaggga ggacgaggag ctgtcctgtg accactactg ccacaactac  480
attggcggct actactgctc ctgccgcttc ggctacatcc tccacacaga caacaggacc  540
tgccgagtgg agtgcagtga caacctcttc actcaaaggg ctggggtgat caccagccct  600
gacttcccaa acccttaccc caagagctct gaatgcctgt ataccatcga gctgaggagg  660
ggtttcatgg tcaacctgca gtttgaggac atatttgaca ttgaggacca tcctgaggtg  720
ccctgcccct atgactacat caagatcaaa gttggtccaa agtttggg gcctttctgt   780
ggagagaaag ccccagaacc catcagcacc cagagccaca gtgtccttat cctgttccat  840
agtgacaact cggagagaa ccggggctgg aggctctcat acagggctgc aggaaatgag   900
tgcccagagc tacagcctcc tgtccatggg aaaatcgagc cctcccaagc caagtatttc  960
ttcaaagacc aagtgctcgt cagctgtgac acaggctaca agtgctgaa ggataatgtg  1020
gagatggaca cattccagat tgagtgtctg aaggatggga cgtggagtaa caagattccc  1080
```

```
acctgtaaaa aaaatgaaat cgatctggag agcgaactca agtcagagca agtgacagag    1140
tga                                                                  1143

SEQ ID NO: 3           moltype = AA  length = 297
FEATURE                Location/Qualifiers
source                 1..297
                       mol_type = protein
                       organism = Homo sapiens
SEQUENCE: 3
MRWLLLYYAL CFSLSKASAH TVELNNMFGQ IQSPGYPDSY PSDSEVTWNI TVPDGFRIKL     60
YFMHFNLESS YLCEYDYVKV ETEDQVLATF CGRETTDTEQ TPGQEVVLSP GSFMSITFRS    120
DFSNEERFTG FDAHYMAVDV DECKEREDEE LSCDHYCHNY IGGYYCSCRF GYILHTDNRT    180
CRVECSDNLF TQRTGVITSP DFPNPYPKSS ECLYTIELEE GFMVNLQFED IFDIEDHPEV    240
PCPYDYIKIK VGPKVLGPFC GEKAPEPIST QSHSVLILFH SDNSGENRGW RLSYRAA       297

SEQ ID NO: 4           moltype = AA  length = 17
FEATURE                Location/Qualifiers
source                 1..17
                       mol_type = protein
                       organism = Homo sapiens
SEQUENCE: 4
KNEIDLESEL KSEQVTE                                                    17

SEQ ID NO: 5           moltype = AA  length = 699
FEATURE                Location/Qualifiers
source                 1..699
                       mol_type = protein
                       organism = Homo sapiens
SEQUENCE: 5
MRWLLLYYAL CFSLSKASAH TVELNNMFGQ IQSPGYPDSY PSDSEVTWNI TVPDGFRIKL     60
YFMHFNLESS YLCEYDYVKV ETEDQVLATF CGRETTDTEQ TPGQEVVLSP GSFMSITFRS    120
DFSNEERFTG FDAHYMAVDV DECKEREDEE LSCDHYCHNY IGGYYCSCRF GYILHTDNRT    180
CRVECSDNLF TQRTGVITSP DFPNPYPKSS ECLYTIELEE GFMVNLQFED IFDIEDHPEV    240
PCPYDYIKIK VGPKVLGPFC GEKAPEPIST QSHSVLILFH SDNSGENRGW RLSYRAAGNE    300
CPELQPPVHG KIEPSQAKYF FKDQVLVSCD TGYKVLKDNV EMDTFQIECL KDGTWSNKIP    360
TCKIVDCRAP GELEHGLITF STRNNLTTYK SEIKYSCQEP YYKMLNNNTG IYTCSAQGVW    420
MNKVLGRSLP TCLPVCGLPK FSRKLMARIF NGRPAQKGTT PWIAMLSHLN GQPFCGGSLL    480
GSSWIVTAAH CLHQSLDPED PTLRDSDLLS PSDFKIILGK HWRLRSDENE QHLGVKHTTL    540
HPQYDPNTFE NDVALVELLE SPVLNAFVMP ICLPEGPQQE GAMVIVSGWG KQFLQRFPET    600
LMEIEIPIVD HSTCQKAYAP LKKKVTRDMI CAGEKEGGKD ACAGDSGGPM VTLNRERGQW    660
YLVGTVSWGD DCGKKDRYGV YSYIHHNKDW IQRVTGVRN                           699

SEQ ID NO: 6           moltype = DNA  length = 4353
FEATURE                Location/Qualifiers
source                 1..4353
                       mol_type = other DNA
                       organism = Homo sapiens
SEQUENCE: 6
gaagtcagcc acacaggata aaggagggaa gggaaggagc agatctttc ggtaggaaga      60
cagattttgt tgtcaggttc ctgggagtgc aagagcaagt caaaggagag agagaggaga    120
gaggaaaagc cagagggaga gaggggagaa ggggatctgt tgcaggcagg ggaaggcgtg    180
acctgaatgg agaatgccag ccaattccag agacacacag ggacctcaga acaaagataa    240
ggcatcacgg acaccacacc gggcacgagc tcacaggcaa gtcaagctgg gaggaccaag    300
gccgggcagc cgggagcacc caaggcagga aaatgaggtg gctgcttctc tattatgctc    360
tgtgcttctc cctgtcaaag gcttcagccc acaccgtgga gctaaacaat atgtttggcc    420
agatccagtc gcctggttat ccagactcct atcccagtga ttcagaggtg acttggaata    480
tcactgtccc agatgggttt cggatcaagc tttacttcat gcacttcaac ttggaatcct    540
cctacctttg tgaatatgac tatgtgaagg tagaaactga ggaccaggtg ctggcaacct    600
tctgtggcag ggagaccaca gacacagagc agactcccgg ccaggaggtg gtcctctcac    660
ctggctcctt catgtccatc actttccggt cagatttctc caatgaggaa cgtttcacag    720
gctttgatgc ccactacatg gctgtggatg tggacgagtg caaggagagg gaggacgagg    780
agctgtcctg tgaccactac tgccacaact acattggcgg ctactactgc tcctgccgct    840
tcggctacat cctccacaca gacaacagga cctgccgagt ggagtgcagt gacaacctct    900
tcactcaaag gactggggtg atcaccagcc ctgacttcc cccaaggct gtataccatc       960
ctgaatgcct gtataccatc gagctggagg agggtttcat ggtcaacctg cagtttgagg   1020
acatatttga cattgaggac catcctgagg tgcctgccc ctatgactac atcaagatca   1080
aagttggtcc aaaagttttg gggcctttct gtggagagaa agcccagaa cccatcagca   1140
cccagagcca cagtgtcctg atcctgttcc atagtgacaa ctcgggagag aaccggggca   1200
ggaggctctc atacagggct gcaggaaatg agtgccagga gctacagcct cctgtccatg   1260
ggaaaatcga gccctcccaa gccagtatt tcttcaaaga ccaagtgtc gtcagctgtg   1320
acacaggcta caagtgctg aaggataatg tggagatgga cacattccag attgagtgtc   1380
tgaaggatgg gacgtggagt aacaagatc cacctgtaa aattgtagac tgtagagccc   1440
caggagagct ggaacacggg ctgatcacct tctctacaag gaacaacctc accacataca   1500
agtctgagat caaatactcc tgtcaggagc cttattacaa gatgctcaac aataacacag   1560
gtatatatac ctgttctgcc caaggagtct ggatgaataa agtattgggg agaagcctac   1620
ccacctgcct tccagtgtgt gggctcccca agttctcccg gaagctgatg gccaggatct   1680
tcaatggacg cccagcccag aaaggcacca ctccctggat tgccatgctg tcacacctga   1740
atgggcagcc cttctgcgga ggctcccttc taggctccag ctggatcgtg accgccgcac   1800
actgcctcca ccagtcactc gatccggaag atccgaccct acgtgattca gacttgctca   1860
```

```
gcccttctga cttcaaaatc atcctgggca agcattggag gctccggtca gatgaaaatg 1920
aacagcatct cggcgtcaaa cacaccactc tccaccccca gtatgatccc aacacattcg 1980
agaatgacgt ggctctggtg gagctgttgg agagcccagt gctgaatgcc ttcgtgatgc 2040
ccatctgtct gcctgaggga ccccagcagg aaggagccat ggtcatcgtc agcggctggg 2100
ggaagcagtt cttgcaaagg ttcccagaga ccctgatgga gattgaaatc ccgattgttg 2160
accacagcac ctgccagaag gcttatgccc cgctgaagaa gaaagtgacc agggacatga 2220
tctgtgctgg ggagaaggaa gggggaaagg acgcctgtgc gggtgactct ggaggcccca 2280
tggtgaccct gaatagagaa agaggccagt ggtacctggt gggcactgtg tcctggggtg 2340
atgactgtgg gaagaaggac cgctacggag tatactctta catccaccac aacaaggact 2400
ggatccagag ggtcaccgga gtgaggaact gaatttggct cctcagcccc agcaccacca 2460
gctgtgggca gtcagtagca gaggacgatc ctccgatgaa agcagccatt tctcctttcc 2520
ttcctcccat cccccctcct tcggcctatc cattactggg caatagagca ggtatcttca 2580
cccccttttc actctcttta aagagatgga gcaagagagt ggtcagaaca caggccgaat 2640
ccaggctcta tcacttacta gtttgcagtg ctgggcaggt gacttcatct cttcgaactt 2700
cagtttcttc ataagatgga aatgctatac cttacctacc tcgtaaaagt ctgatgagga 2760
aaagattaac taatagatgc atagcactta acagagtgca tagcatacac tgttttcaat 2820
aaatgcacct tagcagaagg tcgatgtgtc taccaggcag acgaagctct cttacaaacc 2880
cctgctgggg tcttagcatt gatcagtgac acacctctcc cctcaacctt gaccatctcc 2940
atctgccctt aaatgctgta tgcttttttg ccaccgtgca acttgcccaa catcaatctt 3000
caccctcatc cctaaaaaag taaaacagac aaggttctga gtcctgtggt atgtccccta 3060
gcaaatgtaa ctaggaacat gcactagatg acagattgcg gagggcctg agagaagcag 3120
ggacaggagg gagcctgggg atttgtggtt gggaaggcag acacctggtt ctagaactag 3180
ctctgccctt agcccctgt atgacccctat gcaagtcctc ctccctcatc tcaaagggtc 3240
ctcaaagctc tgacgatcta agatacaatg aagccatttt ccccctgata agatgaggta 3300
aagccaatgt aaccaaaagg caaaaattac aatcggttca aaggaacttt gatgcagaca 3360
aaatgctgct gctgctgctc tcgaaatacc caccccttct cactacggt gggttcccaa 3420
ggacatggga caggcaaagt gtgagccaaa ggatccttcc ttattcctaa gcagagcatc 3480
tgctctgggc cctggcctcc ttcccttctt gggaaactgg gctgcatgag gtgggccctg 3540
gtagtttgta ccccaggccc ctatactctt ccttcctatg tccacagctg accccaagca 3600
gccgttcccc gactcctcac ccctgagcct caccctgaac tccctcatct tgcaaggcca 3660
taagtgtttt ccaagcaaaa tgcctctccc atcctctctc aggaagcttc tagagacttt 3720
atgccctcca gagctccaag atataagccc tccaagggat cagaagctcc aagttcctgt 3780
cttctgtttt atagaaattg atcttccctg ggggactta actcttgacc tgtatgcagc 3840
tgttggagta attccaggtc tcttgaaaaa aaagaggaag ataatggaga atgagaacat 3900
atatatatat atattaagcc ccaggctgaa tactcaggga cagcaattca cagcctgcct 3960
ctggttctat aaacaagtca ttctacctct ttgtgccctg ctgtttattc tgtaagggga 4020
aggtggcaat gggacccagc tccatcgac acttgtcaag ctgcagaaa ctccattttc 4080
aatgccaaag aagaactgta atgctgtttt ggaatcatcc caaggcatcc caagacacca 4140
tatcttccca tttcaagcac tgcctgggca caccccaaca gtcaggctgg tggtggctcc 4200
tgtgggaact acctagatga agagagtatc atttataacct tctaggagct cctattggga 4260
gacatgaaac atatgtaatt gactaccatg taatagaaca aaccctgcca agtgctgctt 4320
tggaaagtca tggaggtaaa agaaagacca ttc                            4353
```

SEQ ID NO: 7          moltype = AA  length = 728
FEATURE             Location/Qualifiers
source              1..728
                    mol_type = protein
                    organism = Homo sapiens
SEQUENCE: 7

```
MRWLLLYYAL CFSLSKASAH TVELNNMFGQ IQSPGYPDSY PSDSEVTWNI TVPDGFRIKL  60
YFMHFNLESS YLCEYDYVKV ETEDQVLATF CGRETTDTEQ TPGQEVVLSP GSFMSITFRS 120
DFSNEERFTG FDAHYMAVDV DECKEREDEE LSCDHYCHNY IGGYYCSCRF GYILHTDNRT 180
CRVECSDNLF TQRTGVITSP DFPNPYPKSS ECLYTIELEE GFMVNLQFED IFDIEDHPEV 240
PCPYDYIKIK VGPKVLGPFC GEKAPEPIST QSHSVLILFH SDNSGENRGW RLSYRAAGNE 300
CPELQPPVHG KIEPSQAKYF FKDQVLVSCD TGYKVLDKNV EMDTFQIECL KDGTWSNKIP 360
TCKIVDCRAP GELEHGLITF STRNNLTTYK SEIKYSCQEP YYKMLNNNTG IYTCSAQGVW 420
MNKVLGRSLP TCLPECGQPS RSLPSLVKRI IGGRNAEPGL FPWQALIVVE DTSRVPNDKW 480
FGSGALLSAS WILTAAHVLR SQRRDTTVIP VSKEHVTVYL GLHDVRDKSG AVNSSAARVV 540
LHPDFNIQNY NHDIALVQLQ EPVPLGPHVM PVCLPRLEPE GPAPHMLGLV AGWGISNPNV 600
TVDEIISSGT RTLSDVLQYV KLPVVPHAEC KTSYESRSGN YSVTENMFCA GYYEGGKDTC 660
LGDSGGAFVI FDDLSQRWVV QGLVSWGGPE ECGSKQVYGV YTKVSNYVDW VWEQMGLPQS 720
VVEPQVER                                                         728
```

SEQ ID NO: 8          moltype = DNA  length = 4137
FEATURE             Location/Qualifiers
source              1..4137
                    mol_type = other DNA
                    organism = Homo sapiens
SEQUENCE: 8

```
gaagtcagcc acacaggata aaggaggaa gggaaggagc agatcttttc ggtaggaaga   60
cagattttgt tgtcaggttc ctgggagtgc aagagcaagt caaaggagag agagaggaga  120
gaggaaaagc cagagggaga gaggggggaga ggggatctgt tgcaggcagg ggaaggcgtg  180
acctgaatgg agaatgccag ccaattccag agacacacag ggacctcaga acaaagataa  240
ggcatcacgg acaccacacc gggcacgagc tcacaggcaa gtcaagctgg gaggaccaag  300
gccgggcagc cgggagcacc caaggcagga aaatgaggtg gctgcttctc tattatgctc  360
tgtgcttctc cctgtcaaag gcttcagccc acacgtgga gctaaacaat atgtttggcc  420
agatccagtc gcctggttat ccagactcct atcccagtga ttcagaggtg acttggaata  480
tcactgtccc agatgggttt cggatcaagc tttacttcat gcacttcaac ttggaatcct  540
cctaccttg tgaatatgac tatgtgaagg tagaaactga ggaccaggtg ctggcaacct  600
```

```
tctgtggcag ggagaccaca gacacagagc agactcccgg ccaggaggtg gtcctctccc    660
ctggctcctt catgtccatc actttccggt cagatttctc caatgaggag cgtttcacag    720
gctttgatgc ccactacatg gctgtggatg tggacgagtg caaggagagg gaggacgagg    780
agctgtcctg tgaccactac tgccacaact acattggcgg ctactactgc tcctgccgct    840
tcggctacat cctccacaca gacaacagga cctgccgagt ggagtgcagt gacaacctct    900
tcactcaaag gactggggtg atcaccagcc ctgacttccc aaaccccttac cccaagagct    960
ctgaatgcct gtataccatc gagctggagg agggtttcat ggtcaacctg cagttttgagg   1020
acatatttga cattgaggac catcctgagg tgccctgccc ctatgactac atcaagatca   1080
aagttggtcc aaaagttttg gggcctttct gtggagagaa agcccccagaa cccatcagca   1140
cccagagcca cagtgtcctg atcctgttcc atagtgacaa ctcgggagag aaccggggct   1200
ggaggctctc atacagggct gcaggaaatg agtgcccaga gctacagcct cctgtccatg   1260
ggaaaatcga gccctcccaa gccaagtatt tcttcaaaga ccaagtgctc gtcagctgtg   1320
acacaggcta caaagtgctg aaggataatg tggagatgga cacattccag attgagtgtc   1380
tgaaggatgg gacgtggagt aacaagattc ccacctgtaa aattgtagac tgtagagccc   1440
caggagagct ggaacacggg ctgatcacct tctctacaag gaacaacctc accacataca   1500
agtctgagat caaatactcc tgtcaggagc cctattacaa gatgctcaac aataacacag   1560
gtatatatac ctgttctgcc caaggagtct ggatgaataa agtattgggg agaagcctac   1620
ccacctgcct tccagagtgt ggtcagccct cccgctccct gccaagcctg gtcaagagga   1680
tcattggggg ccgaaatgct gagcctggcc tcttcccgtg gcaggccctg atagtggtgg   1740
aggacacttc gagagtgcca aatgacaagt ggtttgggag tggggccctg ctctctgcgt   1800
cctggatcct cacagcagct catgtgctgc gctcccagcg tagagacacc acggtgatac   1860
cagtctccaa ggagcatgtc accgtctacc tgggcttgca tgatgtgcga gacaaatcgg   1920
gggcagtcaa cagctcagct gcccgagtgg tgctccaccc agacttcaac atccaaaact   1980
acaaccacga tatagctctg gtgcagctgc aggagcctgt gccccgggga ccccacgtta   2040
tgcctgtctg cctgccaagg cttgagcctg aaggcccggc cccccacatg ctgggcctgg   2100
tggccggctg gggcatctcc aatcccaatg tgacagtgga tgagatcatc acagtggcca   2160
cacggacctt gtcagatgtc ctgcagtatg tcaagttacc cgtggtgcct cacgctgagt   2220
gcaaaactag ctatgagtcc cgctcgggca attacagcgt cacggagaac atgttctgtg   2280
ctggctacta cgagggcggc aaagacacgt gccttggaga tagcggtggg gcctttgtca   2340
tctttgatga cttgagccag cgctgggtgg tgcaaggcct ggtgtcctgg ggggacctg    2400
aagaatgcgg cagcaagcag gtctatggag tctacacaaa ggtctccaat tacgtggact   2460
gggtgtggga gcagatgggc ttaccacaaa gtgttgtgga gccccaggtg gaacggtgag   2520
ctgacttact cctcggggc ctgcctcccc tgagcgaagc tacaccgcac ttccgacagc    2580
acactccaca ttacttatca gaccatatgg aatggaacac actgacctag cggtggcttc   2640
tcctaccgag acagccccca ggacccctgag aggcagagtg tggtataggg aaaaggctcc   2700
aggcaggaga cctgtgttcc tgagcttgtc caagtctctt tccctgtctg ggcctcactc   2760
taccgagtaa tacaatgcag gagctcaacc aaggcctctg tgccaatccc agcactcctt   2820
tccaggccat gcttcttacc ccagtggcct ttattcactc ctgaccactt atcaaaccca   2880
tcggtcctac tgttggtata actgagcttg gacctgacta ttagaaaatg gtttctaaca   2940
ttgaactgaa tgccgcatct gtatatttc ctgctctgcc ttctgggact agccttggcc    3000
taatccttcc tctaggagaa gagcattcag gttttgggag atggctcata gccaagcccc   3060
tctctcttag tgtgatccct tggagcacct tcatgcctgg ggtttctctc ccaaaagctt   3120
cttgcagtct aagccttatc ccttatgttc cccattaaag gaatttcaaa agacatggag   3180
aaagttggga aggtttgtgc tgactgctgg gagcagaata gccgtgggag gcccaccaag   3240
cccttaaatt cccattgtca actcagaaca catttgggcc catatgccac cctgaacac    3300
cagctgacac catgggcgtc cacacctgct gctccagaca agcacaaagc aatctttcag   3360
ccttgaaatg tattatctga aaggctacct gaagcccagg cccgaatatg gggacttagt   3420
cgattacctg gaaaaagaaa agacccacac tgtgtcctgc tgtgcttttg ggcaggaaaa   3480
tggaagaaag agtggggtgg gcacattaga agtcacccaa atcctgccag gctgcctggc   3540
atccctgggg catgagctgg gcggagaatc caccccgcag gatgttcaga gggacccact   3600
ccttcatttt tcagagtcaa aggaatcaga ggctcaccca tggcaggcag tgaaaagagc   3660
caggagtcct gggttctagt ccctgctctg cccccaactg gctgtataac ctttgaaaaa   3720
tcatttttctt tgtctgagtc tctggttctc cgtcagcaac aggctggcat aaggtcccct   3780
gcaggttcct tctagctgga gcactcagag cttccctgac tgctagcagc ctctctggcc   3840
ctcacagggc tgattgttct ccttctccct ggagctctct ctcctgaaaa tctccatcag   3900
agcaaggcag ccagagaagc ccctgagagg gaatgattgg gaagtgtcca ctttctcaac   3960
cggctcatca aacacactcc tttgtctatg aatggcacat gtaaatgatg ttatattttg   4020
tatcttttat atcatatgct tcaccattct gtaaagggcc tctgcattgt tgctcccatc   4080
aggggtctca agtggaaata aaccctcgtg gataaccaaa aaaaaaaaaaa aaaaaa      4137

SEQ ID NO: 9         moltype = AA  length = 686
FEATURE              Location/Qualifiers
source               1..686
                     mol_type = protein
                     organism = Homo sapiens
SEQUENCE: 9
MRLLTLLGLL CGSVATPLGP KWPEPVFGRL ASPGFPGEYA NDQERRWTLT APPGYRLRLY    60
FTHFDLELSH LCEYDFVKLS SGAKVLATLC GQESTDTERA PGKDTFYSLG SSLDITFRSD   120
YSNEKPFTGF EAFYAAEDID ECQVAPGEAP TCDHHCHNHL GGFYCSCRAG YVLHRNKRTC   180
SALCSGQVFT QRSGELSSPE YPRPYPKLSS CTYSISLEEG FSVILDFVES FDVETHPETL   240
CPYDFLKIQT DREEHGPFCG KTLPHRIETK SNTVTITFVT DESGDHTGWK IHYTSTAQPC   300
PYPMAPPNGH VSPVQAKYIL KDSFSIFCET GYELLQGHLP LKSFTAVCQK DGSWDRPMPA   360
CSIVDCGPPD DLPSGRVEYI TGPGVTTYKA VIQYSCEETF YTMKVNDGKY VCEADGFWTS   420
SKGEKSLPVC EPVCGLSART TGGRIYGGQK AKPGDFPWQV LILGGTTAAG ALLYDNWVLT   480
AAHAVYEQKH DASALDIRMG TLKRLSPHYT QAWSEAVFIH EGYTHDAGFD NDIALIKLNN   540
KVVINSNITP ICLPRKEAES FMRTDDIGTA SGWGLTQRGF LARNLMYVDI PIVDHQKCTA   600
AYEKPPYPRG SVTANMLCAG LESGGKDSCR GDSGGALVFL DSETERWFVG GIVSWGSMNC   660
GEAGQYGVYT KVINYIPWIE NIISDF                                        686
```

| SEQ ID NO: 10 | moltype = DNA length = 2460 |
|---|---|
| FEATURE | Location/Qualifiers |
| source | 1..2460 |
| | mol_type = other DNA |
| | organism = Homo sapiens |

SEQUENCE: 10

```
ggccagctgg acgggcacac catgaggctg ctgaccctcc tgggccttct gtgtggctcg   60
gtggccaccc ccttgggccc gaagtggcct gaacctgtgt tcgggcgcct ggcatccccc  120
ggctttccag gggagtatgc caatgaccag gagcggcgct ggaccctgac tgcacccccc  180
ggctaccgcc tgcgcctcta cttcacccac ttcgacctgg agctctccca cctctgcgag  240
tacgacttcg tcaagctgag ctcggggggcc aaggtgctgg ccacgctgtg cgggcaggag  300
agcacagaca cggagcgggc ccctggcaag gacactttct actcgctggg ctccagcctg  360
gacattacct tccgctccga ctactccaac gagaagccgt tcacggggtt cgaggccttc  420
tatgcagccg aggacattga cgagtgccag gtggcccgg gagaggcgcc cacctgcgac  480
caccactgcc acaaccacct gggcggtttc tactgctcct gccgcgcagg ctacgtcctg  540
caccgtaaca agcgcacctg ctcagccctg tgctccggcc aggtcttcac ccagaggtct  600
ggggagctca gcagccctga atacccacgg ccgtatccca aactctccag ttgcacttac  660
agcatcagcc tggaggaggg gttcagtgtc attctggact ttgtgagtc cttcgatgtg  720
gagacacacc ctgaaacccct gtgtccctac gactttctca agattcaaac agacagagaa  780
gaacatggcc cattctgtgg aagacattg ccccacagga ttgaaacaaa aagcaacacg  840
gtgaccatca ccctttgtcac agatgaatca ggagaccaca caggctggaa gatccactac  900
acgagccacag cgcagccttg cccttatccg atggcgcaac ctaatgccgt gctttcacct  960
gtgcaagcca aatacatcct gaaagacagc ttctccatct tttgcgagac tggctatgag 1020
cttctgcaag gtcacttgcc cctgaaatcc tttactgcag tttgtcagaa agatggatct 1080
tgggaccggc caatgccgc gtgcagcatt gttgactgtg ccctcctga tgatctaccc 1140
agtggccgag tggagtacat cacaggtcct ggagtgcca cctacaaagc tgtgattcag 1200
tacagctgtg aagagacctt ctacacaatg aaagtgaatg atggtaaata tgtgtgtgag 1260
gctgatggat tctggacgag ctccaaagga gaaaaatcac tcccagtctg tgagcctgtt 1320
tgtggactat cagcccgcac aacaggaggg cgtatatatg gagggcaaaa ggcaaaacct 1380
ggtgattttc cttggcaagt cctgatatta ggtggaacca cagcagcagg tgcacttttta 1440
tatgacaact gggtcctaac agctgctcat gccgtctatg agcaaaaaca tgatgcatcc 1500
gccctggaca ttcgaatggg caccctgaaa agactatcac ctcattatac caagcctgg 1560
tctgaagctg ttttttataca tgaaggttat actcatgatg ctggctttga caatgacata 1620
gcactgatta aattgaataa caaagttgta atcaatagca acatcacgcc tatttgtctg 1680
ccaagaaaag aagctgaatc ctttatgagg acagatgaca ttggaactgc atctgatgtg 1740
ggattaaccc aaaggggttt tcttgctaga aatcaatgt atgtcgacat accgattgtt 1800
gaccatcaaa aatgtactgc tgcatatgaa aagccaccct atccaagggg aagtgtaact 1860
gctaacatgc tttgtgctgg cttagaaagt gggggcaagg acagctgcag aggtgacagc 1920
ggagggggcac tggtgtttct agatagtgaa acagagaggt ggtttgtggg aggaatagtg 1980
tcctggggtt ccatgaattg tgggggaagca ggtcagtatg gagtctacac aaaagttatt 2040
aactatattc cctggatcga gaacataatt agtgattttt aacttgcgtg tctgcagtca 2100
aggattcttc atttttagaa atgcctgtga agaccttggc agcgacgtgg ctcgagaagc 2160
attcatcatt actgtggaca tggcatttgt tgctccacca aaaaaaacag actccaggtg 2220
aggctgctgt catttctcca cttgccagtt taattccagc cttacccatt gactcaaggg 2280
gacataaacc acgagagtga cagtcatctt tgcccaccca gtgtaatgtc actgctcaaa 2340
ttacatttca ttaccttaaa aagccagtct cttttcatac tggctgttgg catttctgta 2400
aactgcctgt ccatgctctt tgtttttaaa cttgttctta ttgaaaaaaa aaaaaaaaaa 2460
```

| SEQ ID NO: 11 | moltype = AA length = 185 |
|---|---|
| FEATURE | Location/Qualifiers |
| source | 1..185 |
| | mol_type = protein |
| | organism = Homo sapiens |

SEQUENCE: 11

```
MRLLTLLGLL CGSVATPLGP KWPEPVFGRL ASPGFPGEYA NDQERRWTLT APPGYRLRLY   60
FTHFDLELSH LCEYDFVKLS SGAKVLATLC GQESTDTERA PGKDTFYSLG SSLDITFRSD  120
YSNEKPFTGF EAFYAAEDID ECQVAPGEAP TCDHHCHNHL GGFYCSCRAG YVLHRNKRTC  180
SEQSL                                                              185
```

| SEQ ID NO: 12 | moltype = DNA length = 738 |
|---|---|
| FEATURE | Location/Qualifiers |
| source | 1..738 |
| | mol_type = other DNA |
| | organism = Homo sapiens |

SEQUENCE: 12

```
ggccagctgg acgggcacac catgaggctg ctgaccctcc tgggccttct gtgtggctcg   60
gtggccaccc ccttgggccc gaagtggcct gaacctgtgt tcgggcgcct ggcatccccc  120
ggctttccag gggagtatgc caatgaccag gagcggcgct ggaccctgac tgcacccccc  180
ggctaccgcc tgcgcctcta cttcacccac ttcgacctgg agctctccca cctctgcgag  240
tacgacttcg tcaagctgag ctcggggggcc aaggtgctgg ccacgctgtg cgggcaggag  300
agcacagaca cggagcgggc ccctggcaag gacactttct actcgctggg ctccagcctg  360
gacattacct tccgctccga ctactccaac gagaagccgt tcacggggtt cgaggccttc  420
tatgcagccg aggacattga cgagtgccag gtggcccgg gagaggcgcc cacctgcgac  480
caccactgcc acaaccacct gggcggtttc tactgctcct gccgcgcagg ctacgtcctg  540
caccgtaaca agcgcacctg ctcagagcag agcctctagc ctccctgga gctccggcct  600
gcccagcagg tcagaagcca gagccagcct gctggcctca gctccgggtt gggctgagat  660
ggctgtgccc caactcccat tcacccacca tggacccaat aataaacctg gccccacccc  720
aaaaaaaaaa aaaaaaaa                                                738
```

```
SEQ ID NO: 13                 moltype = DNA   length = 18
FEATURE                       Location/Qualifiers
misc_feature                  1..18
                              note = DNA primer
source                        1..18
                              mol_type = other DNA
                              organism = synthetic construct
SEQUENCE: 13
gcacccagag ccacagtg                                                      18

SEQ ID NO: 14                 moltype = DNA   length = 18
FEATURE                       Location/Qualifiers
misc_feature                  1..18
                              note = DNA Primer
source                        1..18
                              mol_type = other DNA
                              organism = synthetic construct
SEQUENCE: 14
gccttccagt gtgtgggc                                                      18

SEQ ID NO: 15                 moltype = DNA   length = 19
FEATURE                       Location/Qualifiers
misc_feature                  1..19
                              note = DNA Primer
source                        1..19
                              mol_type = other DNA
                              organism = synthetic construct
SEQUENCE: 15
gccttccaga gtgtggtca                                                     19

SEQ ID NO: 16                 moltype = DNA   length = 19
FEATURE                       Location/Qualifiers
misc_feature                  1..19
                              note = DNA Primer
source                        1..19
                              mol_type = other DNA
                              organism = synthetic construct
SEQUENCE: 16
cgatctggag agcgaactc                                                     19

SEQ ID NO: 17                 moltype = DNA   length = 19
FEATURE                       Location/Qualifiers
misc_feature                  1..19
                              note = DNA Primer
source                        1..19
                              mol_type = other DNA
                              organism = synthetic construct
SEQUENCE: 17
ctgttcttca cactggctg                                                     19

SEQ ID NO: 18                 moltype = DNA   length = 20
FEATURE                       Location/Qualifiers
misc_feature                  1..20
                              note = DNA Primer
source                        1..20
                              mol_type = other DNA
                              organism = synthetic construct
SEQUENCE: 18
ctgctgagat catgttgttc                                                    20

SEQ ID NO: 19                 moltype = DNA   length = 15
FEATURE                       Location/Qualifiers
misc_feature                  1..15
                              note = DNA Primer
source                        1..15
                              mol_type = other DNA
                              organism = synthetic construct
SEQUENCE: 19
ttatacgact cacta                                                         15

SEQ ID NO: 20                 moltype = AA    length = 1231
FEATURE                       Location/Qualifiers
source                        1..1231
                              mol_type = protein
                              organism = Homo sapiens
SEQUENCE: 20
MRLLAKIICL MLWAICVAED CNELPPRRNT EILTGSWSDQ TYPEGTQAIY KCRPGYRSLG    60
NVIMVCRKGE WVALNPLRKC QKRPCGHPGD TPFGTFTLTG GNVFEYGVKA VYTCNEGYQL   120
LGEINYRECD TDGWTNDIPI CEVVKCLPVT APENGKIVSS AMEPDREYHF GQAVRFVCNS   180
```

```
GYKIEGDEEM HCSDDGFWSK EKPKCVEISC KSPDVINGSP ISQKIIYKEN ERFQYKCNMG    240
YEYSERGDAV CTESGWRPLP SCEEKSCDNP YIPNGDYSPL RIKHRTGDEI TYQCRNGFYP    300
ATRGNTAKCT STGWIPAPRC TLKPCDYPDI KHGGLYHENM RRPYFPVAVG KYYSYYCDEH    360
FETPSGSYWD HIHCTQDGWS PAVPCLRKCY FPYLENGYNQ NHGRKFVQGK SIDVACHPGY    420
ALPKAQTTVT CMENGWSPTP RCIRVKTCSK SSIDIENGFI SESQYTYALK EKAKYQCKLG    480
YVTADGETSG SIRCGKDGWS AQPTCIKSCD IPVFMNARTK NDFTWFKLND TLDYECHDGY    540
ESNTGSTTGS IVCGYNGWSD LPICYERECE LPKIDVHLVP DRKKDQYKVG EVLKFSCKPG    600
FTIVGPNSVQ CYHFGLSPDL PICKEQVQSC GPPPELLNGN VKEKTKEEYG HSEVVEYYCN    660
PRFLMKGPNK IQCVDGEWTT LPVCIVEEST CGDIPELEHG WAQLSSPPYY YGDSVEFNCS    720
ESFTMIGHRS ITCIHGVWTQ LPQCVAIDKL KKCKSSNLII LEEHLKNKKE FDHNSNIRYR    780
CRGKEGWIHT VCINGRWDPE VNCSMAQIQL CPPPPQIPNS HNMTTTLNYR DGEKVSVLCQ    840
ENYLIQEGEE ITCKDGRWQS IPLCVEKIPC SQPPPQIEHGT INSSRSSQES YAHGTKLSYT    900
CEGGFRISEE NETTCYMGKW SSPPQCEGLP CKSPPEISHG VVAHMSDSYQ YGEEVTYKCF    960
EGFGIDGPAI AKCLGEKWSH PPSCIKTDCL SLPSFENAIP MGEKKDVYKA GEQVTYTCAT   1020
YYKMDGASNV TCINSRWTGR PTCRDTSCVN PPTVQNAYIV SRQMSKYPSG ERVRYQCRSP   1080
YEMFGDEEVM CLNGNWTEPP QCKDSTGKCG PPPPIDNGDI TSFPLSVYAP ASSVEYQCQN   1140
LYQLEGNKRI TCRNGQWSEP PKCLHPCVIS REIMENYNIA LRWTAKQKLY SRTGESVEFV   1200
CKRGYRLSSR SHTLRTTCWD GKLEYPTCAK R                                  1231

SEQ ID NO: 21           moltype = AA  length = 597
FEATURE                 Location/Qualifiers
source                  1..597
                        mol_type = protein
                        organism = Homo sapiens
SEQUENCE: 21
MHPPKTPSGA LHRKRKMAAW PFSRLWKVSD PILFQMTLIA ALLPAVLGNC GPPPTLSFAA     60
PMDITLTETR FKTGTTLKYT CLPGYVRSHS TQTLTCNSDG EWVYNTFCIY KRCRHPGELR    120
NGQVEIKTDL SFGSQIEFSC SEGFFLIGST TSRCEVQDRG VGWSHPLPQC EIVKCKPPPD    180
IRNGRHSGEE NFYAYGFSVT YSCDPRFSLL GHASISCTVE NETIGVWRPS PPTCEKITCR    240
KPDVSHGEMV SGFGPIYNYK DTIVFKCQKG FVLRGSSVIH CDADSKWNPS PPACEPNSCI    300
NLPDIPHASW ETYPRPTKED VYVVGTVLRY RCHPGYKPTT DEPTTVICQK NLRWTPYQGC    360
EALCCPEPKL NNGEITQHRK SRPANHCVYF YGDEISFSCH ETSRFSAICQ GDGTWSPRTP    420
SCGDICNFPP KIAHGHYKQS SSYSFFKEEI IYECDKGYIL VGQAKLSCSY SHWSAPAPQC    480
KALCRKPELV NGRLSVDKDQ YVEPENVTIQ CDSGYGVVGP QSITCSGNRT WYPEVPKCEW    540
ETPEGCEQVL TGKRLMQCLP NPEDVKMALE VYKLSLEIEQ LELQRDSARQ STLDKEL      597

SEQ ID NO: 22           moltype = AA  length = 252
FEATURE                 Location/Qualifiers
source                  1..252
                        mol_type = protein
                        organism = Homo sapiens
SEQUENCE: 22
MFFWCACCLM VAWRVSASDA EHCPELPPVD NSIFVAKEVE GQILGTYVCI KGYHLVGKKT     60
LFCNASKEWD NTTTECRLGH CPDPVLVNGE FSSSGPVNVS DKITFMCNDH YILKGSNRSQ    120
CLEDHTWAPP FPICKSRDCD PPGNPVHGYF EGNNFTLGST ISYYCEDRYY LVGVQEQQCV    180
DGEWSSALPV CKLIQEAPKP ECEKALLAFQ ESKNLCEAME NFMQQLKESG MTMEELKYSL    240
ELKKAELKAK LL                                                       252

SEQ ID NO: 23           moltype = AA  length = 583
FEATURE                 Location/Qualifiers
source                  1..583
                        mol_type = protein
                        organism = Homo sapiens
SEQUENCE: 23
MKLLHVFLLF LCFHLRFCKV TYTSQEDLVE KKCLAKKYTH LSCDKVFCQP WQRCIEGTCV     60
CKLPYQCPKN GTAVCATNRR SFPTYCQQKS LECLHPGTKF LNNGTCTAEG KFSVSLKHGN    120
TDSEGIVEVK LVDQDKTMFI CKSSWSMREA NVACLDLGFQ QGADTQRRFK LSDLSINSTE    180
CLHVHCRGLE TSLAECTFTK RRTMGYQDFA DVVCYTQKAD SPMDDFFQCV NGKYISQMKA    240
CDGINDCGDQ SDELCCKACQ GKGPFHCKSGV CIPSQYQCNG EVDCITGEDE VGCAGFASVA    300
QEETEILTAD MDAERRRIKS LLPKLSCGVK NRMHIRRKRI VGGKRAQLGD LPWQVAIKDA    360
SGITCGGIYI GGCWILTAAH CLRASKTHRY QIWTTVVDWI HPDLKRIVIE YVDRIIFHEN    420
YNAGTYQNDI ALIEMKKDGN KKDCELPRSI PACVPWSPYL FQPNDTCIVS GWGREKDNER    480
VFSLQWGEVK LISNCSKFYG NRFYEKEMEC AGTYDGSIDA CKGDSGGPLV CMDANNVTYV    540
WGVVSWGENC GKPEFPGVYT KVANYFDWIS YHVGRPFISQ YNV                     583

SEQ ID NO: 24           moltype = AA  length = 500
FEATURE                 Location/Qualifiers
source                  1..500
                        mol_type = protein
                        organism = Homo sapiens
SEQUENCE: 24
MASRLTLLTL LLLLLAGDRA SSNPNATSSS SQDPESLQDR GEGKVATTVI SKMLFVEPIL     60
EVSSLPTTNS TTNSATKITA NTTDEPTTQP TTEPTTQPTI QPTQPTTQLP TDSPTTPTTG    120
SFCPGPVTLC SDLESHSTEA VLGDALVDFS LKLYHAFSAM KKVETNMAFS PFSIASLLTQ    180
VLLGAGENTK TNLESILSYP KDFTCVHQAL KGFTTKGVTS VSQIFHSPDL AIRDTFVNAS    240
RTLYSSSPRV LSNNSDANLE LINTWVAKNT NNKISRLLDS LPSDTRLVLL NAIYLSAKWK    300
TTFDPKKTRM EPFHFKNSVI KVPMMNSKKY PVAHFIDQTL KAKVGQLQLS HNLSLVILVP    360
QNLKHRLEDM EQALSPSVFK AIMEKLEMSK FQPTLLTLPR IKVTTSQDML SIMEKLEFFD    420
FSYDLNLCGL TEDPDLQVSA MQHQTVLELT ETGVEAAAAS AISVARTLLV FEVQQPFLFV    480
```

```
LWDQQHKFPV FMGRVYDPRA                                                500

SEQ ID NO: 25           moltype = AA  length = 680
FEATURE                 Location/Qualifiers
source                  1..680
                        mol_type = protein
                        organism = Homo sapiens
SEQUENCE: 25
HTVELNNMFG QIQSPGYPDS YPSDSEVTWN ITVPDGFRIK LYFMHFNLES SYLCEYDYVK     60
VETEDQVLAT FCGRETTDTE QTPGQEVVLS PGSFMSITFR SDFSNEERFT GFDAHYMAVD    120
VDECKEREDE ELSCDHYCHN YIGGYYCSCR FGYILHTDNR TCRVECSDNL FTQRTGVITS    180
PDFPNPYPKS SECLYTIELE EGFMVNLQFE DIFDIEDHPE VPCPYDYIKI KVGPKVLGPF    240
CGEKAPEPIS TQSHSVLILF HSDNSGENRG WRLSYRAAGN ECPELQPPVH GKIEPSQAKY    300
FFKDQVLVSC DTGYKVLKDN VEMDTFQIEC LKDGTWSNKI PTCKKNEIDL ESELKSEQVT    360
EGGGGSGGGG SCVAEDCNEL PPRRNTEILT GSWSDQTYPE GTQAIYKCRP GYRSLGNVIM    420
VCRKGEWVAL NPLRKCQKRP CGHPGDTPFG TFTLTGGNVF EYGVKAVYTC NEGYQLLGEI    480
NYRECDTDGW TNDIPICEVV KCLPVTAPEN GKIVSSAMEP DREYHFGQAV RFVCNSGYKI    540
EGDEEMHCSD DGFWSKEKPK CVEISCKSPD VINGSPISQK IIYKENERFQ YKCNMGYEYS    600
ERGDAVCTES GWRPLPSCEE KSCDNPYIPN GDYSPLRIKH RTGDEITYQC RNGFYPATRG    660
NTAKCTSTGW IPAPRCTLKP                                                680

SEQ ID NO: 26           moltype = DNA  length = 2032
FEATURE                 Location/Qualifiers
source                  1..2032
                        mol_type = other DNA
                        organism = Homo sapiens
SEQUENCE: 26
cacaccgtgg agctaaacaa tatgtttggc cagatccagt cgcctggtta tccagactcc     60
tatcccagtg attcagaggt gacttggaat atcactgtcc cagatgggtt tcggatcaag    120
ctttacttca tgcacttcaa cttggaatcc tcctaccgtg tgaatatga ctatgtgaag     180
gtagaaactg aggaccaggt gctggcaacc ttctgtggca gggagaccac agacacagag    240
cagactcccg gccaggaggt ggtcctctcc cctggctcct tcatgtccat cacttttccgg   300
tcagatttct ccaatgagga gcgtttcaca ggctttgatg cccactacat ggctgtggat    360
gtggacgagt gcaaggagag ggaggacgag gagctgtcct gtgaccacta ctgccacaac    420
tacattggcg gctactactg ctcctgccgc ttcggctaca tcctccacac agacaacagg    480
acctgccgag tggagtgcag tgacaacctc ttcactcaaa ggactggggt gatcaccagc    540
cctgacttcc caaaccctta ccccaagagc tctgaatgcc tgtataccat cgagctggag    600
gagggtttca tggtcaacct gcagtttgag gacatatttg acattgagga ccatcctgag    660
gtgccctgcc cctatgacta catcaagatc aaagttggtc caaaagtttt ggggcctttc    720
tgtggagaga aagccccaga acccatcagc acccagagcc acagtgtcct gatcctgttc    780
catagtgaca actcgggaga gaaccggggc tggaggctct catacagggc tgcaggaaat    840
gagtgcccag agctacagcc tcctgtccat gggaaaatcg agccctccca agccaagtat    900
ttcttcaaag accaagtgct cgtcagctgt gacacagatt ggctggataca gaaggataaa    960
gtggagatgg acacattcca gattgagtgt ctgaaggatg ggacgtggag taacaagatt   1020
cccacctgta aaaaaaatga aatcgatctg gagagcgaac tcaagtcaga gcaagtgaca   1080
gagggcggag gtgggtcggg tggcggcgga tcttgtgtag cagaagattg caatgaactt   1140
cctccaagaa gaaatacaga aattctgaca ggttcctggt ctgaccaaac atatccagaa   1200
ggcacccagg ctatctataa atgccgccct ggatatagat ctcttgggaa tgtaataatg   1260
gtatgcagga agggagaatg ggttgctctt aatccattaa ggaaatgtca gaaaaggccc   1320
tgtggacatc ctggagatac tcctttggt acttttaccc ttacaggagg aaatgtgttt    1380
gaatatggtg taaaagctgt gtatacatgt aatgagggt atcaattgct aggtgagatt    1440
aattaccgtg aatgtgacac agatggatgg accaatgata ttcctatatg tgaagttgtg   1500
aagtgtttac cagtgacagc accagagaat ggaaaaattg tcagtagtgc aatggaacca   1560
gatcgggaat accattttgg acaagcagta cggtttgtat gtaactcagg ctacaagatt   1620
gaaggagatg aagaaatgca ttgttcagac gatggttttt ggagtaaaga gaaaccaaag   1680
tgtgtggaaa tttcatgcaa atccccagat gttataaatg gatctcctat atctcagaag   1740
attatttata aggagaatga acgatttcaa tataaatgta acatgggtta tgaatacagt   1800
gaaagaggag atgctgtatg cactgaatct ggatggcgtc cgttgccttc atgtgaagaa   1860
aaatcatgtg ataatccta ttccaaat ggtgactact cacctttaag gattaaacac   1920
agaactggga tgaaatcac gtaccagtgt agaaatggtt tttatcctgc aacccgggga   1980
aatacagcaa aatgcacaag tactggctgg atacctgctc cgagatgtac ct           2032

SEQ ID NO: 27           moltype = AA  length = 680
FEATURE                 Location/Qualifiers
source                  1..680
                        mol_type = protein
                        organism = Homo sapiens
SEQUENCE: 27
CVAEDCNELP PRRNTEILTG SWSDQTYPEG TQAIYKCRPG YRSLGNVIMV CRKGEWVALN     60
PLRKCQKRPC GHPGDTPFGT FTLTGGNVFE YGVKAVYTCN EGYQLLGEIN YRECDTDGWT    120
NDIPICEVVK CLPVTAPENG KIVSSAMEPD REYHFGQAVR FVCNSGYKIE GDEEMHCSDD    180
GFWSKEKPKC VEISCKSPDV INGSPISQKI IYKENERFQY KCNMGYEYSE RGDAVCTESG    240
WRPLPSCEEK SCDNPYIPNG DYSPLRIKHR TGDEITYQCR NGFYPATRGN TAKCTSTGWI    300
PAPRCTLKPG GGGSGGGGSH TVELNNMFGI QSPGYPDSY PSDSEVTWNI TVPDGFRIKL    360
YFMHFNLESS YLCEYDYVKV ETEDQVLATF CGRETTDTEQ TPGQEVVLSP GSFMSITFRS    420
DFSNEERFTG FDAHYMAVDV DECEREDEE LSCDHYCHNY IGGYYCSCRF GYILHTDNRT     480
CRVECSDNLF TQRTGVITSP DFPNPYPKSS ECLYTIELEE GFMVNLQFED IFDIEDHPEV    540
PCPYDYIKIK VGPKVLGPFC GEKAPEPIST QSHSVLILFH SDNSGENGW RLSYRAAGNE    600
CPELQPPVHG KIEPSQAKYF FKDQVLVSCD TGYKVLKDNV EMDTFQIECL KDGTWSNKIP    660
```

TCKKNEIDLE SELKSEQVTE                                                680

SEQ ID NO: 28           moltype = DNA   length = 2032
FEATURE                 Location/Qualifiers
source                  1..2032
                        mol_type = other DNA
                        organism = Homo sapiens
SEQUENCE: 28
tgtgtagcag aagattgcaa tgaacttcct ccaagaagaa atacagaaat tctgacaggt   60
tcctggtctg accaaacata tccagaaggc acccaggcta tctataaatg ccgccctgga  120
tatagatctc ttggaaatgt aataatggta tgcaggaagg gagatgggt tgctcttaat   180
ccattaagga aatgtcagaa aaggccctgt ggacatcctg gagatactcc ttttggtact  240
tttacccctta caggaggaaa tgtgtttgaa tatggtgtaa aagctgtgta tacatgtaat  300
gagggggtatc aattgctagg tgagattaat taccgtgagt gtgacacaga tggatggacc  360
aatgatattc ctatatgtga agttgtgaag tgtttaccag tgacagcacc agagaatgga  420
aaaattgtca gtagtgcaat ggaaccagat cgggaatacc attttggaca agcagtacgg  480
tttgtatgta actcaggcta caagattgaa ggagatgaag aaatgcattg ttcagacgat  540
ggttttttgga gtaaagagaa accaaagtgt gtggaaattt catgcaaatc cccagatgtt  600
ataaatggat ctcctatatc tcagaagatt atttataagg agaatgaacg atttcaatat  660
aaatgtaaca tgggttatga atacagtgaa agaggagatg ctgtatgcac tgaatctgga  720
tggcgtccgt tgccttcatg tgaagaaaaa tcatgtgata tccttatat tccaaatggt   780
gactactcac ctttaaggat taaacacaga actggaagta aaatcacgta ccagtgtaga  840
aatggttttt atcctgcaac ccggggaaat acagcaaaat gcacaagtac tggctggata  900
cctgctccga gatgtacctg gcggaggtgg gtcgggtggc ggcggatctc acaccgtgga  960
gctaaacaat atgtttggcc agatccagtc gcctggttat ccagactcct atcccagtga 1020
ttcagaggtg acttggaata tcactgtccc agatgggttt cggatcaagc tttacttcat 1080
gcacttcaac ttggaatcct cctaccttttg tgaatatgac tatgtgaagg tagaaactga 1140
ggaccaggtg ctggcaacct tctgtggcag ggagaccaca gacacagagc agactcccgg 1200
ccaggaggtg gtcctctccc ctggctcctt catgtccatc actttccggt cagatttctc 1260
caatgaggag cgtttcacag gctttgatgc ccactacatg gctgtggatg tggacgagga 1320
caaggagagg gaggacgagg agctgtcctg tgaccactac tgccacaact acattggcgg 1380
ctactactgc tcctgccgct tcggctacat cctccacaca gacaacagga cctgccgagt 1440
ggagtgcagt gacaacctct tcactcaaag gactggggtg atcaccagcc ctgacttccc 1500
aaaaccttac cccaagagct ctgaatgcct gtataccatc gagctggagg aggtttcat  1560
ggtcaacctg cagtttgagg acatatttga cattgaggac atcctgagg tgccctgccc  1620
ctatgactac atcaagatca aagttggtcc aaaagttttg gggcctttct gtggagagaa 1680
agccccagaa cccatcagca cccagagcca cagtgtcctg atcctgttcc atagtgacaa 1740
ctcgggagag aaccgggggct ggaggctctc atacagggct gcaggaaatg agtgcccaga 1800
gctacagcct cctgtccatg ggaaaatcga gccctcccaa gccaagtatt tcttcaaaga 1860
ccaagtgctc gtcagctgtg acacaggcta caagtgctg aaggataatg tggagatgga  1920
cacattccag attgagtgtc tgaagggatgg gacgtggagt aacaagattc ccacctgtaa 1980
aaaaaatgaa atcgatctgg agagcgaact caagtcagag caagtgacag ag         2032

SEQ ID NO: 29           moltype = AA   length = 363
FEATURE                 Location/Qualifiers
source                  1..363
                        mol_type = protein
                        organism = Homo sapiens
SEQUENCE: 29
MRWLLLYYAL CFSLSKASAH TVELNNMFGQ IQSPGYPDSY PSDSEVTWNI TVPDGFRIKL   60
YFMHFNLESS YLCEYDYVKV ETEDQVLATF CGRETTDTEQ TPGQEVVLSP GSFMSITFRS  120
DFSNEERFTG FDAHYMAVDV DECKEREDEE LSCDHYCHNY IGGYYCSCRF GYILHTDNRT  180
CRVECSDNLF TQRTGVITSP DFPNPYPKSS ECLYTIELEE GFMVNLQFED IFDIEDHPEV  240
PCPYDYIKIK VGPKVLGPFC GEKAPEPIST QSHSVLILFH SDNSGENRGW RLSYRAAGNE  300
CPELQPPVHG KIEPSQAKYF FKDQVLVSCD TGYKVLKDNV EMDTFQIECL KDGTWSNKIP  360
TCK                                                                363

SEQ ID NO: 30           moltype = AA   length = 295
FEATURE                 Location/Qualifiers
source                  1..295
                        mol_type = protein
                        organism = Homo sapiens
SEQUENCE: 30
WLLLYYALCF SLSKASAHTV ELNNMFGQIQ SPGYPDSYPS DSEVTWNITV PDGFRIKLYF   60
MHFNLESSYL CEYDYVKVET EDQVLATFCG RETTDTEQTP GQEVVLSPGS FMSITFRSDF  120
SNEERFTGFD AHYMAVDVDE CKEREDEELS CDHYCHNYIG GYYCSCRFGY ILHTDNRTCR  180
VECSDNLFTQ RTGVITSPDF PNPYPKSSEC LYTIELEEGF MVNLQFEDIF DIEDHPEVPC  240
PYDYIKIKVG PKVLGPFCGE KAPEPISTQS HSVLILFHSD NSGENRGWRL SYRAA       295

SEQ ID NO: 31           moltype = AA   length = 198
FEATURE                 Location/Qualifiers
source                  1..198
                        mol_type = protein
                        organism = Homo sapiens
SEQUENCE: 31
VECSDNLFTQ RTGVITSPDF PNPYPKSSEC LYTIELEEGF MVNLQFEDIF DIEDHPEVPC   60
PYDYIKIKVG PKVLGPFCGE KAPEPISTQS HSVLILFHSD NSGENRGWRL SYRAAGNECP  120
ELQPPVHGKI EPSQAYYFFK DQVLVSCDTG YKVLKDNVEM DTFQIECLKD GTWSNKIPTC  180
KKNEIDLESE LKSEQVTE                                                198

```
SEQ ID NO: 32              moltype = AA  length = 264
FEATURE                    Location/Qualifiers
source                     1..264
                           mol_type = protein
                           organism = Homo sapiens
SEQUENCE: 32
MRLLAKIICL MLWAICVAED CNELPPRRNT EILTGSWSDQ TYPEGTQAIY KCRPGYRSLG   60
NVIMVCRKGE WVALNPLRKC QKRPCGHPGD TPFGTFTLTG GNVFEYGVKA VYTCNEGYQL  120
LGEINYRECD TDGWTNDIPI CEVVKCLPVT APENGKIVSS AMEPDREYHF GQAVRFVCNS  180
GYKIEGDEEM HCSDDGFWSK EKPKCVEISC KSPDVINGSP ISQKIIYKEN ERFQYKCNMG  240
YEYSERGDAV CTESGWRPLP SCEE                                        264

SEQ ID NO: 33              moltype = AA  length = 845
FEATURE                    Location/Qualifiers
source                     1..845
                           mol_type = protein
                           organism = Homo sapiens
SEQUENCE: 33
RKCYFPYLEN GYNQNHGRKF VQGKSIDVAC HPGYALPKAQ TTVTCMENGW SPTPRCIRVK   60
TCSKSSIDIE NGFISESQYT YALKEKAKYQ CKLGYVTADG ETSGSIRCGK DGWSAQPTCI  120
KSCDIPVFMN ARTKNDFTWF KLNDTLDYEC HDGYESNTGS TTGSIVCGYN GWSDLPICYE  180
RECELPKIDV HLVPDRKKDQ YKVGEVLKFS CKPGFTIVGP NSVQCYHFGL SPDLPICKEQ  240
VQSCGPPPEL LNGNVKEKTK EEYGHSEVVE YYCNPRFLMK GPNKIQCVDG EWTTLPVCIV  300
EESTCGDIPE LEHGWAQLSS PPYYYGDSVE FNCSESFTMI GHRSITCIHG VWTQLPQCVA  360
IDKLKKCKSS NLIILEEHLK NKKEFDHNSN IRYRCRGKEG WIHTVCINGR WDPEVNCSMA  420
QIQLCPPPPQ IPNSHNMTTT LNYRDGEKVS VLCQENYLIQ EGEEITCKDG RWQSIPLCVE  480
KIPCSQPPQI EHGTINSSRS SQESYAHGTK LSYTCEGGFR ISEENETTCY MGKWSSPPQC  540
EGLPCKSPPE ISHGVVAHMS DSYQYGEEVT YKCFEGFGID GPAIAKCLGE KWSHPPSCIK  600
TDCLSLPSFE NAIPMGEKKD VYKAGEQVTY TCATYYKMDG ASNVTCINSR WTGRPTCRDT  660
SCVNPPTVQN AYIVSRQMSK YPSGERVRYQ CRSPYEMFGD EEVMCLNGNW TEPPQCKDST  720
GKCGPPPPID NGDITSFPLS VYAPASSVEY QCQNLYQLEG NKRITCRNGQ WSEPPKCLHP  780
CVISREIMEN YNIALRWTAK QKLYSRTGES VEFVCKRGYR LSSRSHTLRT TCWDGKLEYP  840
TCAKR                                                             845

SEQ ID NO: 34              moltype = AA  length = 483
FEATURE                    Location/Qualifiers
source                     1..483
                           mol_type = protein
                           organism = Homo sapiens
SEQUENCE: 34
KTCSKSSIDI ENGFISESQY TYALKEKAKY QCKLGYVTAD GETSGSIRCG KDGWSAQPTC   60
IKSCDIPVFM NARTKNDFTW FKLNDTLDYE CHDGYESNTG STTGSIVCGY NGWSDLPICY  120
ERECELPKID VHLVPDRKKD QYKVGEVLKF SCKPGFTIVG PNSVQCYHFG LSPDLPICKE  180
QVQSCGPPPE LLNGNVKEKT KEEYGHSEVV EYYCNPRFLM KGPNKIQCVD GEWTTLPVCI  240
VEESTCGDIP ELEHGWAQLS SPPYYYGDSV EFNCSESFTM IGHRSITCIH GVWTQLPQCV  300
AIDKLKKCKS SNLIILEEHL KNKKEFDHNS NIRYRCRGKE GWIHTVCING RWDPEVNCSM  360
AQIQLCPPPP QIPNSHNMTT TLNYRDGEKV SVLCQENYLI QEGEEITCKD GRWQSIPLCV  420
EKIPCSQPPQ IEHGTINSSR SSQESYAHGT KLSYTCEGGF RISEENETTC YMGKWSSPPQ  480
CEG                                                               483

SEQ ID NO: 35              moltype = AA  length = 180
FEATURE                    Location/Qualifiers
source                     1..180
                           mol_type = protein
                           organism = Homo sapiens
SEQUENCE: 35
ESTCGDIPEL EHGWAQLSSP PYYYGDSVEF NCSESFTMIG HRSITCIHGV WTQLPQCVAI   60
DKLKKCKSSN LIILEEHLKN KKEFDHNSNI RYRCRGKEGW IHTVCINGRW DPEVNCSMAQ  120
IQLCPPPPQI PNSHNMTTTL NYRDGEKVSV LCQENYLIQE GEEITCKDGR WQSIPLCVEK  180

SEQ ID NO: 36              moltype = AA  length = 126
FEATURE                    Location/Qualifiers
source                     1..126
                           mol_type = protein
                           organism = Homo sapiens
SEQUENCE: 36
TGKCGPPPPI DNGDITSFPL SVYAPASSVE YQCQNLYQLE GNKRITCRNG QWSEPPKCLH   60
PCVISREIME NYNIALRWTA KQKLYSRTGE SVEFVCKRGY RLSSRSHTLR TTCWDGKLEY  120
PTCAKR                                                            126

SEQ ID NO: 37              moltype = AA  length = 188
FEATURE                    Location/Qualifiers
source                     1..188
                           mol_type = protein
                           organism = Homo sapiens
SEQUENCE: 37
NCGPPPTLSF AAPMDITLTE TRFKTGTTLK YTCLPGYVRS HSTQTLTCNS DGEWVYNTFC   60
IYKRCRHPGE LRNGQVEIKT DLSFGSQIEF SCSEGFFLIG STTSRCEVQD RGVGWSHPLP  120
```

```
QCEIVKCKPP PDIRNGRHSG EENFYAYGFS VTYSCDPRFS LLGHASISCT VENETIGVWR    180
PSPPTCEK                                                             188

SEQ ID NO: 38           moltype = AA  length = 246
FEATURE                 Location/Qualifiers
source                  1..246
                        mol_type = protein
                        organism = Homo sapiens
SEQUENCE: 38
NCGPPPTLSF AAPMDITLTE TRFKTGTTLK YTCLPGYVRS HSTQTLTCNS DGEWVYNTFC    60
IYKRCRHPGE LRNGQVEIKT DLSFGSQIEF SCSEGFFLIG STTSRCEVQD RGVGWSHPLP    120
QCEIVKCKPP PDIRNGRHSG EENFYAYGFS VTYSCDPRFS LLGHASISCT VENETIGVWR    180
PSPPTCEKGH CPDPVLVNGE FSSSGPVNVS DKITFMCNDH YILKGSNRSQ CLEDHTWAPP    240
FPICKS                                                               246

SEQ ID NO: 39           moltype = AA  length = 304
FEATURE                 Location/Qualifiers
source                  1..304
                        mol_type = protein
                        organism = Homo sapiens
SEQUENCE: 39
NCGPPPTLSF AAPMDITLTE TRFKTGTTLK YTCLPGYVRS HSTQTLTCNS DGEWVYNTFC    60
IYKRCRHPGE LRNGQVEIKT DLSFGSQIEF SCSEGFFLIG STTSRCEVQD RGVGWSHPLP    120
QCEIVKCKPP PDIRNGRHSG EENFYAYGFS VTYSCDPRFS LLGHASISCT VENETIGVWR    180
PSPPTCEKEH CPELPPVDNS IFVAKEVEGQ ILGTYVCIKG YHLVGKKTLF CNASKEWDNT    240
TTECRLGHCP DPVLVNGEFS SSGPVNVSDK ITFMCNDHYI LKGSNRSQCL EDHTWAPPFP    300
ICKS                                                                 304

SEQ ID NO: 40           moltype = AA  length = 665
FEATURE                 Location/Qualifiers
source                  1..665
                        mol_type = protein
                        organism = Homo sapiens
SEQUENCE: 40
NCGPPPTLSF AAPMDITLTE TRFKTGTTLK YTCLPGYVRS HSTQTLTCNS DGEWVYNTFC    60
IYKRCRHPGE LRNGQVEIKT DLSFGSQIEF SCSEGFFLIG STTSRCEVQD RGVGWSHPLP    120
QCEIVKCKPP PDIRNGRHSG EENFYAYGFS VTYSCDPRFS LLGHASISCT VENETIGVWR    180
PSPPTCEKIT CRKPDVSHGE MVSGFGPIYN YKDTIVFKCQ KGFVLRGSSV IHCDADSKWN    240
PSPPACEPNS CINLPDIPHA SWETYPRPTK EDVYVVGTVL RYRCHPGYKP TTDEPTTVIC    300
QKNLRWTPYQ GCEALCCPEP KLNNGEITQH RKSRPANHCV YFYGDEISFS CHETSRFSAI    360
CQGDGTWSPR TPSCGDICNF PPKIAHGHYK QSSSYSFFKE EIIYECDKGY ILVGQAKLSC    420
SYSHWSAPAP QCKALCRKPE LVNGRLSVDK DQYVEPENVT IQCDSGYGVV GPQSITCSGN    480
RTWYPEVPKC EWEHCPELPP VDNSIFVAKE VEGQILGTYV CIKGYHLVGK KTLFCNASKE    540
WDNTTTECRL GHCPDPVLVN GEFSSSGPVN VSDKITFMCN DHYILKGSNR SQCLEDHTWA    600
PPFPICKSRD CDPPGNPVHG YFEGNNFTLG STISYYCEDR YYLVGVQEQQ CVDGEWSSAL    660
PVCKL                                                                665

SEQ ID NO: 41           moltype = AA  length = 473
FEATURE                 Location/Qualifiers
source                  1..473
                        mol_type = protein
                        organism = Homo sapiens
SEQUENCE: 41
KFSVSLKHGN TDSEGIVEVK LVDQDKTMFI CKSSWSMREA NVACLDLGFQ QGADTQRRFK    60
LSDLSINSTE CLHVHCRGLE TSLAECTFTK RRTMGYQDFA DVVCYTQCAD SPMDDFFQCV    120
NGKYISQMKA CDGINDCGDQ SDELCCKACQ GKGFHCKSGV CIPSQYQCNG EVDCITGEDE    180
VGCAGFASVA QEETEILTAD MDAERRRIKS LLPKLSCGVK NRMHIRRKRI VGGKRAQLGD    240
LPWQVAIKDA SGITCGGIYI GGCWILTAAH CLRASKTHRY QIWTTVVDWI HPDLKRIVIE    300
YVDRIIFHEN YNAGTYQNDI ALIEMKKDGN KKDCELPRSI PACVPWSPYL FQPNDTCIVS    360
GWGREKDNER VFSLQWGEVK LISNCSKFYG NRFYEKEMEC AGTYDGSIDA CKGDSGGPLV    420
CMDANNVTYV WGVVSWGENC GKPEFPGVYT KVANYFDWIS YHVGRPFISQ YNV           473

SEQ ID NO: 42           moltype = AA  length = 366
FEATURE                 Location/Qualifiers
source                  1..366
                        mol_type = protein
                        organism = Homo sapiens
SEQUENCE: 42
KADSPMDDFF QCVNGKYISQ MKACDGINDC GDQSDELCCK ACQGKGFHCK SGVCIPSQYQ    60
CNGEVDCITG EDEVGCAGFA SVAQEETEIL TADMDAERRR IKSLLPKLSC GVKNRMHIRR    120
KRIVGGKRAQ LGDLPWQVAI KDASGITCGG IYIGGCWILT AAHCLRASKT HRYQIWTTVV    180
DWIHPDLKRI VIEYVDRIIF HENYNAGTYQ NDIALIEMKK DGNKKDCELP RSIPACVPWS    240
PYLFQPNDTC IVSGWGREKD NERVFSLQWG EVKLISNCSK FYGNRFYEKE MECAGTYDGS    300
IDACKGDSGG PLVCMDANNV TYVWGVVSWG ENCGKPEFPG VYTKVANYFD WISYHVGRPF    360
ISQYNV                                                               366

SEQ ID NO: 43           moltype = AA  length = 327
FEATURE                 Location/Qualifiers
source                  1..327
```

```
                        mol_type = protein
                        organism = Homo sapiens
SEQUENCE: 43
KACQGKGFHC KSGVCIPSQY QCNGEVDCIT GEDEVGCAGF ASVAQEETEI LTADMDAERR    60
RIKSLLPKLS CGVKNRMHIR RKRIVGGKRA QLGDLPWQVA IKDASGITCG GIYIGGCWIL   120
TAAHCLRASK THRYQIWTTV VDWIHPDLKR IVIEYVDRII FHENYNAGTY QNDIALIEMK   180
KDGNKKDCEL PRSIPACVPW SPYLFQPNDT CIVSGWGREK DNERVFSLQW GEVKLISNCS   240
KFYGNRFYEK EMECAGTYDG SIDACKGDSG GPLVCMDANN VTYVWGVVSW GENCGKPEFP   300
GVYTKVANYF DWISYHVGRP FISQYNV                                      327

SEQ ID NO: 44           moltype = AA  length = 285
FEATURE                 Location/Qualifiers
source                  1..285
                        mol_type = protein
                        organism = Homo sapiens
SEQUENCE: 44
VAQEETEILT ADMDAERRRI KSLLPKLSCG VKNRMHIRRK RIVGGKRAQL GDLPWQVAIK    60
DASGITCGGI YIGGCWILTA AHCLRASKTH RYQIWTTVVD WIHPDLKRIV IEYVDRIIFH   120
ENYNAGTYQN DIALIEMKKD GNKKDCELPR SIPACVPWSP YLFQPNDTCI VSGWGREKDN   180
ERVFSLQWGE VKLISNCSKF YGNRFYEKEM ECAGTYDGSI DACKGDSGGP LVCMDANNVT   240
YVWGVVSWGE NCGKPEFPGV YTKVANYFDW ISYHVGRPFI SQYNV                  285

SEQ ID NO: 45           moltype = AA  length = 365
FEATURE                 Location/Qualifiers
source                  1..365
                        mol_type = protein
                        organism = Homo sapiens
SEQUENCE: 45
HSTEAVLGDA LVDFSLKLYH AFSAMKKVET NMAFSPFSIA SLLTQVLLGA GENTKTNLES    60
ILSYPKDFTC VHQALKGFTT KGVTSVSQIF HSPDLAIRDT FVNASRTLYS SSPRVLSNNS   120
DANLELINTW VAKNTNNKIS RLLDSLPSDT RLVLLNAIYL SAKWKTTFDP KKTRMEPFHF   180
KNSVIKPMM NSKKYPVAHF IDQTLKAKVG QLQLSHNLSL VILVPQNLKH RLEDMEQALS    240
PSVFKAIMEK LEMSKFQPTL LTLPRIKVTT SQDMLSIMEK LEFFDFSYDL NLCGLTEDPD   300
LQVSAMQHQT VLELTETGVE AAAASAISVA RTLLVFEVQQ PFLFVLWDQQ HKFPVFMGRV   360
YDPRA                                                              365

SEQ ID NO: 46           moltype = AA  length = 678
FEATURE                 Location/Qualifiers
source                  1..678
                        mol_type = protein
                        organism = Homo sapiens
SEQUENCE: 46
MAPSLSPGPA ALRRAPQLLL LLLAAECALA ALLPAREATQ FLRPRQRRAF QVFEEAKQGH    60
LERECVEELC SREEAREVFE NDPETDYFYP RYLDCINKYG SPYTKNSGFA TCVQNLPDQC   120
TPNPCDRKGT QACQDLMGNF FCLCKAGWGG RLCDKDVNEC SQENGGCLQI CHNKPGSFHC   180
SCHSGFELSS DGRTCQDIDE CADSEACGEA RCKNLPGSYS CLCDEGFAYS SQEKACRDVD   240
ECLQGRCEQV CVNSPGSYTC HCDGRGGLKL SQDMDTCEDI LPCVPFSVAK SVKSLYLGRM   300
FSGTPVIRLR FKRLQPTRLV AEFDFRTFDP EGILLFAGGH QDSTWIVLAL RAGRLELQLR   360
YNGVGRVTSS GPVINHGMWQ TISVEELARN LVIKVNRDAV MKIAVAGDLF QPERGLYHLN   420
LTVGGIPFHE KDLVQPINPR LDGCMRSWNW LNGEDTTIQE TVKVNTRMQC FSVTERGSFY   480
PGSSFAFYSL DYMRTPLDVG TESTWEVEVV AHIRPAADTG VLFALWAPDL RAVPLSVALV   540
DYHSTKKLKK QLVVLAVEHT ALALMEIKVC DGQEHVVTVS LRDGEATLEV DGTRGQSEVS   600
AAQLQERLAV LERHLSPVL TFAGGLPDVP VTSAPVTAFY RGCMTLEVNR RLLDLDEAAY   660
KHSDITAHSC PPVEPAAA                                                678

SEQ ID NO: 47           moltype = DNA  length = 2041
FEATURE                 Location/Qualifiers
source                  1..2041
                        mol_type = other DNA
                        organism = Homo sapiens
SEQUENCE: 47
gccacctgcg tgcaaaacct gcctgaccag tgcacgccca ccccctgcga taggaagggg    60
acccaagcct gccaggacct catgggcaac ttcttctgcc tgtgtaaagc tggctggggg   120
ggccggctct gcgacaaaga tgtcaacgaa tgcagccagg agaacggggg ctgcctccag   180
atctgccaca caaagccggg tagcttccac tgttcctgcc acagcggctt cgagctctcc   240
tctgatggca ggacctgcca agacatagac gagtgcgcag actcggaggc ctgcggggag   300
gcgcgctgca agaacctgcc cggctcctac tcctgcctct gtgacgaggg cttttgcgtac   360
agctcccagg agaaggcttg ccgagatgtg gacgagtgtc tgcagggccg ctgtgagcga   420
gtctgcgtga actcccagg gagctacacc tgccactgtg acgggcgtgg gggcctcaag   480
ctgtcccagg acatggacac ctgtgaggac atcttgccgt gcgtgccctt cagcgtggcc   540
aagagtgtga agtccttgta cctgggccgg atgttcagtg gaccccccgt gatccgactg   600
cgcttcaaga ggctgcagcc caccaggctg gtagctgagt ttgacttccg gaccttgac    660
cccgagggca tcctcctctt tgccggaggc accaggacag gcacctggat cgtgctggcc   720
ctgagagcg gccgcctgga gctgcagctg cgctacaacg gtgtcggccg tgtcaccggc   780
agcggcccgg tcatcaacca tggcatgtgg cagacaatct ctgttgagga gctggcgcgg   840
aatctggtca tcaaggtcaa cagggatgct gtcatgaaaa tcgcggtggc cggggacttg   900
ttccaaccgg agcgaggact gtatcatctg aacctgaccg tgggaggtat tccccttccat   960
gagaaggacc tcgtgcagcc tataaaccct cgtctggatg gctgcatgag gagctggaac  1020
tggctgaacg gagaagacac caccatccag gaaacggtga agtgaacac gaggatgcag   1080
```

```
tgcttctcgg tgacggagag aggctctttc tacccccggga gcggcttcgc cttctacagc 1140
ctggactaca tgcggacccc tctgacgtc gggactgaat caacctggga agtagaagtc 1200
gtggctcaca tccgcccagc cgcagacaca ggcgtgctgt ttgcgctctg gcccccgac  1260
ctccgtgccg tgcctctctc tgtggcactg gtagactatc actccacgaa gaaactcaag 1320
aagcagctgg tggtcctggc cgtggagcat acggccttgc ccctaatgga gatcaaggtc 1380
tgcgacggcc aagagcacgt ggtcaccgtc tcgctgaggg acggtgaggc caccctggag 1440
gtggacggca ccaggggcca gagcgaggtg agcgccgcgc agctgcagga gagctggcc   1500
gtgctcgaga ggcacctgcg gagccccgtg ctcaccttg ctggcggcct gccagatgtg   1560
ccggtgactt cagcgccagt caccgcgttc taccgcggct gcatgacact ggaggtcaac  1620
cggaggctgc tggacctgga cgaggcggcg tacaagcaca gcgacatcac ggcccactcc  1680
tgccccccg tggagcccgc cgcagcctag gccccacgg gacgcggcag gcttctcagt    1740
ctctgtccga cacagccggg aggagcctgg gggctcctca ccacgtgggg ccatgctgag  1800
agctgggctt tcctctgtga ccatcccggc ctgtaacata tctgtaaata gtgagatgga  1860
cttgggcctt ctgacgccgc gcactcagcc gtgggcccgg gcgcggggag gccggccag   1920
cgcagagcgg gctcgaagaa aataattctc tattattttt attaccaagc gcttctttct  1980
gactctaaaa tatggaaaat aaaatattta cagaaagctt tgtaaaaaaa aaaaaaaaa   2040
a                                                                  2041

SEQ ID NO: 48         moltype = AA  length = 405
FEATURE               Location/Qualifiers
source                1..405
                      mol_type = protein
                      organism = Homo sapiens
SEQUENCE: 48
MDTCEDILPC VPFSVAKSVK SLYLGRMFSG TPVIRLRFKR LQPTRLVAEF DFRTFDPEGI 60
LLFAGGHQDS TWIVLALRAG RLELQLRYNG VGRVTSSGPV INHGMWQTIS VEELARNLVI 120
KVNRDAVMKI AVAGDLFQPE RGLYHLNLTV GGIPFHEKDL VQPINPRLDG CMRSWNWLNG 180
EDTTIQETVK VNTRMQCFSV TERGSFYPGS GFAFYSLDYM RTPLDVGTES TWEVEVVAHI 240
RPAADTGVLF ALWAPDLRAV PLSVALVDYH STKKLKKQLV VLAVEHTALA LMEIKVCDGQ 300
EHVVTVSLRD GEATLEVDGT RGQSEVSAAQ LQERLAVLER HLRSPVLTFA GGLPDVPVTS 360
APVTAFYRGC MTLEVNRRLL DLDEAAYKHS DITAHSCPPV EPAAA                 405

SEQ ID NO: 49         moltype = DNA  length = 2188
FEATURE               Location/Qualifiers
source                1..2188
                      mol_type = other DNA
                      organism = Homo sapiens
SEQUENCE: 49
ttgattgaaa ccagtaaatg cttctctttg gggttgggt tttagtttca aatgccccg    60
gggggttact tttacggcc ccgtgtcctg tagcaccgtc atttaaatgg aacagcacag   120
cgtgcaccgc cgcccccac ccctccacca agcagggccc ttcccagctc tccacctgct   180
gggctgaagt cagccttccc agccgggcct tgatcagaag cgtgcaccaa caccccggga  240
gctgcccggt caggggagga gggcagggaa atggggcgag gcgcgctgg ccccacagag   300
tctggatgcg acctctgggt ggtgccctgg ccagtccctg cagccgcctg ccccagcccc  360
gtctgagatg ccgctgtgct gcggttggcc ggttttttt tgcttgcaga catagacgag   420
tgcgcagact cggaggcctg cggggaggcg cgctgcaaga acctgcccgg ctcctactcc  480
tgcctctgtg acgagggctt tgcgtacagc tcccaggaga aggcttgccg agatgtggac  540
gagtgtctgc agggccgctg tgagcaggtc tgcgtgaact cccccaggag ctacacctgc  600
cactgtgacg ggcgtggggg cctcaagctg tcccaggaca tggacacctg tgaggacatc  660
ttgccgtgcg tgcccttcag cgtggccaag agtgtgaagt ccttgtacct gggccggatg  720
ttcagtggga ccccccgtgat ccgactgcgc ttcaagaggc tgcagcccac caggctgtga  780
gctgagtttg acttccggac cttgacccc gagggcatcc tcctctttgc cggaggccac   840
caggacagca cctggatcgt gctggcccct agagccggcc ggctgagct gcagctgcgc   900
tacaacggtg tcggccgtgt caccagcagc ggcccgtca tcaaccatgg catgtggcag   960
acaatctctg ttgaggagct ggcgcggaat ctggtcatca aggtcaacag ggatgctgtc  1020
atgaaaatcg cggtggccgg ggacttgttc caaccggagc gaggactgta tcatctgaac  1080
ctgaccgtgg gaggtattcc cttccatgag aaggaccctcg tgcagcctat aaaccctcgt  1140
ctggatggct gcatgaggag ctggaactgg ctgaacggag aagacaccac catccaggaa  1200
acggtgaaag tgaacacgag gatgcagtgc ttctcggtga cggagagagg ctcttttctac  1260
cccggggagcg gcttcgcctt ctacagcctg gactacatgc ggacccctct ggacgtcggga 1320
actgaatcaa cctgggaagt agaagtcgtg gctcacatcc gcccagccgc agacacaggc  1380
gtgctgtttg cgctctggc cccgacctc cgtgccgtgc ctctctctgt ggcactggta    1440
gactatcact ccacgaagaa actcaagaag cagctggtgt tcctggccgt ggagcatacg  1500
gccttggccc taatggagat caaggtctgc gacggccaag agcacgttg gtcaccgtct   1560
cgctgaggga cgtgaggccac cctggaggtg gacggcacca ggggccagag cgaggtgagc  1620
gccgcgcagc tgcaggagag gctggccgtg ctcgagaggc acctgcggag ccccgtgctc  1680
acctttgctg gcggcctgcc agatgtgccg gtgacttcag cgccagtcac cgcgttctac  1740
cgcggctgca tgacactgga ggtcaaccgg aggctgctgg acctggacga ggcggcgtac  1800
aagcacagcg acatcacggc ccactcctgc cccccgtgg agcccgccgc agcctaggcc   1860
cccacgggac gcggcaggct tctcagtctc tgtccgagac agccgggagg agcctggggg  1920
ctcctcacca cgtgggcca tgctgagagc tgggcttttc tctgtgacca tcccggcctg   1980
taacatatct gtaaatagtg agatggactt ggggcctctg acgccgcgca ctcagccgtg  2040
ggcccgggcg cggggaggcc ggcgcagcgc agagcgggct cgaagaaaat aattctctat  2100
tattttttatt accaagcgct tctttctgac tctaaaatat ggaaataaa atatttacag  2160
aaagctttgt aaaaaaaaaa aaaaaaa                                      2188

SEQ ID NO: 50         moltype = AA  length = 379
FEATURE               Location/Qualifiers
source                1..379
```

```
                           mol_type = protein
                           organism = Homo sapiens
SEQUENCE: 50
MFSGTPVIRL RFKRLQPTRL VAEFDFRTFD PEGILLFAGG HQDSTWIVLA LRAGRLELQL    60
RYNGVGRVTS SGPVINHGMW QTISVEELAR NLVIKVNRDA VMKIAVAGDL FQPERGLYHL   120
NLTVGGIPFH EKDLVQPINP RLDGCMRSWN WLNGEDTTIQ ETVKVNTRMQ CFSVTERGSF   180
YPGSGFAFYS LDYMRTPLDV GTESTWEVEV VAHIRPAADT GVLFALWAPD LRAVPLSVAL   240
VDYHSTKKLK KQLVVLAVEH TALALMEIKV CDGQEHVVTV SLRDGEATLE VDGTRGQSEV   300
SAAQLQERLA VLERHLRSPV LTFAGGLPDV PVTSAPVTAF YRGCMTLEVN RRLLDLDEAA   360
YKHSDITAHS CPPVEPAAA                                                379

SEQ ID NO: 51              moltype = DNA  length = 2523
FEATURE                    Location/Qualifiers
source                     1..2523
                           mol_type = other DNA
                           organism = Homo sapiens
SEQUENCE: 51
cacaccgacc tgtcacaccg gtgcctgtca caccactgcc tgtcacactg acttgtcacc    60
ggtgtctgtc acaccgacct gtcacactgg tgcctgtcac actggtgcct gtcacaccga   120
cctgtcacac cggtgcctgt cacaccgacc tgtcacactg acctgtcaca ccggtaggaa   180
tgcagtaccc acatgtggac gtttctgggc agggcggctc ttgtctttcc tcttcagcct   240
gggcctgtgc ctgggggttg atgagagtga gcatttattt aaaaagcaaa accacaggtg   300
gaaagagtca ccaggacagc ttctcggagt cgcagacctg ggatgcagcc gtggggctct   360
tgggtctggg ctgcgacgtt cagggcttcc agccagccct cgccttgagg ttcttttgcct   420
cgctgcctca tgtactcatg cagagggtgt cggacccctg cgagatgtcc agctcaccct   480
ggctgcccac ggtgggcagg gcaggcctgc ctcagccgca cccctccat cttccaggtg    540
tgtcagctca caccggcttt ggttctgtcc cccttcgggc agcgtggaga accacagcc    600
cagaacaggg aactttccag gacagccatc ttcaaggcat ccatatctat ttcataatag   660
tgtatacttt ttaatgattc tctgtaattt ttgtatgctt gaaatatttc ataatttaaa   720
aataaagggt caagggaaat gagcagggaa ggagatgacg gggaccccg agaagccctg    780
tgggaagcgc ctgctgcaag cccgcccttc acctggagt cccagtgggg caggtgtgac    840
agcctctggg gtctcagcag ctagaggcgg ggtggccact cccgaggcac aggagggaca   900
gtggaccccgc tgcgcggccg gggcgtgggg ctcaggggag caggagtgaa ggccacatcc   960
ccgaccggcg tggccccccgt ccgtggcagg acatcttgcc gtgcgtgccc ttcagctgg   1020
ccaagatgtg gaagtccttg tacctgggcc ggatgttcac tgggaccccc gtgatccgac  1080
tgcgcttcaa gaggctgcag cccaccaggc tggtagctga gtttgacttc cggaccttgg  1140
accccgaggg catcctcctc tttgccgagg gccaccagga cagcacctgg atcgtgctgg  1200
ccctgagagc cggccggctg gagctgcagc tgcgctacaa cggtgtcggc cgtgtcacca  1260
gcagcgggcc ggtcatcaac catgccatgt ggcagacaat ctctgttgag gagctggcgc  1320
ggaatctggt catcaaggtc aacagggatg ctgtcatgaa aatcgcggtg gccggggact  1380
tgttccaacc ggagcgagga ctgtatcatc tgaacctgac cgtgggaggt attcccttcc  1440
atgagaagga cctcgtgcag cctataaacc ctcgtctgga tggctgcatg aggagctgga  1500
actggctgaa cggagaagac accaccatcc aggaaacggt gaaagtgaac acgaggatgc  1560
agtgcttctc ggtgacgag agaggctctt tctaccccgg gagcggcttc gccttctaca  1620
gcctggacta catgcggacc cctctggacg tcgggactga atcaacctgg gaagtagaag  1680
tcgtggctca catccgccca gccgcagaca caggcgtgct gtttgcgctc tgggcccccg  1740
acctccgtgc cgtgcctctc tctgtggcac tggtagacta tcactccacg aagaactca   1800
agaagcagct ggtggtcctg gccgtggagc atacggcctt ggccctaatg agatcaagg   1860
tctgcgacgg ccaagagcac gtggtcaccg tctcgctgag ggacggtgag gccaccctgg  1920
aggtggacgg caccagggc cagagcgagg tgagcgccgc gcagctgcag gagaggctgg   1980
ccgtgctcga gaggcacctg cggagccccg tgctcacctt tgctggcggc ctgccagatg  2040
tgccggtgac ttcagcgcca gtcaccgcgt tctaccgcgg ctgcatgaca ctggaggtca  2100
accggaggct gctggacctg gacgaggcgg cgtacaagca cagcgacatc acggcccact  2160
cctgcccccc cgtggagccc gccgcagcct aggcccccac gggacgcggc aggcttctca  2220
gtctctgtcc gagacagccg gaggagcct ggggggctct caccacgtgg ggcatgctg    2280
agagctgggc tttcctctgt gaccatcccg gcctgtaaca tatctgtaaa tagtgagatg  2340
gacttggggc ctctgacgcc gcgcactcag ccgtgggccc gggcgcgggg aggccggcgc  2400
agcgcagagc gggctcgaag aaaataatc tctattattt ttattaccaa gcgcttcttt   2460
ctgactctaa aatatggaaa ataaaatatt tacagaaagc tttgtaaaaa aaaaaaaaaa  2520
aaa                                                                 2523

SEQ ID NO: 52              moltype = AA  length = 676
FEATURE                    Location/Qualifiers
source                     1..676
                           mol_type = protein
                           organism = Homo sapiens
SEQUENCE: 52
MRVLGGRCGA LLACLLLVLP VSEANFLSKQ QASQVLVRKR RANSLLEETK QGNLERECIE    60
ELCNKEEARE VFENDPETDY FYPKYLVCLR SFQTGLFTAA RQSTNAYPDL RSCVNAIPDQ   120
CSPLPCNEDG YMSCKDGKAS FTCTCKPGWQ GEKCEFDINE CKDPSNINGG CSQICDNTPG   180
SYHCSCKNGF VMLSNKKDCK DVDECSLKPS ICGTAVCKNI PGDFECECPE GYRYNLKSKS   240
CEDIDECSEN MCAQLCVNYP GGYTCYCDGK KGFKLAQDQK SCEVVSVCLP LNLDTKYELL   300
YLAEQFAGVV LYLKFRLPEI SRFSAEFDFR TYDSEGVILY AESIDHSAWL LIALRGGKIE   360
VQLKNEHTSK ITTGGDVINN GLWNMVSVEE LEHSISIKIA KEAVMDINKP GPLFKPENGL   420
LETKVYFAGF PRKVESELIK PINPRLDGCI RSWNLMKQGA SGIKEIIQEK QNKHCLVTVE   480
KGSYYPGSGI AQFHIDYNNV SSAEGWHVNV TLNIRPSTGT GVMLALVSGN NTVPFAVSLV   540
DSTSEKSQDI LLSVENTVIY RIQALSLCSD QQSHLEFRVN RNNLESTPL KIETISHEDL    600
QRQLAVLDKA MKAKVATYLG GLPDVPFSAT PVNAFYNGCM EVNINGVQLD LDEAISKHND   660
IRAHSCPSVW KKTKNS                                                   676
```

| SEQ ID NO: 53 | moltype = DNA  length = 3595 |
|---|---|
| FEATURE | Location/Qualifiers |
| source | 1..3595 |
| | mol_type = other DNA |
| | organism = Homo sapiens |

SEQUENCE: 53

```
tttggaaacg tcacactgtg gaggaaaagc agcaactagg gagctggtga agaaggatgt    60
ctcagcagtg tttactaggc ctccaacact agagcccatc ccccagctcc gaaaagcttc   120
ctggaaatgt ccttgttatc acttcccctc tcgggctggg cgctgggagc gggcggtctc   180
ctccgccccc ggctgttccg ccgaggctcg ctgggtcgct ggcgccgccg cgcagcacgg   240
ctcagaccga ggcgcacagg ctcgcagctc cgcggcgcct agcgctccgg tccccgccgc   300
gacgcgccac cgtccctgcc ggcgcctccg cgcgcttcga aatgagggtc ctgggtgggc   360
gctgcgggc gctgctggcg tgtctcctcc tagtgcttcc cgtctcagag gcaaactttc    420
tgtcaaagca acaggcttca caagtcctgg ttaggaagcg tcgtgcaaat tctttacttg   480
aagaaaccaa acagggtaat cttgaaagag aatgcatcga agaactgtgc aataaagaag   540
aagccaggga ggtcttttgaa aatgacccgg aaacggatta tttttatcca aaatacttag   600
tttgtcttcg ctctttttcaa actggttat tcactgctgc acgtcagtca actaatgctt    660
atcctgacct aagaagctgt gtcaatgcca ttccagacca gtgtagtcct ctgccatgca   720
atgaagatgg atatatgagc tgcaaagatg gaaaagcttc ttttacttgc acttgtaaac   780
caggttggca aggagaaaag tgtgaatttg acataaatga atgcaaagat ccctcaaata   840
taaatggagg ttgcagtcaa atttgtgata atacacctga aagttaccac tgttcctgta   900
aaaatggttt tgttatgctt tcaaataaga aagattgtaa agatgtggat gaatgctctt   960
tgaagccaag catttgtggc acagctgtgt gcaagaacat cccaggagat tttgaatgtg  1020
aatgccccga aggctacaga tataatctca aatcaaagtc ttgtgaagat atagatgaat  1080
gctctgagaa catgtgtgct cagctttgtg tcaattacaa tggaggttac acttgctatt  1140
gtgatgggaa gaaaggattc aaacttgccc aagatcagaa gagttgtgag gttgtttcag  1200
tgtgccttcc cttgaacctt gacacaaagt atgaattact ttacttggcg gagcagtttg  1260
cagggggttgt tttatattta aaatttcgtt tgccagaaat cagcagattt tcagcagaat  1320
ttgatttccg gacatatgat tcagaaggcg tgatactgta cgcagaatct atcgatcact  1380
cagcgtggct cctgattgca cttcgtggtg gaaagattga agttcagctt aagaatgaac  1440
atacatccaa aatcacaact ggaggtgatg ttattaataa tggtcatgg aatatggtgt   1500
ctgtggaaga attagaacat agtattgca ttaaaatagc taagaagct gtgatggata    1560
taaataaacc tggaccctt tttaagccgg aaaatggatt gctggaaacc aaagtatact   1620
ttgcaggatt ccctcggaaa gtggaaagtg aactcattaa accgattaac cctcgtctag  1680
atggatgtat acgaagctgg aatttgatga gcaaggagc ttctggaata aaggaaatta   1740
ttcaagaaaa acaaaataag cattgcctgg ttactgtgga aagggctcc tactatcctg    1800
gttctggaat tgctcaatttt cacatagatt ataataatgt atccagtgct gagggttggc  1860
atgtaaatgt gaccttgaat attcgtccat ccacgggcac tggtgttatg cttgccttgg  1920
tttctggtaa caacacagtg ccctttgctg tgtccttgct ggactccacc tctgaaaaat  1980
cacaggatat tctgttatct gttgaaaata ctgtaatata tcggatacag gccctaagtc  2040
tatgttccga tcaacaatct catctggaat ttagagtcaa cagaaacaat ctggagttgt  2100
cgcacaccact taaaatagaa accatctccc atgaagacct tcaaagacaa cttgccgtct   2160
tggacaaagc aatgaaagca aaagtggcca catacctggg tggccttcca gatgttccat   2220
tcagtgccac accagtgaat gccttttata atggctgcat ggaagtgaat attaatggtg  2280
tacagttgga tctggatgaa gccatttcta acataatga tattagagct cactcatgtc    2340
catcagtttg gaaaaagaca aagaattctt aaggcatctt ttctctgctt ataatccttt  2400
ttccttgtgt gtaattatac ttatgtttca ataacagctg aagggtttta tttacaatgt  2460
gcagtctttg attattttgt ggtccttcca tgggattttt aaaaggtcct ttgtcaagga  2520
aaaaattct gttgtgatat aaatcacagt aaagaaattc ttacttctct tgctatctaa   2580
gaatagtgaa aaataacaat tttaaatttg aattttttttc ctacaaatga cagtttcaat  2640
tttttgtttgt aaaactaaat tttaatttta tcatcatgaa ctagtgtcta aataccatg   2700
tttttttttcag aaagcaagga agtaaactca aacaaaagtg cgtgtaatta aatactatta  2760
atcataggca gatactattt tgtttatgtt tttgttttt tcctgatgaa ggcagaagag    2820
atggtggtct attaaatatg aattgaatgg agggtcctaa tgcctattt caaaacaatt   2880
cctcaggggg aacagctttg gcttcatctt tctcttgtgt ggcttcacat ttaaccagt   2940
atctttattg aattagaaaa caagtgggac atatttcct gagagcagca caggaatctt   3000
cttcttggca gctgcagtct gtcaggatga gatatcagat taggttggat aggtggggaa   3060
atctgaagtg ggtacatttt ttaaattttg ctgtgtgggt cacacaaggt ctacattaca  3120
aaagacagaa ttcagggatg gaaaggagaa tgaacaaatg tgggagttca tagtttttcct  3180
tgaatccaac ttttaattac cagagtaagt tgccaaaatg tgattgttga agtacaaaag  3240
gaactatgaa aaccagaaca aattttaaca aaaggacaac cacagaggga tatagtgaat  3300
atcgtatcat tgtaatcaaa gaagtaagga ggtaagattg ccacgtgcct gctggtactg  3360
tgatgcattt caagtggcag tttttatcacg tttgaatcta ccagatgtgt            3420
atcagatgtt tcactgacag ttttttaacaa taaattcttt tcactgtatt ttatatcact  3480
tataatataaat cggtgtataa ttttaaaatg catgtgaata tctttattat atcaactgtt  3540
tgaataaaac aaaattacat aatagacatt taactcttca aaaaaaaaaa aaaaa         3595
```

| SEQ ID NO: 54 | moltype = AA  length = 1019 |
|---|---|
| FEATURE | Location/Qualifiers |
| source | 1..1019 |
| | mol_type = protein |
| | organism = Homo sapiens |

SEQUENCE: 54

```
HTVELNNMFG QIQSPGYPDS YPSDSEVTWN ITVPDGFRIK LYFMHFNLES SYLCEYDYVK    60
VETEDQVLAT FCGRETTDTE QTPGQEVVLS PGSFMSITFR SDFSNEERFT GFDAHYMAVD   120
VDECKEREDE ELSCDHYCHN YIGGYYCSCR FGYILHTDNR TCRVECSDNL FTQRTGVITS   180
PDFPNPYPKS SECLYTIELE EGFMVNLQFE DIFDIEDHPE VPCPYDYIKI KVGPKVLGPF   240
CGEKAPEPIS TQSHSVLILF HSDNSGENRG WRLSYRAAGN ECPELQPPVH GKIEPSQAKY   300
```

```
FFKDQVLVSC DTGYKVLKDN VEMDTFQIEC LKDGTWSNKI PTCKKNEIDL ESELKSEQVT  360
EGGGGSGGGG SALLPAREAT QFLRPRQRRA FQVFEEAKQG HLERECVEEL CSREEAREVF  420
ENDPETDYFY PRYLDCINKY GSPYTKNSGF ATCVQNLPDQ CTPNPCDRKG TQACQDLMGN  480
FFCLCKAGWG GRLCDKDVNE CSQENGGCLQ ICHNKPGSFH CSCHSGFELS SDGRTCQDID  540
ECADSEACGE ARCKNLPGSY SCLCDEGFAY SSQEKACRDV DECLQGRCEQ VCVNSPGSYT  600
CHCDGRGGLK LSQDMDTCED ILPCVPFSVA KSVKSLYLGR MFSGTPVIRL RFKRLQPTRL  660
VAEFDFRTFD PEGILLFAGG HQDSTWIVLA LRAGRLELQL RYNGVGRVTS SGPVINHGMW  720
QTISVEELAR NLVIKVNRDA VMKIAVAGDL FQPERGLYHL NLTVGGIPFH EKDLVQPINP  780
RLDGCMRSWN WLNGEDTTIQ ETVKVNTRMQ CFSVTERGSF YPGSGFAFYS LDYMRTPLDV  840
GTESTWEVEV VAHIRPAADT GVLFALWAPD LRAVPLSVAL VDYHSTKKLK KQLVVLAVEH  900
TALALMEIKV CDGQEHVVTV SLRDGEATLE VDGTRGQSEV SAAQLQERLA VLERHLRSPV  960
LTFAGGLPDV PVTSAPVTAF YRGCMTLEVN RRLLDLDEAA YKHSDITAHS CPPVEPAAA  1019

SEQ ID NO: 55           moltype = AA   length = 1019
FEATURE                 Location/Qualifiers
source                  1..1019
                        mol_type = protein
                        organism = Homo sapiens
SEQUENCE: 55
ALLPAREATQ FLRPRQRRAF QVFEEAKQGH LERECVEELC SREEAREVFE NDPETDYFYP   60
RYLDCINKYG SPYTKNSGFA TCVQNLPDQC TPNPCDRKGT QACQDLMGNF FCLCKAGWGG  120
RLCDKDVNEC SQENGGCLQI CHNKPGSFHC SCHSGFELSS DGRTCQDIDE CADSEACGEA  180
RCKNLPGSYS CLCDEGFAYS SQEKACRDVD ECLQGRCEQV CVNSPGSYTC HCDGRGGLKL  240
SQDMDTCEDI LPCVPFSVAK SVKSLYLGRM FSGTPVIRLR FKRLQPTRLV AEFDFRTFDP  300
EGILLFAGGH QDSTWIVLAL RAGRLELQLR YNGVGRVTSS GPVINHGMWQ TISVEELARN  360
LVIKVNRDAV MKIAVAGDLF QPERGLYHLN LTVGGIPFHE KDLVQPINPR LDGCMRSWNW  420
LNGEDTTIQE TVKVNTRMQC FSVTERGSFY PGSGFAFYSL DYMRTPLDVG TESTWEVEVV  480
AHIRPAADTG VLFALWAPDL RAVPLSVALV DYHSTKKLKK QLVVLAVEHT ALALMEIKVC  540
DGQEHVVTVS LRDGEATLEV DGTRGQSEVS AAQLQERLAV LERHLRSPVL TFAGGLPDVP  600
VTSAPVTAFY RGCMTLEVNR RLLDLDEAAY KHSDITAHSC PPVEPAAAGG GGSGGGGSHT  660
VELNNMFGQI QSPGYPDSYP SDSEVTWNIT VPDGFRIKLY FMHFNLESSY LCEYDYVKVE  720
TEDQVLATFC GRETTDTEQT PGQEVVLSPG SFMSITFRSD FSNEERFTGF DAHYMAVDVD  780
ECKEREDEEL SCDHYCHNYI GGYYCSCRFG YILHTDNRTC RVECSDNLFT QRTGVITSPD  840
FPNPYPKSSE CLYTIELEEG FMVNLQFEDI FDIEDHPEVP CPYDYIKIKV GPKVLGPFCG  900
EKAPEPISTQ SHSVLILFHS DNSGENRGWR LSYRAAGNEC PELQPPVHGK IEPSQAKYFF  960
KDQVLVSCDT GYKVLKDNVE MDTFQIECLK DGTWSNKIPT CKKNEIDLES ELKSEQVTE  1019

SEQ ID NO: 56           moltype = AA   length = 1030
FEATURE                 Location/Qualifiers
source                  1..1030
                        mol_type = protein
                        organism = Homo sapiens
SEQUENCE: 56
HTVELNNMFG QIQSPGYPDS YPSDSEVTWN ITVPDGFRIK LYFMHFNLES SYLCEYDYVK   60
VETEDQVLAT FCGRETTDTE QTPGQEVVLS PGSFMSITFR SDFSNEERFT GFDAHYMAVD  120
VDECKEREDE ELSCDHYCHN YIGGYYCSCR FGYILHTDNR TCRVECSDNL FTQRTGVITS  180
PDFPNPYPKS SECLYTIELE EGFMVNLQFE DIFDIEDHPE VPCPYDYIKI KVGPKVLGPF  240
CGEKAPEPIS TQSHSVLILF HSDNSGENRG WRLSYRAAGN ECPELQPPVH GKIEPSQAKY  300
FFKDQVLVSC DTGYKVLKDN VEMDTFQIEC LKDGTWSNKI PTCKKNEIDL ESELKSEQVT  360
EGGGGSGGGG SGSGGGGSNF LSKQQASQVL VRKRRANSLL EETKQGNLER ECIEELCNKE  420
EAREVFENDP ETDYFYPKYL VCLRSFQTGL FTAARQSTNA YPDLRSCVNA IPDQCSPLPC  480
NEDGYMSCKD GKASFTCTCK PGWQGEKCEF DINECKDPSN INGGCSQICD NTPGSYHCSC  540
KNGFVMLSNK KDCKDVDECS LKPSICGTAV CKNIPGDFEC ECPEGYRYNL KSKSCEDIDE  600
CSENMCAQLC VNYPGGYTCY CDGKKGFKLA QDQKSCEVVS VCLPLNLDTK YELLYLAEQF  660
AGVVLYLKFR LPEISRFSAE FDFRTYDSEG VILYAESIDH SAWLLIALRG GKIEVQLKNE  720
HTSKITTGGD VINNGLWNMV SVEELEHSIS IKIAKEAVMD INKPGPLFKP ENGLLETKVY  780
FAGFPRKVES ELIKPINPRL DGCIRSWNLM KQGASGIKEI IQEKQNKHCL VTVEKGSYYP  840
GSGIAQFHID YNNVSSAEGW HVNVTLNIRP STGTGVMLAL VSGNNTVPFA VSLVDSTSEK  900
SQDILLSVEN TVIYRIQALS LCSDQQSHLE FRVNRNNLEL STPLKIETIS HEDLQRQLAV  960
LDKAMKAKVA TYLGGLPDVP FSATPVNAFY NGCMEVNING VQLDLDEAIS KHNDIRAHSC 1020
PSVWKKTKNS                                                       1030

SEQ ID NO: 57           moltype = AA   length = 1020
FEATURE                 Location/Qualifiers
source                  1..1020
                        mol_type = protein
                        organism = Homo sapiens
SEQUENCE: 57
NFLSKQQASQ VLVRKRRANS LLEETKQGNL ERECIEELCN KEEAREVFEN DPETDYFYPK   60
YLVCLRSFQT GLFTAARQST NAYPDLRSCV NAIPDQCSPL PCNEDGYMSC KDGKASFTCT  120
CKPGWQGEKC EFDINECKDP SNINGGCSQI CDNTPGSYHC SCKNGFVMLS NKKDCKDVDE  180
CSLKPSICGT AVCKNIPGDF ECECPEGYRY NLKSKSCEDI DECSENMCAQ LCVNYPGGYT  240
CYCDGKKGFK LAQDQKSCEV VSVCLPLNLD TKYELLYLAE QFAGVVLYLK FRLPEISRFS  300
AEFDFRTYDS EGVILYAESI DHSAWLLIAL RGGKIEVQLK NEHTSKITTG GDVINNGLWN  360
MVSVEELEHS ISIKIAKEAV MDINKPGPLF KPENGLLETK VYFAGFPRKV ESELIKPINP  420
RLDGCIRSWN LMKQGASGIK EIIQEKQNKH CLVTVEKGSY YPGSGIAQFH IDYNNVSSAE  480
GWHVNVTLNI RPSTGTGVML ALVSGNNTVP FAVSLVDSTS EKSQDILLSV ENTVIYRIQA  540
LSLCSDQQSH LEFRVNRNNL ELSTPLKIET ISHEDLQRQL AVLDKAMKAK VATYLGGLPD  600
VPFSATPVNA FYNGCMEVNI NGVQLDLDEA ISKHNDIRAH SCPSVWKKTK NSGSGGGGSH  660
```

```
TVELNNMFGQ IQSPGYPDSY PSDSEVTWNI TVPDGFRIKL YFMHFNLESS YLCEYDYVKV    720
ETEDQVLATF CGRETTDTEQ TPGQEVVLSP GSFMSITFRS DFSNEERFTG FDAHYMAVDV    780
DECKEREDEE LSCDHYCHNY IGGYYCSCRF GYILHTDNRT CRVECSDNLF TQRTGVITSP    840
DFPNPYPKSS ECLYTIELEE GFMVNLQFED IFDIEDHPEV PCPYDYIKIK VGPKVLGPFC    900
GEKAPEPIST QSHSVLILFH SDNSGENRGW RLSYRAAGNE CPELQPPVHG KIEPSQAKYF    960
FKDQVLVSCD TGYKVLKDNV EMDTFQIECL KDGTWSNKIP TCKKNEIDLE SELKSEQVTE   1020

SEQ ID NO: 58          moltype = AA   length = 13
FEATURE                Location/Qualifiers
source                 1..13
                       mol_type = protein
                       organism = Homo sapiens
SEQUENCE: 58
ICVVQDWGHH RCT                                                       13

SEQ ID NO: 59          moltype = DNA  length = 18
FEATURE                Location/Qualifiers
misc_feature           1..18
                       note = synthetic
misc_feature           1..18
                       note = exon 6 forward primer
source                 1..18
                       mol_type = other DNA
                       organism = synthetic construct
SEQUENCE: 59
gcacccagag ccacagtg                                                  18

SEQ ID NO: 60          moltype = DNA  length = 18
FEATURE                Location/Qualifiers
misc_feature           1..18
                       note = synthetic
misc_feature           1..18
                       note = reverse primer MASP1 in exon 12
source                 1..18
                       mol_type = other DNA
                       organism = synthetic construct
SEQUENCE: 60
gccttccagt gtgtgggc                                                  18

SEQ ID NO: 61          moltype = DNA  length = 19
FEATURE                Location/Qualifiers
misc_feature           1..19
                       note = synthetic
misc_feature           1..19
                       note = reverse primer for MASP3 in exon 11
source                 1..19
                       mol_type = other DNA
                       organism = synthetic construct
SEQUENCE: 61
gccttccaga gtgtggtca                                                 19

SEQ ID NO: 62          moltype = DNA  length = 19
FEATURE                Location/Qualifiers
misc_feature           1..19
                       note = synthetic
misc_feature           1..19
                       note = reverse primer for FAP in exon 8a
source                 1..19
                       mol_type = other DNA
                       organism = synthetic construct
SEQUENCE: 62
cgatctggag agcgaactc                                                 19

SEQ ID NO: 63          moltype = DNA  length = 19
FEATURE                Location/Qualifiers
misc_feature           1..19
                       note = synthetic
misc_feature           1..19
                       note = forward primer for exon 8a
source                 1..19
                       mol_type = other DNA
                       organism = synthetic construct
SEQUENCE: 63
cgatctggag agcgaactc                                                 19

SEQ ID NO: 64          moltype = DNA  length = 20
FEATURE                Location/Qualifiers
misc_feature           1..20
                       note = synthetic
```

```
misc_feature            1..20
                        note = reverse primer for exon 8a
source                  1..20
                        mol_type = other DNA
                        organism = synthetic construct
SEQUENCE: 64
ctgctgagat catgttgttc                                                    20

SEQ ID NO: 65           moltype = DNA  length = 15
FEATURE                 Location/Qualifiers
misc_feature            1..15
                        note = synthetic
misc_feature            1..15
                        note = T7 sequence
source                  1..15
                        mol_type = other DNA
                        organism = synthetic construct
SEQUENCE: 65
ttatacgact cacta                                                         15

SEQ ID NO: 66           moltype = AA  length = 7
FEATURE                 Location/Qualifiers
REGION                  1..7
                        note = synthetic
source                  1..7
                        mol_type = protein
                        organism = synthetic construct
SEQUENCE: 66
VSVFPLE                                                                   7

SEQ ID NO: 67           moltype = AA  length = 5
FEATURE                 Location/Qualifiers
REGION                  1..5
                        note = synthetic
source                  1..5
                        mol_type = protein
                        organism = synthetic construct
SEQUENCE: 67
GGGGS                                                                     5

SEQ ID NO: 68           moltype = AA  length = 10
FEATURE                 Location/Qualifiers
REGION                  1..10
                        note = Synthetic
source                  1..10
                        mol_type = protein
                        organism = synthetic construct
SEQUENCE: 68
GGGGSGGGGS                                                               10

SEQ ID NO: 69           moltype = AA  length = 15
FEATURE                 Location/Qualifiers
REGION                  1..15
                        note = Synthetic
source                  1..15
                        mol_type = protein
                        organism = synthetic construct
SEQUENCE: 69
GGGGSGGGGS GGGGS                                                         15

SEQ ID NO: 70           moltype = AA  length = 16
FEATURE                 Location/Qualifiers
REGION                  1..16
                        note = Synthetic
source                  1..16
                        mol_type = protein
                        organism = synthetic construct
SEQUENCE: 70
GGGSGGGSGG GSGGGS                                                        16

SEQ ID NO: 71           moltype = AA  length = 5
FEATURE                 Location/Qualifiers
REGION                  1..5
                        note = Synthetic
source                  1..5
                        mol_type = protein
                        organism = synthetic construct
SEQUENCE: 71
SGGGG                                                                     5
```

```
SEQ ID NO: 72          moltype = AA  length = 10
FEATURE                Location/Qualifiers
REGION                 1..10
                       note = synthetic
source                 1..10
                       mol_type = protein
                       organism = synthetic construct
SEQUENCE: 72
SGGGGSGGGG                                                              10

SEQ ID NO: 73          moltype = AA  length = 15
FEATURE                Location/Qualifiers
REGION                 1..15
                       note = synthetic
source                 1..15
                       mol_type = protein
                       organism = synthetic construct
SEQUENCE: 73
SGGGGSGGGG SGGGG                                                        15

SEQ ID NO: 74          moltype = AA  length = 20
FEATURE                Location/Qualifiers
REGION                 1..20
                       note = Synthetic
source                 1..20
                       mol_type = protein
                       organism = synthetic construct
SEQUENCE: 74
SGGGGSGGGG SGGGGSGGGG                                                   20

SEQ ID NO: 75          moltype = AA  length = 146
FEATURE                Location/Qualifiers
REGION                 1..146
                       note = human GULP - engulfment adaptor PTB domain
                        containing 1 variant
source                 1..146
                       mol_type = protein
                       organism = Homo sapiens
SEQUENCE: 75
ETENMELKNK VQDLENQLRI TQVSAPPAGS MTPKSPSTDI FDMIPFSPIS HQSSMPTRNG        60
TQPPPVPSRS TEIKRDLFGA EPFDPFNCGA ADFPPDIQSK LDEMQVTILI DWPINDLFHF       120
DMGQRECYVP KLWFPSIIFA IKTRLK                                            146
```